US012772728B2

(12) United States Patent
Park et al.

(10) Patent No.: US 12,772,728 B2
(45) Date of Patent: Oct. 20, 2026

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

(71) Applicant: SAMSUNG SDI CO., LTD., Yongin-si (KR)

(72) Inventors: Junmo Park, Suwon-si (KR); Dong Min Kang, Suwon-si (KR); Byungku Kim, Suwon-si (KR); Hansol Seo, Suwon-si (KR); Byoungkwan Lee, Suwon-si (KR); Jonghoon Ko, Suwon-si (KR); Jin Sook Kim, Suwon-si (KR); Hyunjung Kim, Suwon-si (KR); Sunwoong Shin, Suwon-si (KR); Kipo Jang, Suwon-si (KR); Sung-Hyun Jung, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 1084 days.

(21) Appl. No.: 17/741,013

(22) Filed: May 10, 2022

(65) Prior Publication Data

US 2022/0407010 A1 Dec. 22, 2022

(30) Foreign Application Priority Data

May 11, 2021 (KR) ........................ 10-2021-0060893
Apr. 27, 2022 (KR) ........................ 10-2022-0052335

(51) Int. Cl.

| | |
|---|---|
| ***H10K 85/60*** | (2023.01) |
| ***C07D 209/80*** | (2006.01) |
| ***C07D 307/77*** | (2006.01) |
| ***C07D 405/10*** | (2006.01) |
| ***C07D 409/10*** | (2006.01) |
| ***C09K 11/06*** | (2006.01) |
| ***H10K 50/11*** | (2023.01) |
| ***H10K 101/00*** | (2023.01) |
| ***H10K 101/10*** | (2023.01) |
| ***H10K 101/30*** | (2023.01) |

(52) U.S. Cl.

CPC ......... *H10K 85/654* (2023.02); *C07D 209/80* (2013.01); *C07D 307/77* (2013.01); *C07D 405/10* (2013.01); *C07D 409/10* (2013.01); *C09K 11/06* (2013.01); *H10K 85/633* (2023.02); *H10K 85/636* (2023.02); *H10K 85/6574* (2023.02); *H10K 85/6576* (2023.02); *C09K 2211/1018* (2013.01); *H10K 50/11* (2023.02); *H10K 85/615* (2023.02); *H10K 85/6572* (2023.02); *H10K 2101/10* (2023.02); *H10K 2101/30* (2023.02); *H10K 2101/90* (2023.02)

(58) Field of Classification Search

None

See application file for complete search history.

(56) References Cited

U.S. PATENT DOCUMENTS

| | | | | |
|---|---|---|---|---|
| 5,061,569 A | 10/1991 | Vanslyke et al. | | |
| 2010/0001636 A1 | 1/2010 | Yabunouchi | | |
| 2012/0112174 A1* | 5/2012 | Lee | C07D 333/50 548/440 | |
| 2019/0312215 A1* | 10/2019 | Kang | H10K 85/6572 | |
| 2022/0199911 A1* | 6/2022 | Lee | H10K 85/615 | |

FOREIGN PATENT DOCUMENTS

| | | | |
|---|---|---|---|
| CN | 113549059 A * | 10/2021 | C07D 405/04 |
| JP | 1993-009471 A | 1/1993 | |
| JP | 1995-126615 A | 5/1995 | |
| JP | 1998-095973 A | 4/1998 | |
| KR | 10-2011-0011647 A | 2/2011 | |
| KR | 10-1814875 B1 | 1/2018 | |
| KR | 10-2018-0022574 A | 3/2018 | |
| KR | 10-2019-0013353 A | 2/2019 | |

(Continued)

OTHER PUBLICATIONS

Xu et al., machine translation of CN-113549059-A (2021) pp. 1-93. (Year: 2021).*

(Continued)

*Primary Examiner* — Dylan C Kershner
(74) *Attorney, Agent, or Firm* — Lee IP Law, P.C.

(57) ABSTRACT

A compound for an organic optoelectronic device, a composition for an organic optoelectronic device including the same, an organic optoelectronic device, and a display device, the compound being represented by Chemical Formula 1:

[Chemical Formula 1]

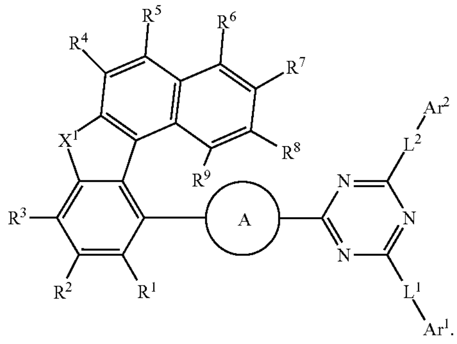

11 Claims, 1 Drawing Sheet

(56) References Cited

FOREIGN PATENT DOCUMENTS

| | | | | | |
|---|---|---|---|---|---|
| KR | 10-2020-0092897 | A | | 8/2020 | |
| KR | 10-2021-0002014 | A | | 1/2021 | |
| KR | 10-2022-0014504 | A | | 2/2022 | |
| WO | WO 1995/009147 | A1 | | 4/1995 | |
| WO | WO 2013/077352 | A1 | | 5/2013 | |
| WO | WO 2018-038464 | A1 | | 3/2018 | |
| WO | WO-2020226300 | A1 | * | 11/2020 | ............. H10K 50/00 |

OTHER PUBLICATIONS

Korean Notice of Allowance dated Jan. 1, 2025.

Chinese Office Action (including a search report) dated Mar. 14, 2024, of the corresponding Chinese Patent Application No. 202210504846.3.

Provisional double patenting rejection from U.S. Appl. No. 17/978,417 dated Jul. 7, 2026.

* cited by examiner

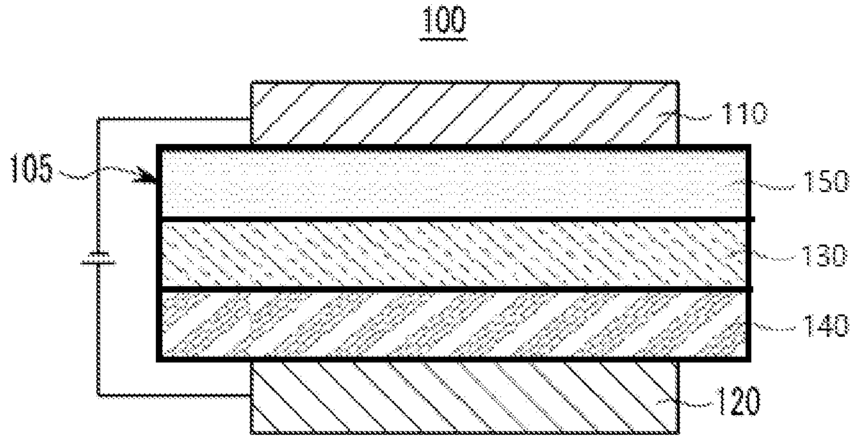
100
110
105
150
130
140
120

COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

CROSS-REFERENCE TO RELATED APPLICATIONS

This application claims priority to and the benefit of Korean Patent Application No. 10-2021-0060893 filed in the Korean Intellectual Property Office on May 11, 2021, and Korean Patent Application No. 10-2022-0052335 filed in the Korean Intellectual Property Office on Apr. 27, 2022, the entire contents of which are incorporated herein by reference.

BACKGROUND

1. Field

Embodiments relate to a compound for an organic optoelectronic device, a composition for an organic optoelectronic device, an organic optoelectronic device, and a display device.

2. Description of the Related Art

An organic optoelectronic device (e.g., organic optoelectronic diode) is a device capable of converting electrical energy and optical energy to each other.

An organic optoelectronic device may be classified as follows in accordance with its driving principles. One is a photoelectric device that generates electrical energy by separating excitons formed by light energy into electrons and holes, and transferring the electrons and holes to different electrodes, respectively and the other is light emitting device that generates light energy from electrical energy by supplying voltage or current to the electrodes.

Examples of the organic optoelectronic device may include an organic photoelectric element, an organic light emitting diode, an organic solar cell, and an organic photo conductor drum.

Of these, an organic light emitting diode (OLED) has recently drawn attention due to an increase in demand for flat panel displays. The organic light emitting diode is a device that converts electrical energy into light, and the performance of the organic light emitting diode is greatly influenced by an organic material between electrodes.

SUMMARY

The embodiments may be realized by providing a compound for an organic optoelectronic device, the compound being represented by Chemical Formula 1:

[Chemical Formula 1]

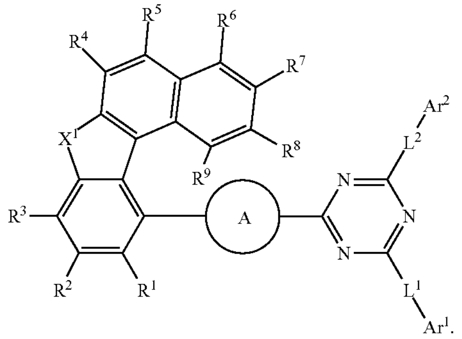

wherein, in Chemical Formula 1, $X^1$ is O or S, $L^1$ and $L^2$ are each independently a single bond or a substituted or unsubstituted C6 to C20 arylene group, $Ar^1$ and $Ar^2$ are each independently a substituted or unsubstituted C6 to C30 aryl group or a substituted or unsubstituted C2 to C30 heterocyclic group, $R^1$ to $R^9$ are each independently hydrogen, deuterium, a halogen, a substituted or unsubstituted C1 to C20 alkyl group, or a substituted or unsubstituted C6 to C20 aryl group, and A is a linking group of Group I,

[Group I]

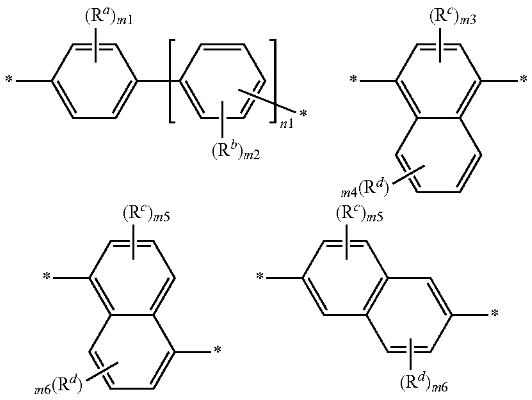

wherein, in Group I, $R^a$, $R^b$, $R^c$, and $R^d$ are each independently hydrogen, deuterium, or a substituted or unsubstituted C1 to C10 alkyl group, n1 is 0 or 1, m1, m2, and m4 are each independently an integer of 1 to 4, m3 is 1 or 2, m5 and m6 are each independently an integer of 1 to 3, and * is a linking point.

The embodiments may be realized by providing a composition for an organic optoelectronic device, the composition including a first compound; and a second compound, wherein the first compound is the compound for an organic optoelectronic device according to an embodiment, the second compound is a compound for an organic optoelectronic device represented by Chemical Formula 2:

[Chemical Formula 2]

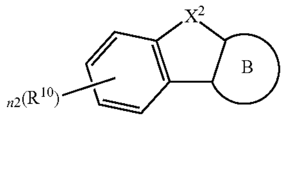

in Chemical Formula 2, $X^2$ is O, S, N-$L^a$-$R^e$, $CR^fR^g$, or $SiR^hR^i$, $L^a$ is a single bond or a substituted or unsubstituted C6 to C12 arylene group, $R^e$, $R^f$, $R^g$, $R^h$, $R^i$, and $R^{10}$ are each independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, n2 is an integer of 1 to 4, and B is a ring of Group III,

[Group III]

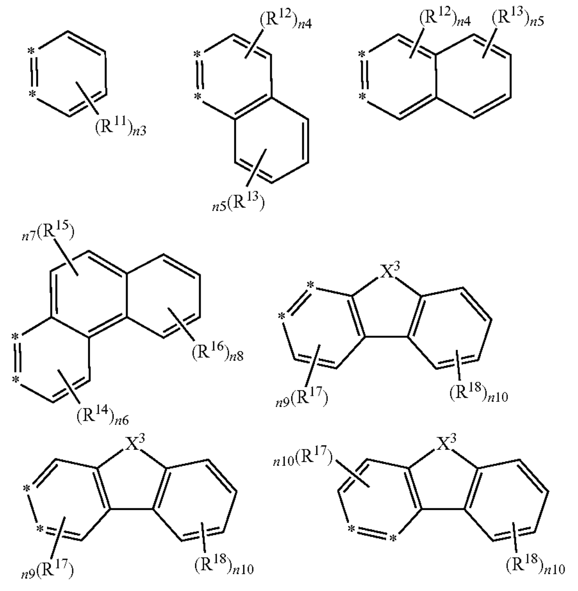

in Group III, * are linking carbons, $X^3$ is O, S, $CR^jR^k$, or $SiR^lR^m$, $R^j$, $R^k$, $R^l$, $R^m$, and $R^{11}$ to $R^{18}$ are each independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, n3, n5, n8 and n10 are each independently an integer of 1 to 4, n4, n6, n7, and n9 are each independently 1 or 2, and at least one of $R^e$ and $R^{10}$ to $R^{18}$ is a substituted amine group represented by Chemical Formula a,

[Chemical Formula a]

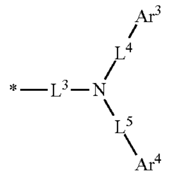

in Chemical Formula a, $L^3$ to $L^5$ are each independently a single bond or a substituted or unsubstituted C6 to C30 arylene group, $Ar^3$ and $Ar^4$ are each independently a substituted or unsubstituted amine group, a substituted or unsubstituted C6 to C30 aryl group, or a substituted or unsubstituted C2 to C30 heterocyclic group, and * is a linking point.

The embodiments may be realized by providing an organic optoelectronic device including an anode and a cathode facing each other, and at least one organic layer between the anode and the cathode, wherein the at least one organic layer includes the compound for an organic optoelectronic device according to an embodiment.

The embodiments may be realized by providing an organic optoelectronic device including an anode and a cathode facing each other, and at least one organic layer between the anode and the cathode, wherein the at least one organic layer includes the composition for an organic optoelectronic device according to an embodiment.

The embodiments may be realized by providing a display device including the organic optoelectronic device according to an embodiment.

BRIEF DESCRIPTION OF THE DRAWING

Features will be apparent to those of skill in the art by describing in detail exemplary embodiments with reference to the attached drawing in which:

the FIGURE is a cross-sectional view of an organic light emitting diode according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

In one example of the present disclosure, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof. As used herein, the term "or" is not an exclusive term, e.g., "A or B" would include A, B, or A and B.

In specific example of the present disclosure, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In specific example of the present disclosure, the "substituted" refers to replacement of at least one hydrogen of a substituent or a compound by deuterium, a C1 to C20 alkyl group, a C6 to C30 aryl group, or a cyano group. In specific example of the present disclosure, the "substituted" refers to replacement of at least one hydrogen of a substituent or a compound by deuterium, a C1 to C5 alkyl group, a C6 to C18 aryl group, or a cyano group. In specific example of the present disclosure, the "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

As used herein, "unsubstituted" refers to hydrogen remaining without substituting to or replacing with any other substituents.

As used herein, "hydrogen substitution (—H)" may also include "deuterium substitution (-D)" or "tritium substitution (-T)".

As used herein, when a definition is not otherwise provided, "hetero" refers to one including one to three heteroatoms selected from N, O, S, P, and Si, and remaining carbons in one functional group.

As used herein, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic, or fused ring polycyclic (i.e., rings sharing adjacent pairs of carbon atoms) functional group.

As used herein, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted benzophenanthrenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or a combination thereof, but is not limited thereto.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, a substituted or unsubstituted benzonaphthofuranyl group, a substituted or unsubstituted benzonaphthothiophenyl group, a substituted or unsubstituted benzofuranofluorenyl group, a substituted or unsubstituted benzothiophenefluorenyl group, or a combination thereof, but is not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic device according to an embodiment is described.

A compound for an organic optoelectronic device according to an embodiment may be, e.g., represented by Chemical Formula 1.

[Chemical Formula 1]

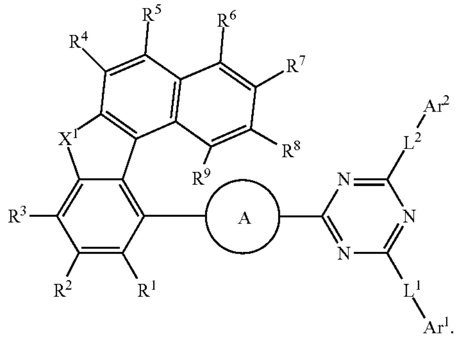

In Chemical Formula 1, $X^1$ may be, e.g., O or S.

$L^1$ and $L^2$ may each independently be or include, e.g., a single bond or a substituted or unsubstituted C6 to C20 arylene group.

$Ar^1$ and $Ar^2$ may each independently be or include, e.g., a substituted or unsubstituted C6 to C30 aryl group, or a substituted or unsubstituted C2 to C30 heterocyclic group.

$R^1$ to $R^9$ may each independently be or include, e.g., hydrogen, deuterium, a halogen, a substituted or unsubstituted C1 to C20 alkyl group, or a substituted or unsubstituted C6 to C20 aryl group.

A may be, e.g., a linking group of Group I.

[Group I]

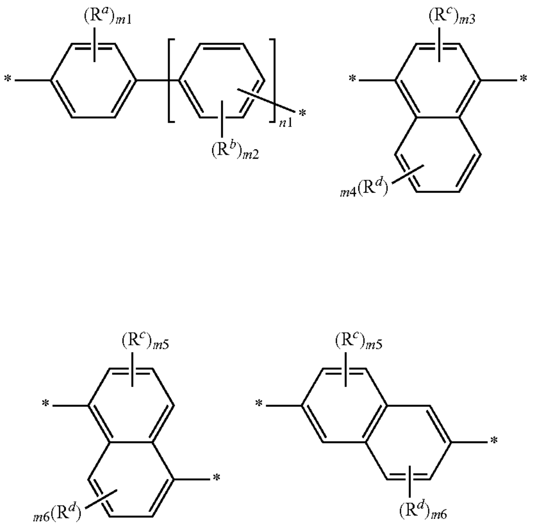

In Group I, $R^a$, $R^b$, $R^c$, and $R^d$ may each independently be or include, e.g., hydrogen, deuterium, or a substituted or unsubstituted C1 to C10 alkyl group.

n1 may be, e.g., 0 or 1.

m1, m2, and m4 may each independently be, e.g., an integer of 1 to 4.

m3 may be, e.g., 1 or 2.

m5 and m6 may each independently be, e.g., an integer of 1 to 3.

* is a linking point.

The compound represented by Chemical Formula 1 may have a structure in which the benzo[b]naphtho[1,2-d]furan (or benzo[b]naphtho[1,2-d]thiophene) skeleton is substituted with an ET unit or moiety at the 11-position thereof. In an implementation, as a twist angle between the benzo[b]naphtho[1,2-d]furan (or benzo[b]naphtho[1,2-d]thiophene) skeleton and the ET moiety increases, HOMO-LUMO separation may increase and electron mobility may increase, and Tg relative to Tev may be increased because movement of molecules is restricted.

Accordingly, an organic light emitting diode including the compound represented by Chemical Formula 1 may secure a stable driving voltage and excellent efficiency characteristics. The high glass transition temperature may maintain a stable film even against Joule heat generated during device driving, thereby ensuring stable device characteristics and enabling devices with excellent life-span.

In Chemical Formula 1, the linking group A may be linked with a para position or orientation, e.g., it may be represented by one of Chemical Formula 1-I to Chemical Formula 1-VI.

[Chemical Formula 1-I]

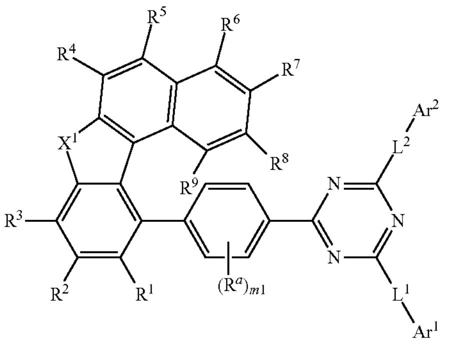

[Chemical Formula 1-II]

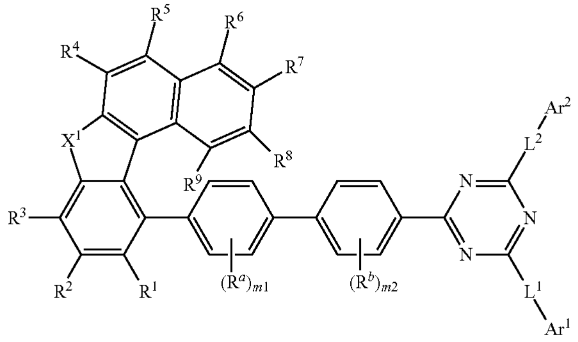

[Chemical Formula 1-III]

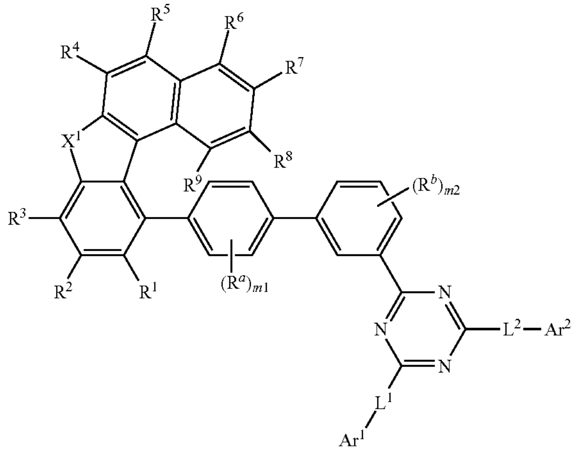

[Chemical Formula 1-IV]

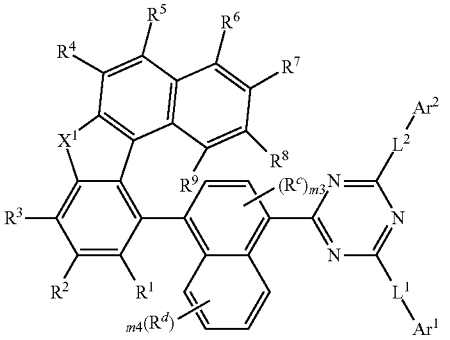

-continued

[Chemical Formula 1-V]

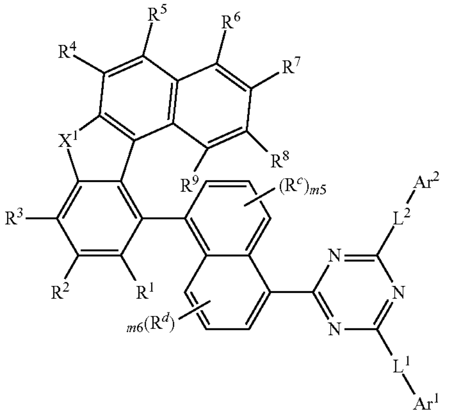

[Chemical Formula 1-VI]

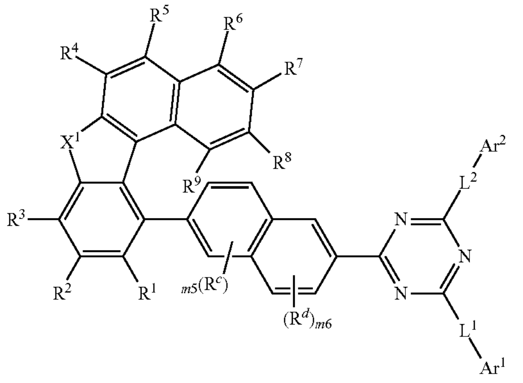

In Chemical Formula 1-I to Chemical Formula 1-VI, $X^1$, $L^1$, $L^2$, $Ar^1$, $Ar^2$, $R^1$ to $R^9$, $R^a$, $R^b$, $R^c$, $R^d$, and m1 to m6 may be defined the same as those described above (e.g., in Chemical Formula 1).

In an implementation, $Ar^1$ and $Ar^2$ may each independently be, e.g., a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, a substituted or unsubstituted chrysenyl group, or a substituted or unsubstituted triphenylene group, a substituted or unsubstituted fluorenyl group, a substituted or unsubstituted dibenzofuranyl group, a substituted or unsubstituted dibenzothiophenyl group, or a substituted or unsubstituted dibenzosilolyl group.

In an implementation, $Ar^1$ and $Ar^2$ may each independently be, e.g., a substituted or unsubstituted phenyl group, a substituted or unsubstituted biphenyl group, a substituted or unsubstituted naphthyl group, a substituted or unsubstituted fluorenyl group, a substituted or unsubstituted dibenzofuranyl group, a substituted or unsubstituted dibenzothiophenyl group, or a substituted or unsubstituted dibenzosilolyl group.

In an implementation, $L^1$ and $L^2$ may each independently be, e.g., a single bond or a substituted or unsubstituted phenylene group.

In an implementation, moieties $*-L^1-Ar^1$ and $*-L^2-Ar^2$ may each independently be, e.g., a moiety of Group II.

[Group II]

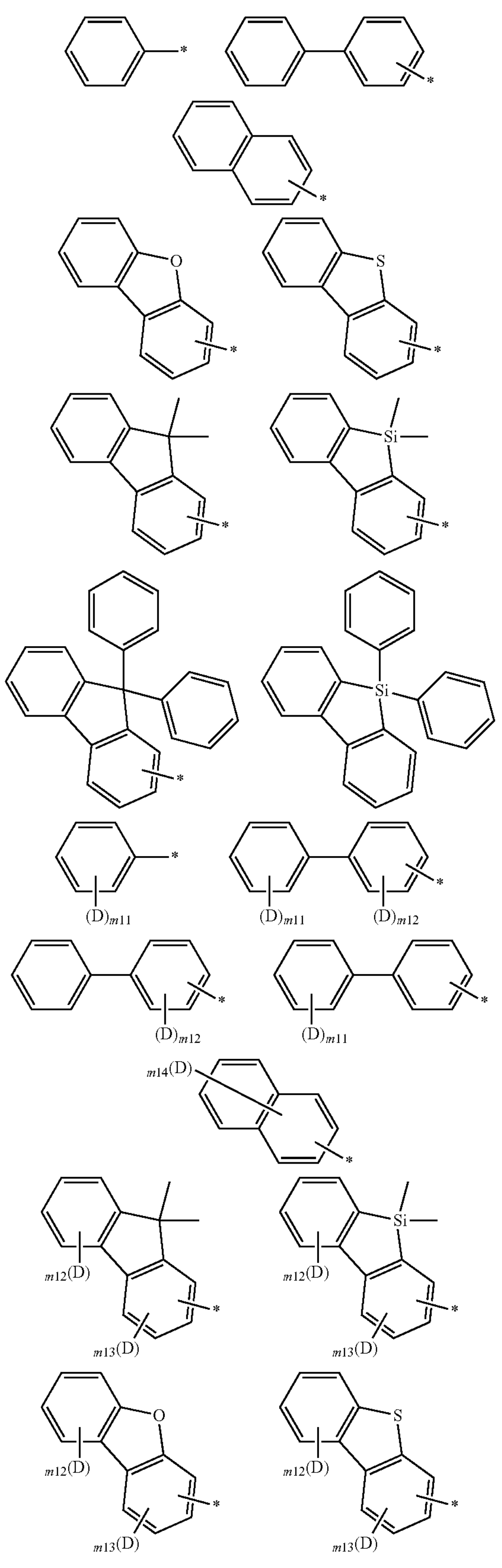

-continued

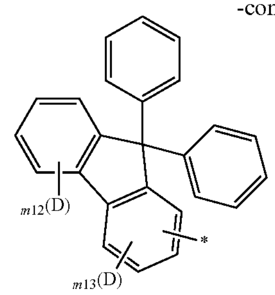
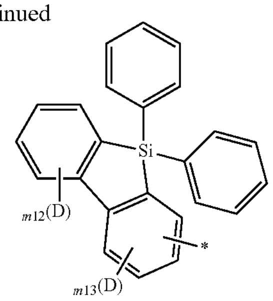
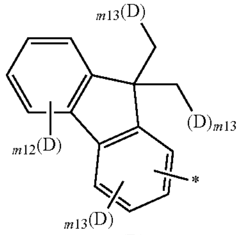
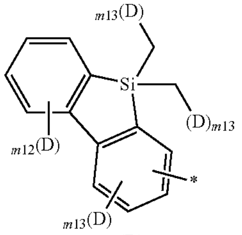
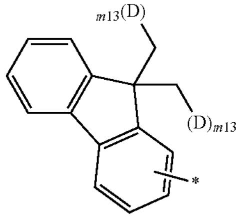
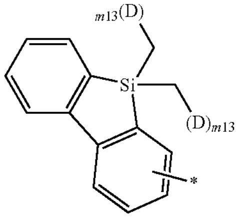
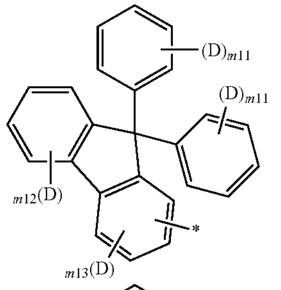
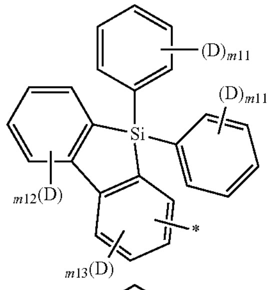
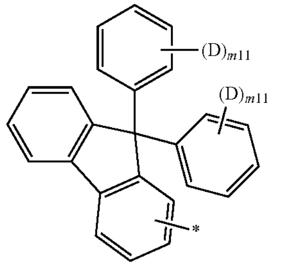
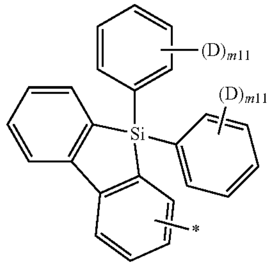

In Group II, D is deuterium.

m11 may be, e.g., an integer of 1 to 5.

m12 may be, e.g., an integer of 1 to 4.

m13 may be, e.g., an integer of 1 to 3.

m14 may be, e.g., an integer of 1 to 7.

* is a linking point.

In an implementation, $R^1$ to $R^9$ may each independently be, e.g., hydrogen, deuterium, a substituted or unsubstituted C1 to C10 alkyl group, or a substituted or unsubstituted C6 to C12 aryl group.

In an implementation, $R^1$ to $R^9$ may each independently be, e.g., hydrogen, deuterium, a substituted or unsubstituted C1 to C5 alkyl group, a substituted or unsubstituted phenyl group, a substituted or unsubstituted biphenyl group, or a substituted or unsubstituted naphthyl group.

In an implementation, $R^1$ to $R^9$ may each independently be, e.g., hydrogen or deuterium.

In an implementation, the compound for an organic optoelectronic device represented by Chemical Formula 1 may be, e.g., a compound of Group 1.

[Group 1]

[1-1]

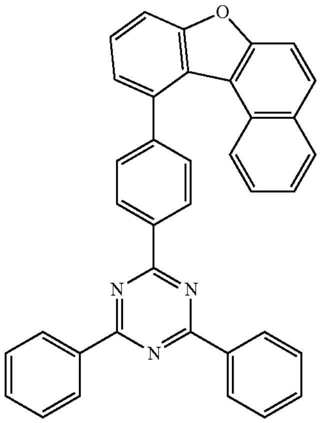

[1-2]

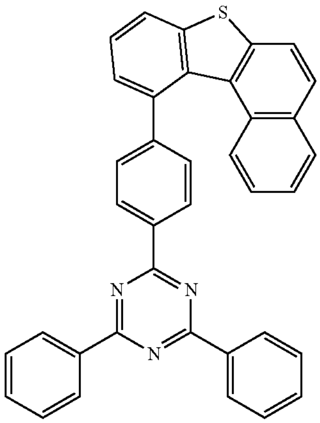

[1-3]

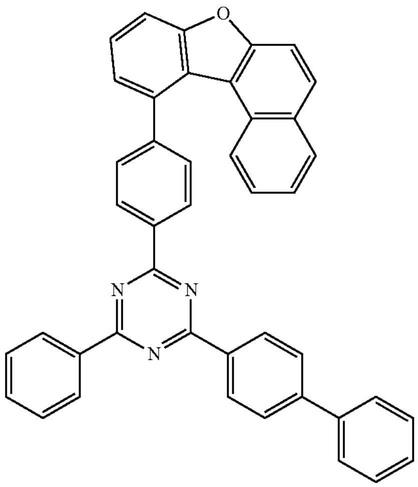

-continued
[1-4]
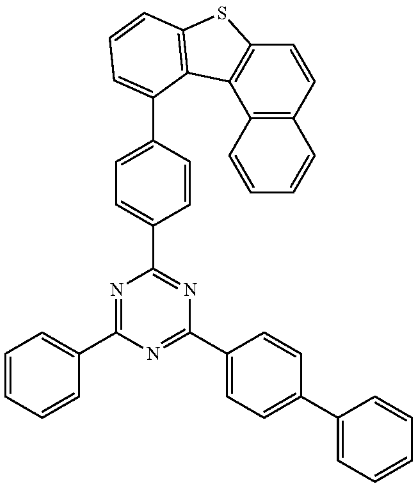
[1-5]
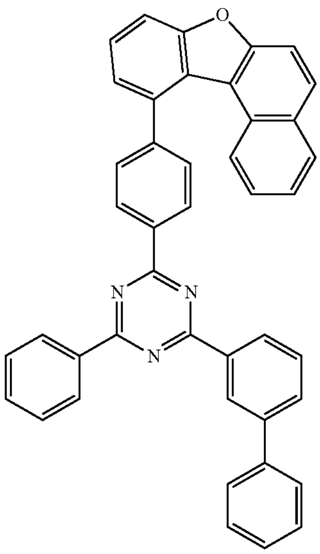
[1-6]
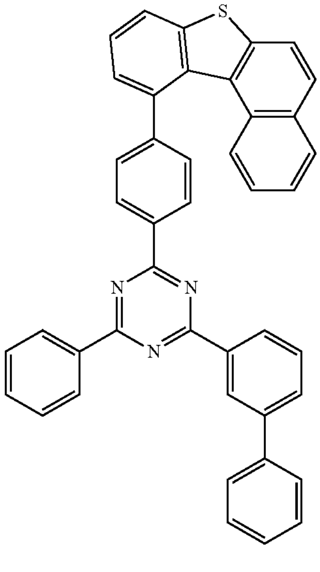
-continued
[1-7]
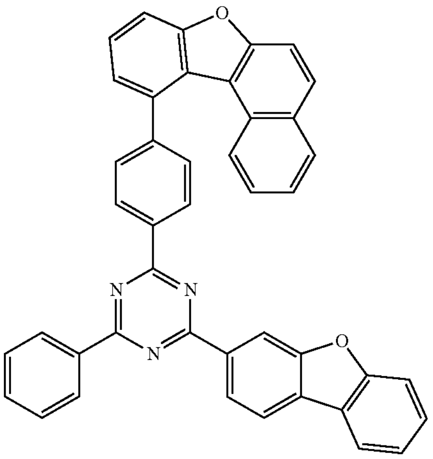
[1-8]
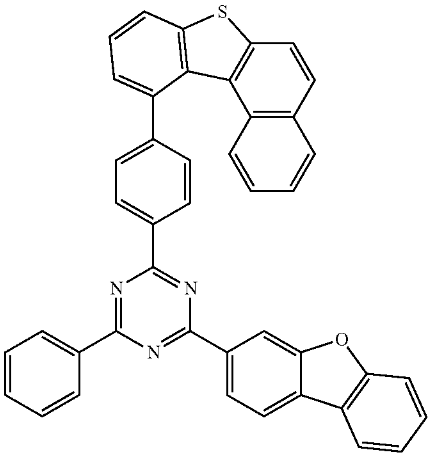
[1-9]
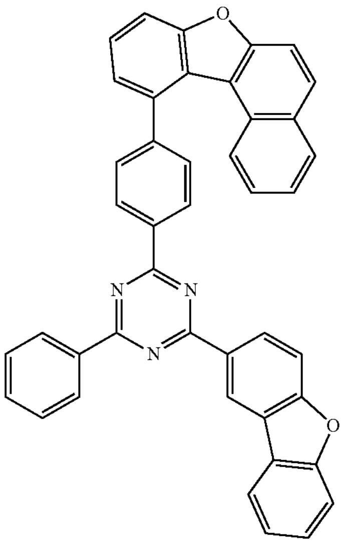

-continued
[1-10]
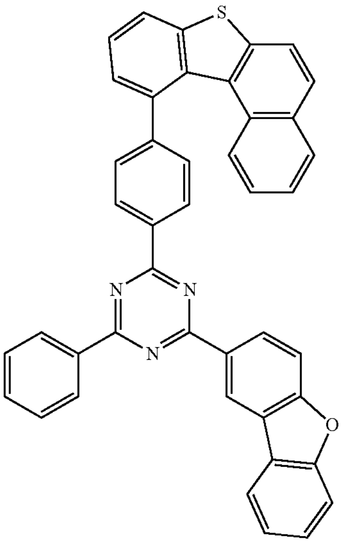
[1-11]
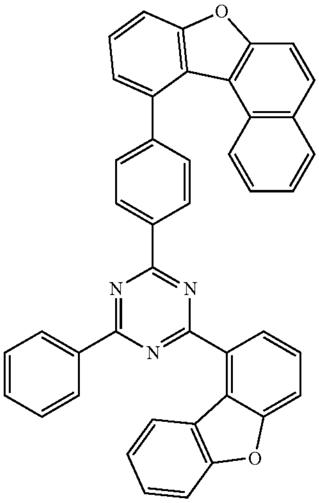
[1-12]
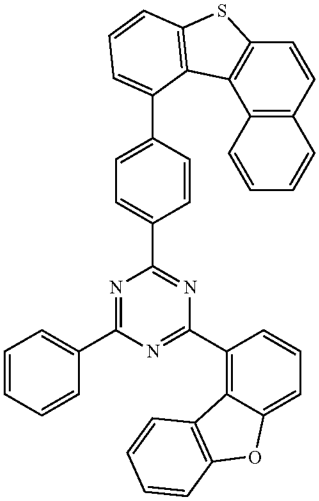
-continued
[1-13]
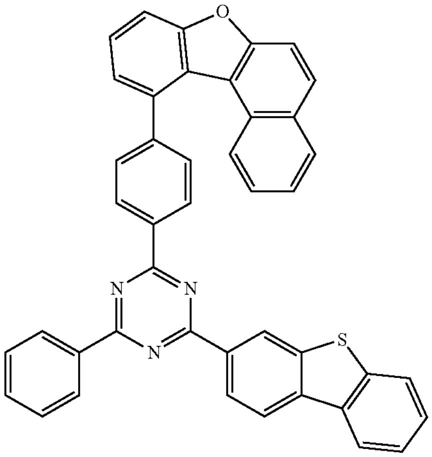
[1-14]
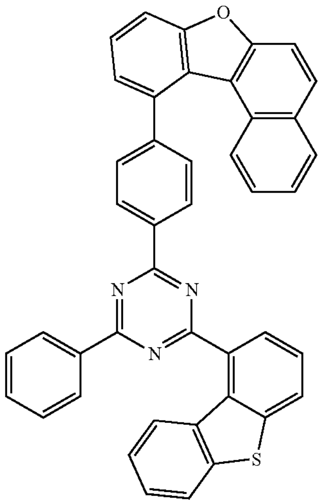
[1-15]
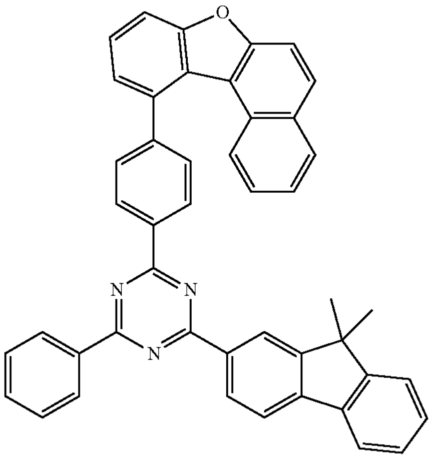

-continued
[1-16]
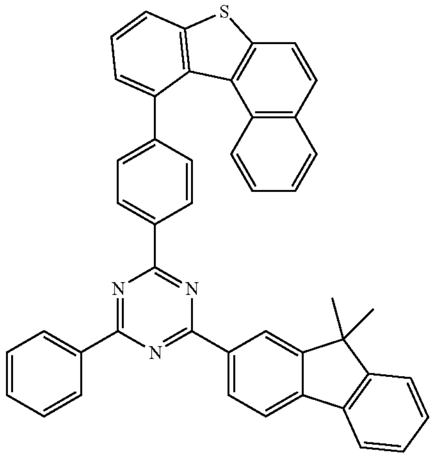
[1-17]
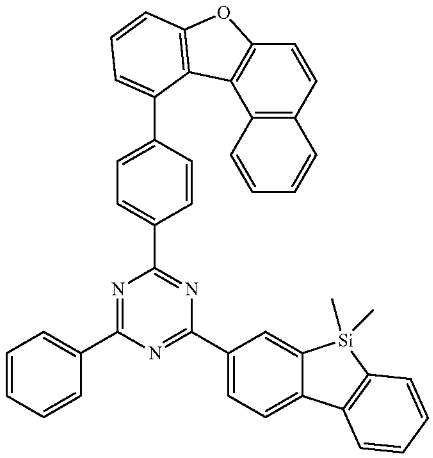
[1-18]
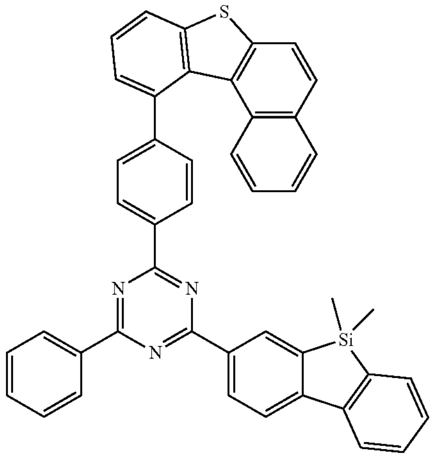
-continued
[1-19]
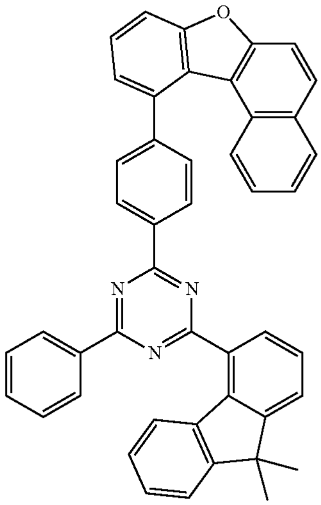
[1-20]
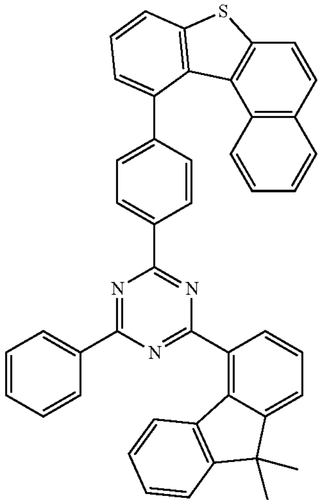
[1-21]
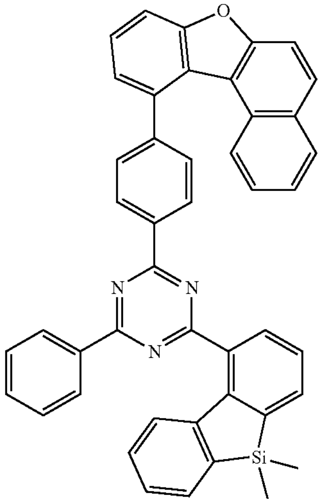

-continued
[1-22]
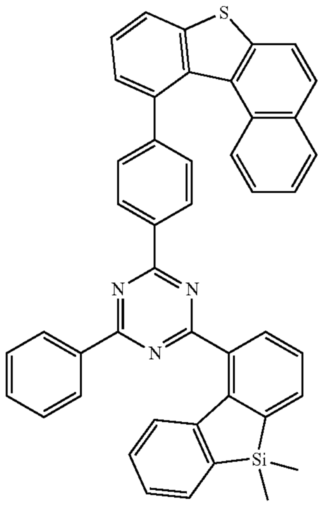
[1-23]
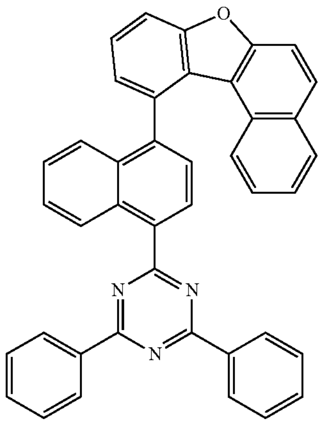
[1-24]
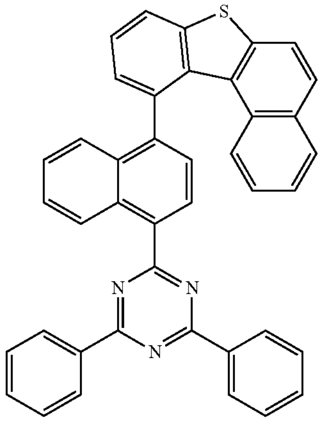
-continued
[1-25]
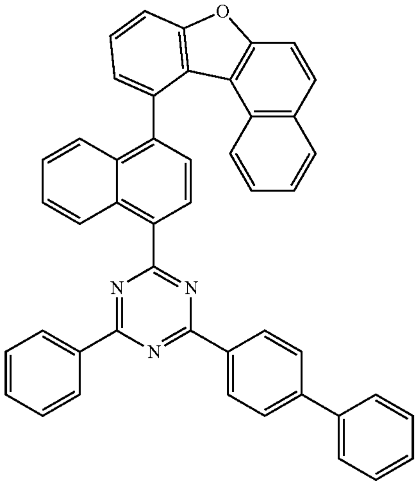
[1-26]
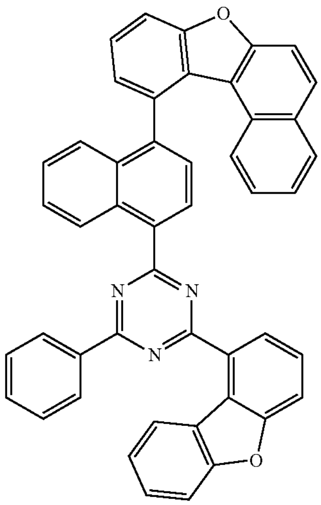
[1-27]
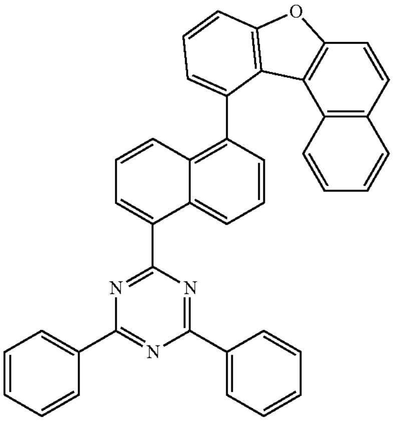

-continued
[1-28]
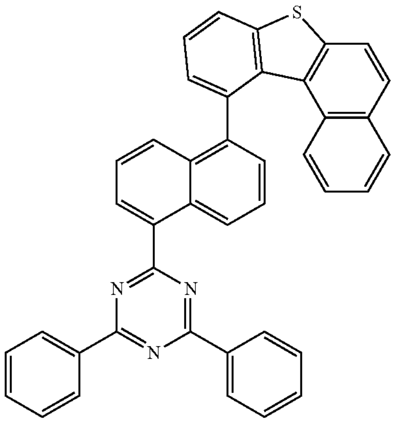
[1-29]
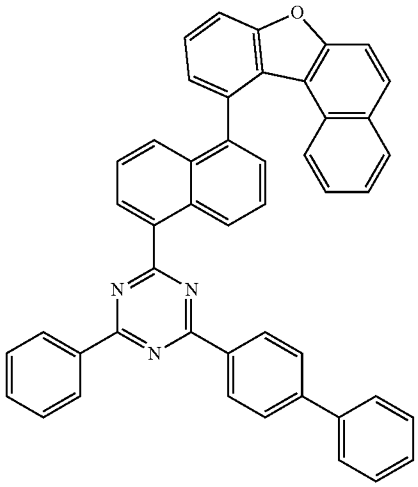
[1-30]
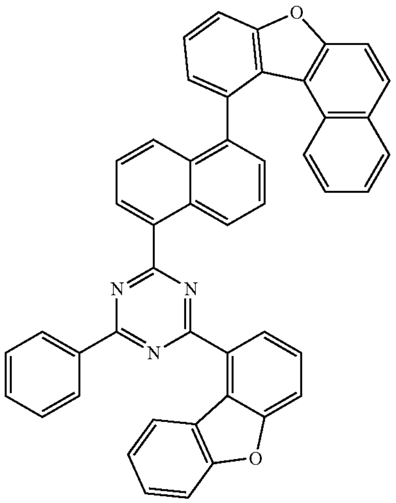
-continued
[1-31]
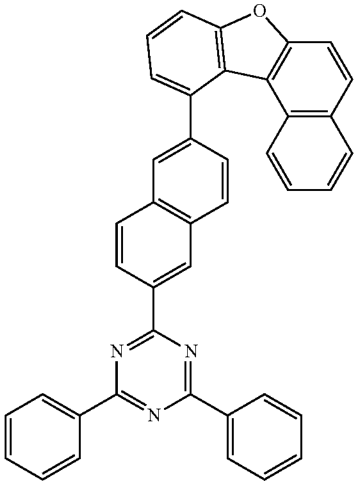
[1-32]
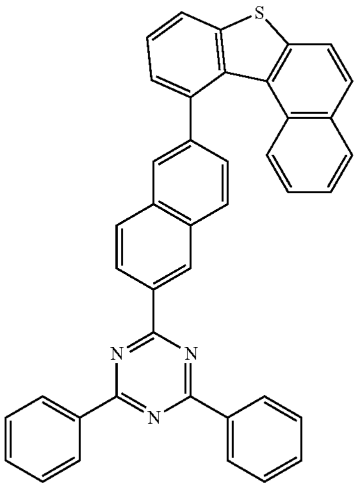
[1-33]
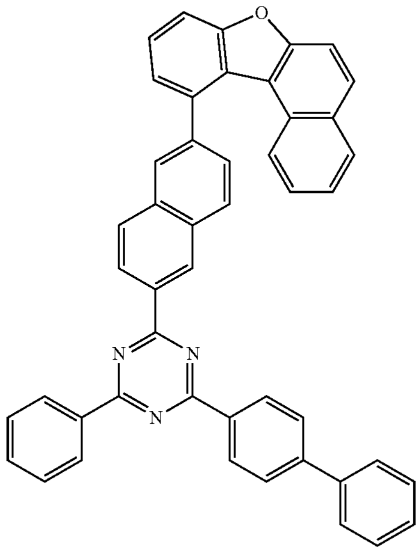

-continued
[1-34]
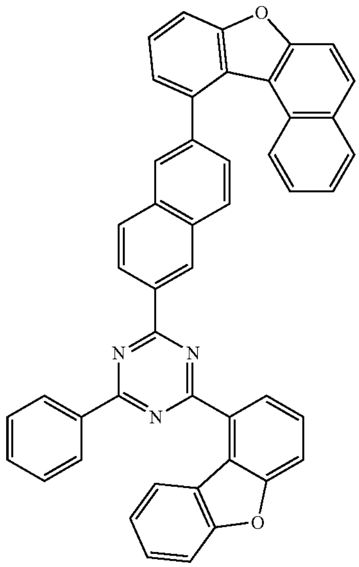
[1-35]
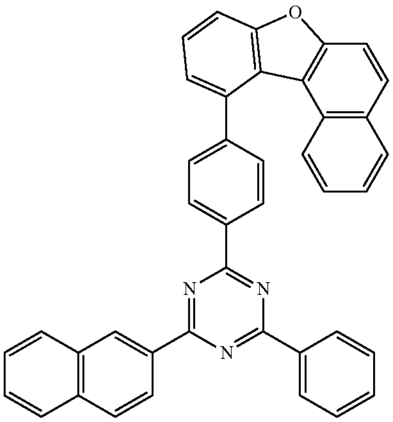
[1-36]
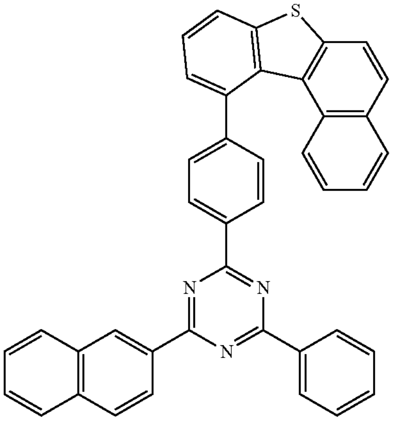
-continued
[1-37]
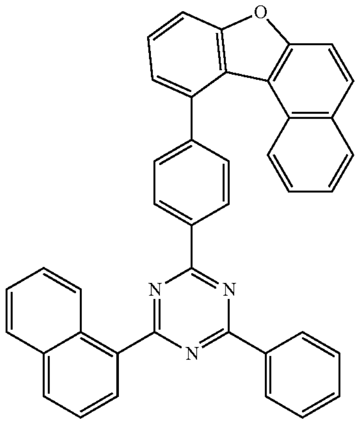
[1-38]
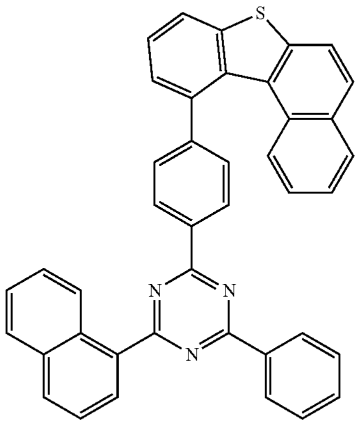
[1-39]
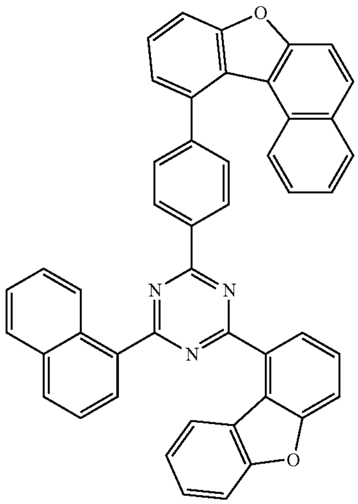

-continued
[1-40]
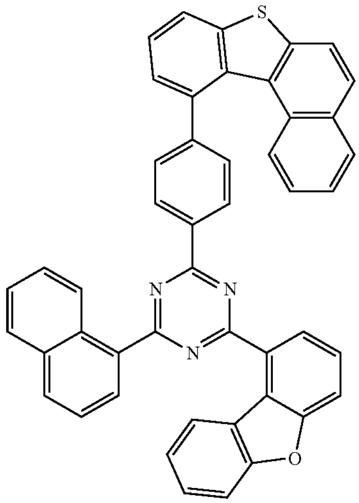
[1-41]
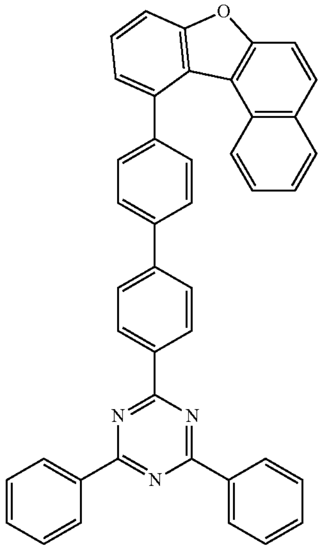
[1-42]
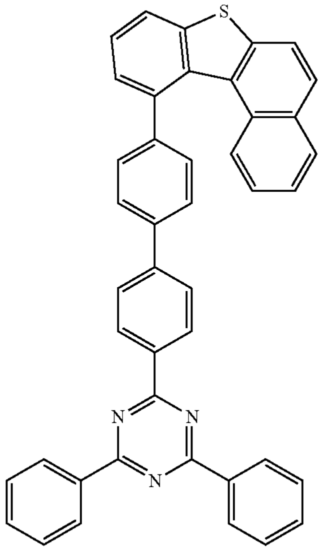
-continued
[1-43]
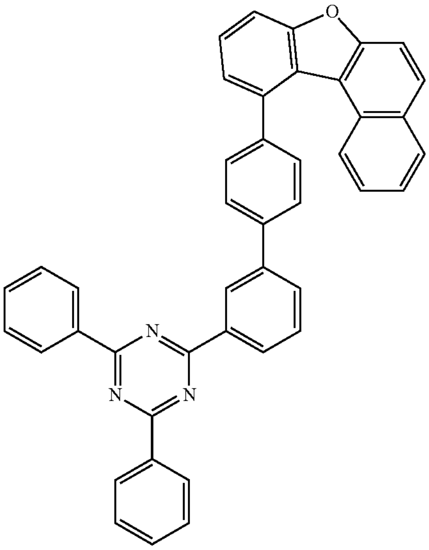
[1-44]
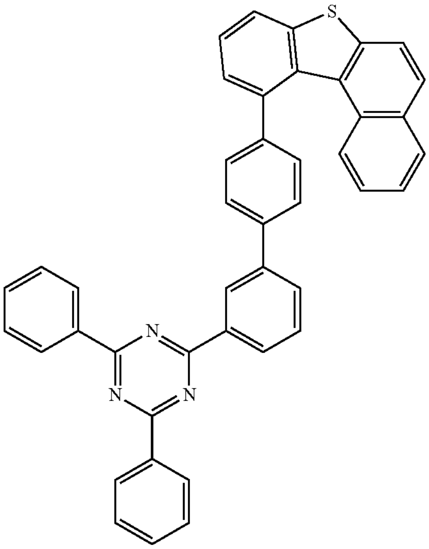
[1-45]
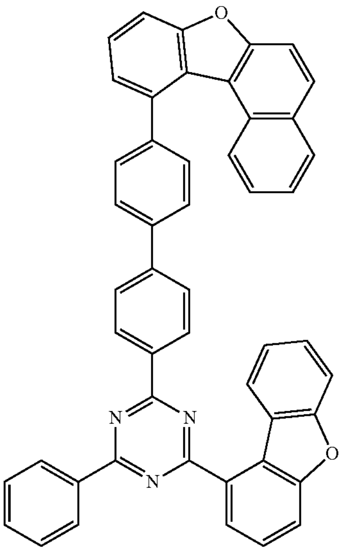

-continued
[1-46]
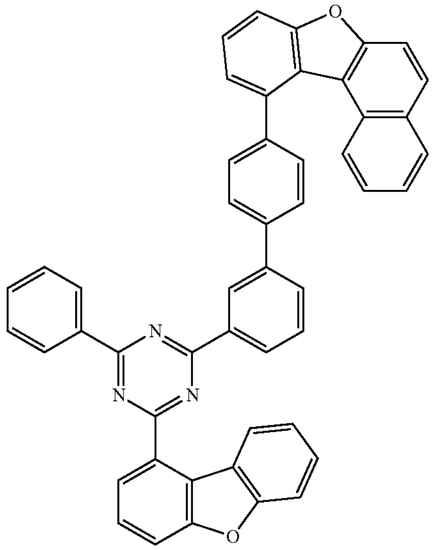
[1-47]
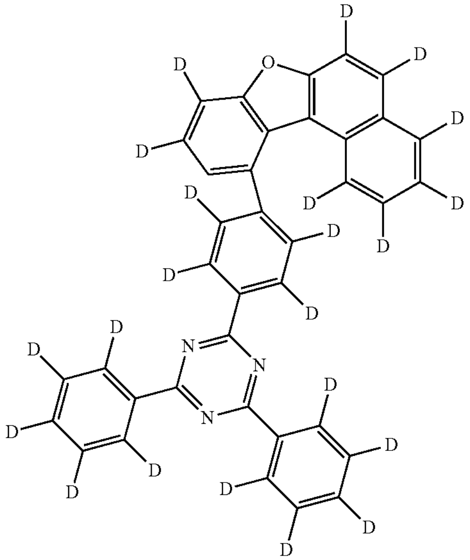
-continued
[1-48]
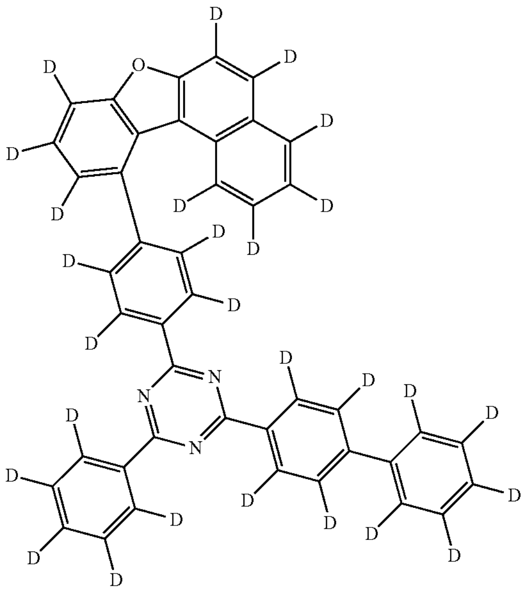
[1-49]
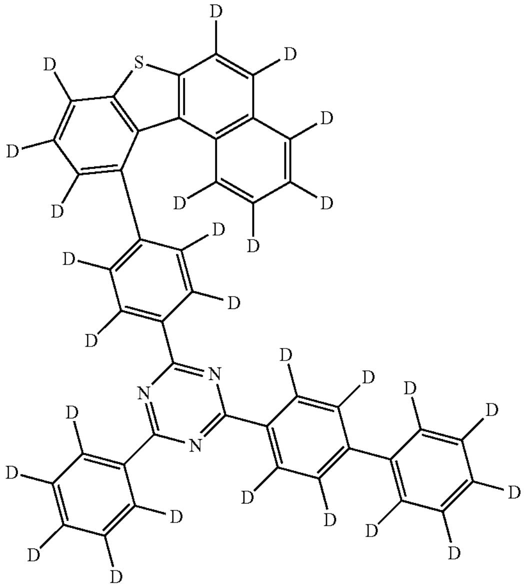

-continued
[1-50]
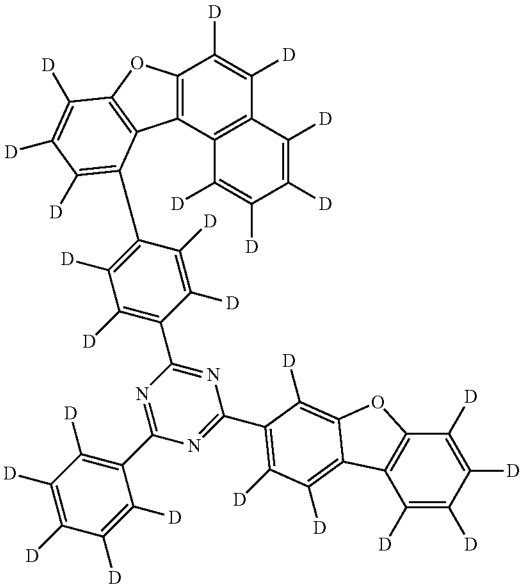
[1-51]
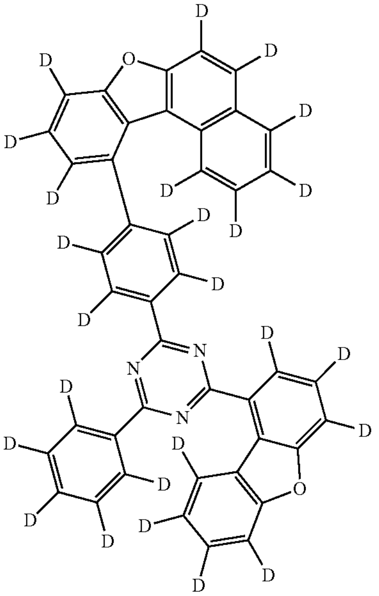
-continued
[1-52]
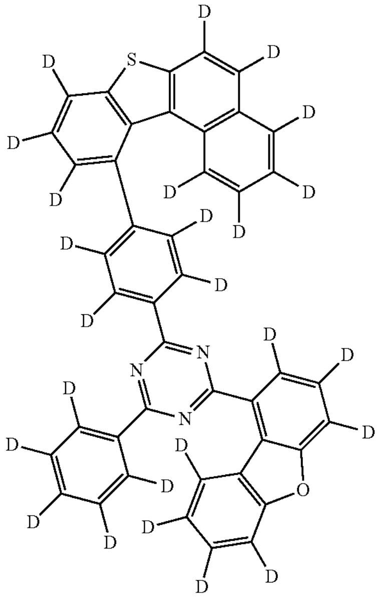
[1-53]
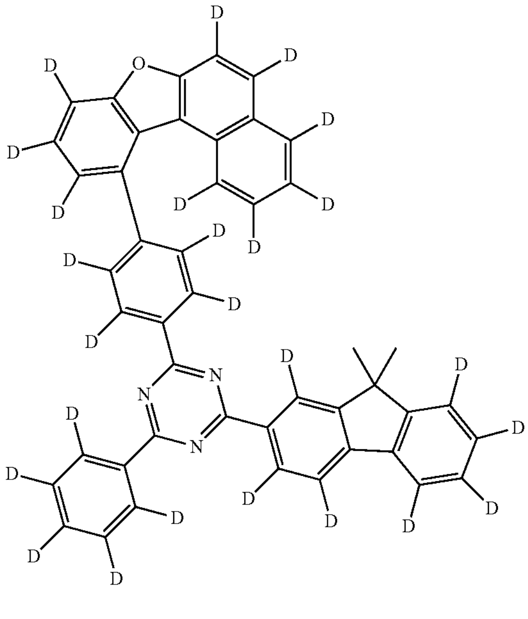

-continued
[1-54]
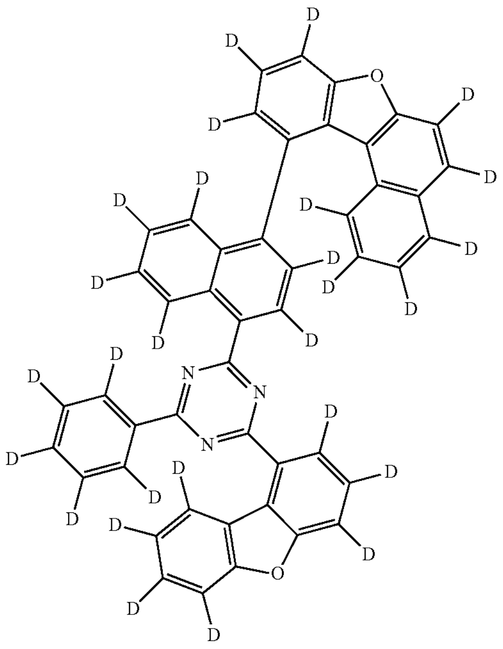
[1-55]
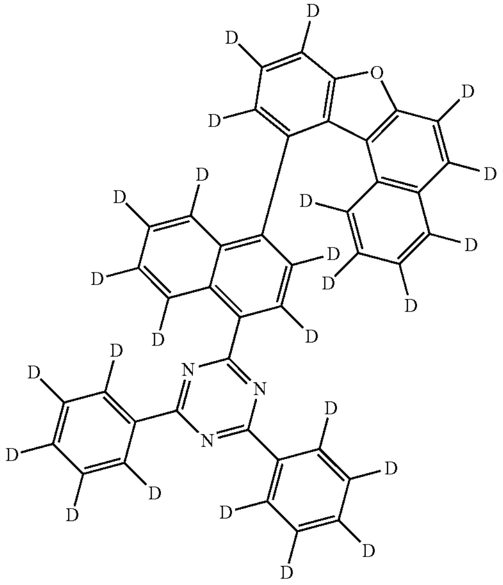
-continued
[1-56]
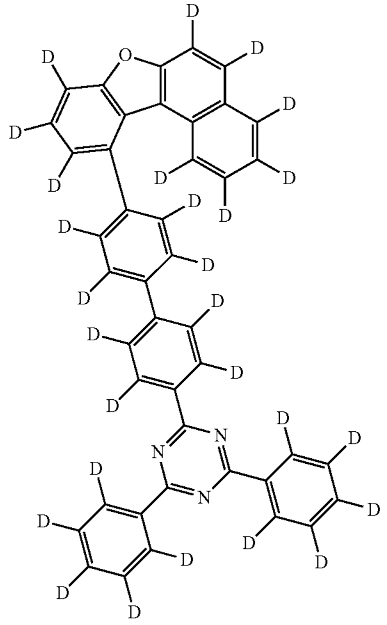
[1-57]
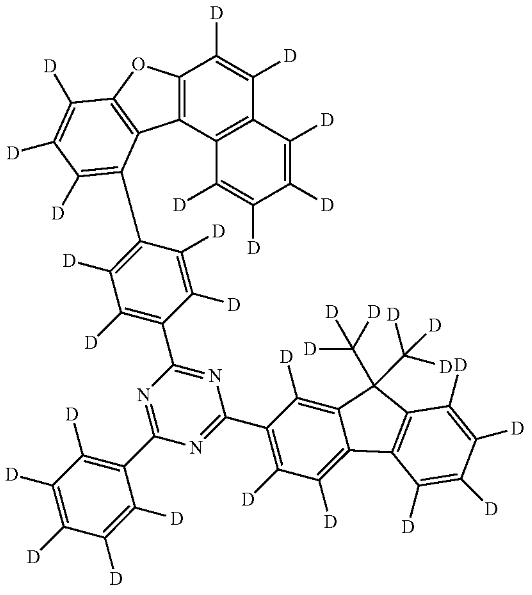

-continued

[1-58]

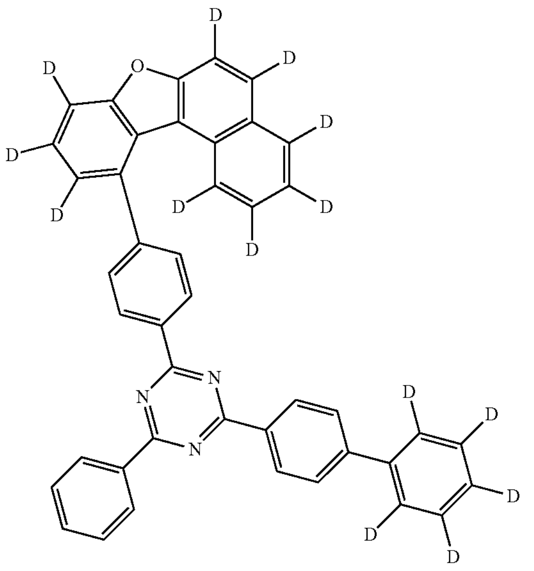

[1-59]

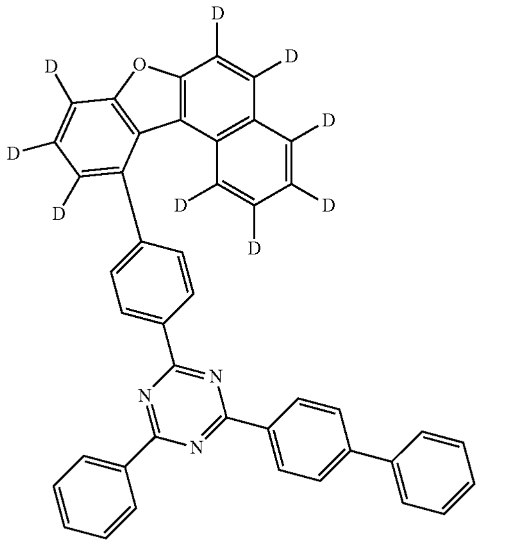

A composition for an organic optoelectronic device according to another embodiment may include, e.g., a first compound and a second compound. In an implementation, the first compound may be the aforementioned compound for an organic optoelectronic device represented by Chemical Formula 1. In an implementation, the second compound may be, e.g., a compound for an organic optoelectronic device represented by Chemical Formula 2.

[Chemical Formula 2]

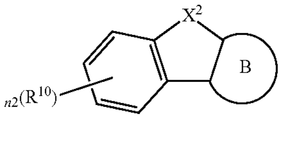

In Chemical Formula 2, $X^2$ may be, e.g., O, S, N-$L^a$-$R^e$, $CR^fR^g$, or $SiR^hR^i$.

$L^a$ may be or may include, e.g., a single bond or a substituted or unsubstituted C6 to C12 arylene group.

$R^e$, $R^f$, $R^g$, $R^h$, $R^i$, and $R^{10}$ may each independently be or include, e.g., hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

n2 may be, e.g., an integer of 1 to 4.

B may be, e.g., a ring of Group III.

[Group III]

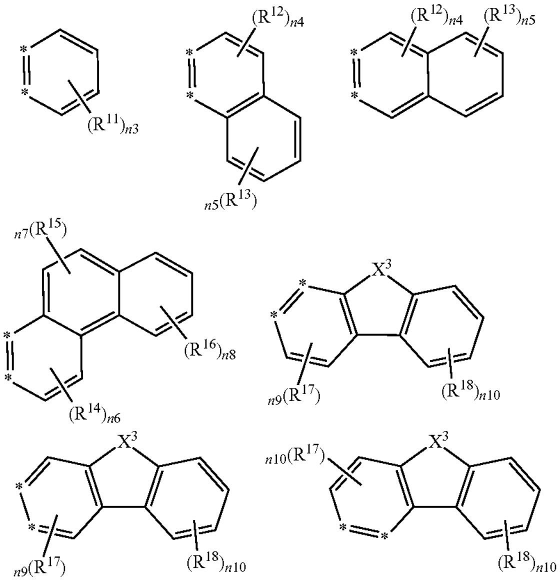

In Group III, * are linking carbons. As used herein, the term "linking carbon" refers to a shared carbon at which fused rings are linked.

$X^3$ may be, e.g., O, S, $CR^jR^k$, or $SiR^lR^m$.

$R^j$, $R^k$, $R^l$, $R^m$, and $R^{11}$ to $R^{18}$ may each independently be or include, e.g., hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

n3, n5, n8 and n10 may each independently be, e.g., an integer of 1 to 4.

n4, n6, n7, and n9 may each independently be, e.g., 1 or 2.

In an implementation, at least one of $R^e$ and $R^{10}$ to $R^{18}$ may be, e.g., a (substituted amine) group represented by Chemical Formula a.

[Chemical Formula a]

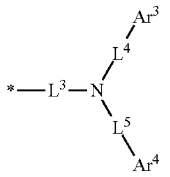

In Chemical Formula a, $L^3$ to $L^5$ may each independently be or include, e.g., a single bond or a substituted or unsubstituted C6 to C30 arylene group.

$Ar^3$ and $Ar^4$ may each independently be or include, e.g., a substituted or unsubstituted amine group, a substituted or unsubstituted C6 to C30 aryl group, or a substituted or unsubstituted C2 to C30 heterocyclic group.

* is a linking point.

The second compound may be used in the light emitting layer together with the first compound (e.g., the first compound and the second compound may be mixed) to increase charge mobility and improve stability, thereby improving luminous efficiency and life-span characteristics.

The second compound may have a structure in which carbazole/fused carbazole/fused dibenzofuran/fused dibenzothiophene/fused dibenzosilole is substituted with an amine. In an implementation, the second compound may be represented by, e.g., one of Chemical Formula 2-I to Chemical Formula 2-IX, depending on the type and fusion position of the additional benzene ring.

[Chemical Formula 2-I]

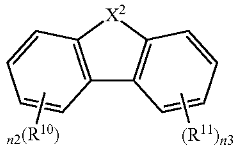

[Chemical Formula 2-II]

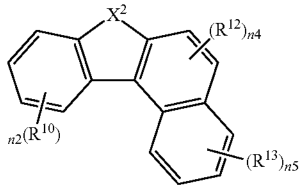

[Chemical Formula 2-III]

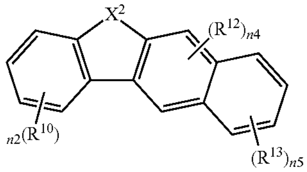

[Chemical Formula 2-IV]

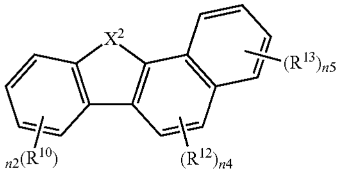

[Chemical Formula 2-V]

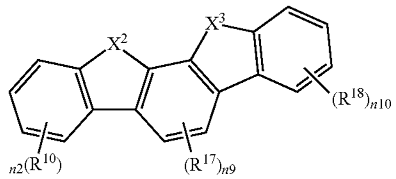

[Chemical Formula 2-VI]

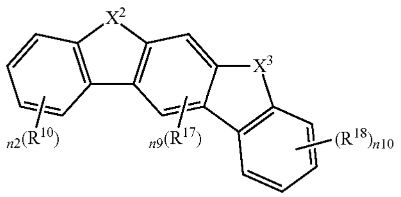

-continued

[Chemical Formula 2-VII]

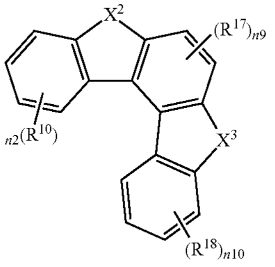

[Chemical Formula 2-VIII]

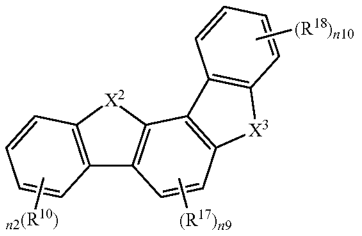

[Chemical Formula 2-IX]

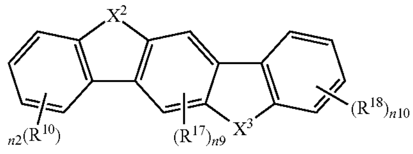

[Chemical Formula 2-X]

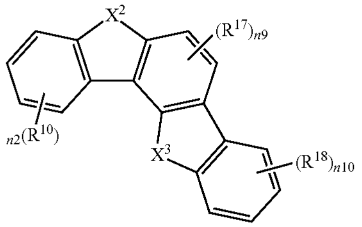

In Chemical Formula 2-I to Chemical Formula 2-X, $X^2$, $X^3$, $R^{10}$ to $R^{13}$, $R^{17}$, $R^{18}$, n2 to n5, n9, and n10 may be defined the same as those described above (e.g., with respect to Chemical Formula 2).

In an implementation, the second compound may be represented by, e.g., one of Chemical Formula 2-IA to Chemical Formula 2-X A, Chemical Formula 2-IIB to Chemical Formula 2-IVB and Chemical Formula 2-IIC to Chemical Formula 2-XC, depending on the substitution direction of the amine group.

[Chemical Formula 2-IA]

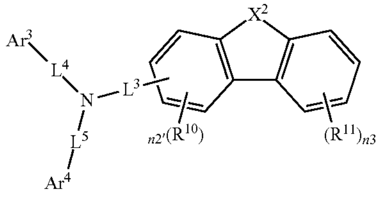

-continued

[Chemical Formula 2-IIA]

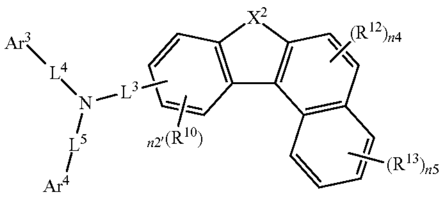

[Chemical Formula 2-IIIA]

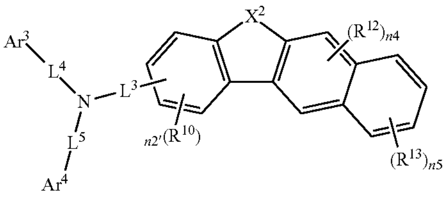

[Chemical Formula 2-IVA]

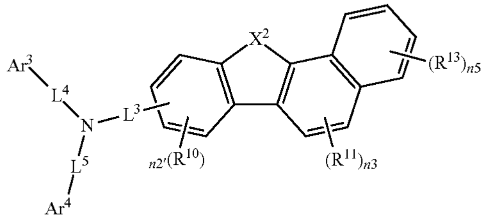

[Chemical Formula 2-VA]

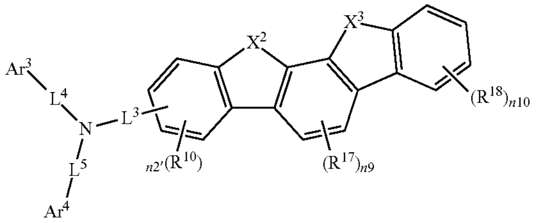

[Chemical Formula 2-VIA]

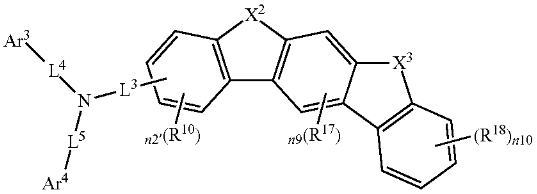

[Chemical Formula 2-VIIA]

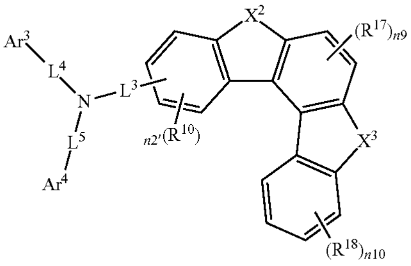

-continued

[Chemical Formula 2-VIIIA]

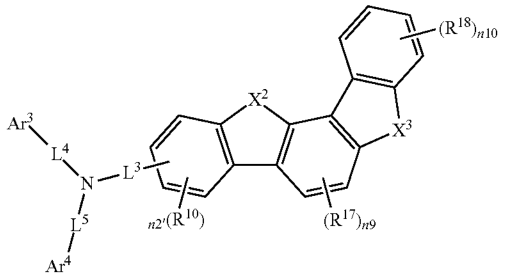

[Chemical Formula 2-IXA]

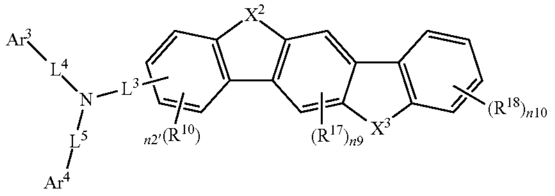

[Chemical Formula 2-XA]

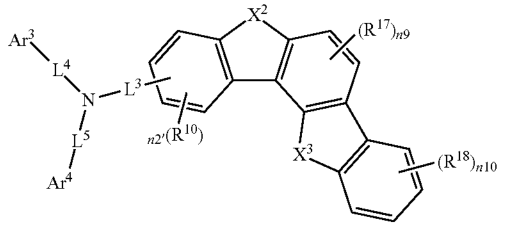

In Chemical Formula 2-IA to Chemical Formula 2-X A, $X^2$, $X^3$, $L^3$ to $L^5$, $Ar^3$, $R^{10}$ to $R^{13}$, $R^{17}$, $R^8$, $Ar^4$, n3 to n5, n9, and n10 may be defined the same as those described above.

n2' may be, e.g., an integer of 1 to 3.

[Chemical Formula 2-IIB]

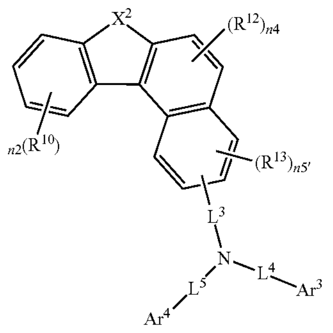

[Chemical Formula 2-IIIB]

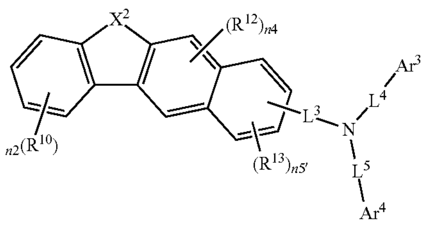

-continued

[Chemical Formula 2-IVB]

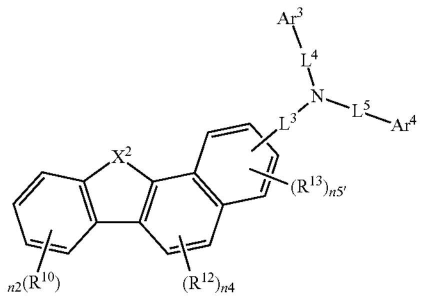

In Chemical Formula 2-IIB to Chemical Formula 2-IVB, $X^2$, $L^3$ to $L^5$, $R^{10}$, $R^{12}$, $R^{13}$, $Ar^3$, $Ar^4$, n2, and n4 may be defined the same as those described above.

n5' may be, e.g., an integer of 1 to 3.

[Chemical Formula 2-IIC]

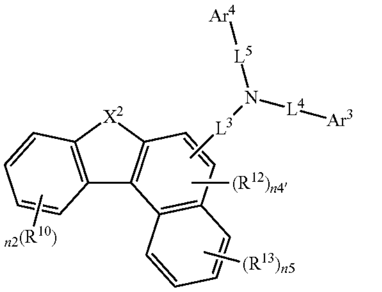

[Chemical Formula 2-IIIC]

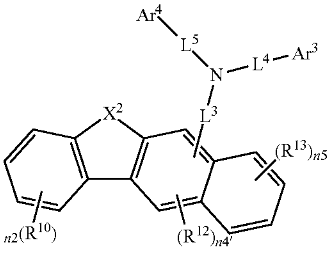

[Chemical Formula 2-IVC]

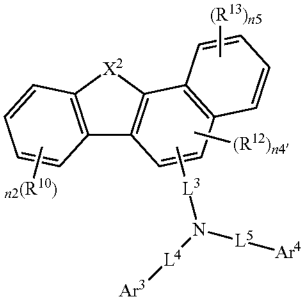

In Chemical Formula 2-II C to Chemical Formula 2-IVC, $X^2$, $L^3$ to $L^5$, $R^{10}$, $R^{12}$, $R^{13}$, $Ar^3$, $Ar^4$, n2, and n5 may be defined the same as those described above.

n4' may be, e.g., an integer of 1.

[Chemical Formula 2-VC]

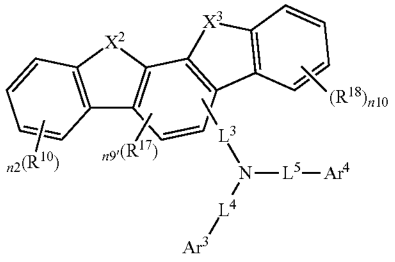

[Chemical Formula 2-VIC]

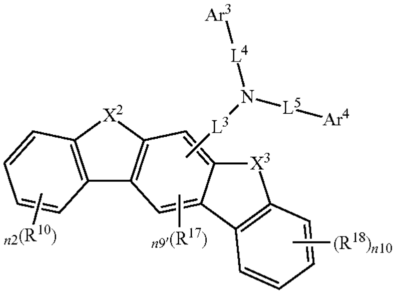

[Chemical Formula 2-VIIC]

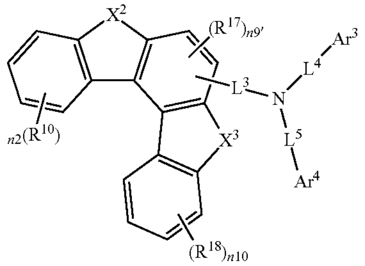

[Chemical Formula 2-VIIIC]

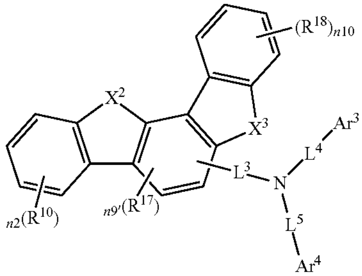

[Chemical Formula 2-IXC]

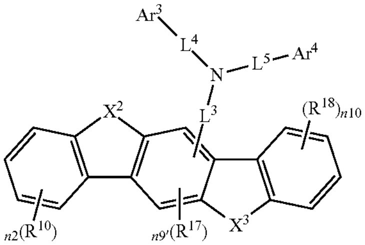

-continued

[Chemical Formula 2-XC]

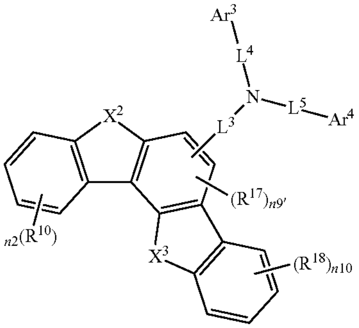

In Chemical Formula 2-VC to Chemical Formula 2-XC, $X^2$, $X^3$, $L^3$ to $L^5$, $Ar^3$, $Ar^4$, $R^{10}$, $R^{17}$, $R^{18}$, n2, and n10 may be defined the same as those described above.

n9' may be, e.g., an integer of 1.

In an implementation, $R^{10}$ to $R^{13}$, $R^{17}$, and $R^{18}$ may each independently be, e.g., hydrogen, deuterium, a substituted or unsubstituted C1 to C30 alkyl group, or a substituted or unsubstituted C6 to C30 aryl group.

In an implementation, $Ar^3$ and $Ar^4$ may each independently be, e.g., a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, a substituted or unsubstituted triphenylene group, a substituted or unsubstituted chrysenyl group, a substituted or unsubstituted fluorenyl group, a substituted or unsubstituted benzophenanthrenyl group, a substituted or unsubstituted carbazolyl group, a substituted or unsubstituted dibenzofuranyl group, a substituted or unsubstituted dibenzothiophenyl group, a substituted or unsubstituted benzofuranofluorenyl group, or a substituted or unsubstituted benzothiophenefluorenyl group.

In an implementation, $Ar^3$ and $Ar^4$ may each independently be, e.g., a substituted or unsubstituted phenyl group, a substituted or unsubstituted biphenyl group, or a substituted or unsubstituted naphthyl group.

In an implementation, $L^3$ to $L^5$ may each independently be, e.g., a single bond, a substituted or unsubstituted phenylene group, or a substituted or unsubstituted biphenylene group.

In an implementation, $L^3$ may be, e.g., a single bond or a substituted or unsubstituted phenylene group, and $L^4$ and $L^5$ may each independently be, e.g., a single bond, a substituted or unsubstituted phenylene group, or a substituted or unsubstituted biphenylene group.

In an implementation, $L^3$ may be, e.g., a single bond, and $L^4$ and $L^5$ may each independently be, e.g., a single bond or a substituted or unsubstituted phenylene group.

In an implementation, $X^2$ may be, e.g., O, S, $N\text{-}L^a\text{-}R^e$, $CR^fR^g$, or $SiR^hR^i$.

In an implementation, $X^2$ may be, e.g., $N\text{-}L^a\text{-}R^e$, $CR^fR^g$, or $SiR^hR^i$.

In an implementation, $X^3$ may be, e.g., O, S, $CR^jR^k$, or $SiR^lR^m$.

In an implementation, $X^3$ may be, e.g., O, or S.

In an implementation, $R^e$ may be, e.g., a substituted or unsubstituted phenyl group.

In an implementation, $R^f$, $R^g$, $R^h$, $R^i$, $R^j$, $R^k$, $R^l$, and $R^m$ may each independently be, e.g., a substituted or unsubstituted C1 to C5 alkyl group or a substituted or unsubstituted C6 to C12 aryl group.

In an implementation, $R^f$, $R^g$, $R^h$, $R^i$, $R^j$, $R^j$, $R^k$, $R^l$, and $R^m$ may each independently be, e.g., a substituted or unsubstituted methyl group or a substituted or unsubstituted phenyl group.

In an implementation, $R^{10}$ to $R^{13}$, $R^{17}$, and $R^{18}$ may each independently be, e.g., hydrogen, deuterium, a substituted or unsubstituted C1 to C5 alkyl group, or a substituted or unsubstituted C6 to C12 aryl group.

In an implementation, $R^{10}$ to $R^{13}$, $R^{17}$, and $R^{18}$ may each independently be, e.g., hydrogen or deuterium.

The second compound according to an embodiment may be represented by, e.g., Chemical Formula 2-IA, Chemical Formula 2-IVB, Chemical Formula 2-X A.

In an implementation, in Chemical Formula 2-IVB, $X^2$ may be, e.g., O, S, or $N\text{-}L^a\text{-}R^e$, $L^a$ may be a single bond, and $R^e$ may be, e.g., a substituted or unsubstituted phenyl group.

In an implementation, in Chemical Formula 2-X A, $X^2$ may be, e.g., $N\text{-}L^a\text{-}R^e$, $CR^fR^g$, or $SiR^hR^i$, $L^a$ may be, e.g., a single bond, $R^e$ may be, e.g., a substituted or unsubstituted phenyl group, $R^f$, $R^g$, $R^h$, $R^i$, $R^j$, $R^k$, $R^l$, and $R^m$ may each independently be, e.g., a substituted or unsubstituted methyl group or a substituted or unsubstituted phenyl group, $X^3$ may be, e.g., O, or S.

In an implementation, the second compound may be represented by, e.g., Chemical Formula 2-IA-3, Chemical Formula 2-IVB-2, or Chemical Formula 2-XA-2.

[Chemical Formula 2-IA-3]

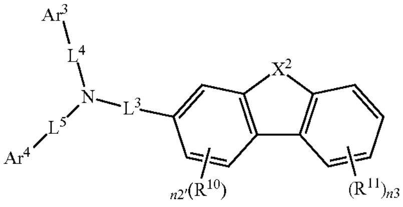

[Chemical Formula 2-IVB-2]

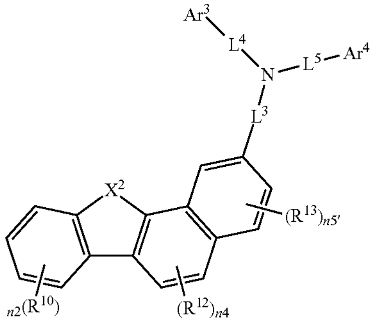

[Chemical Formula 2-XA-2]

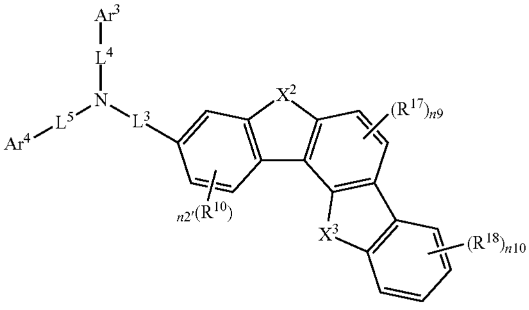

In Chemical Formula 2-IA-3, Chemical Formula 2-IVB-2, and Chemical Formula 2-XA-2, $L^3$ may be, e.g., a single bond, $L^4$ and $L^5$ may each independently be, e.g., a single bond or a substituted or unsubstituted phenylene group.

$Ar^3$ and $Ar^4$ may each independently be, e.g., a substituted or unsubstituted phenyl group, a substituted or unsubstituted biphenyl group, or a substituted or unsubstituted naphthyl group.

$X^2$ may be, e.g., N-$L^a$-$R^e$, $CR^fR^g$, or $SiR^hR^i$.

$X^3$ may be, e.g., O or S, $L^a$ may be, e.g., a single bond, $R^e$, $R^f$, $R^g$, $R^h$, and $R^i$ may each independently be, e.g., a substituted or unsubstituted C1 to C5 alkyl group or a substituted or unsubstituted C6 to C12 aryl group.

$R^{10}$ to $R^{13}$, $R^{17}$, and $R^{18}$ may each independently be, e.g., hydrogen, deuterium, a substituted or unsubstituted C1 to C5 alkyl group or a substituted or unsubstituted C6 to C12 aryl group.

n2 to n5, n2', n5', n9, and n10 may be defined the same as those described above.

In an implementation, the second compound may be, e.g., a compound of Group 2.

[Group 2]

A-1

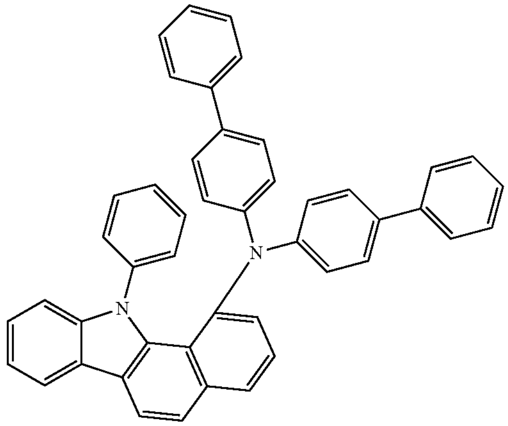

A-2

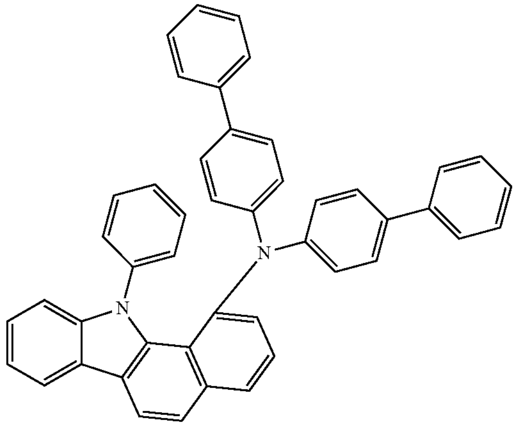

-continued

A-3

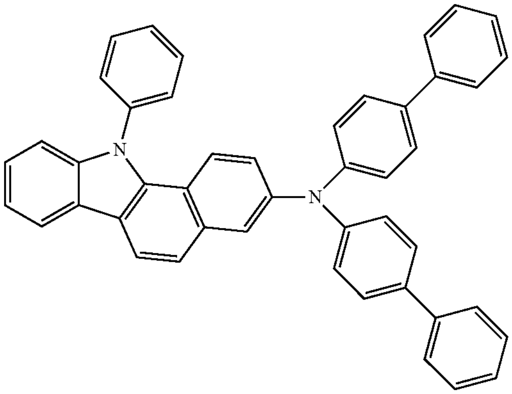

A-4

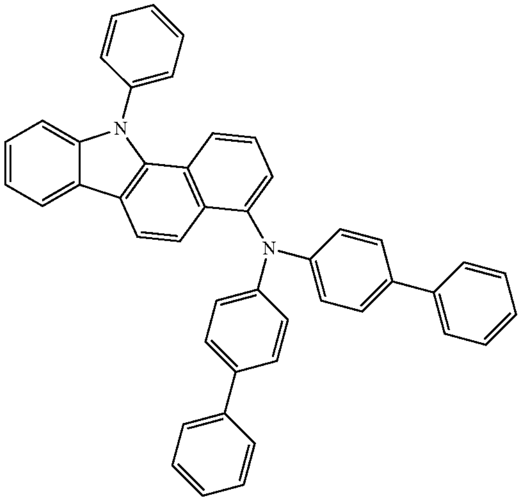

A-5

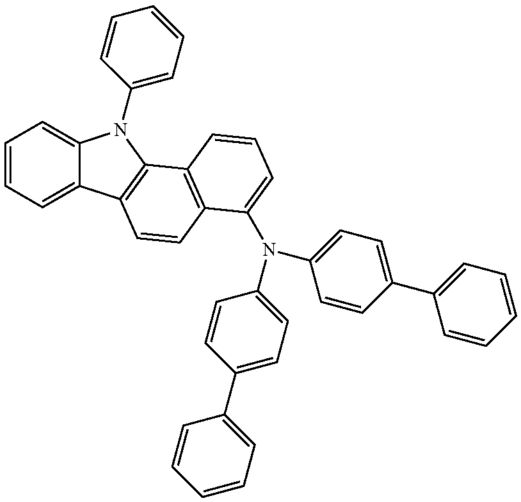

-continued
A-6
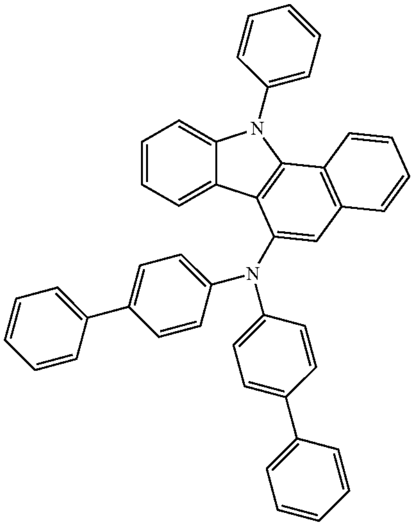
A-7
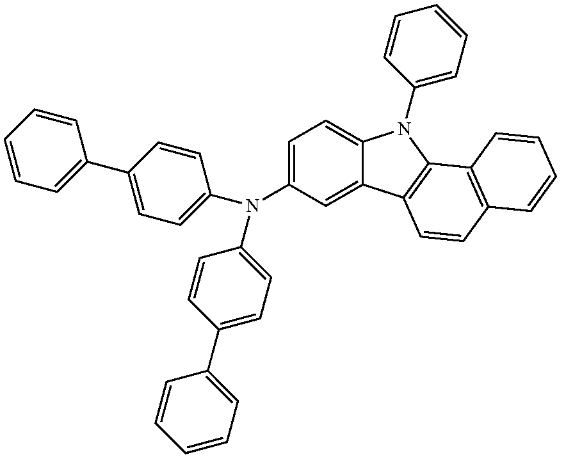
A-8
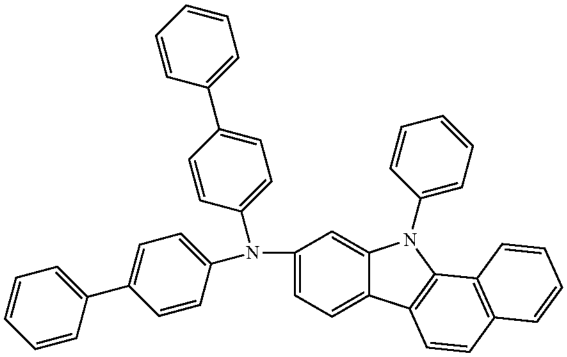
-continued
A-9
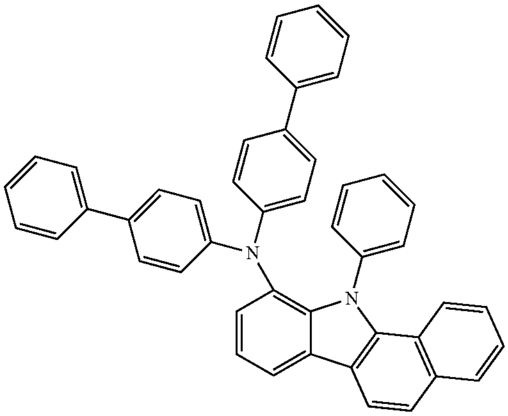
A-10
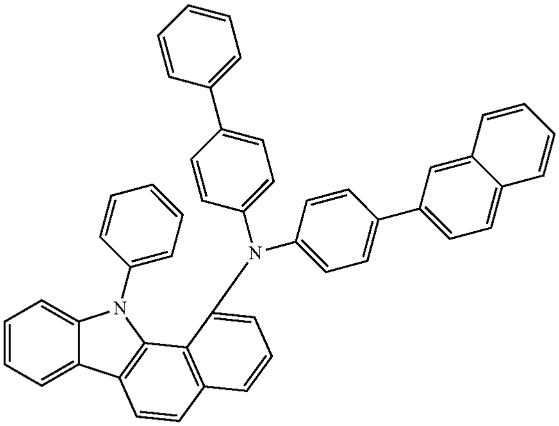
A-11
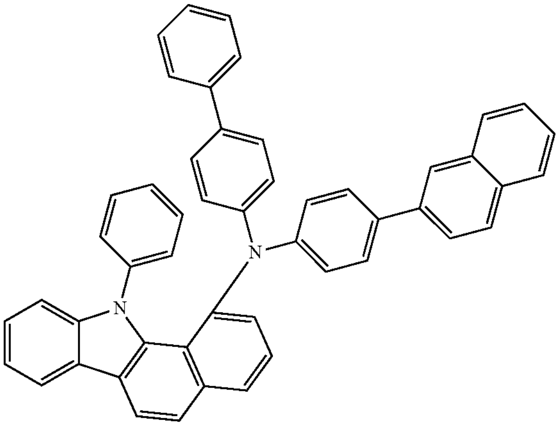

-continued
A-12
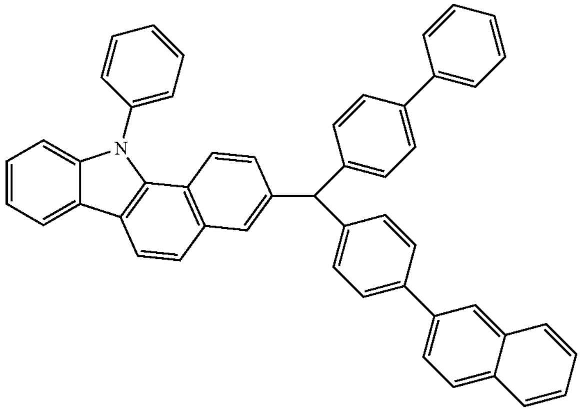
A-13
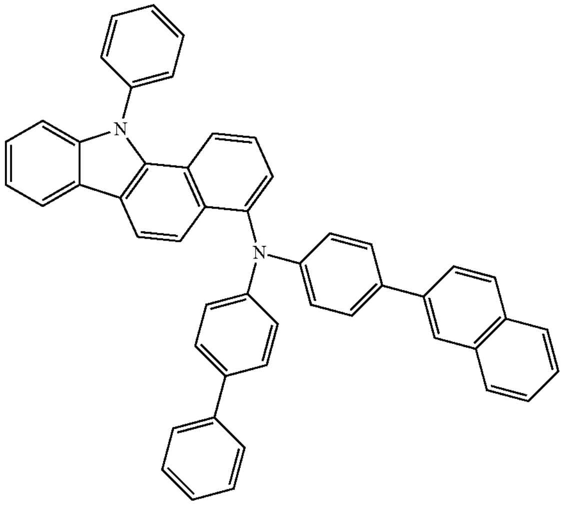
A-14
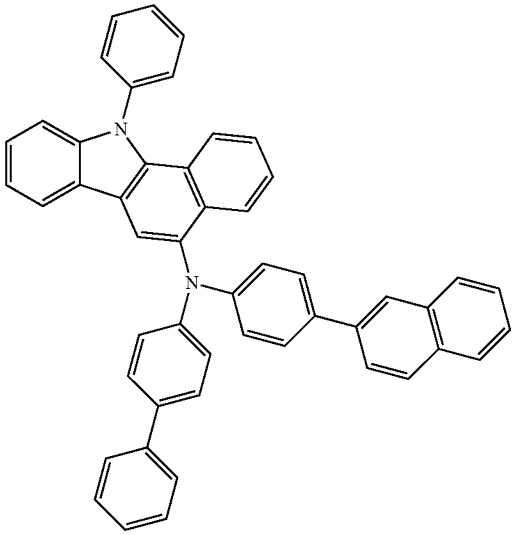
-continued
A-15
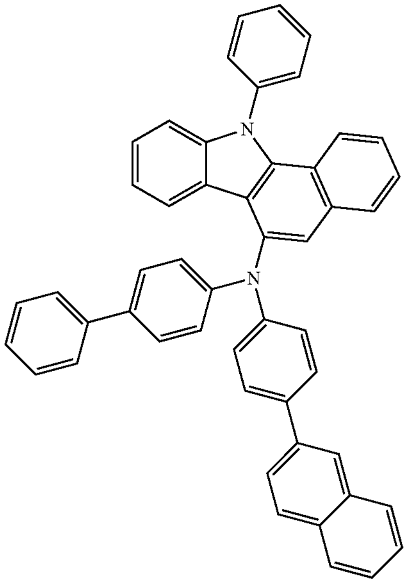
A-16
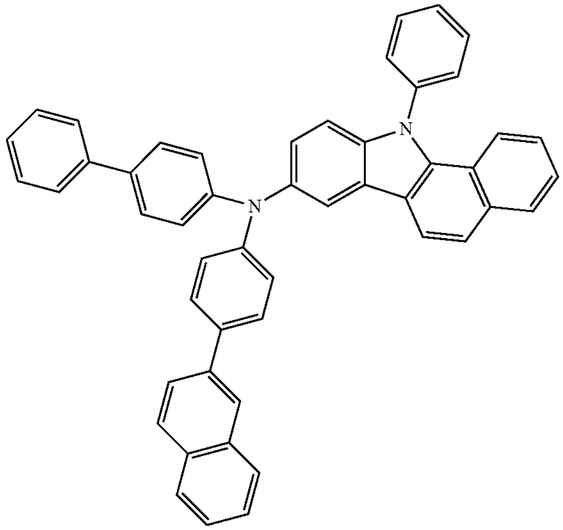
A-17
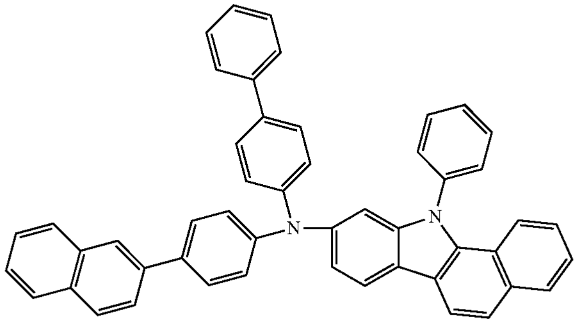

-continued
A-18
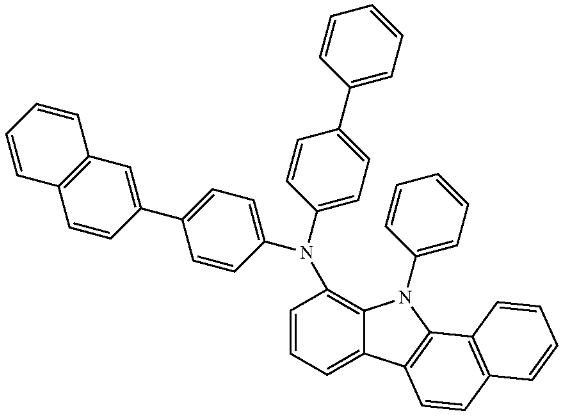
A-19
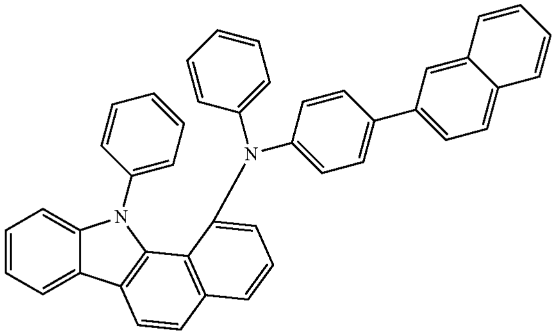
A-20
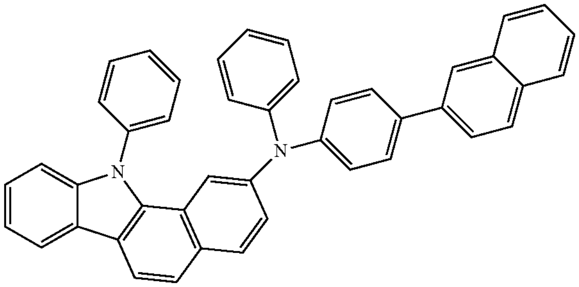
A-21
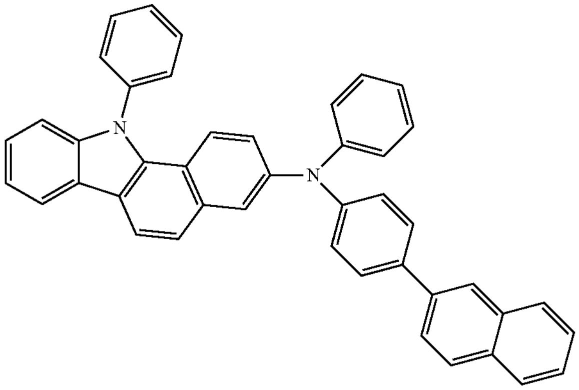
-continued
A-22
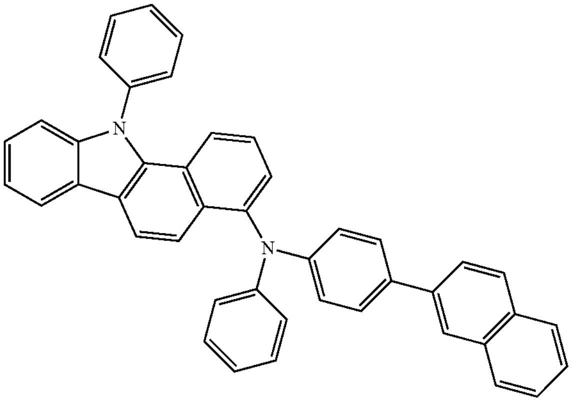
A-23
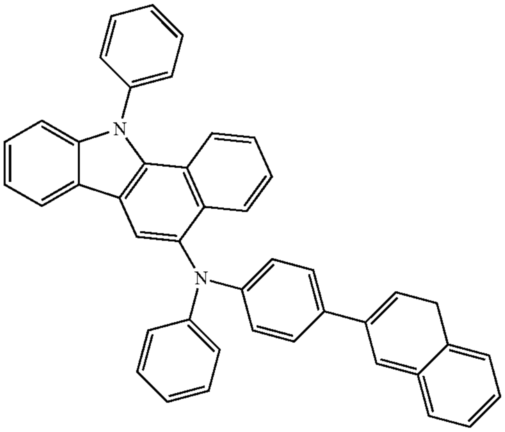
A-24
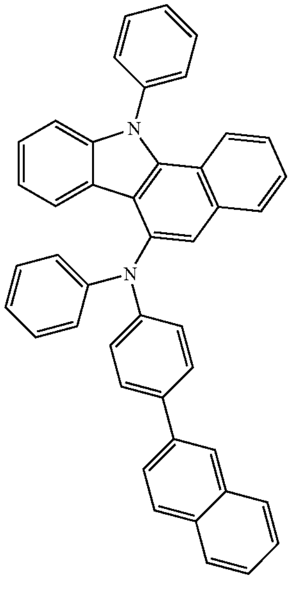

-continued
A-25
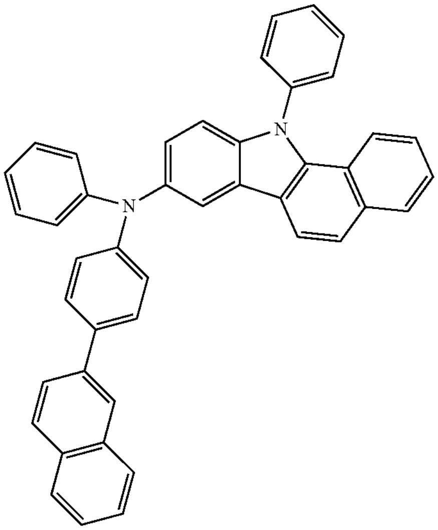
A-26
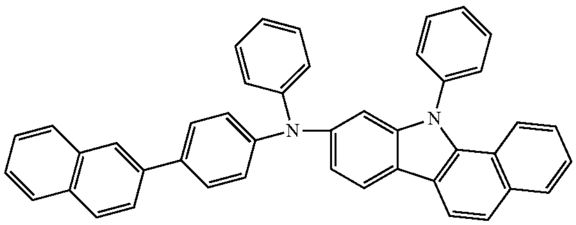
A-27
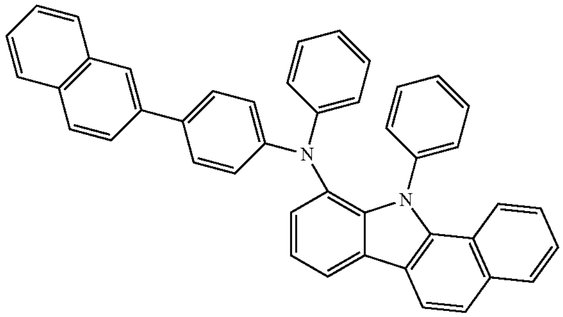
A-28
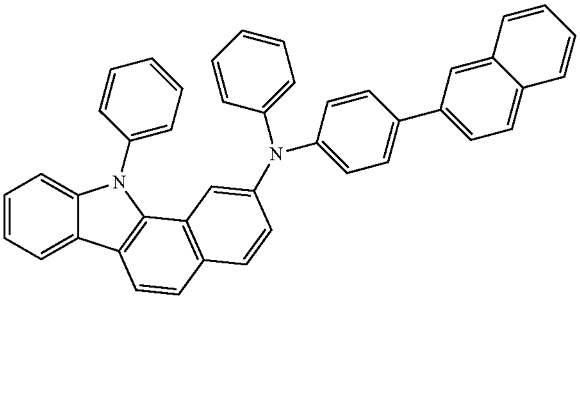
-continued
A-45
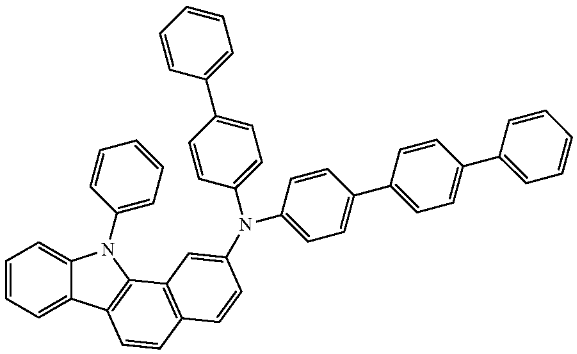
A-46
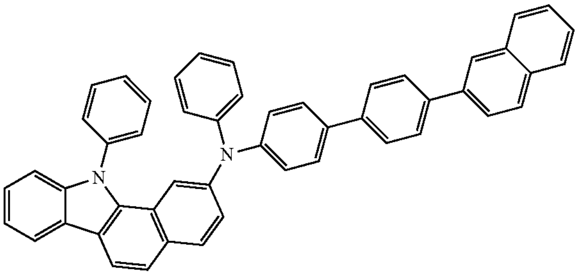
A-47
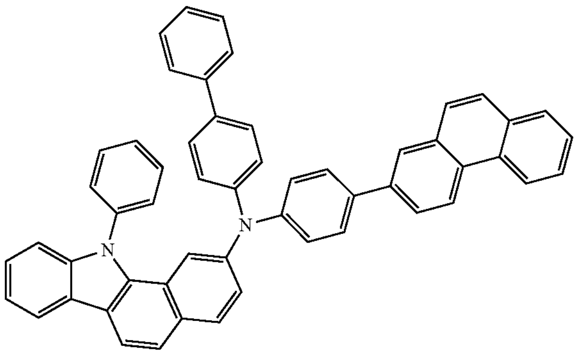
A-48
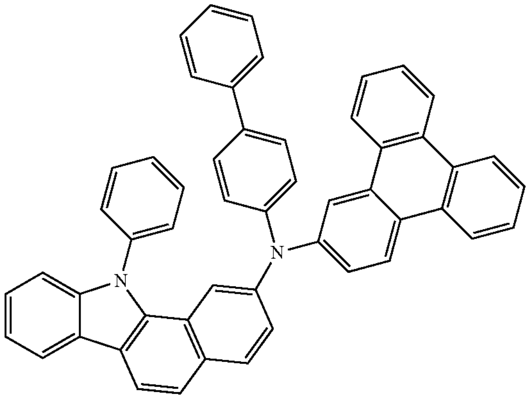

-continued
A-49
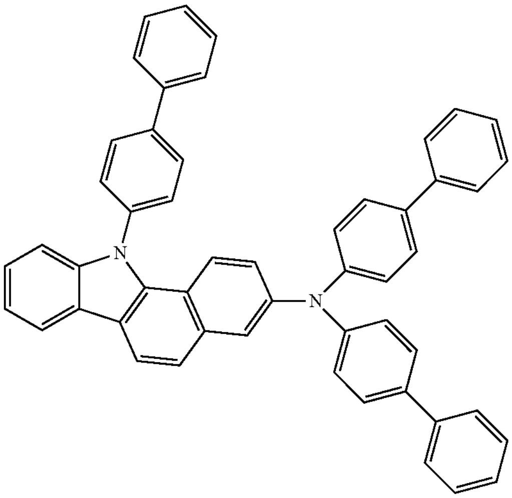
A-50
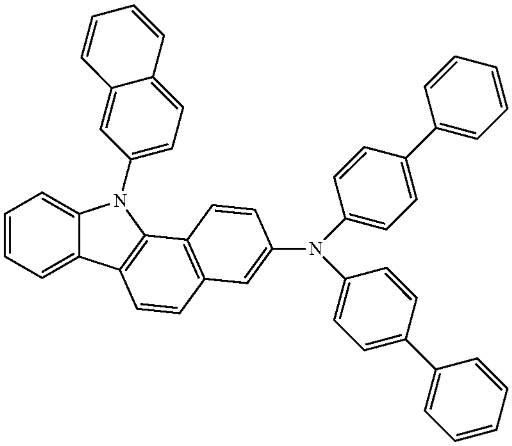
A-51
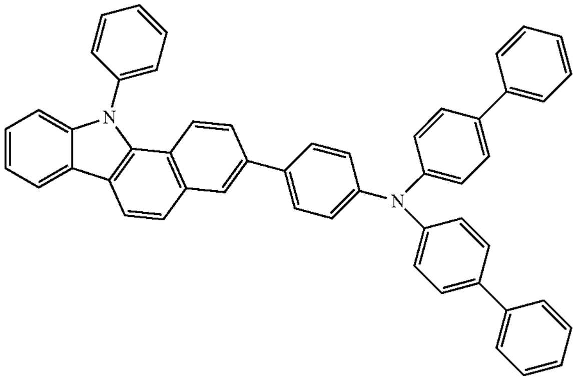
-continued
A-52
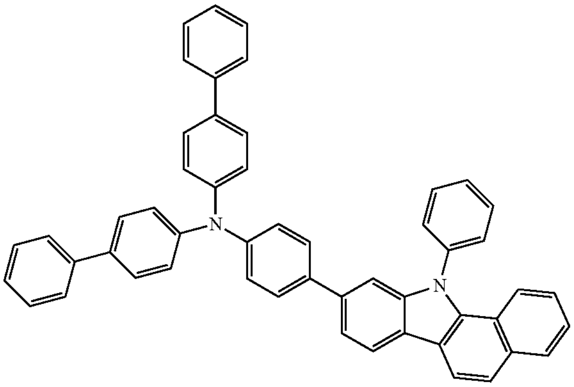
A-53
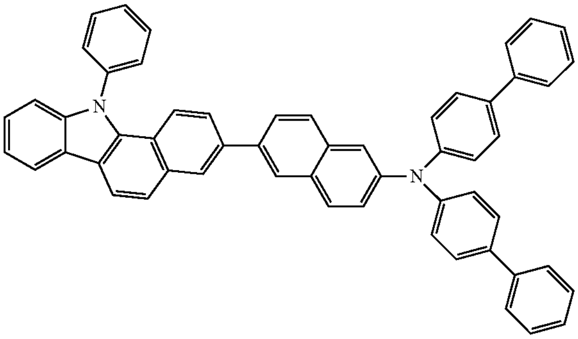
A-54
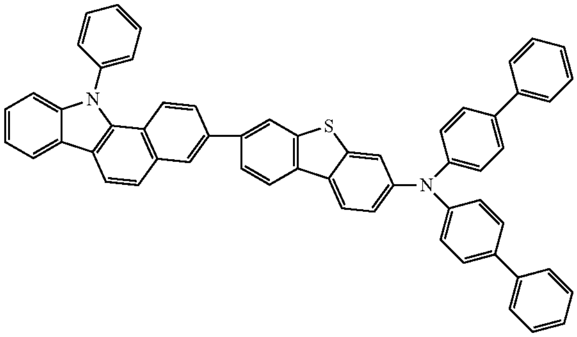
A-55
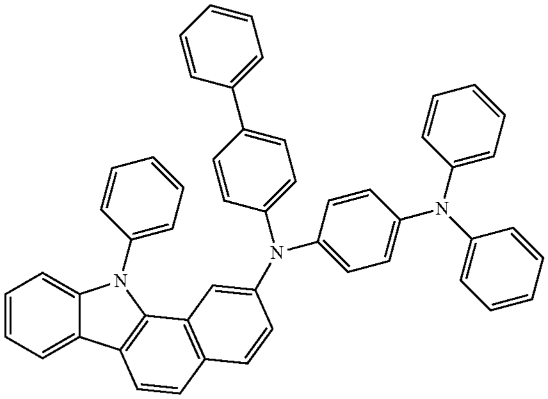

-continued
A-56
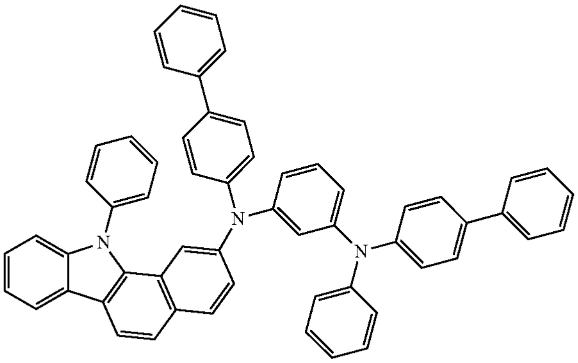
A-57
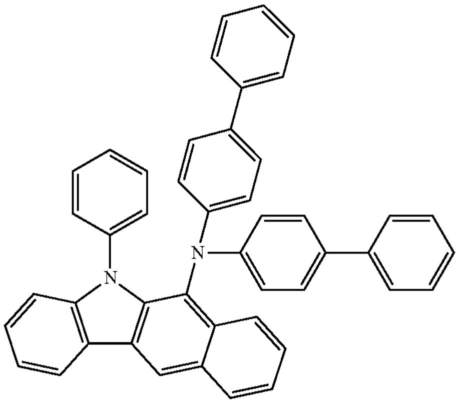
A-58
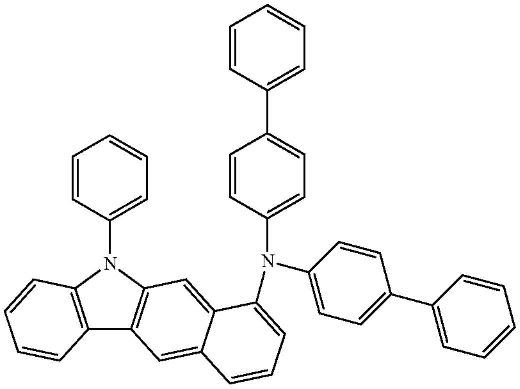
A-59
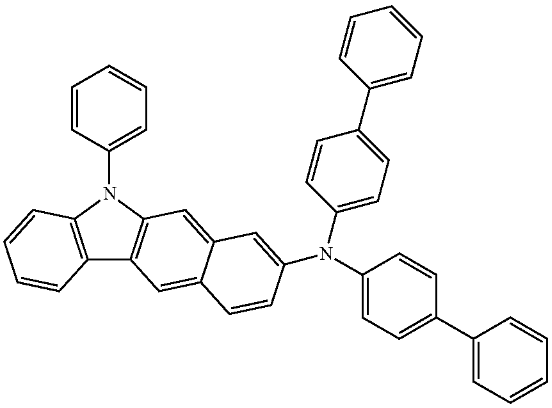
-continued
A-60
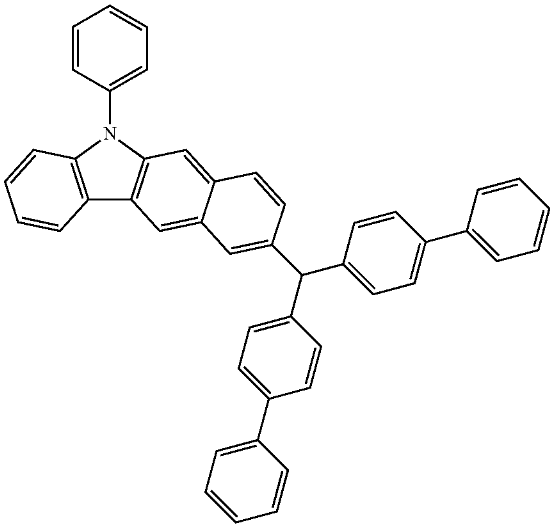
A-61
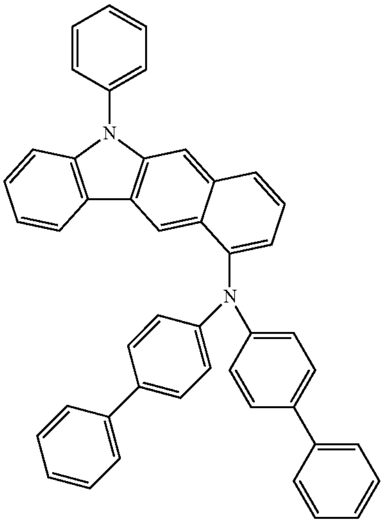
A-62
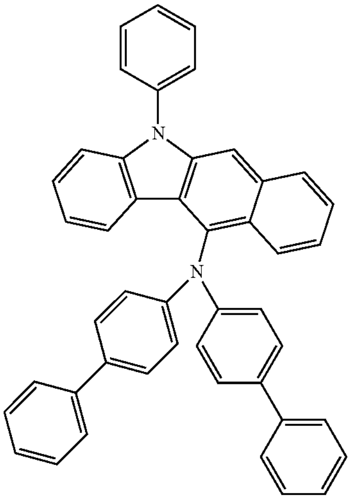

-continued
A-63
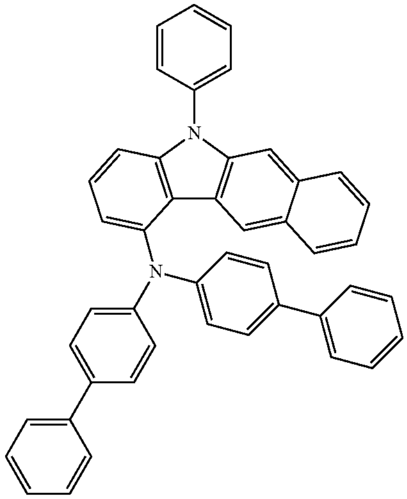
A-64
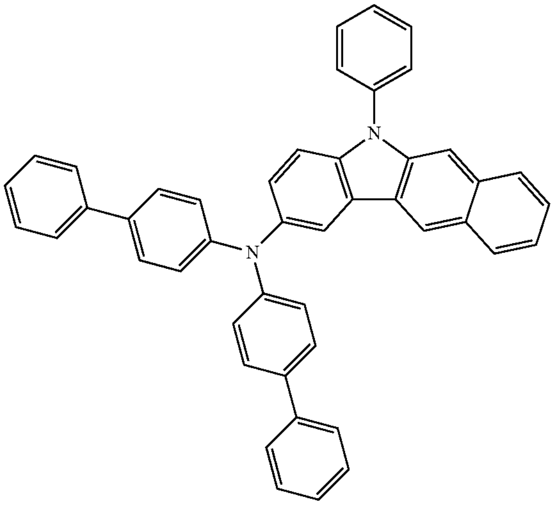
A-65
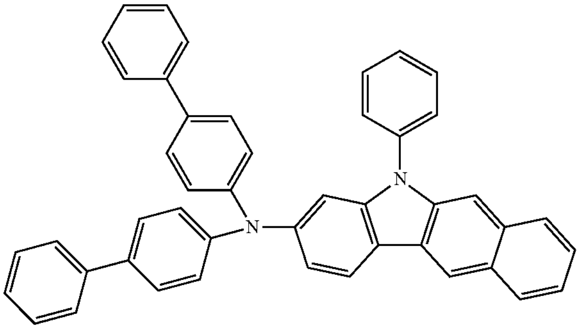
-continued
A-66
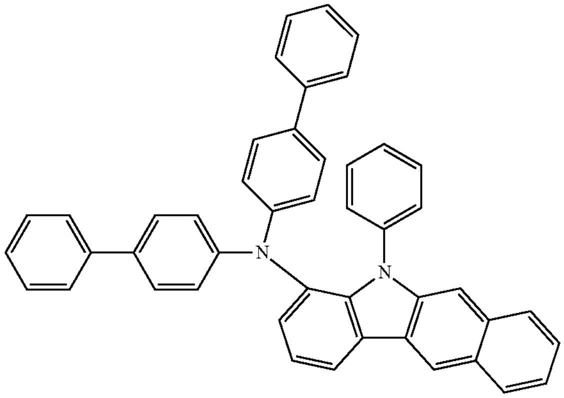
A-67
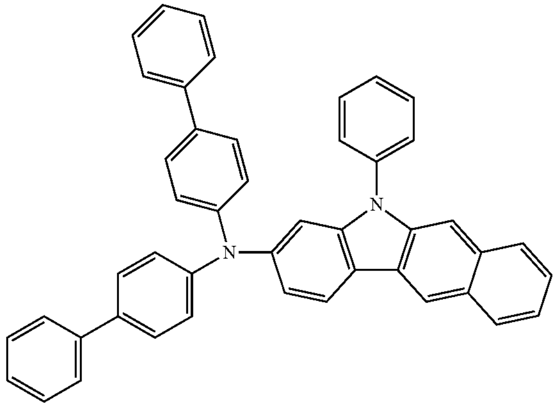
A-68
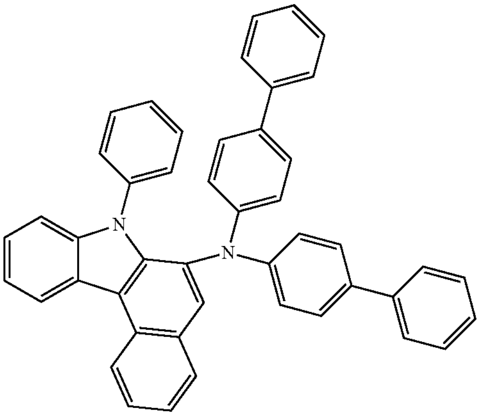
A-69
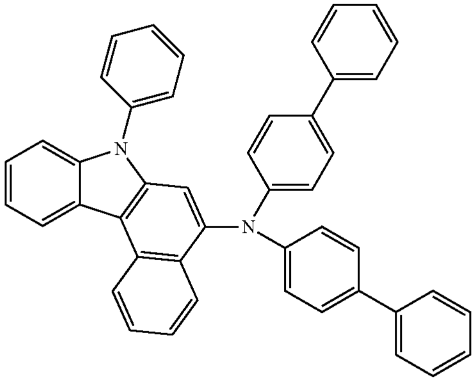

-continued
A-70
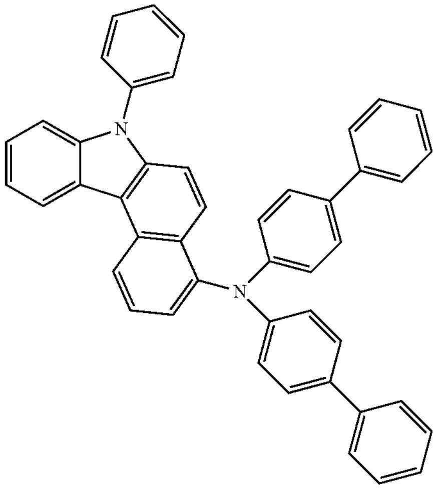
A-71
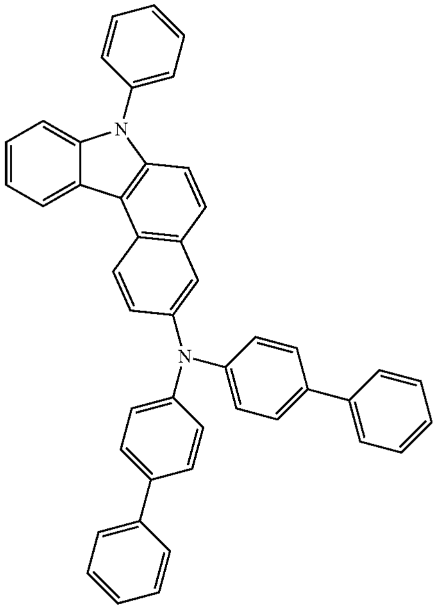
-continued
A-72
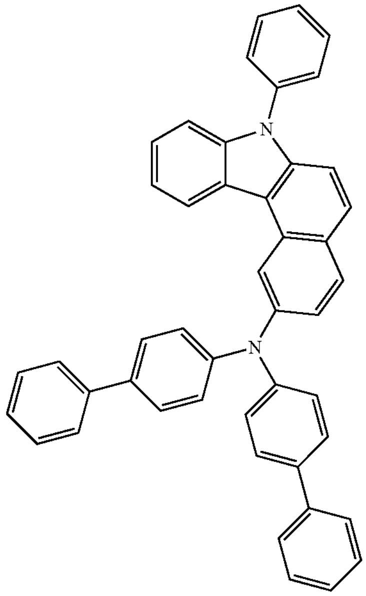
A-73
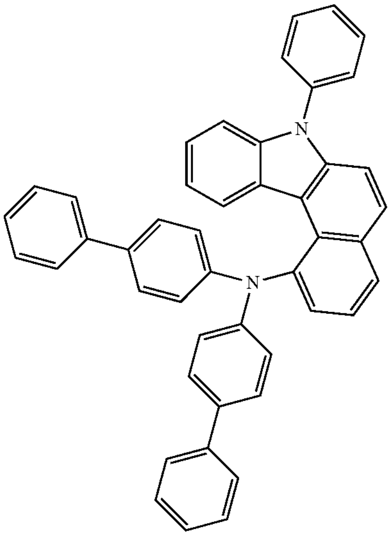
A-74
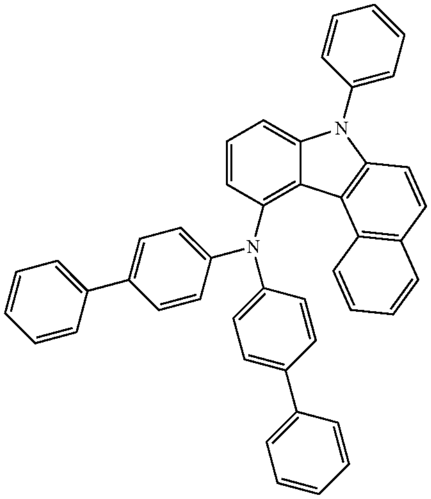

-continued
A-75
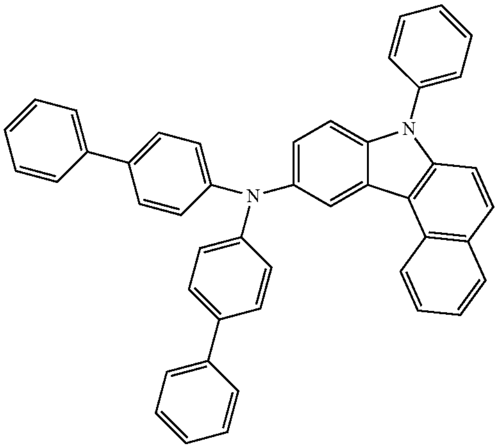
A-76
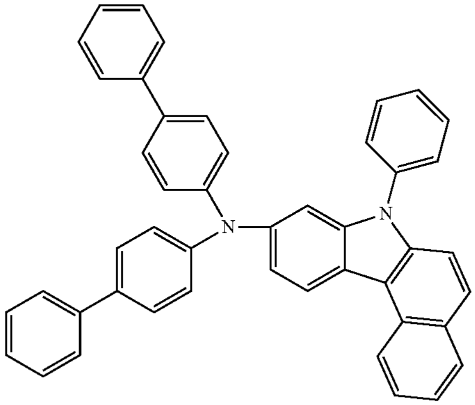
A-77
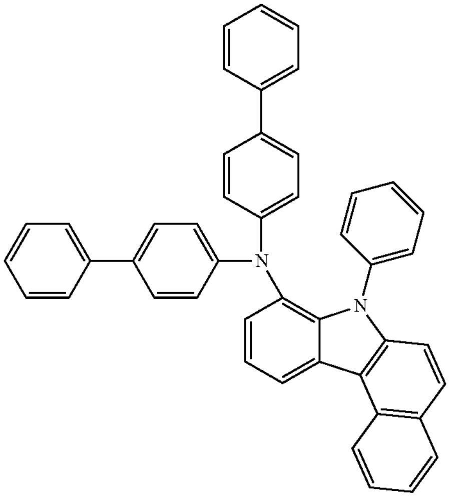
-continued
A-78
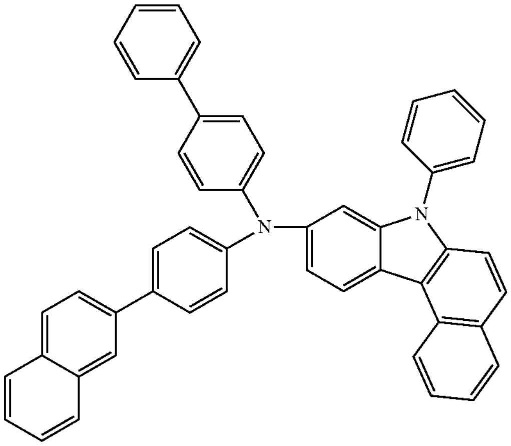
A-79
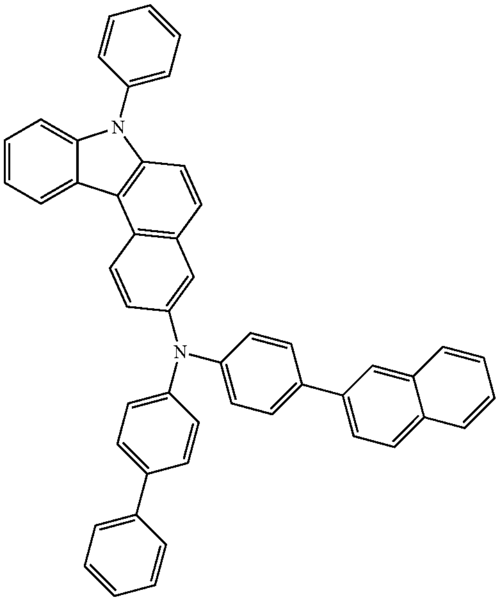
A-80
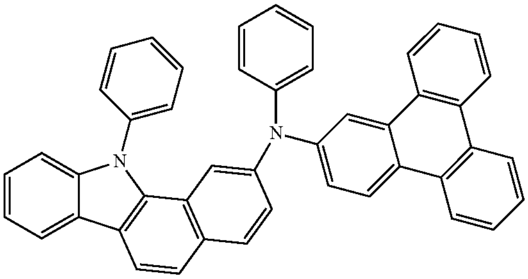

-continued
A-81
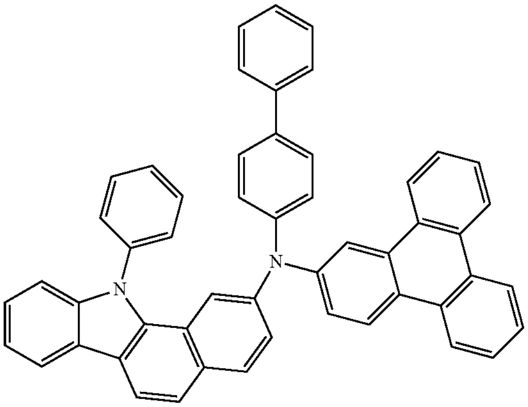
A-82
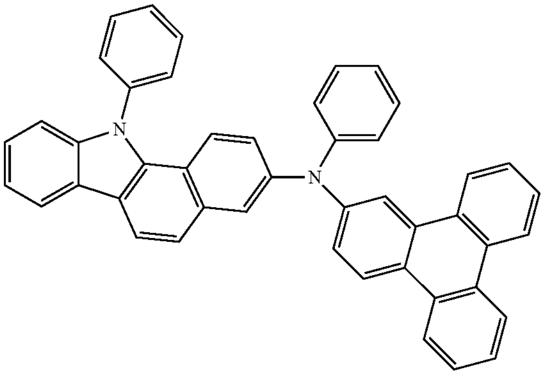
A-83
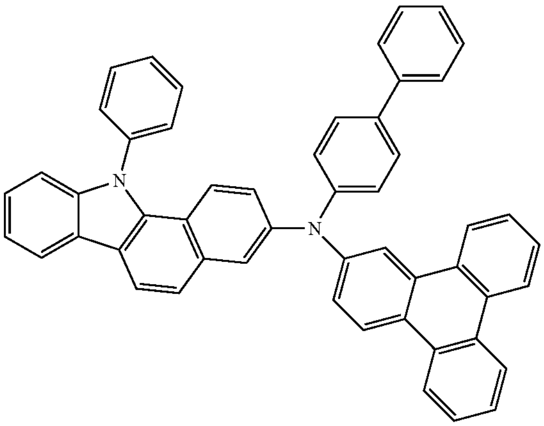
-continued
A-84
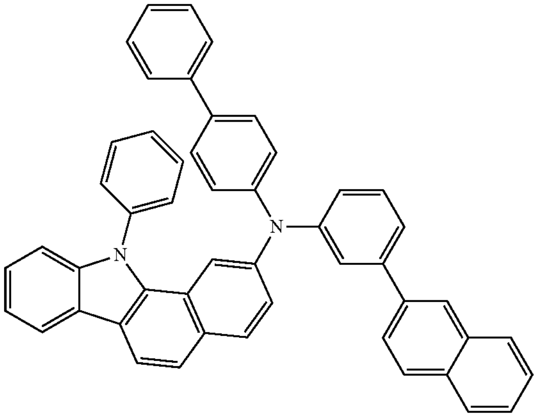
2-1
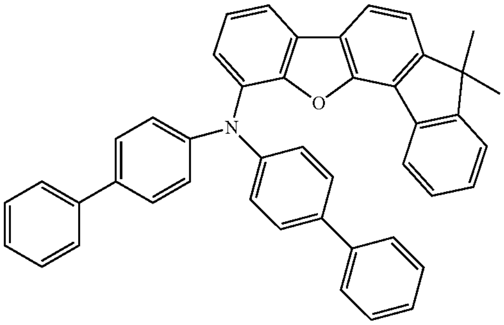
2-2
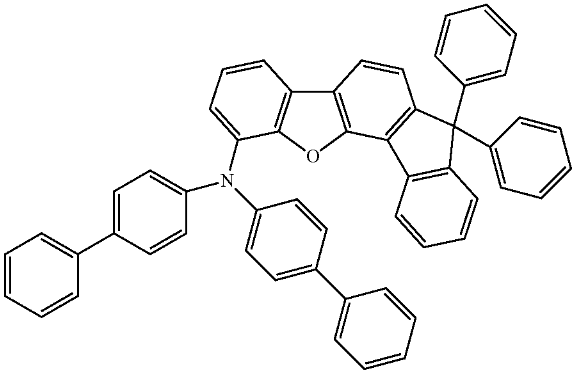
2-3
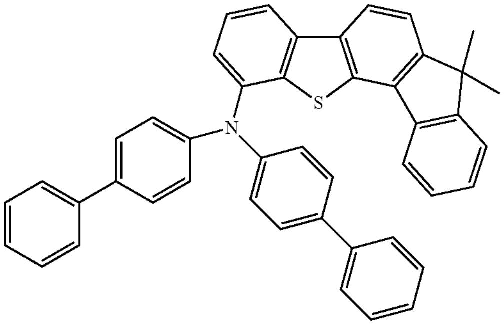

-continued
2-4
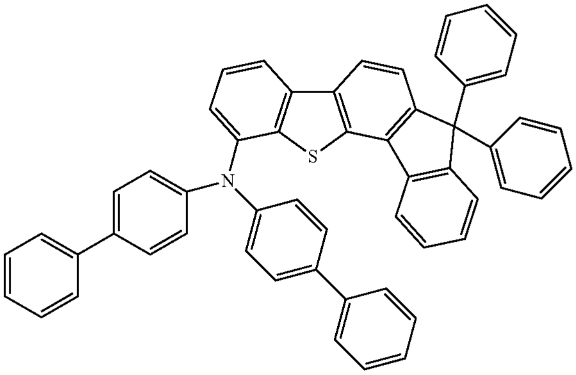
2-5
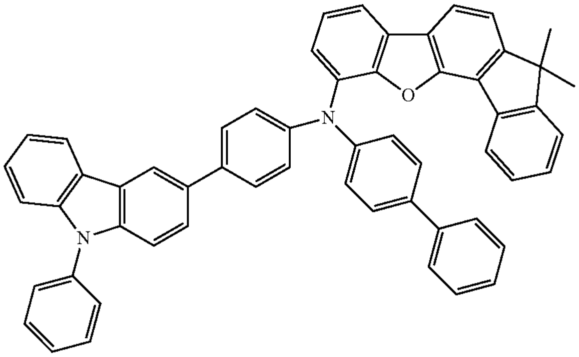
2-6
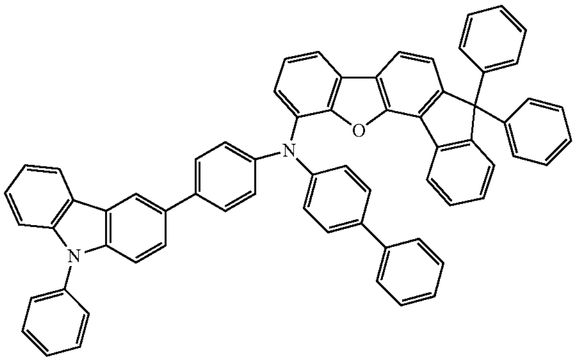
2-7
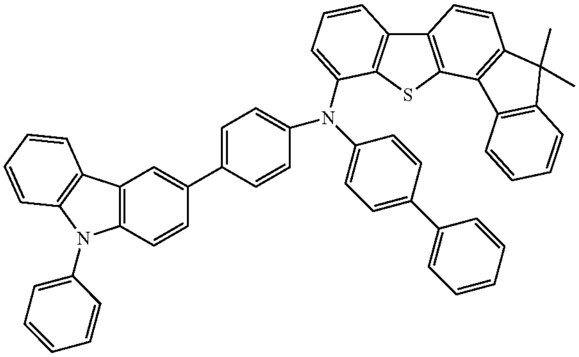
-continued
2-8
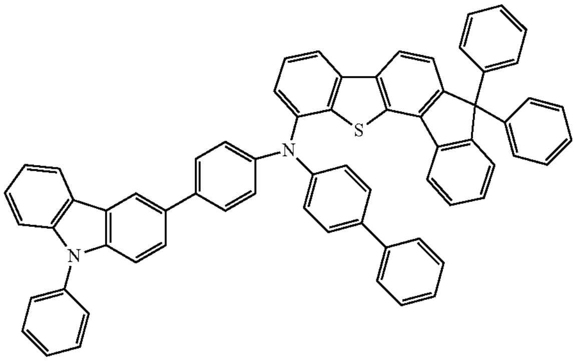
2-9
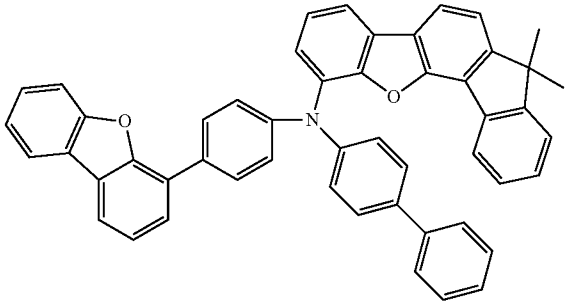
2-10
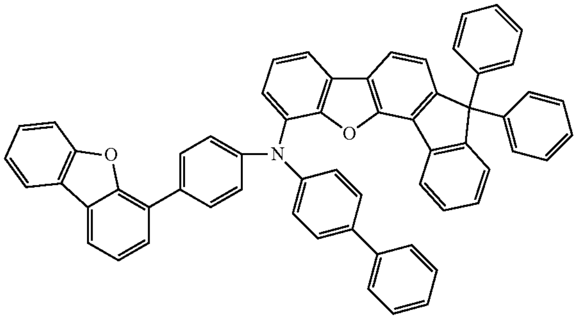
2-11
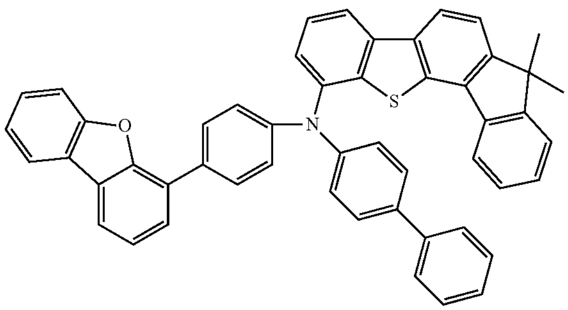

-continued
2-12
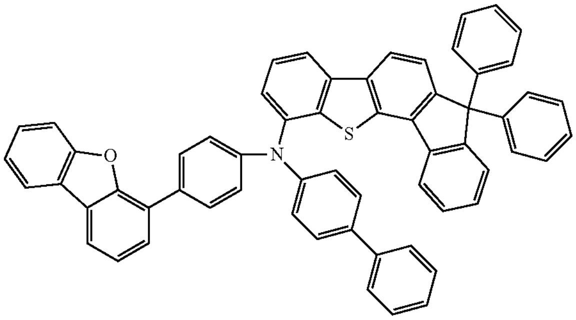
2-13
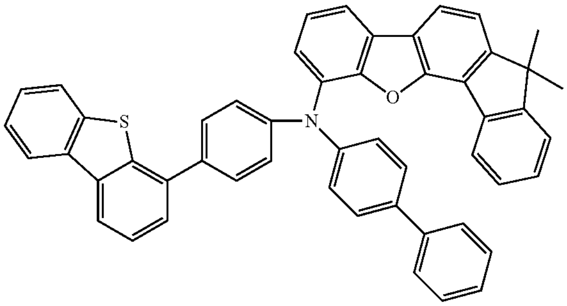
2-14
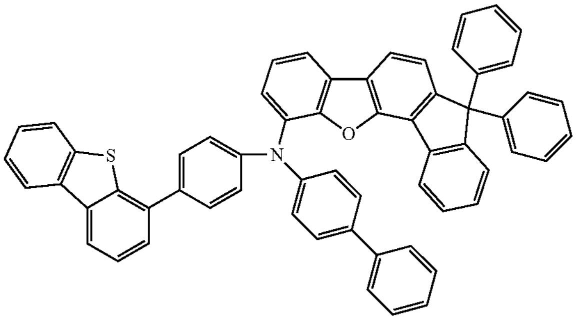
2-15
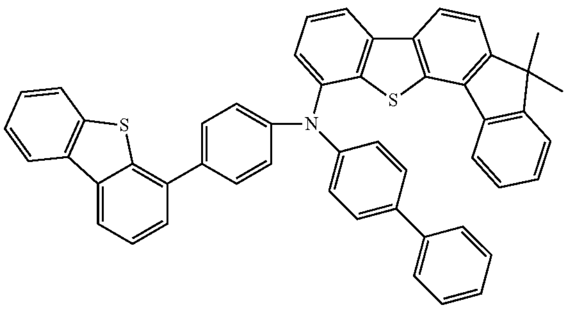
-continued
2-16
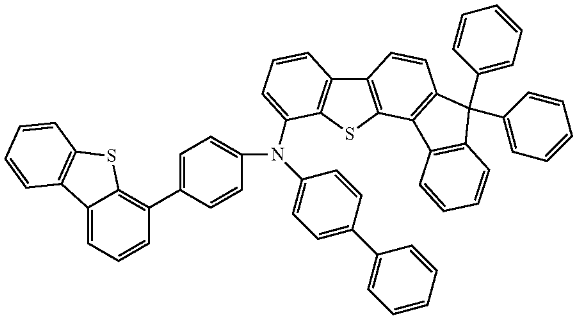
2-17
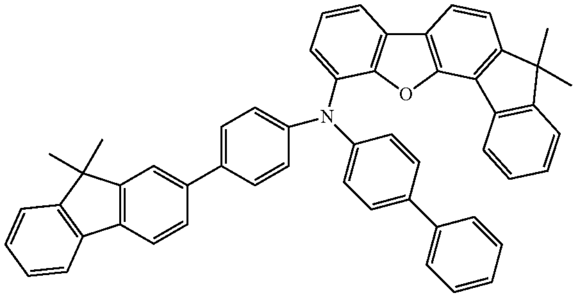
2-18
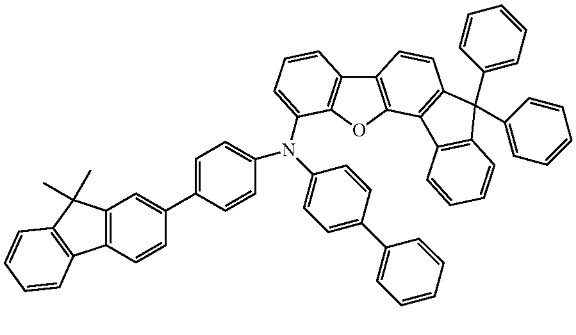
2-19
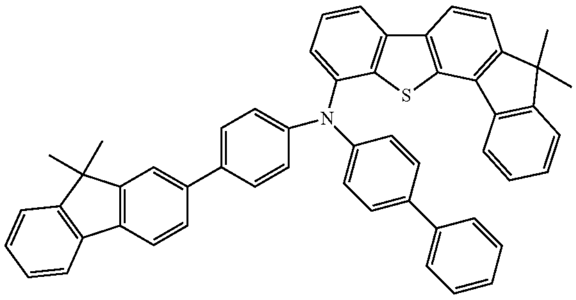

-continued
2-20
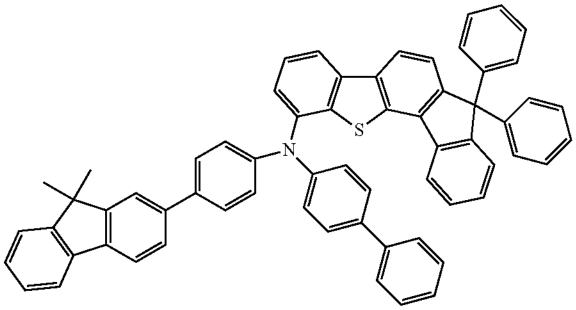
2-21
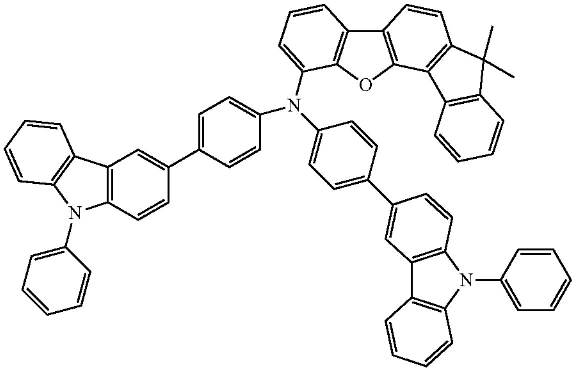
2-22
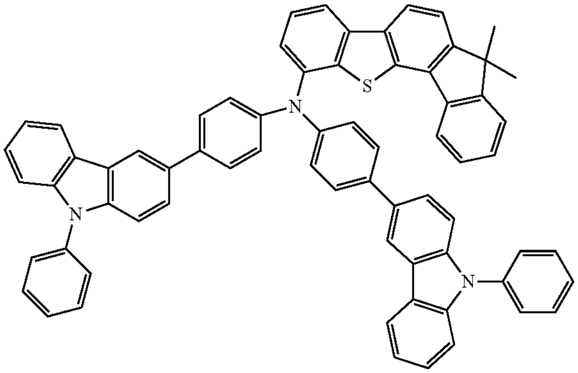
2-23
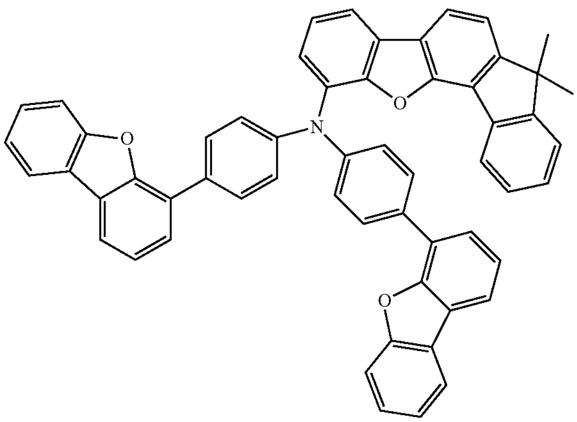
-continued
2-24
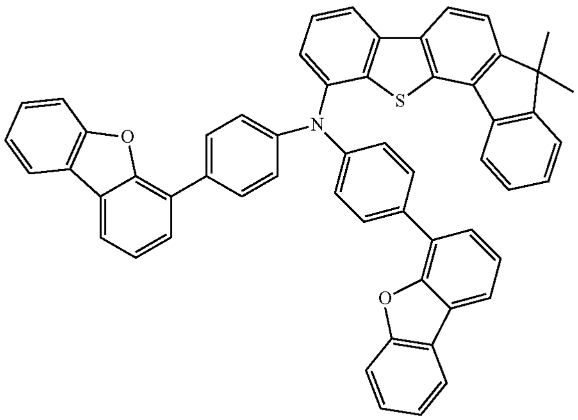
2-25
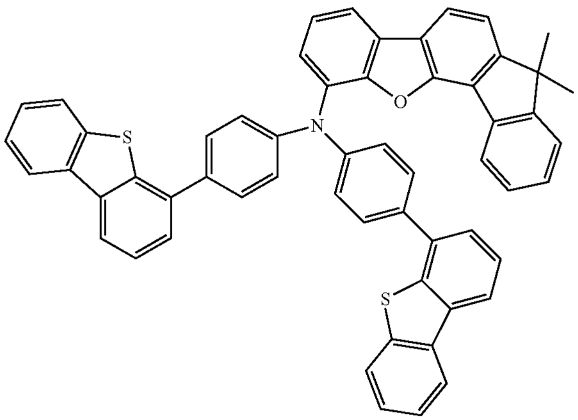
2-26
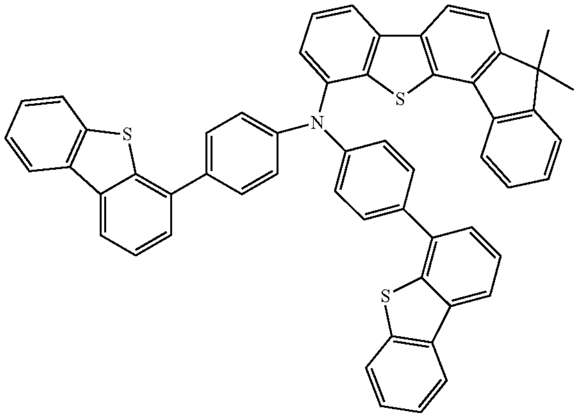

-continued
2-27
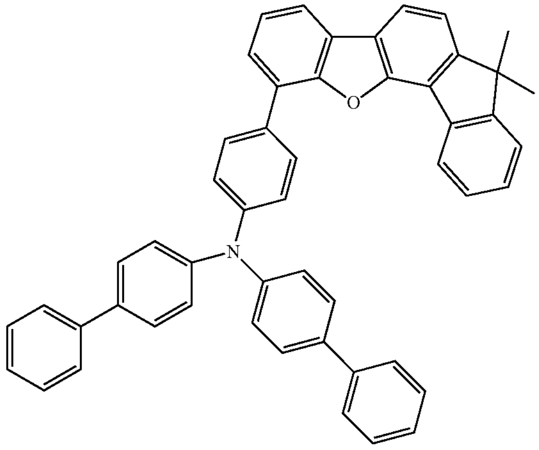
2-28
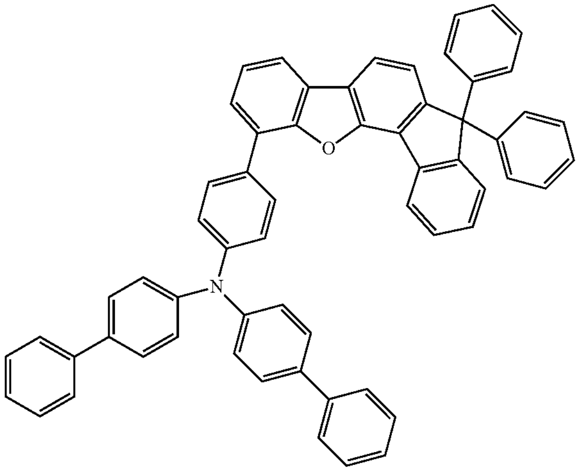
2-29
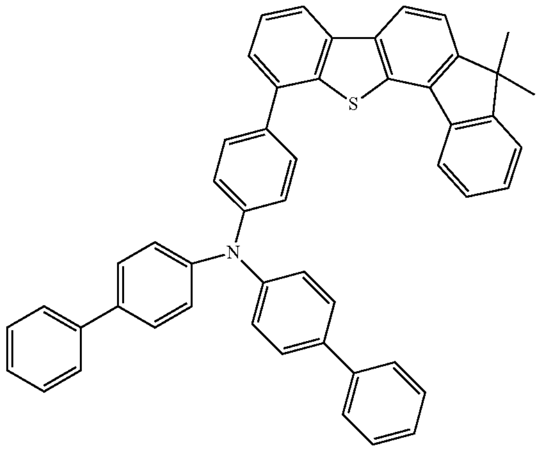
-continued
2-30
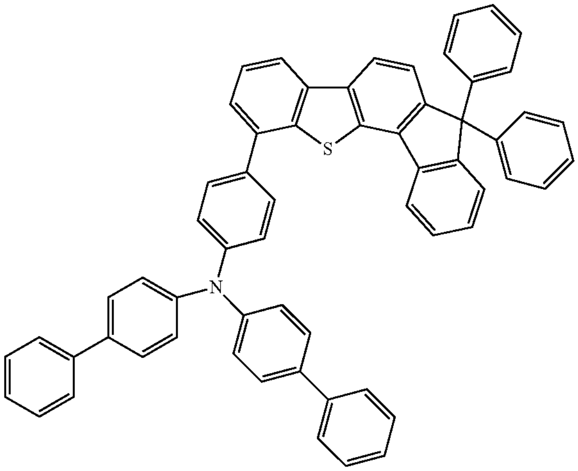
2-31
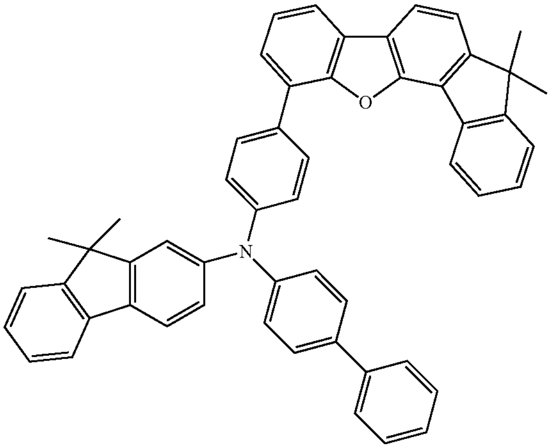
2-32
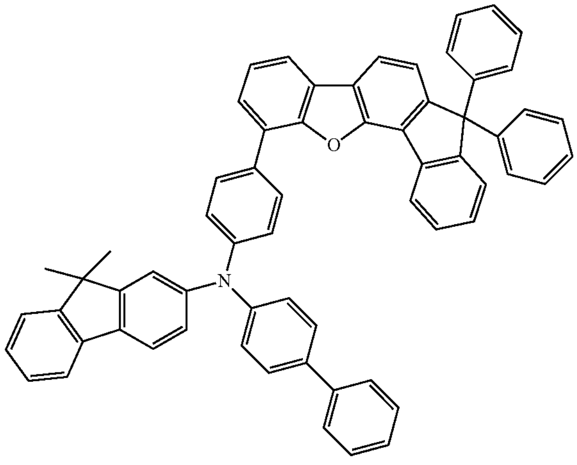

-continued
2-33
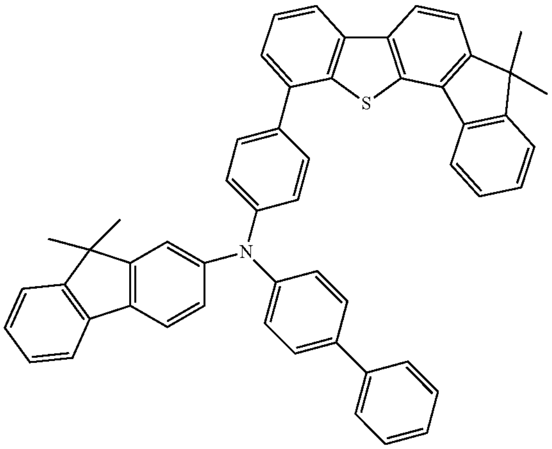
2-34
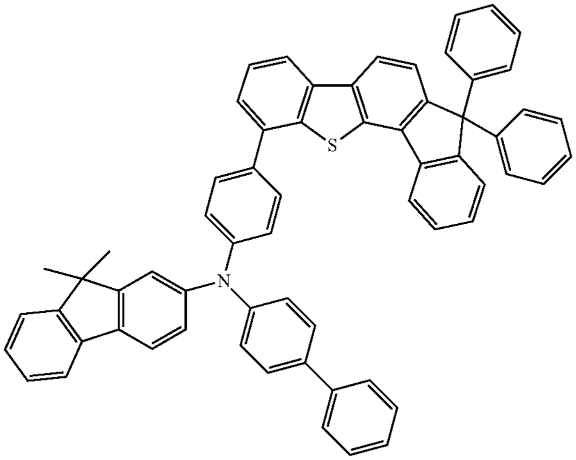
2-35
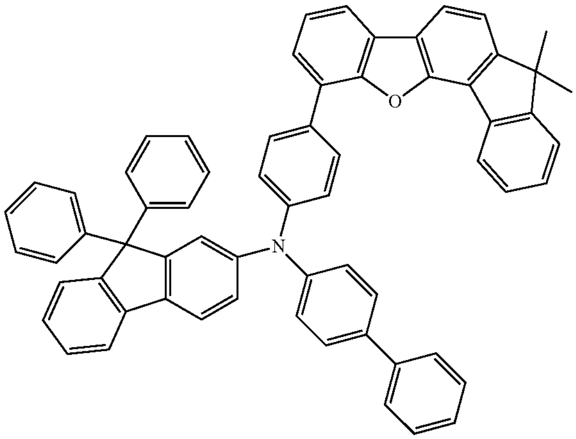
-continued
2-36
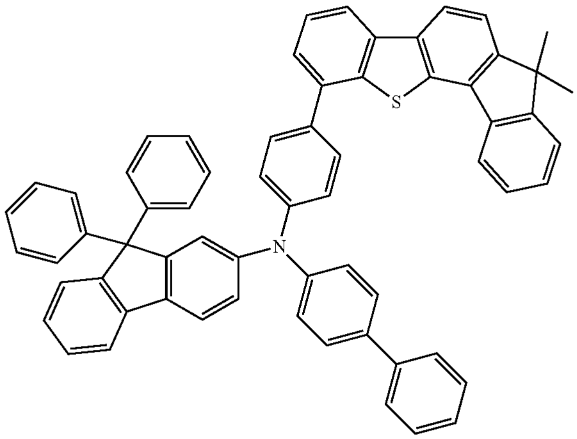
2-37
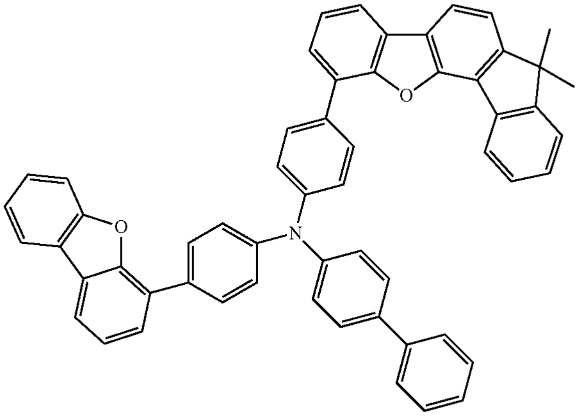
2-38
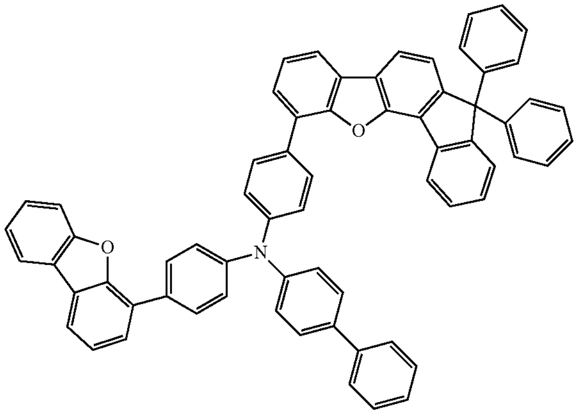

-continued
2-39
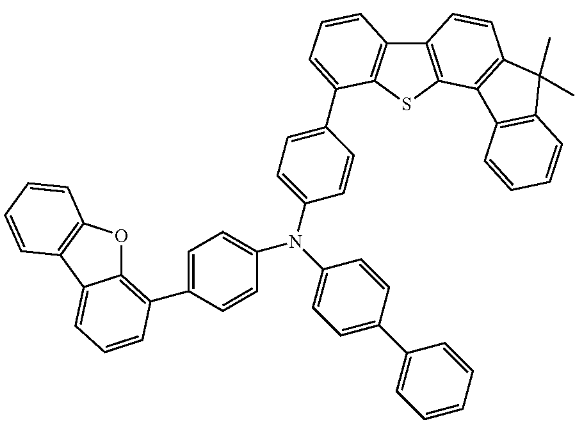
2-40
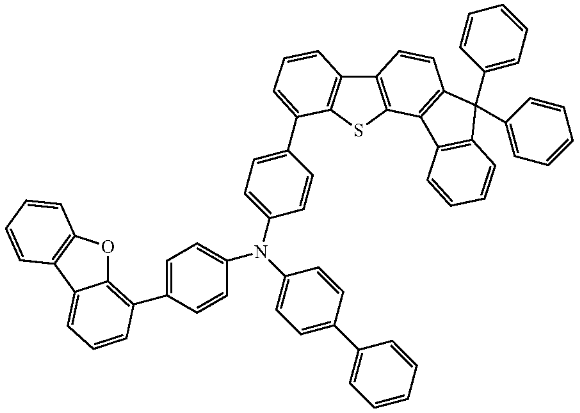
2-41
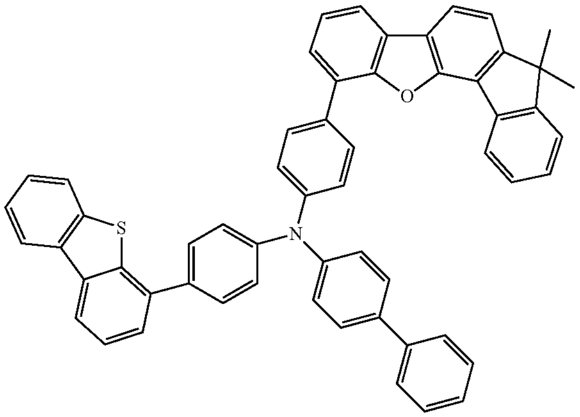
-continued
2-42
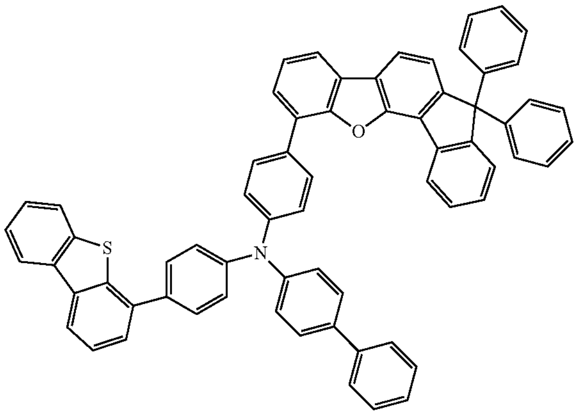
2-43
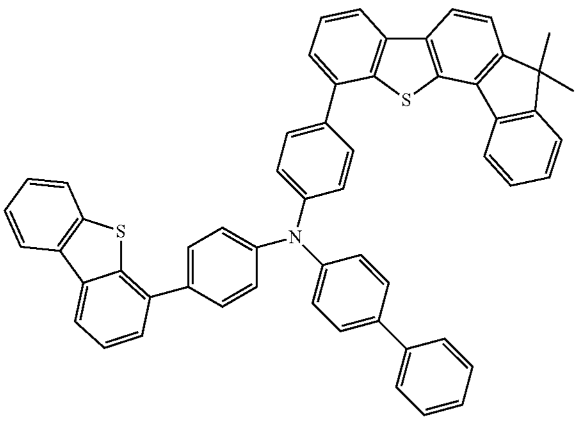
2-44
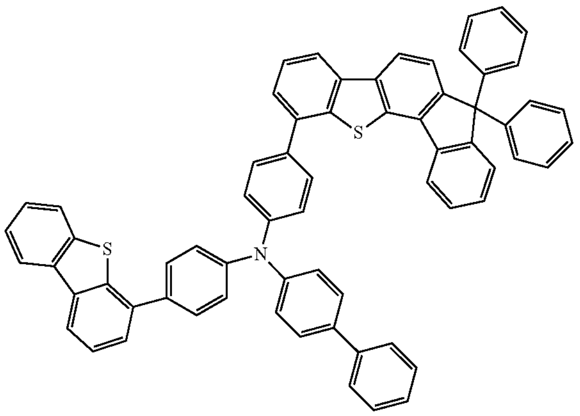

-continued
2-45
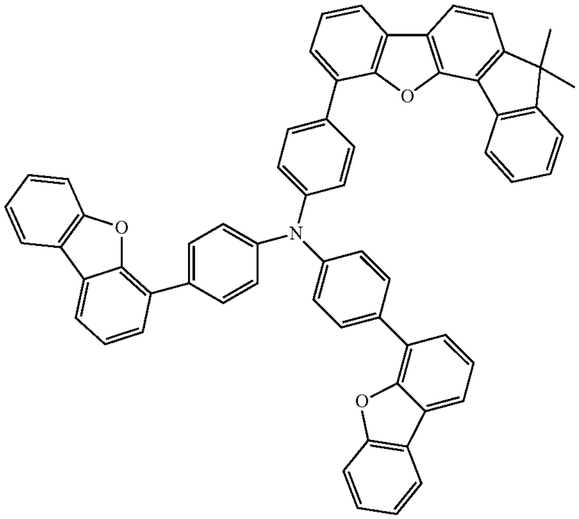
2-46
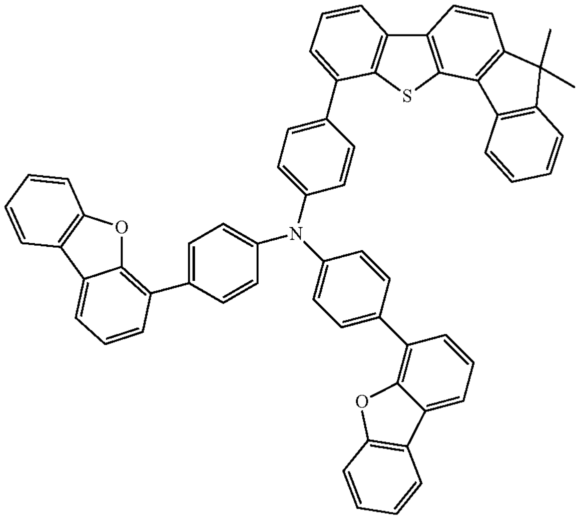
2-47
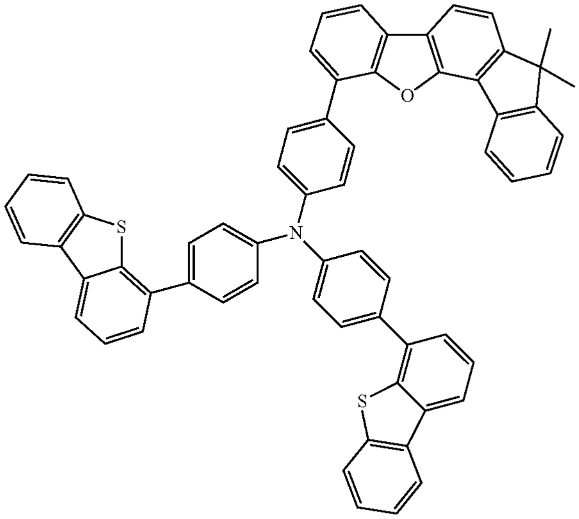
-continued
2-48
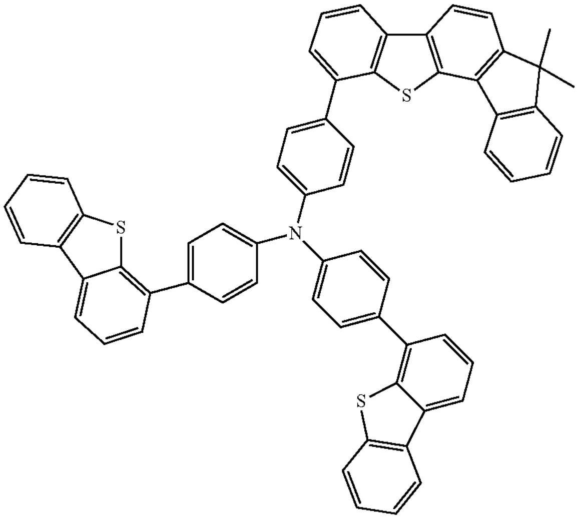
2-49
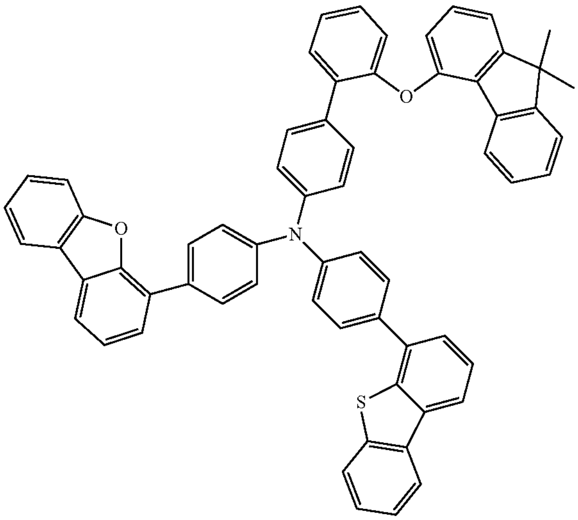
2-50
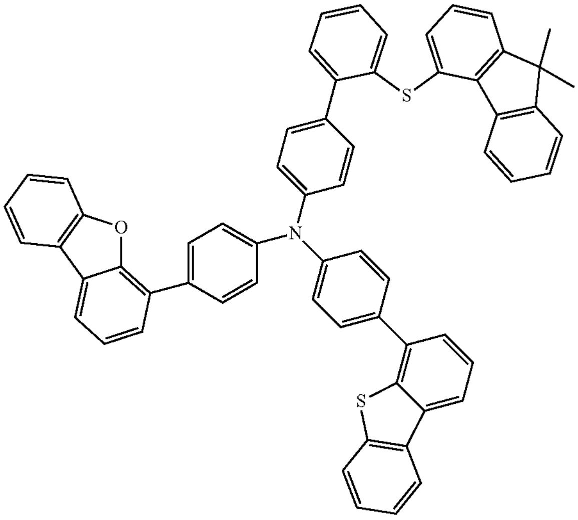

-continued
2-51
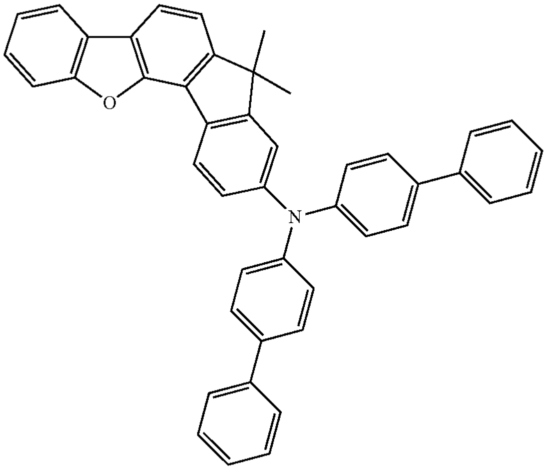
2-52
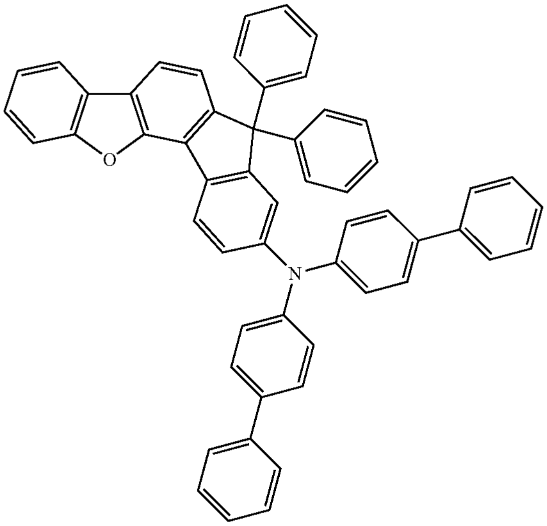
2-53
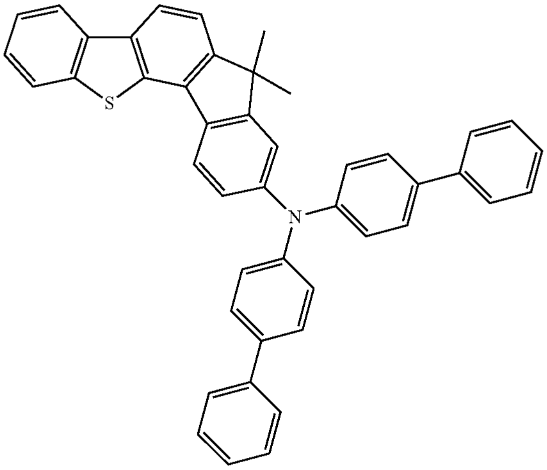
-continued
2-54
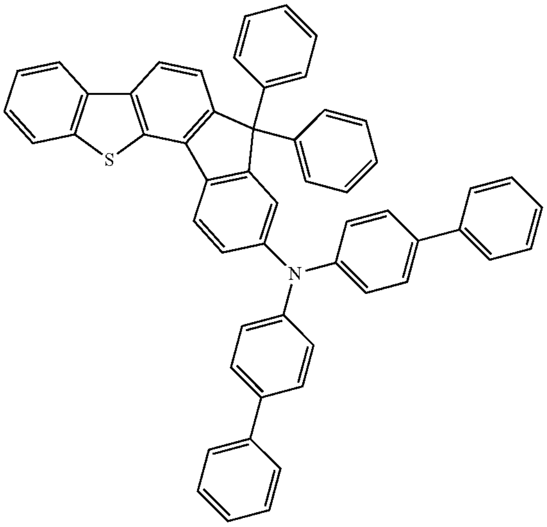
2-55
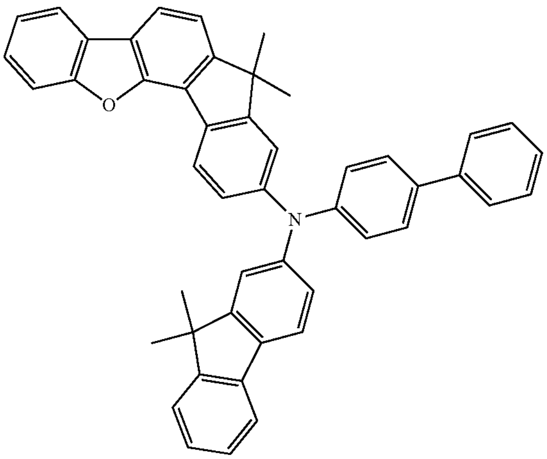
2-56
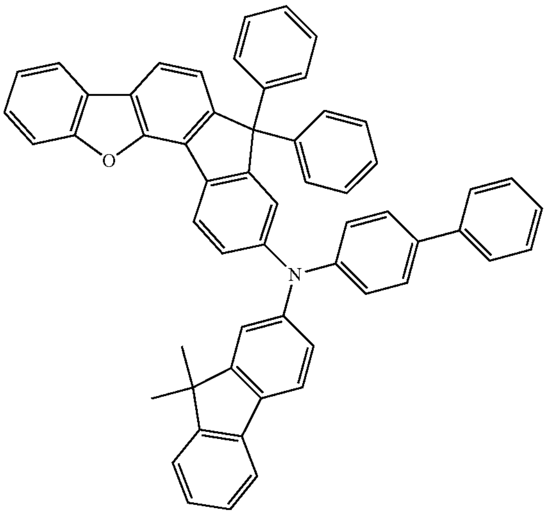

-continued
2-57
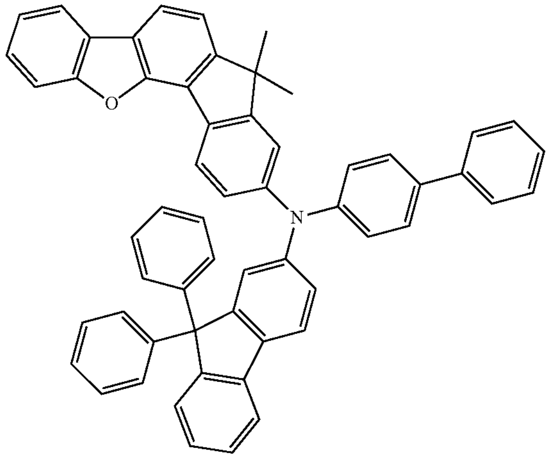
2-58
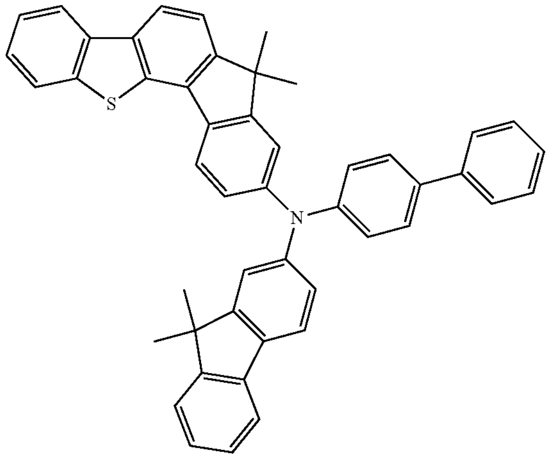
2-59
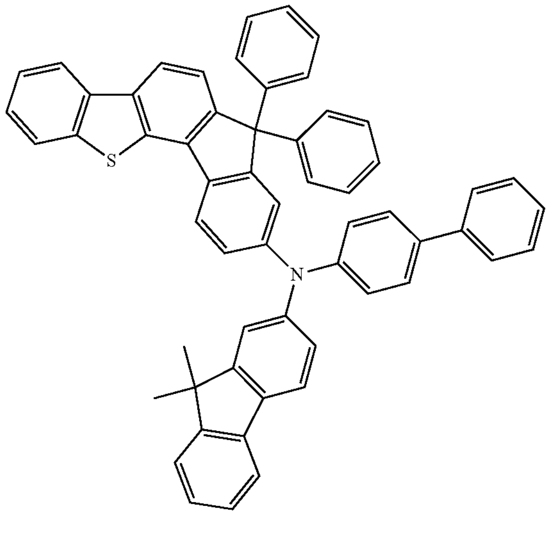
-continued
2-60
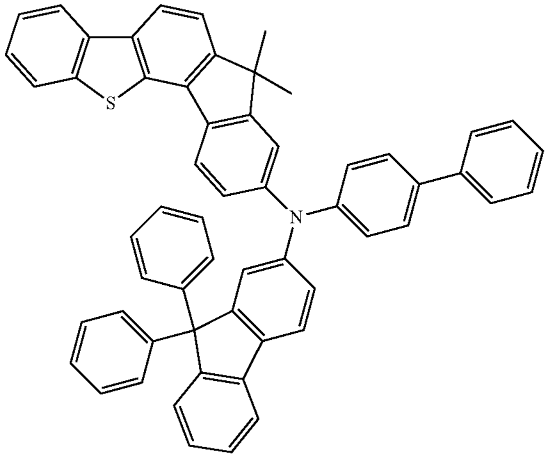
2-61
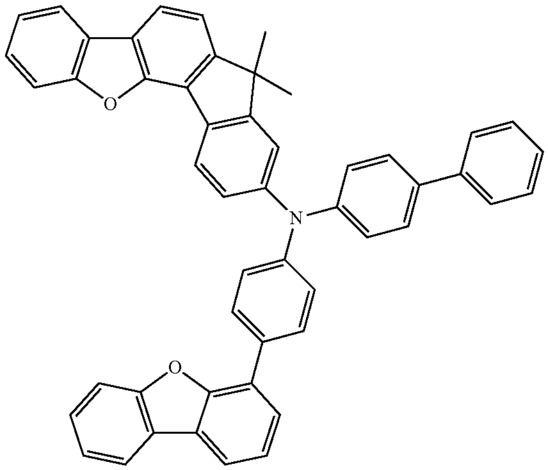
2-62
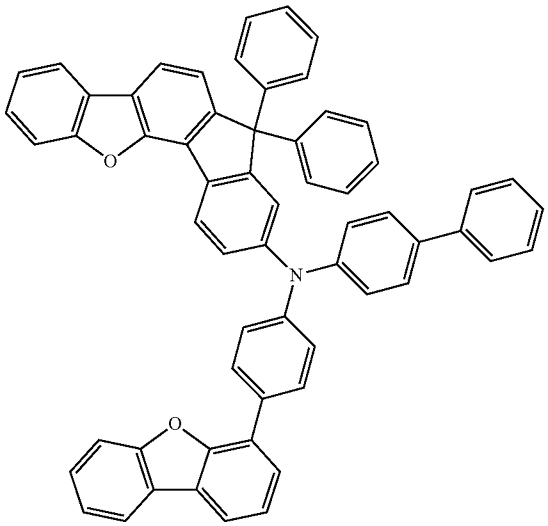

-continued
2-63
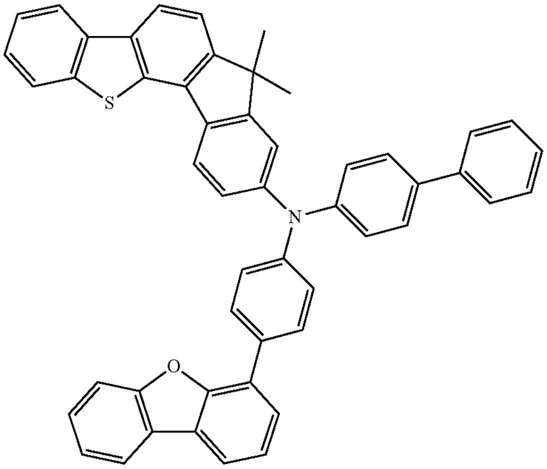
2-64
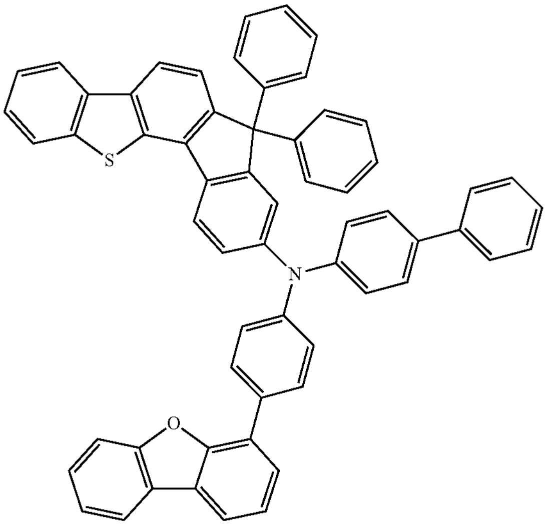
2-65
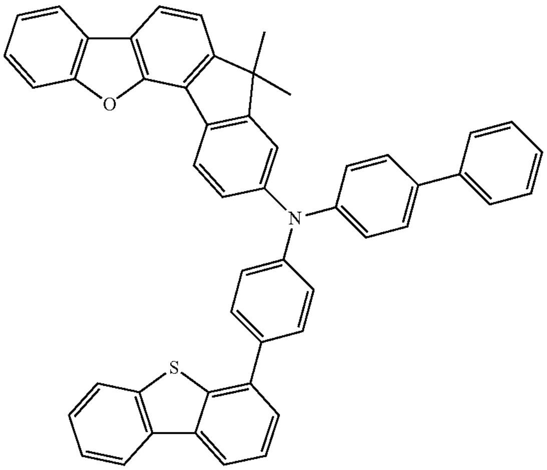
-continued
2-66
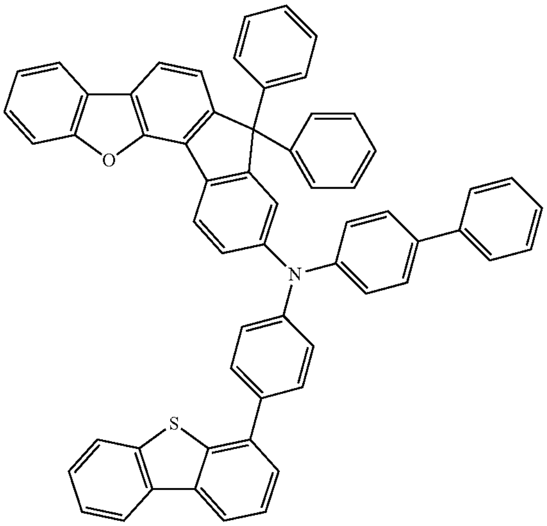
2-67
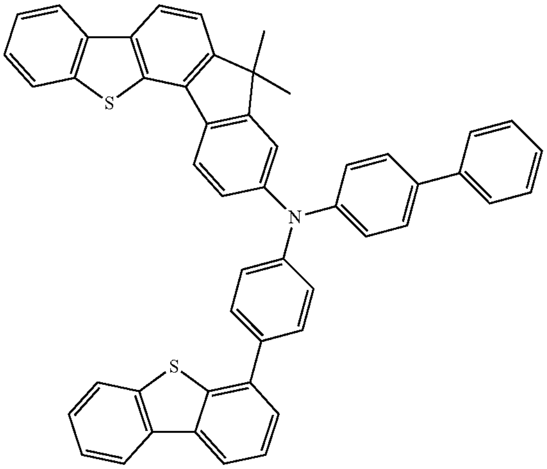
2-68
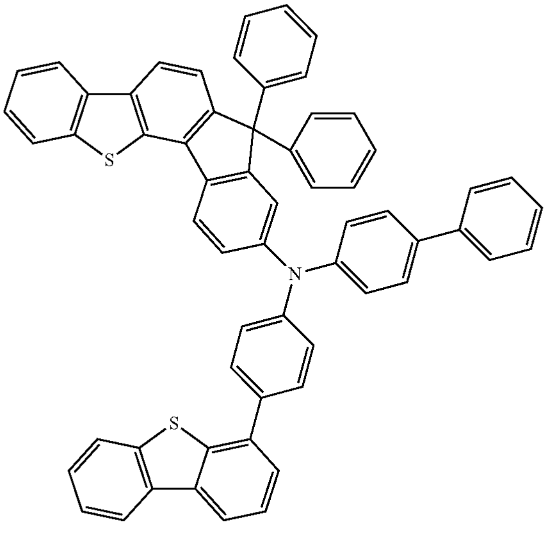

-continued
2-69
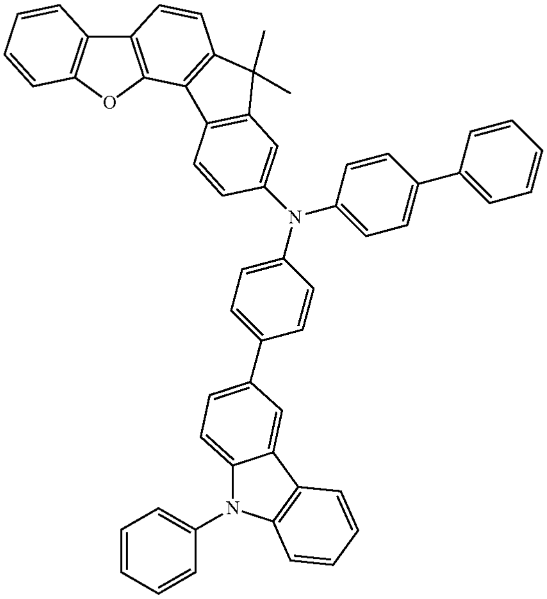
2-70
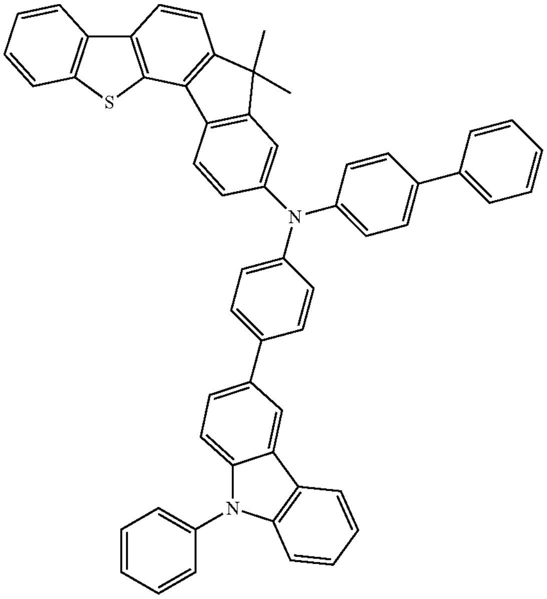
-continued
2-71
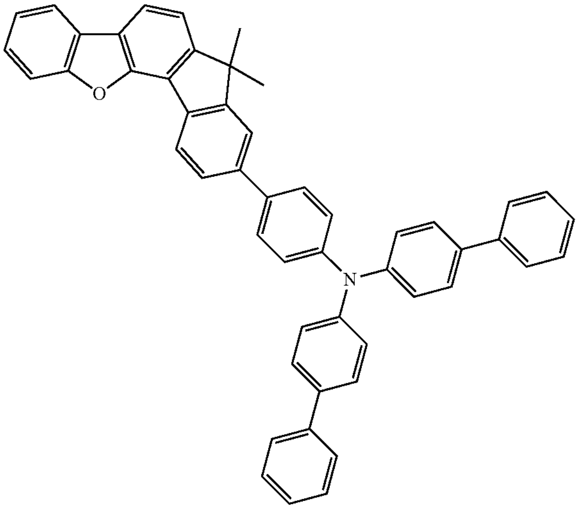
2-72
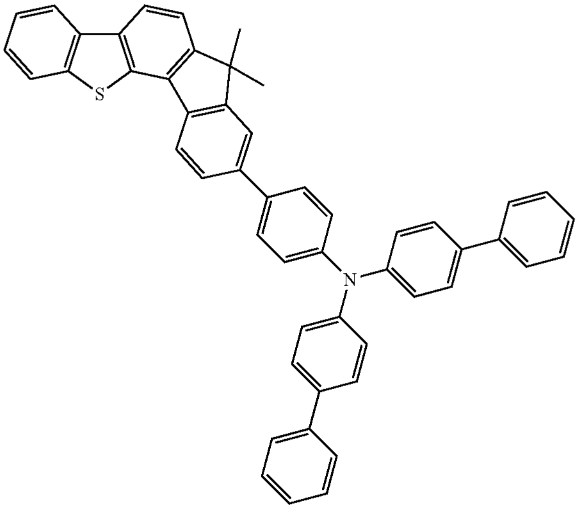
2-73
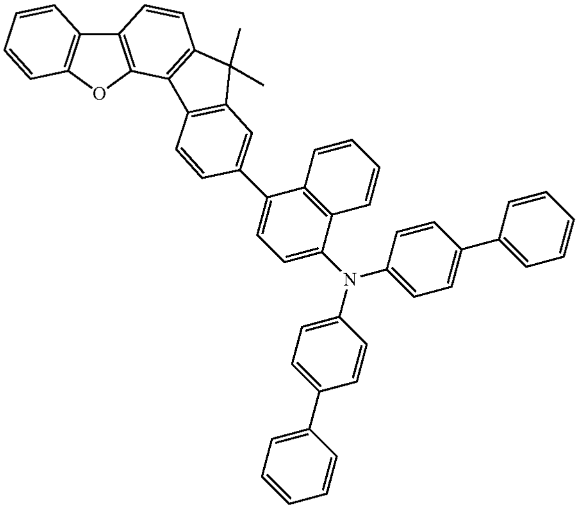

-continued
2-74
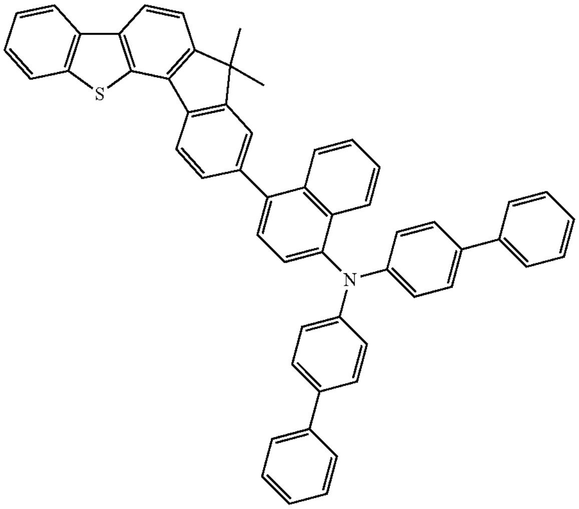
2-75
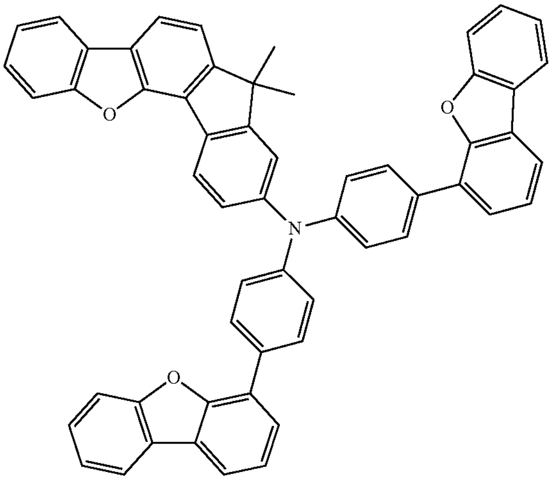
2-76
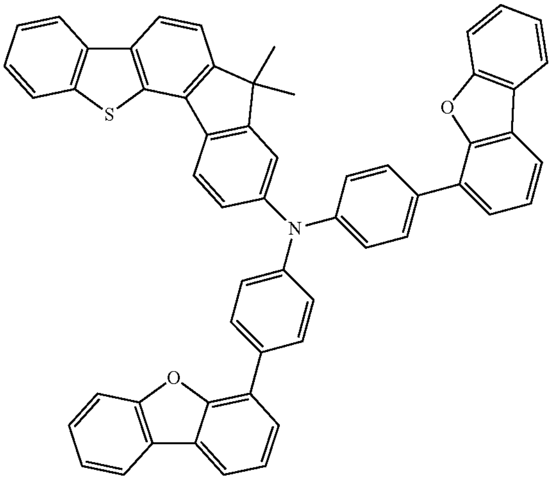
-continued
2-77
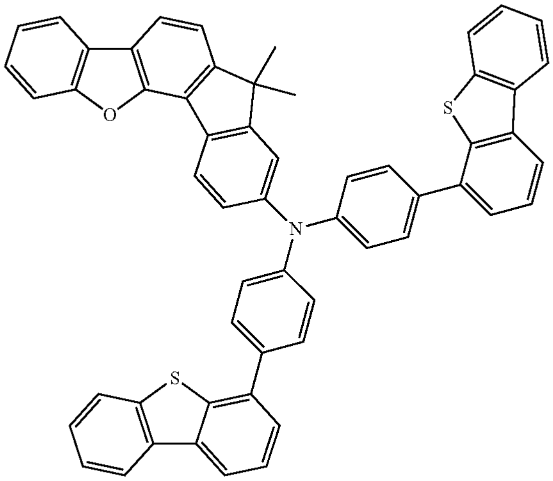
2-78
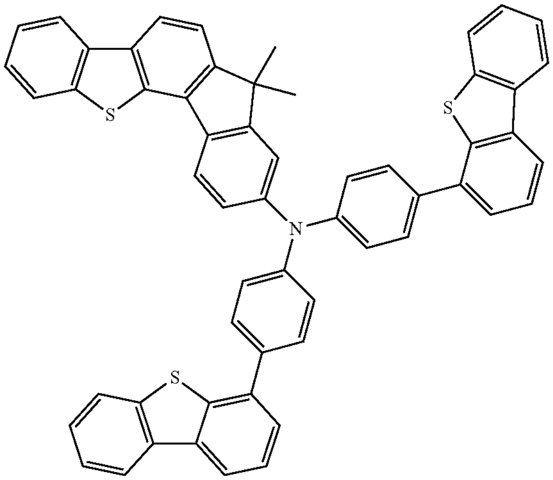
2-79
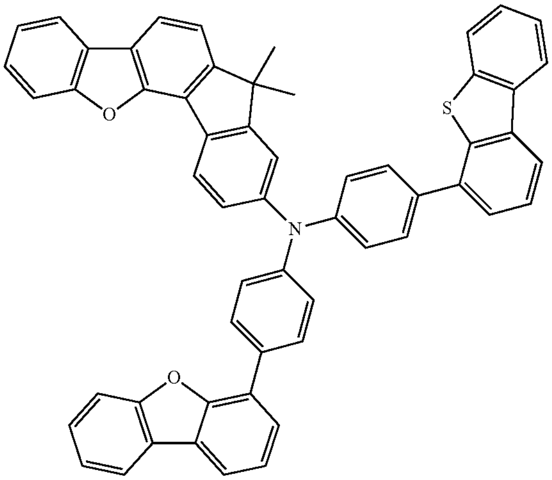

-continued
2-80
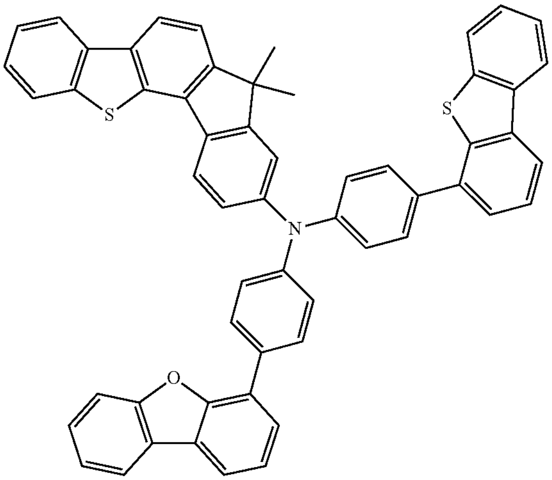
2-81
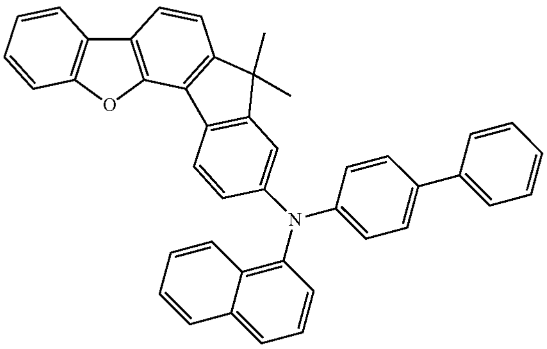
2-82
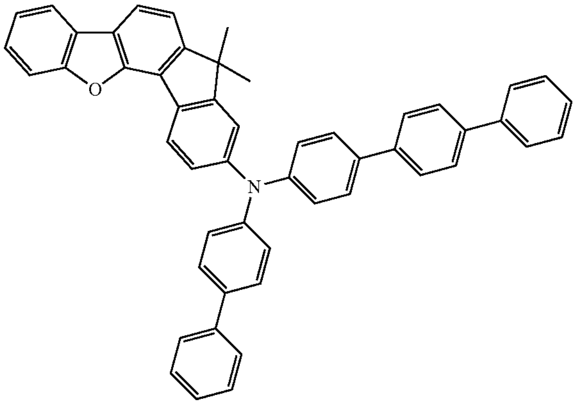
-continued
2-83
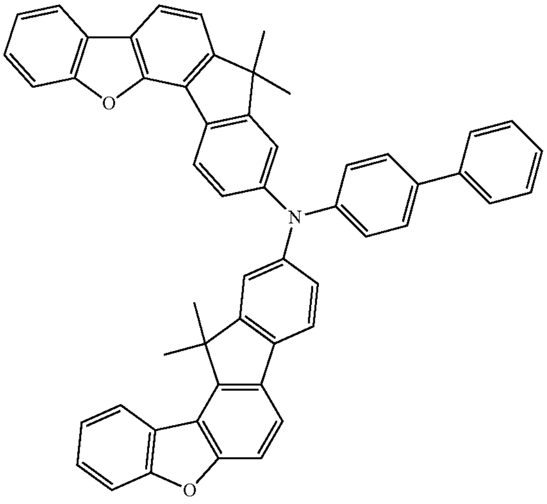
2-84
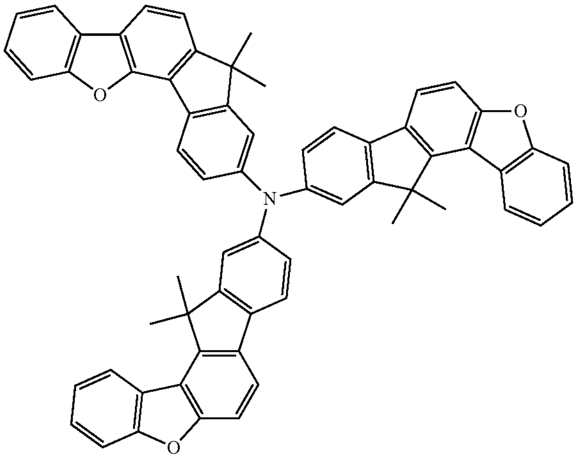
2-85
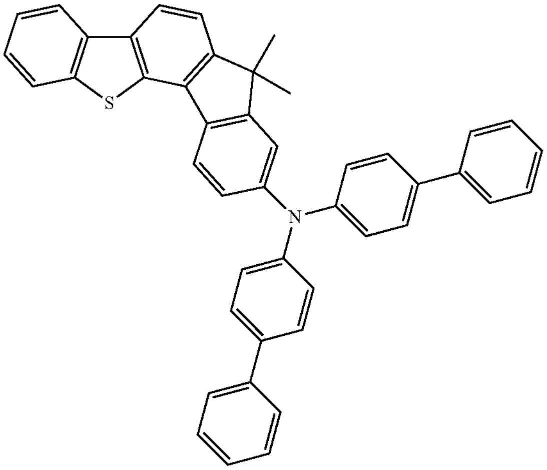

-continued
2-86
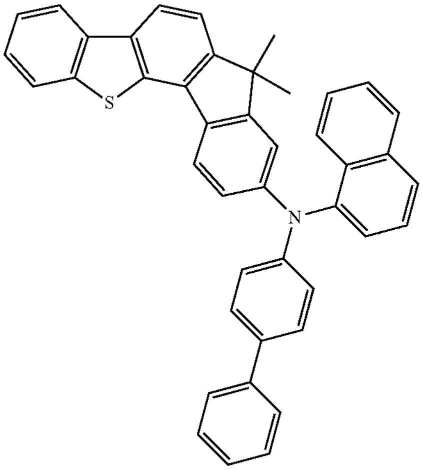
2-87
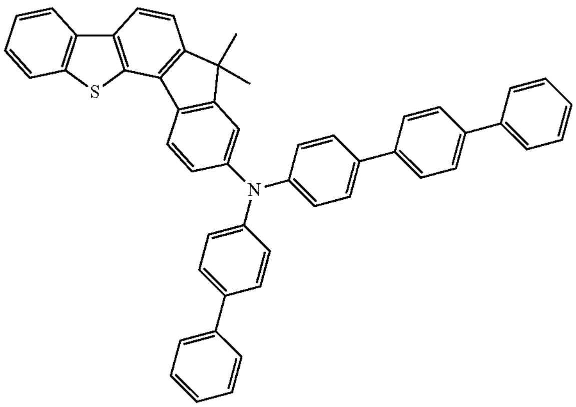
2-88
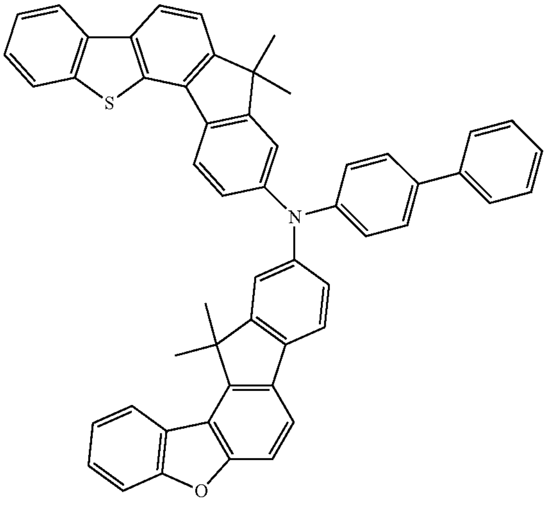
-continued
2-89
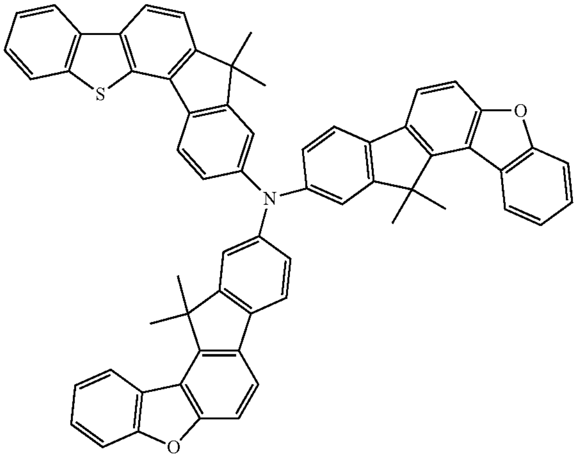
2-90
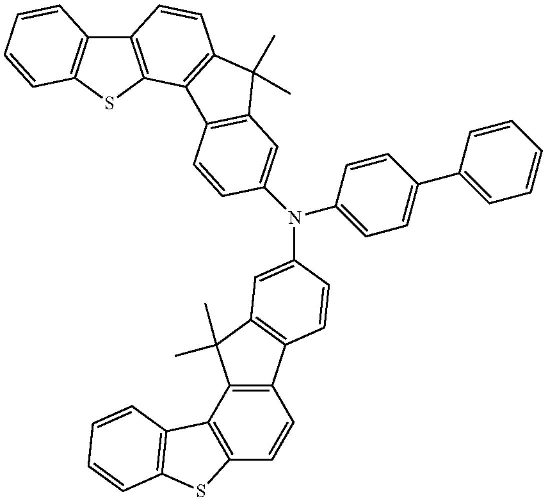
2-91
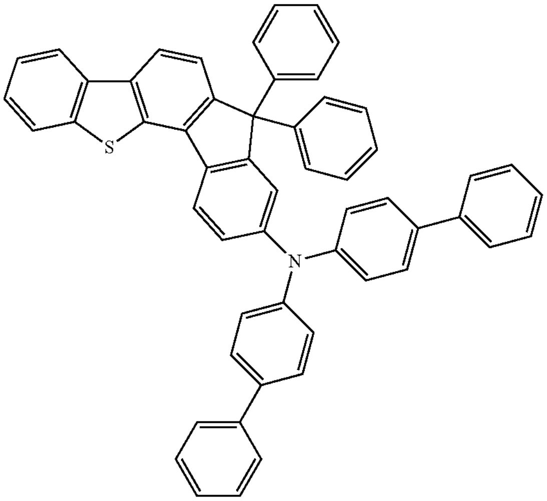

-continued
2-92
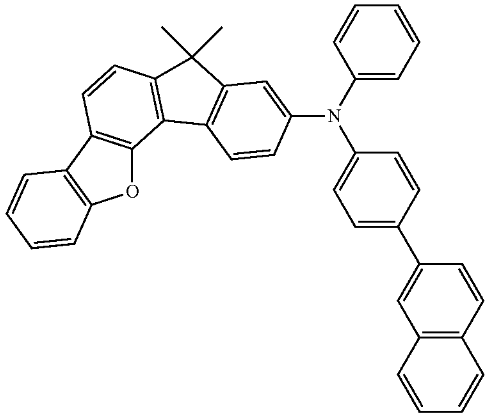
2-93
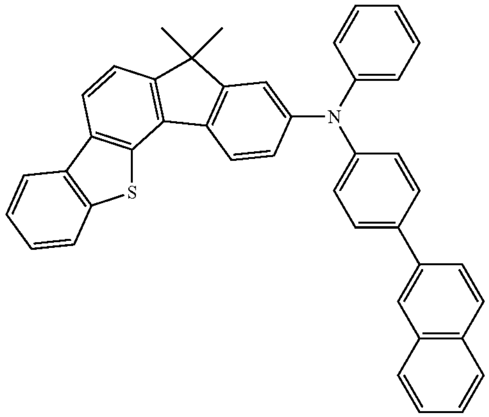
2-94
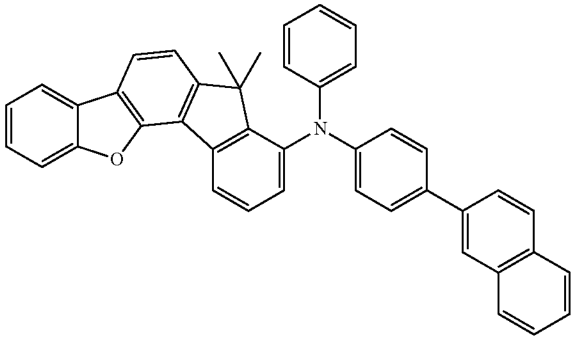
2-95
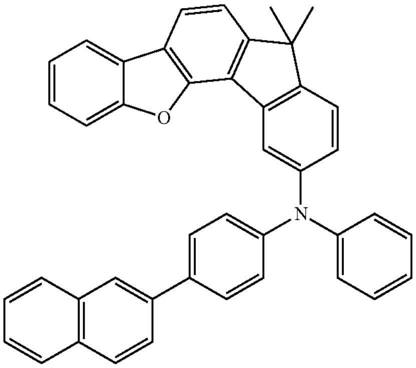
-continued
2-96
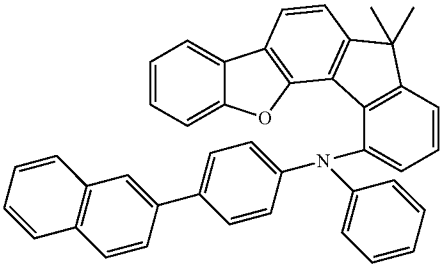
2-97
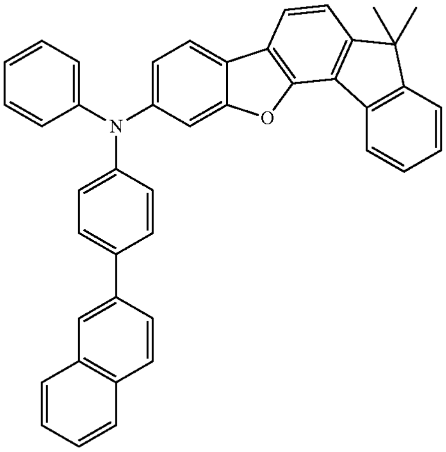
2-98
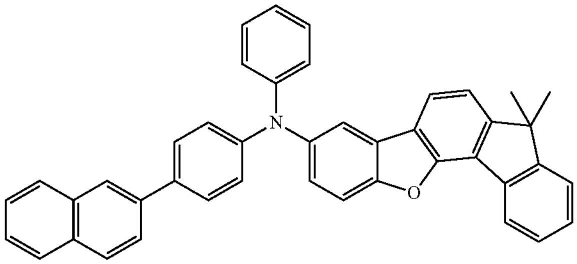
2-99
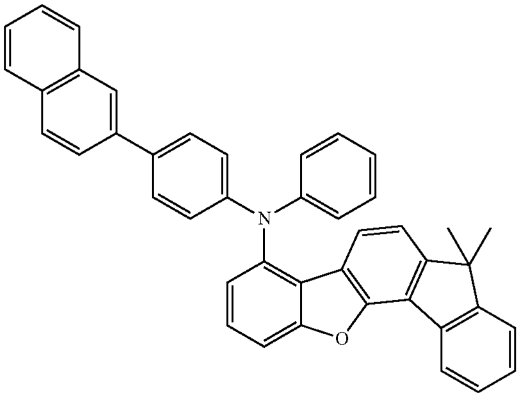

-continued
2-100
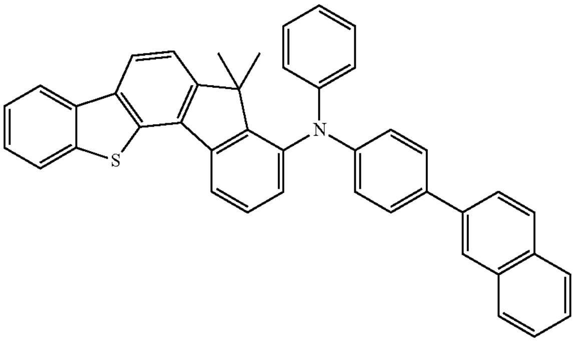
2-101
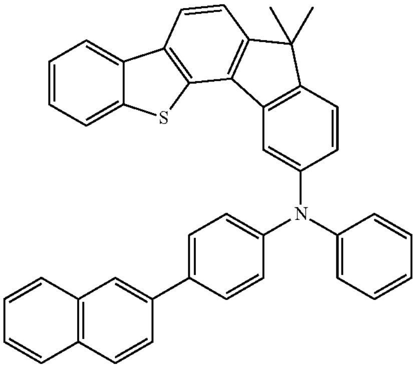
2-102
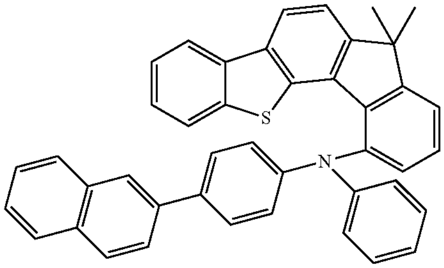
2-103
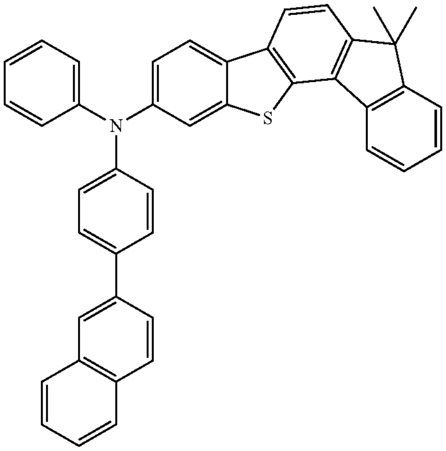
-continued
2-104
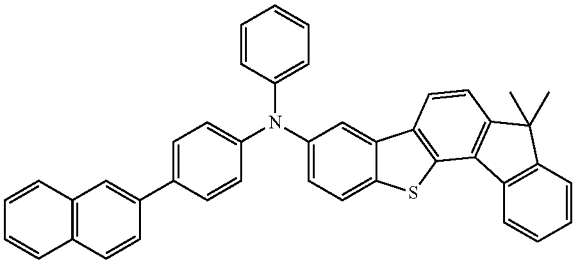
2-105
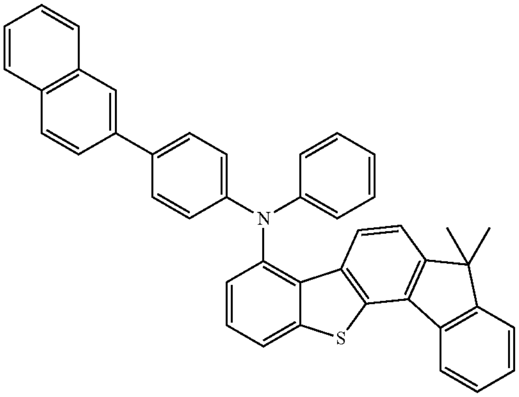
2-106
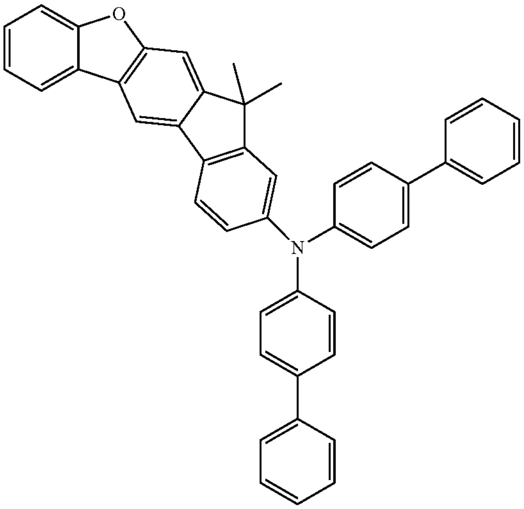

2-107
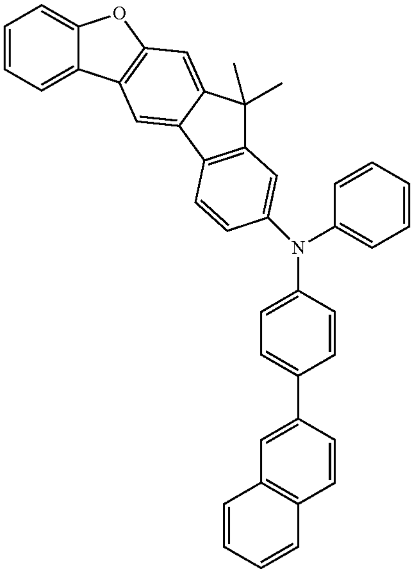
2-108
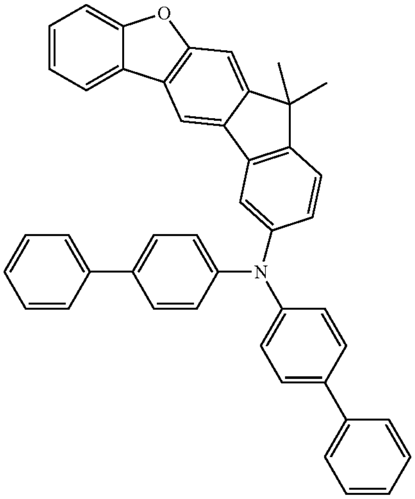
2-109
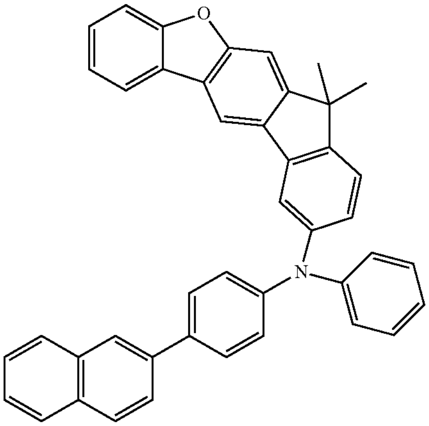
2-110
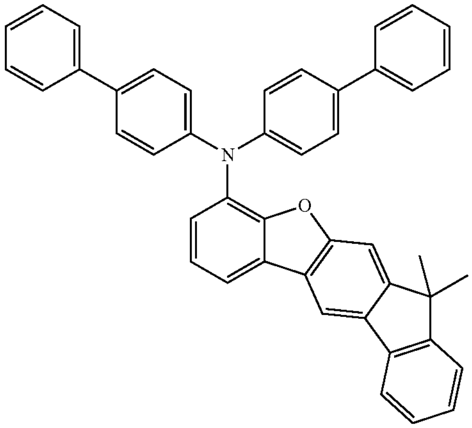
2-111
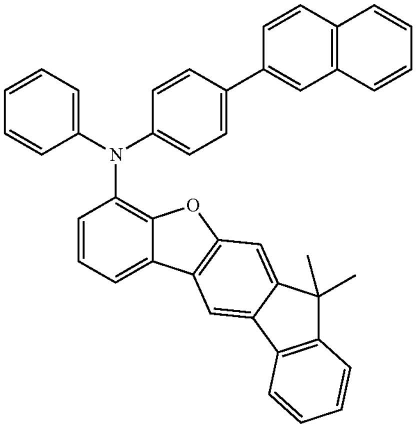
2-112
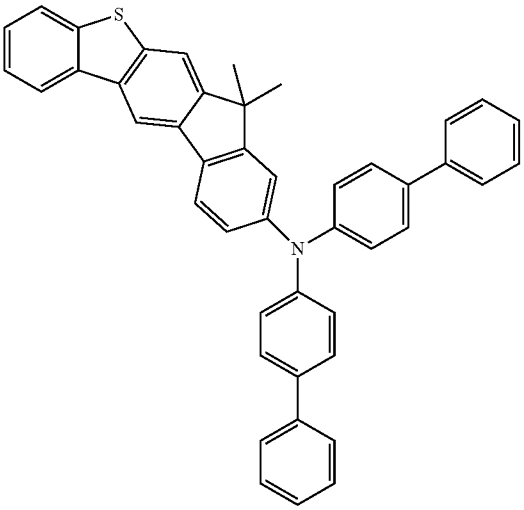

-continued
2-113
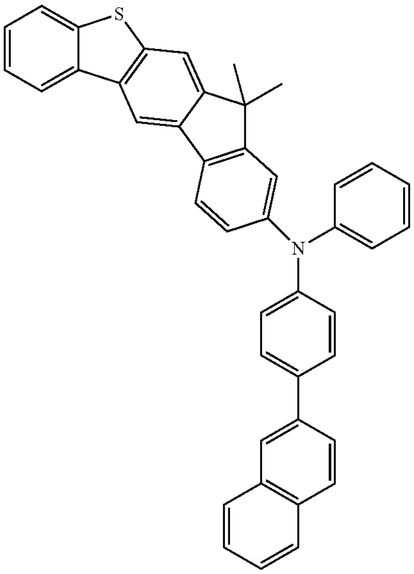
2-114
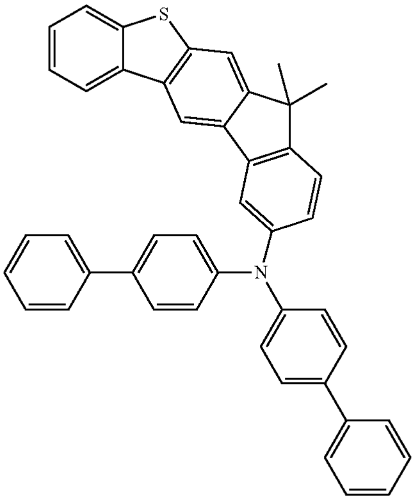
2-115
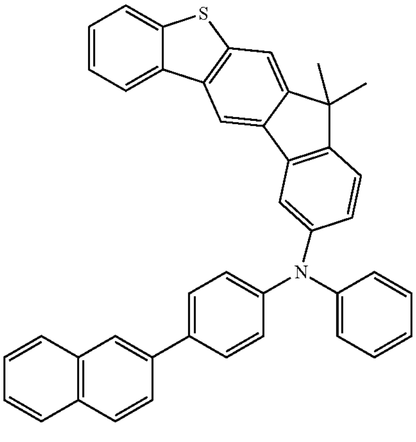
-continued
2-116
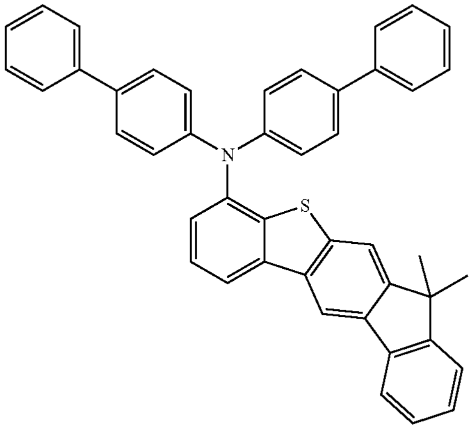
2-117
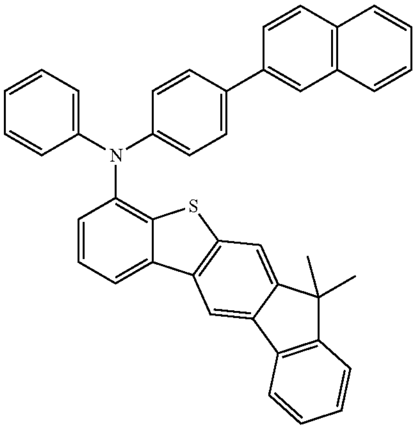
2-118
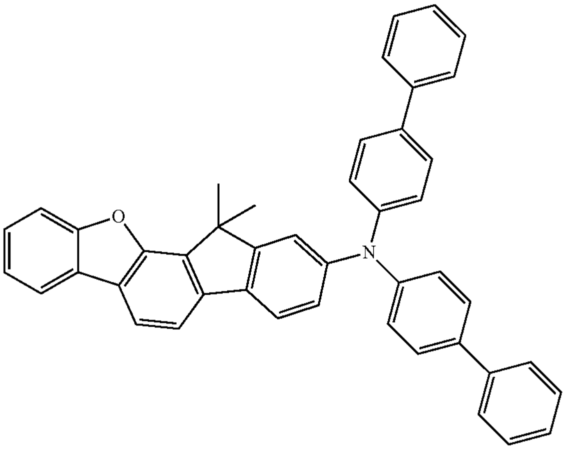

-continued
2-119
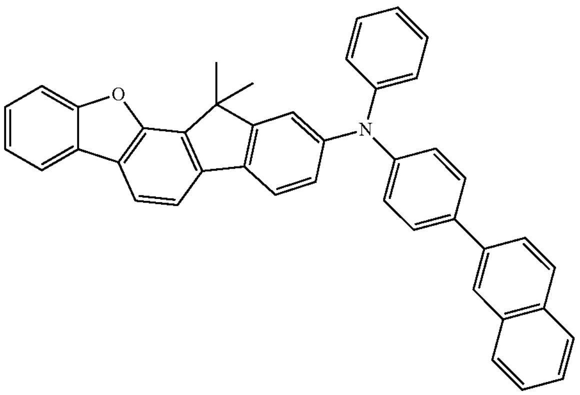
2-120
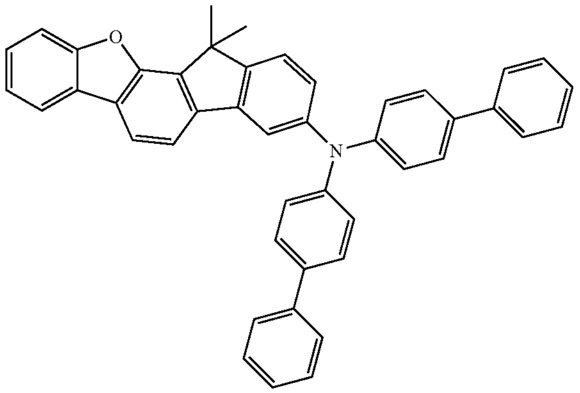
2-121
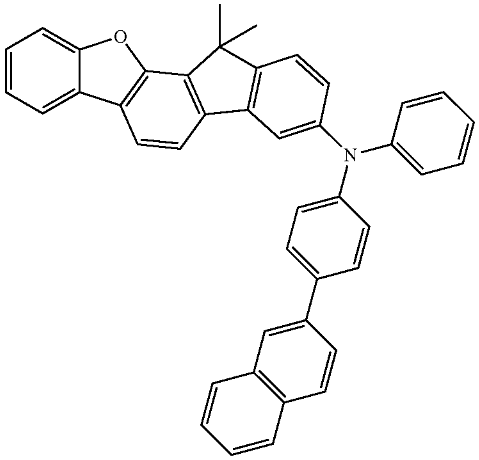
2-122
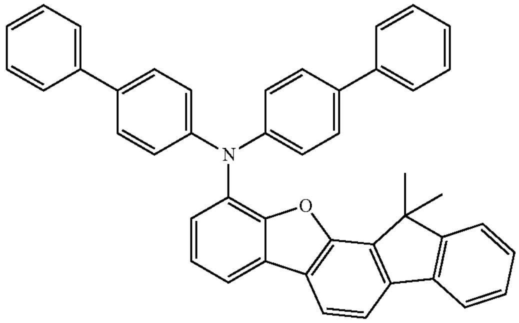
-continued
2-123
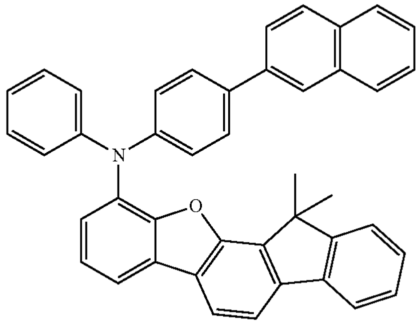
2-124
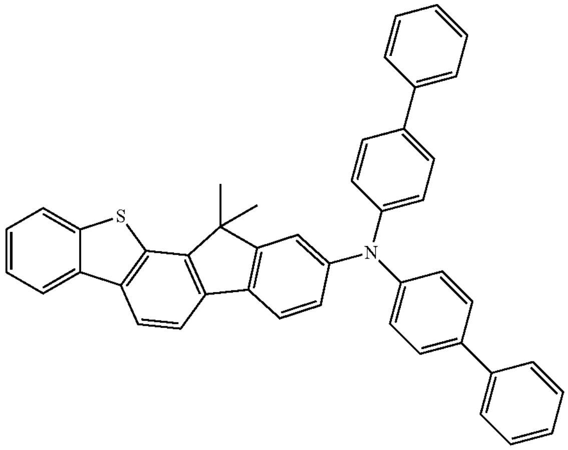
2-125
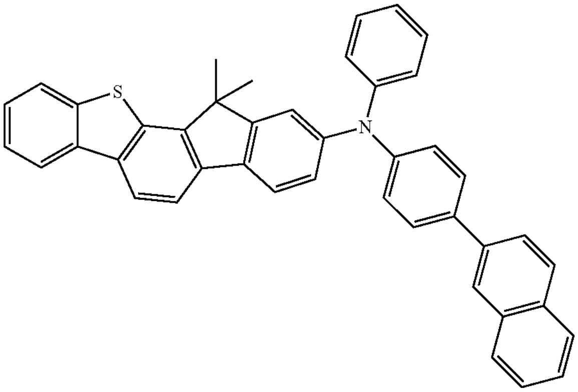
2-126
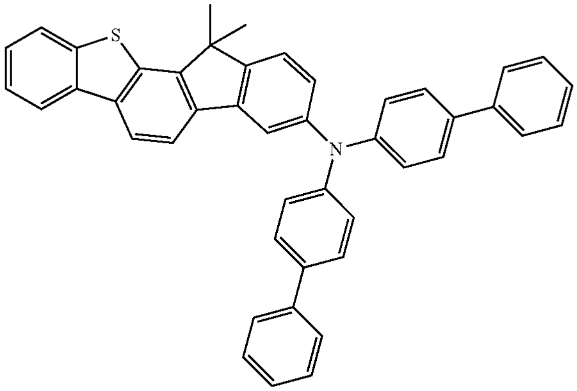

-continued
2-127
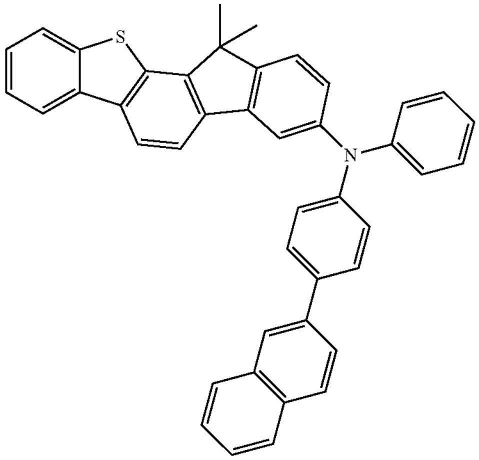
2-128
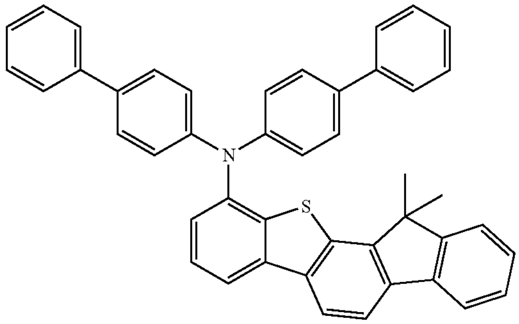
2-129
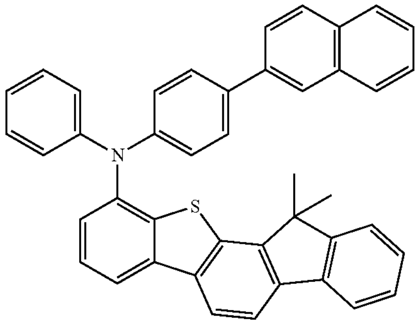
2-130
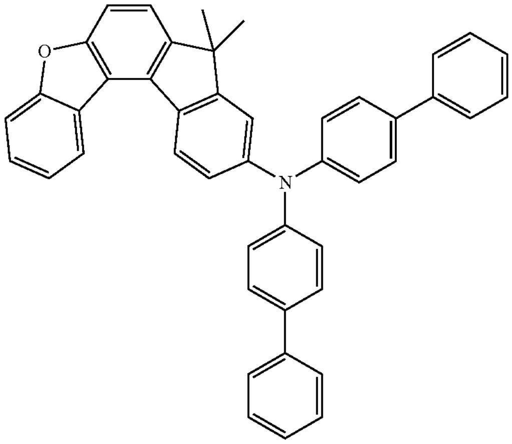
-continued
2-131
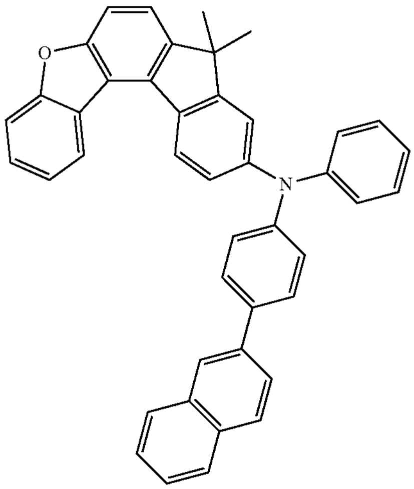
2-132
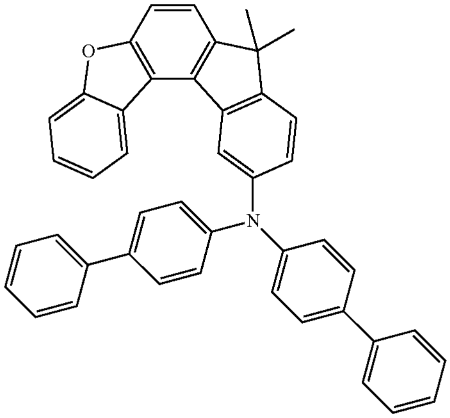
2-133
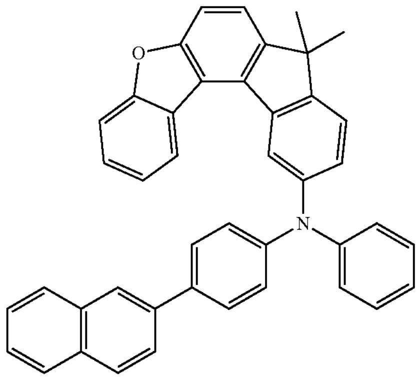

-continued
2-134
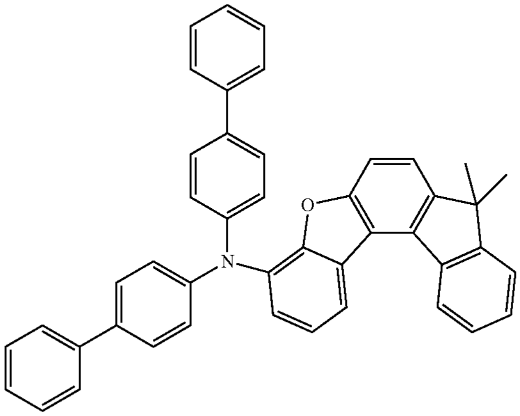
2-135
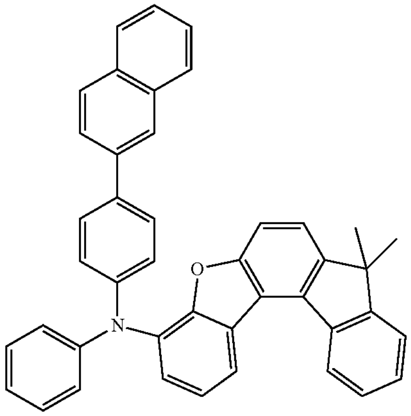
2-136
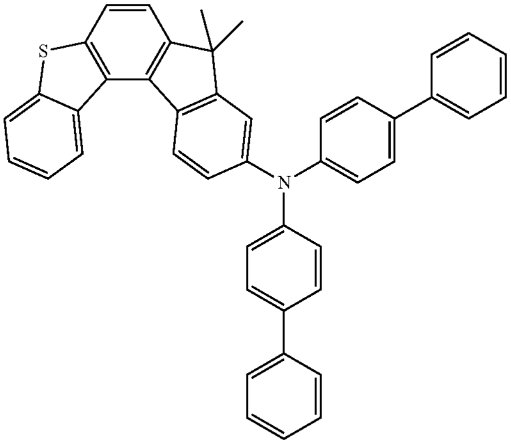
-continued
2-137
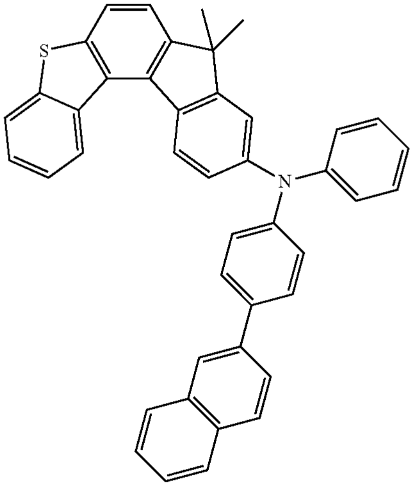
2-138
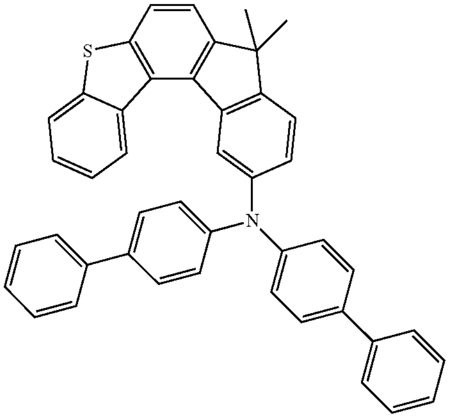
2-139
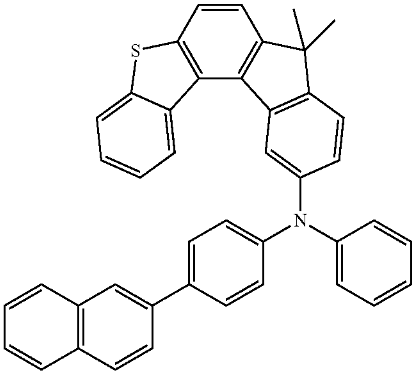

-continued
2-140
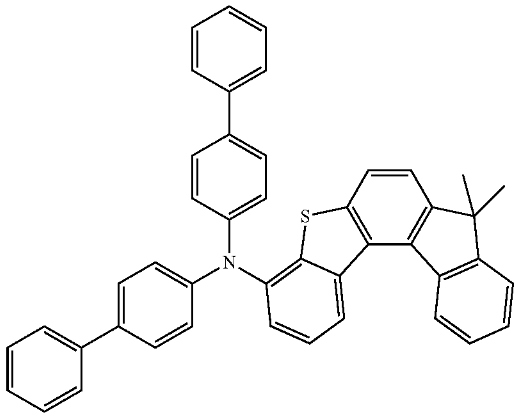
2-141
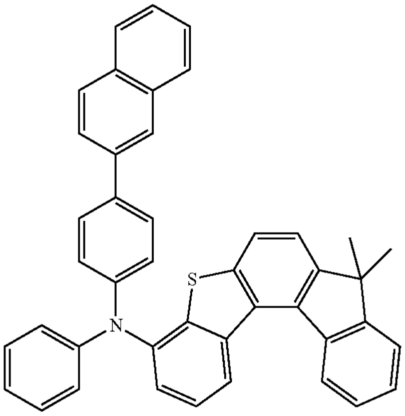
2-142
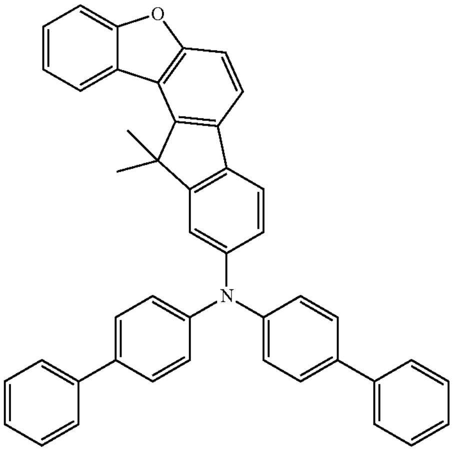
-continued
2-143
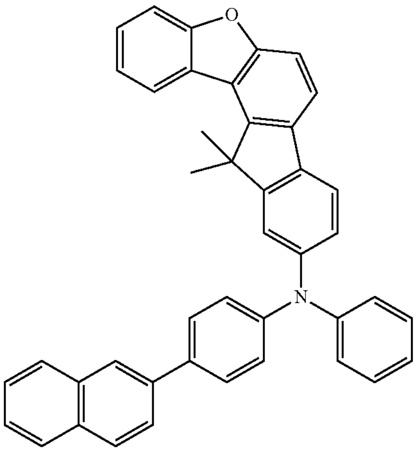
2-144
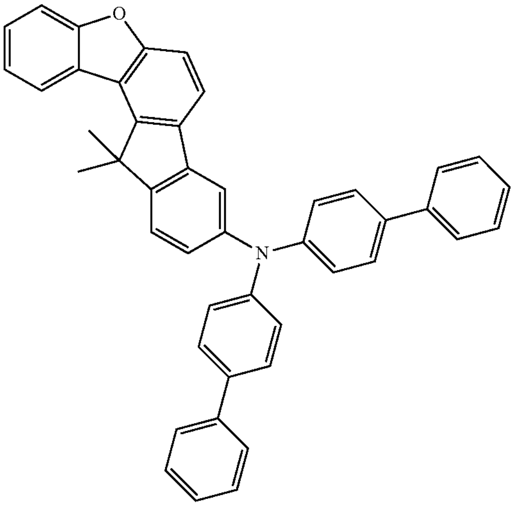
2-145
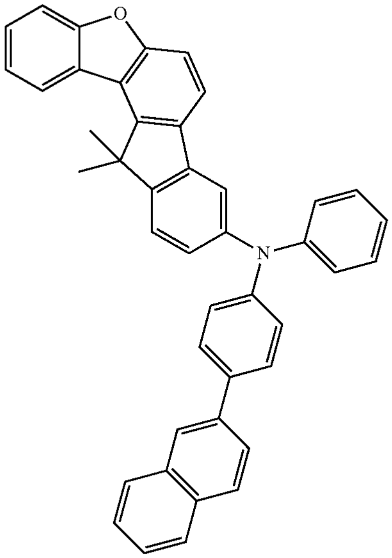

-continued
2-146
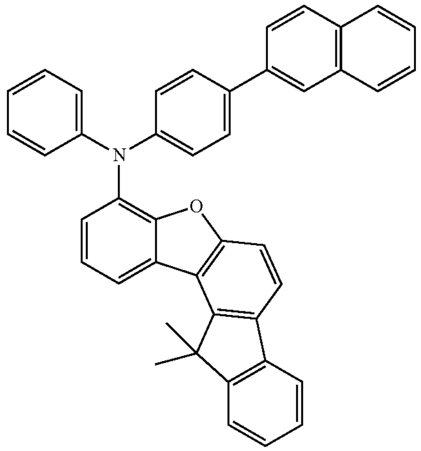
2-147
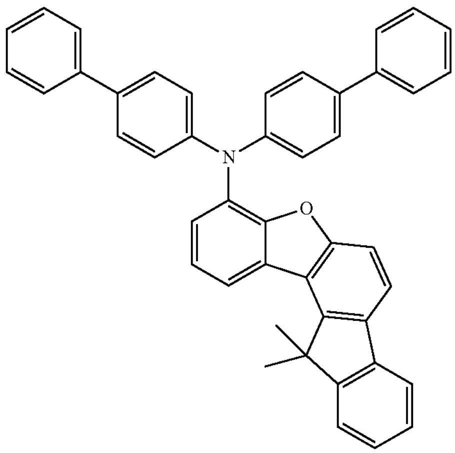
2-148
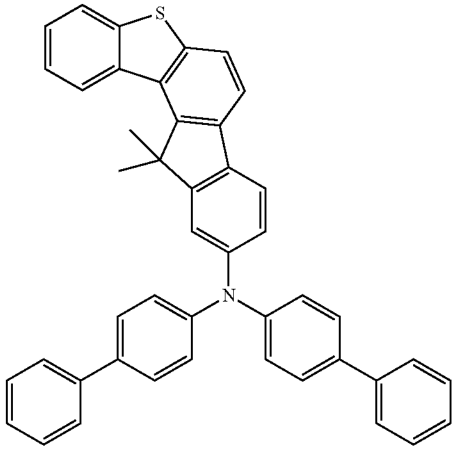
-continued
2-149
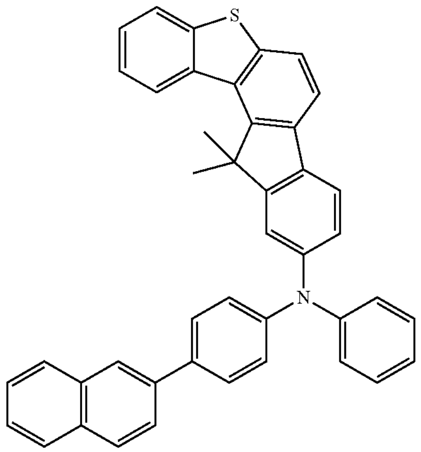
2-150
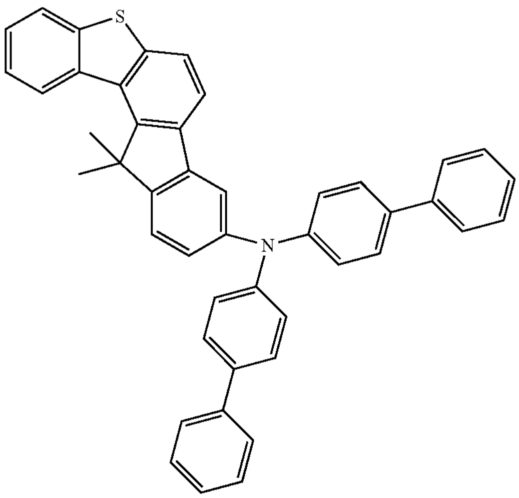
2-151
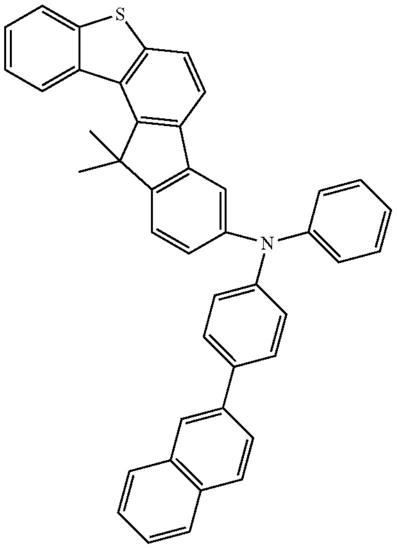

-continued
2-152
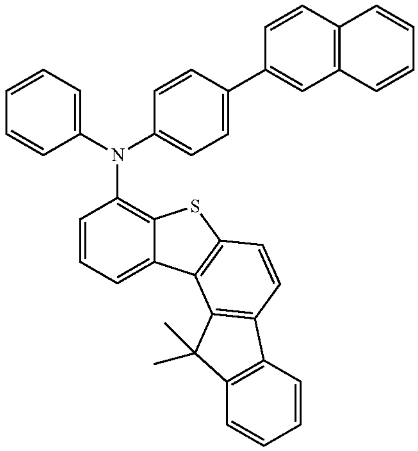
2-153
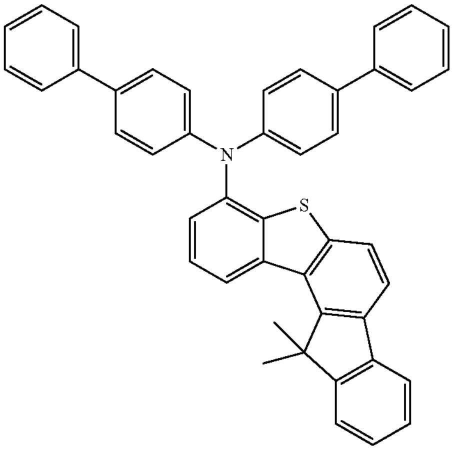
2-154
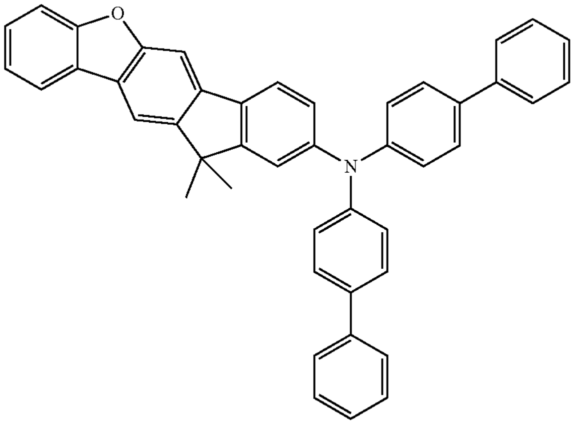
-continued
2-155
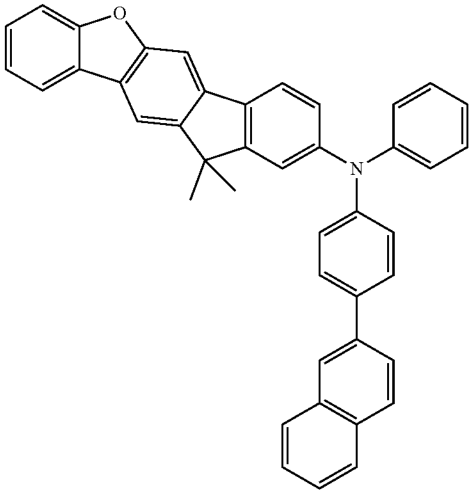
2-156
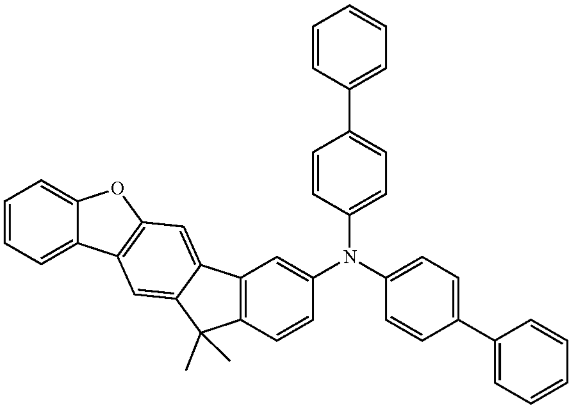
2-157
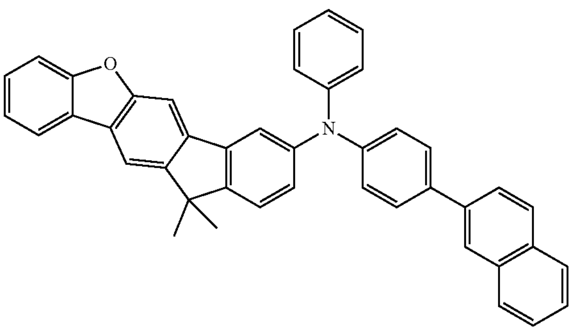

-continued
2-158
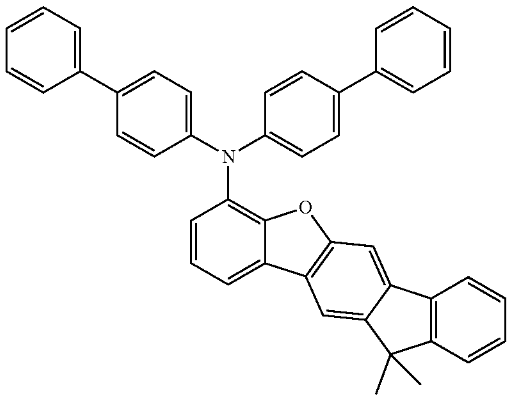
2-159
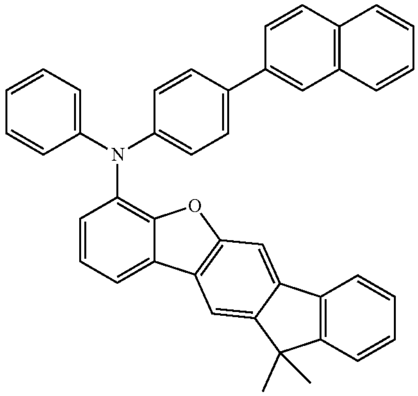
2-160
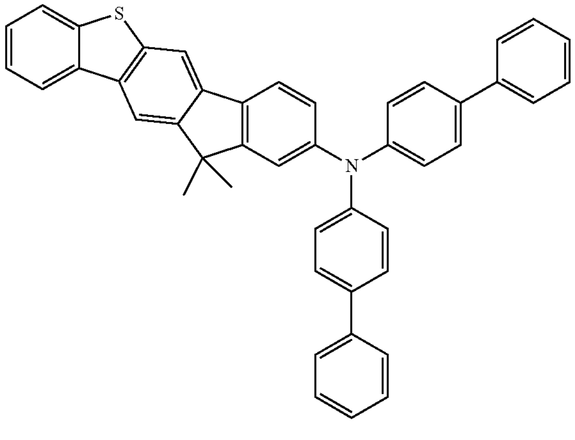
-continued
2-161
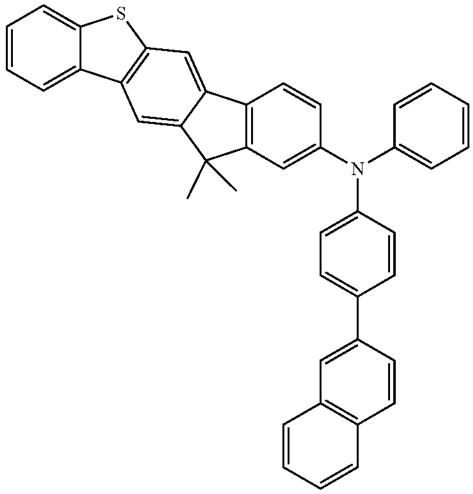
2-162
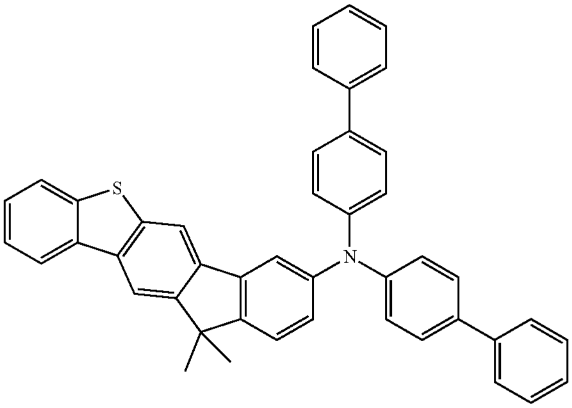
2-163
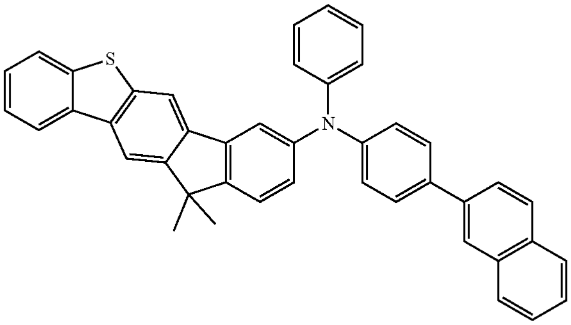

-continued
2-164
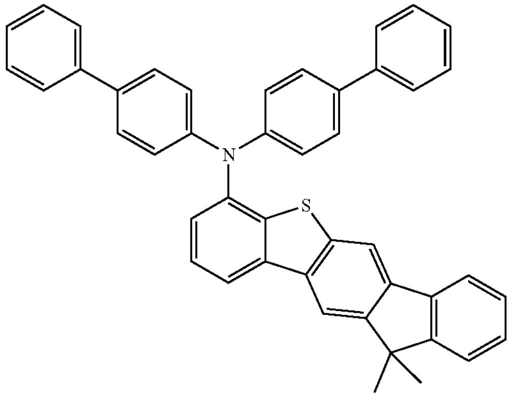
2-165
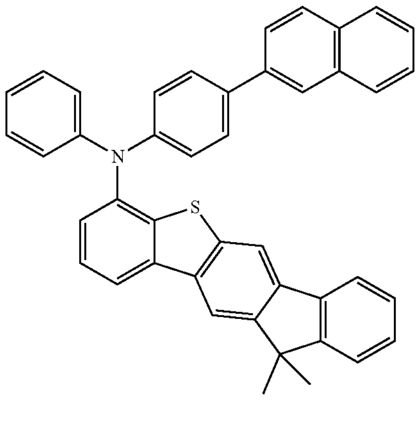
2-166
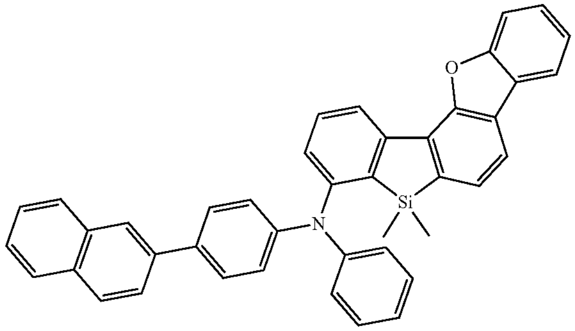
2-167
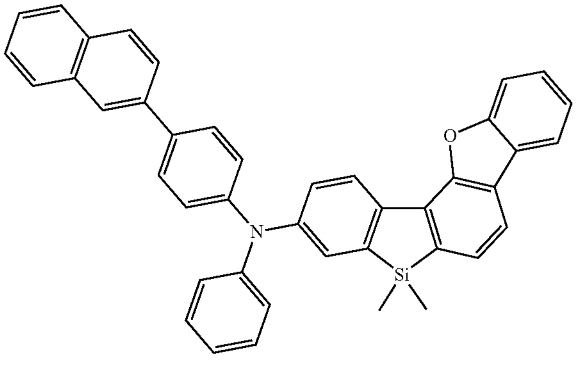
-continued
2-168
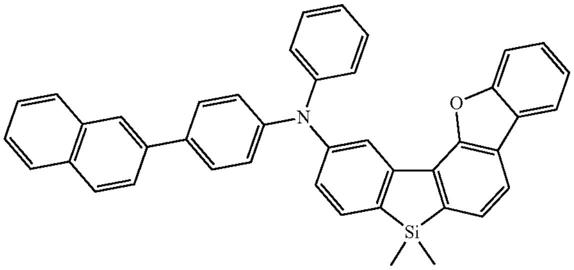
2-169
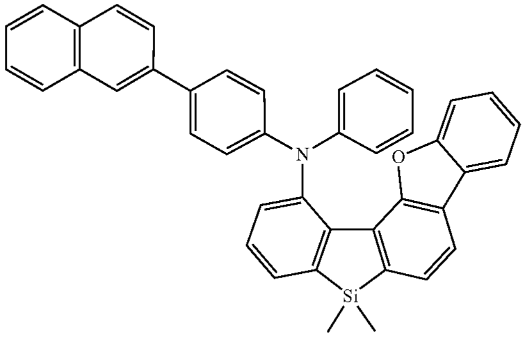
2-170
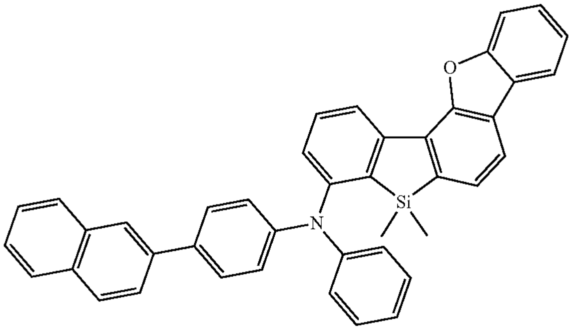
2-171
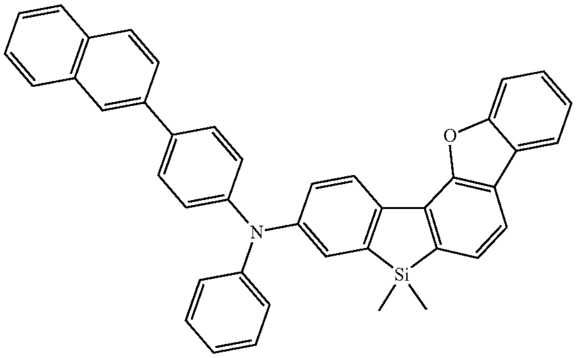

-continued
2-172
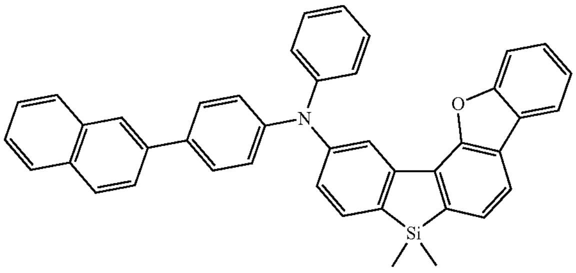
2-173
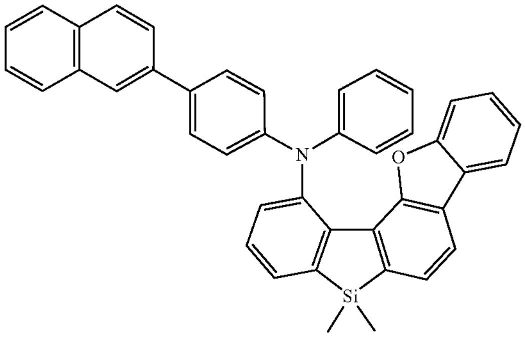
2-174
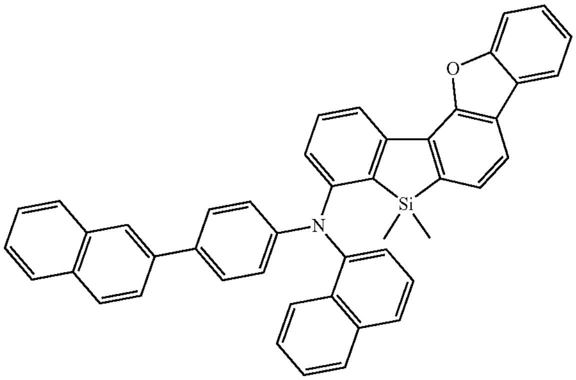
2-175
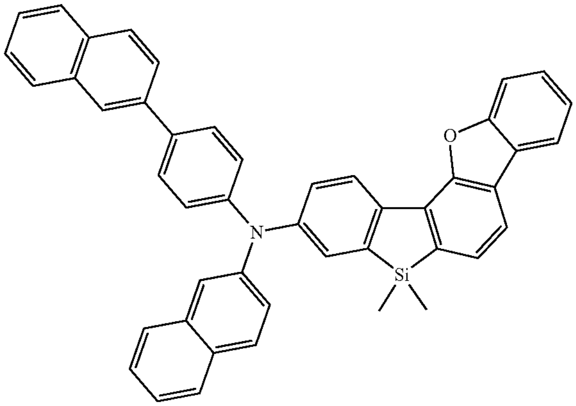
-continued
2-176
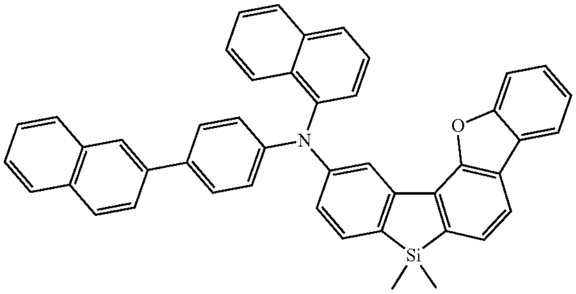
2-177
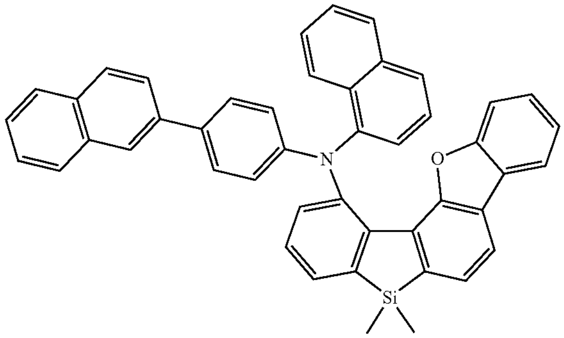
2-178
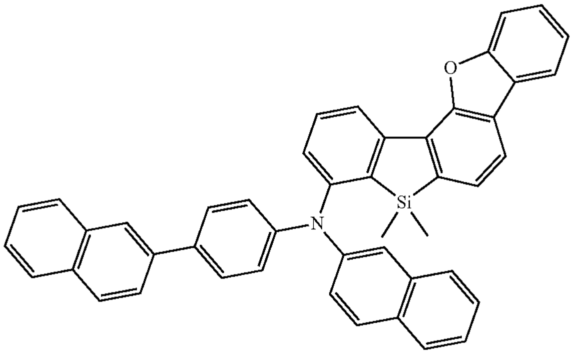
2-179
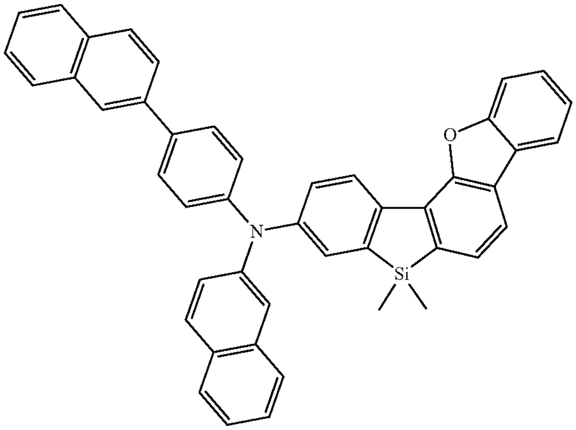

-continued
2-180
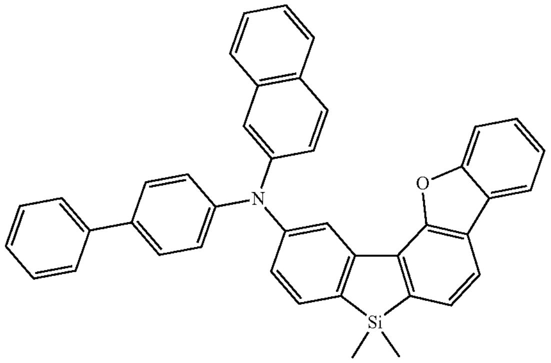
2-181
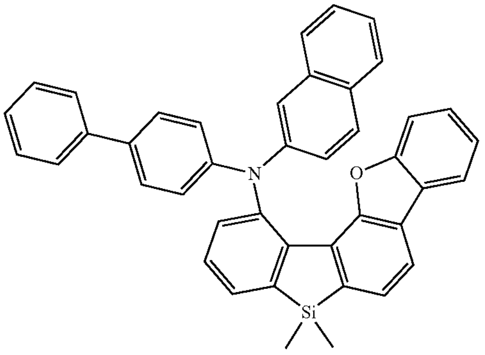
2-182
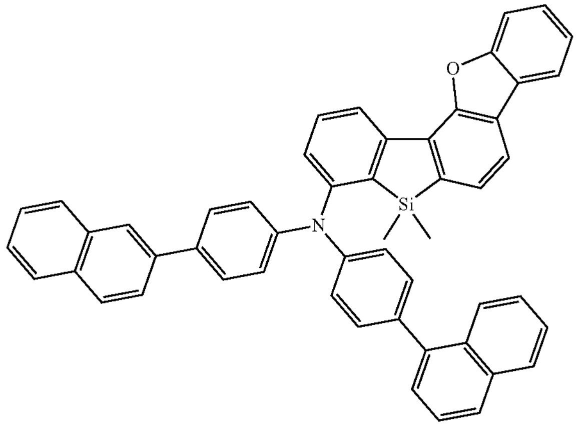
-continued
2-183
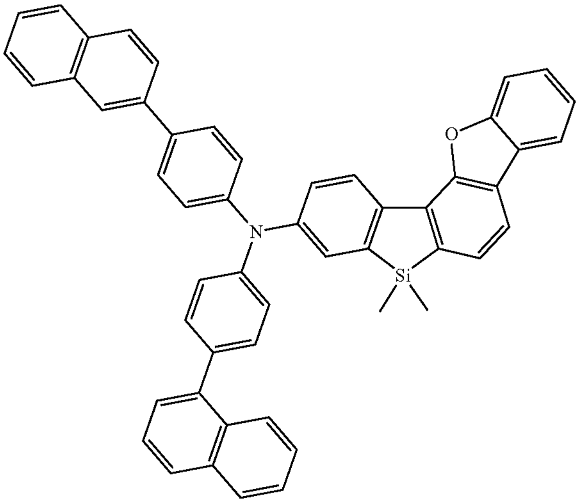
2-184
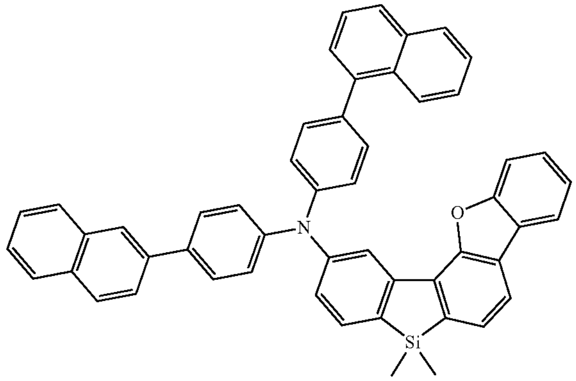
2-185
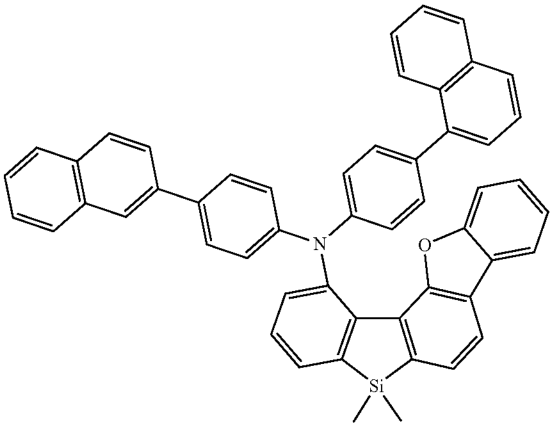

2-186
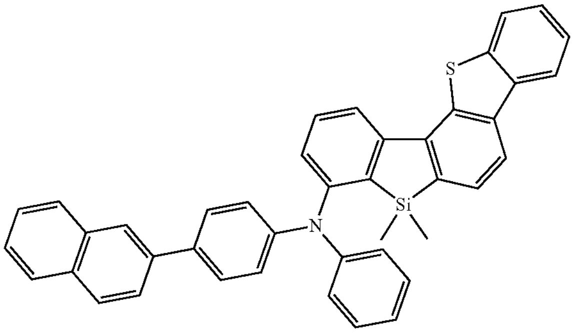
2-187
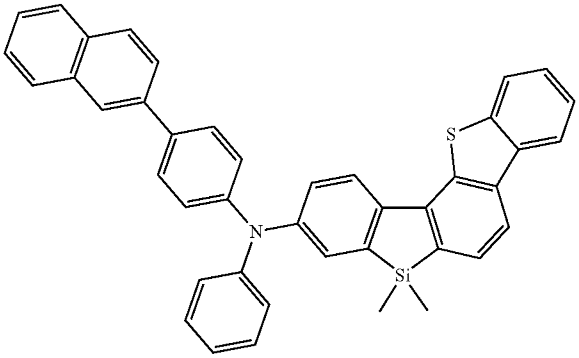
2-188
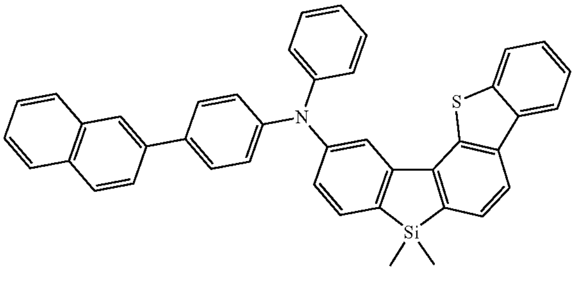
2-189
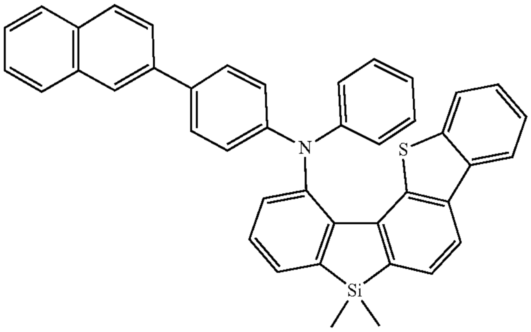
2-190
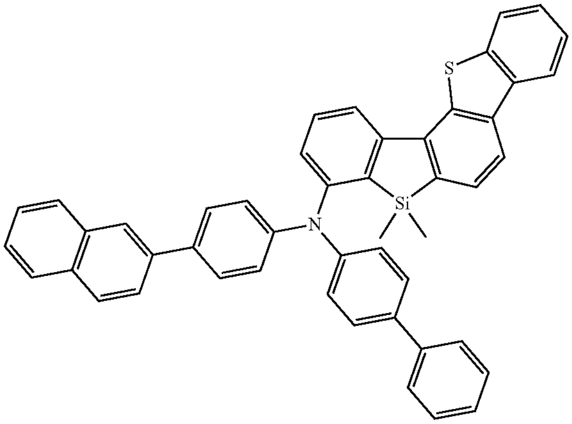
2-191
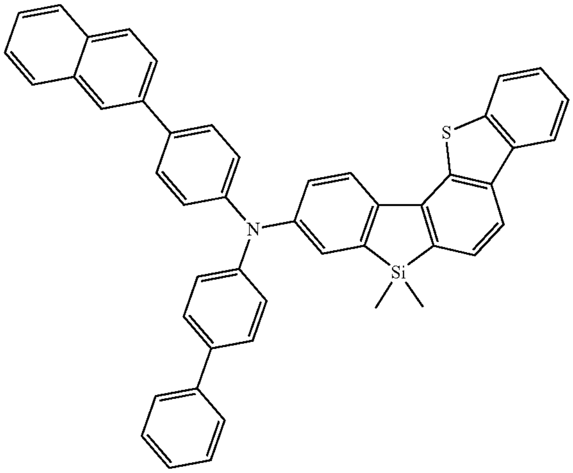
2-192
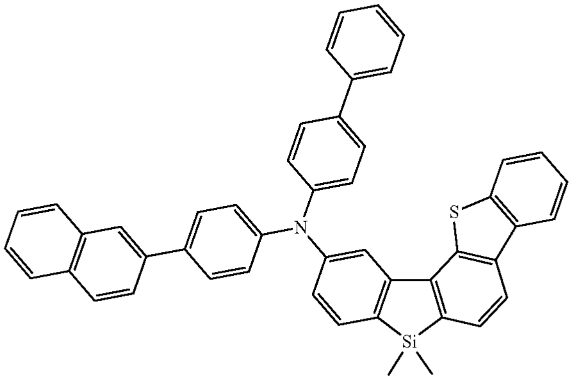

-continued
2-193
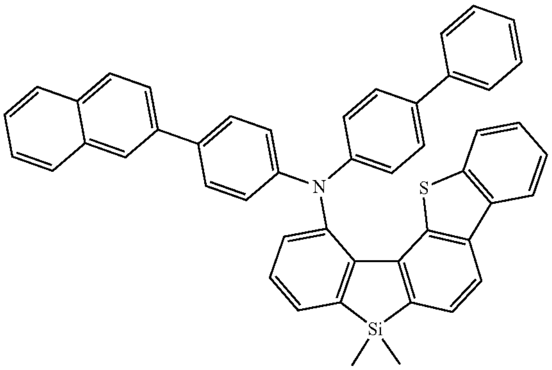
2-194
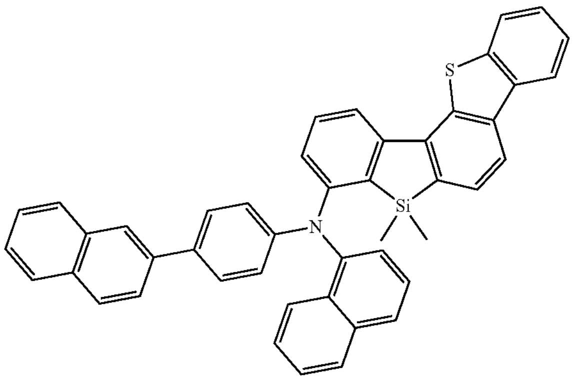
2-195
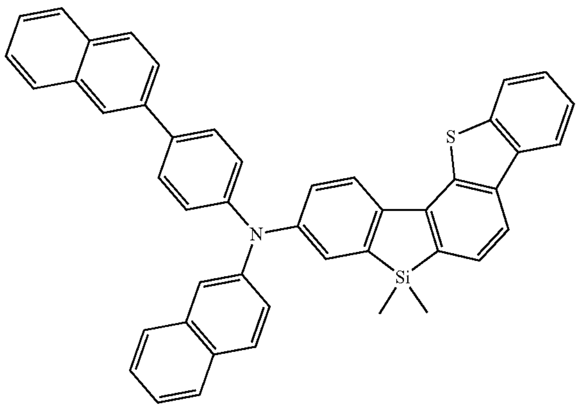
2-196
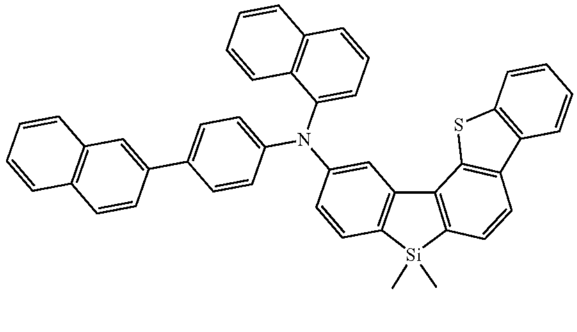
-continued
2-197
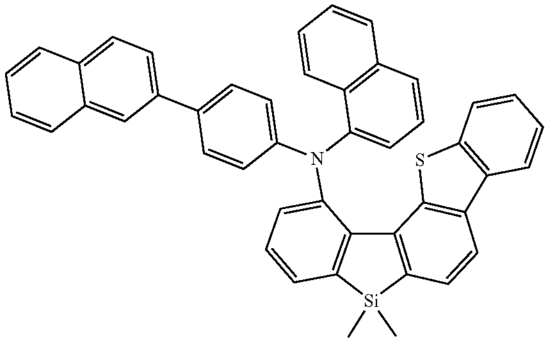
2-198
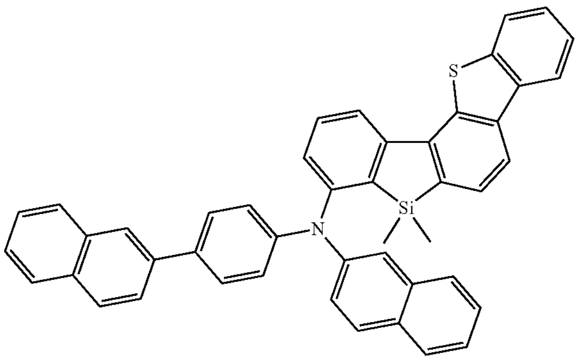
2-199
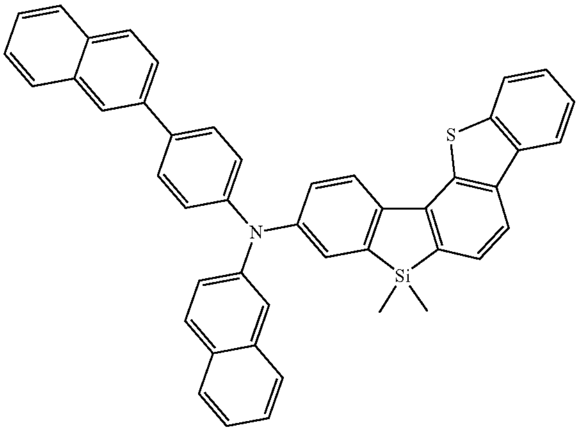
2-200
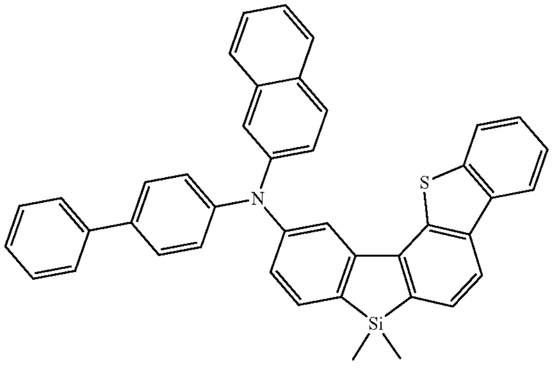

-continued
2-201
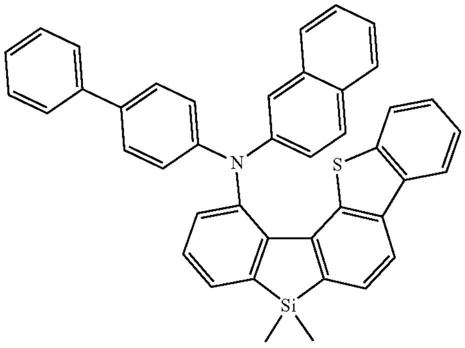
2-202
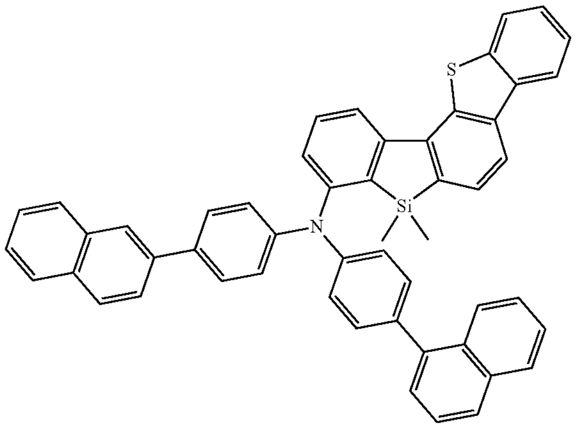
2-203
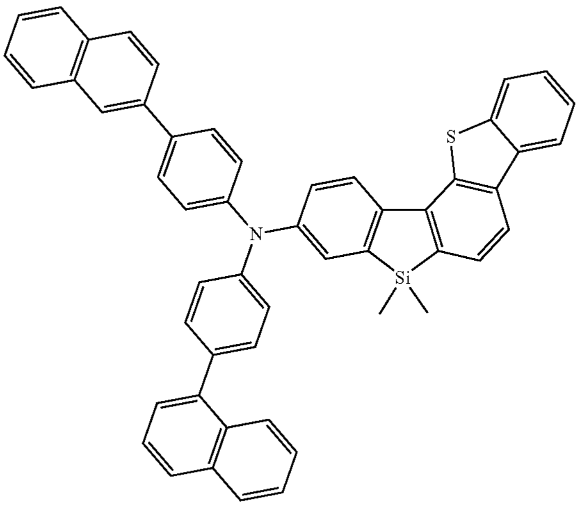
-continued
2-204
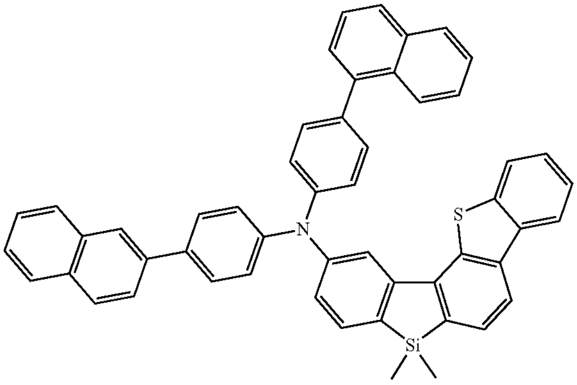
2-205
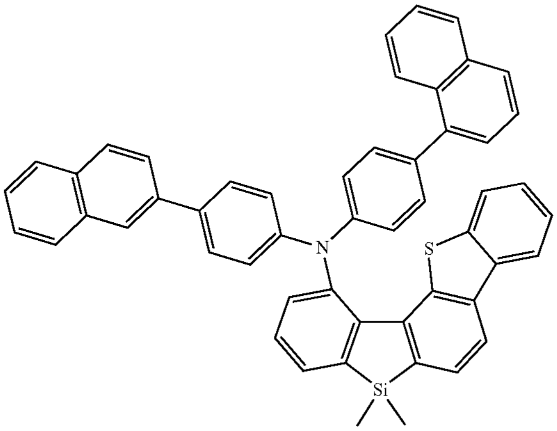
2-206
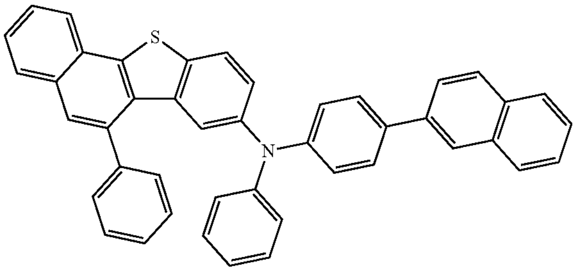
2-207
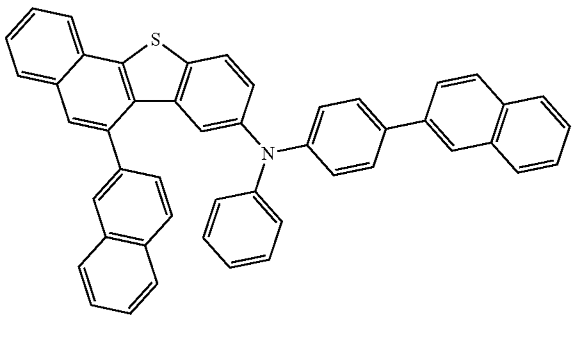

-continued
2-208
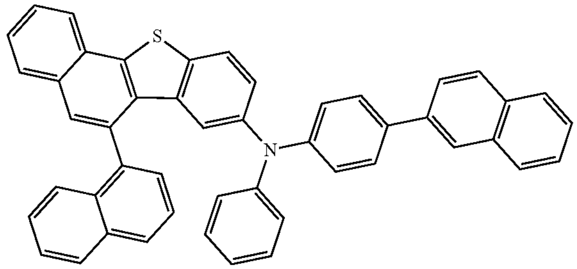
2-209
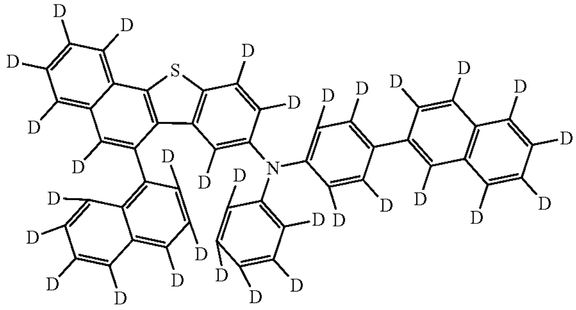
2-210
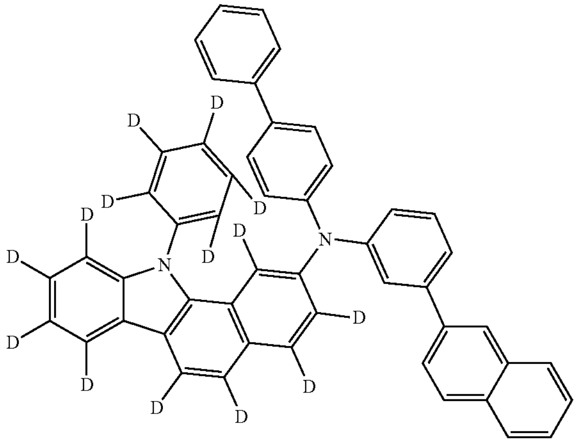
2-211
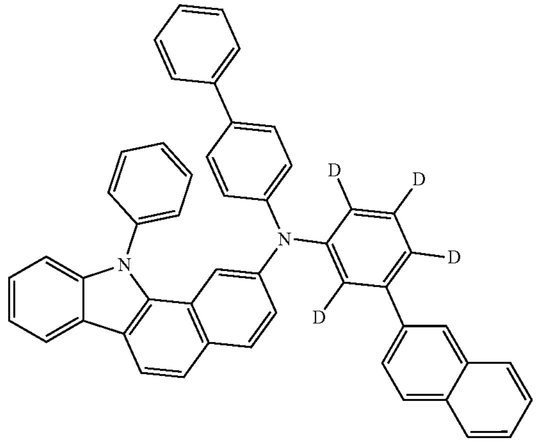
-continued
2-212
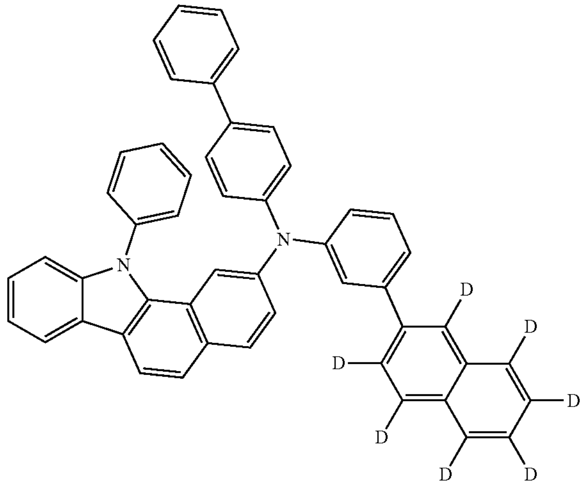
2-213
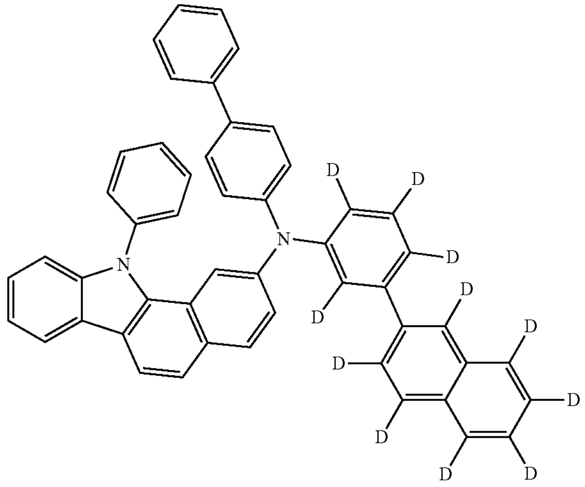
2-214
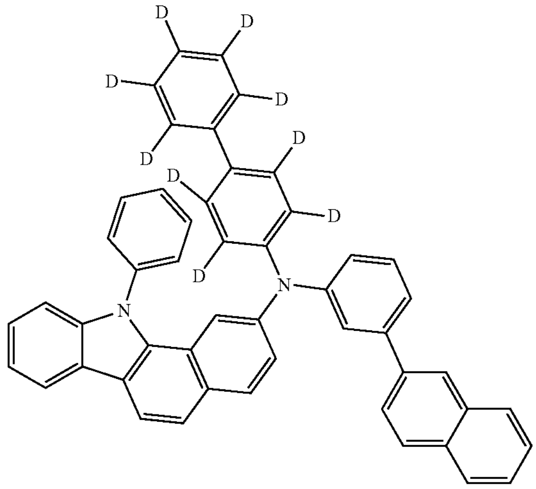

2-215
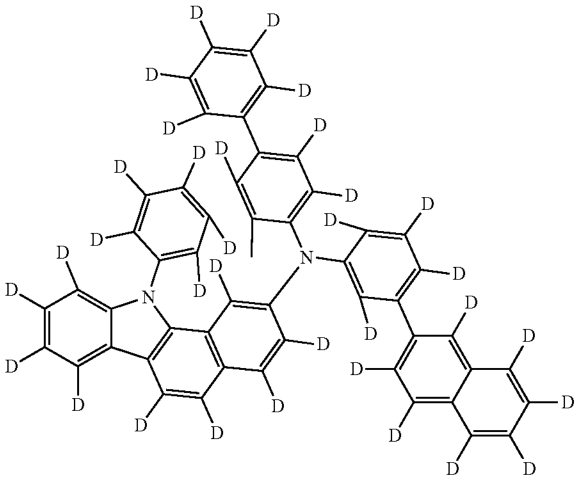
2-216
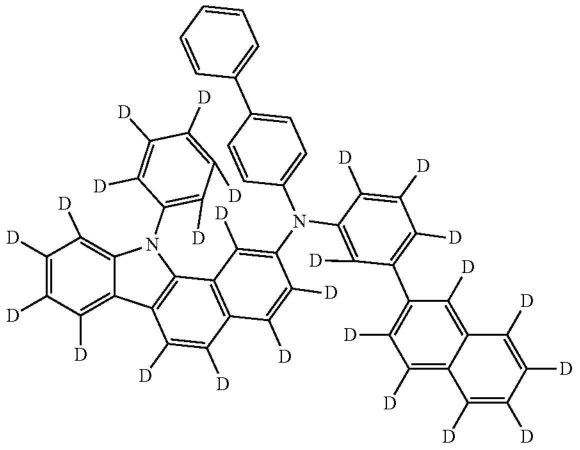
2-217
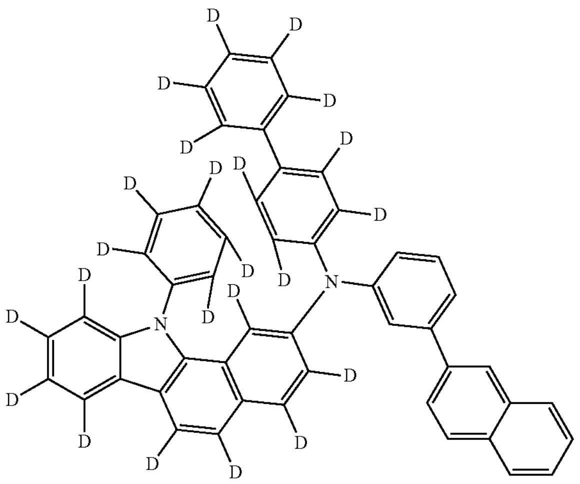
2-218
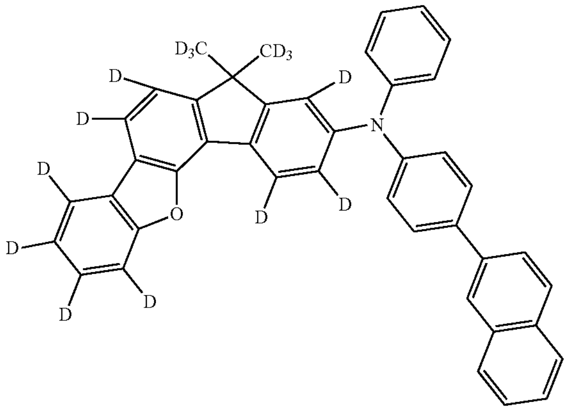
2-219
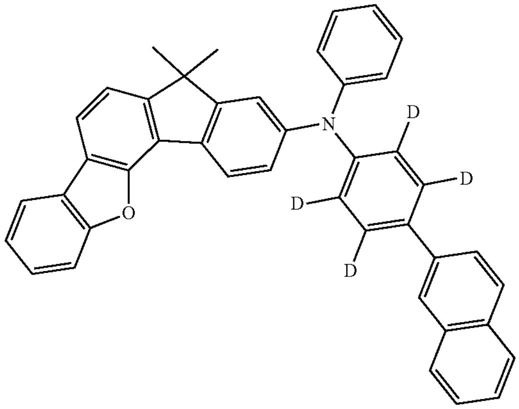
2-220
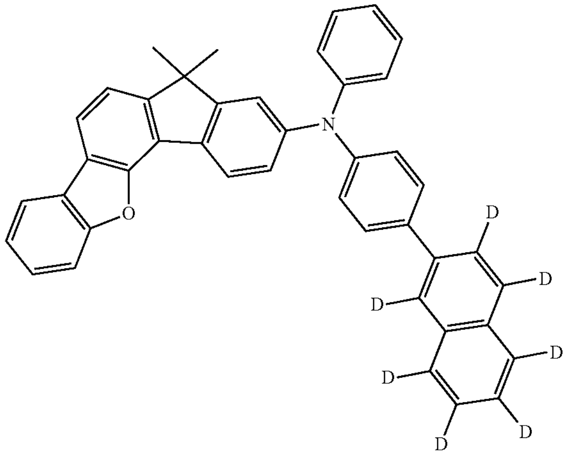

-continued 2-221

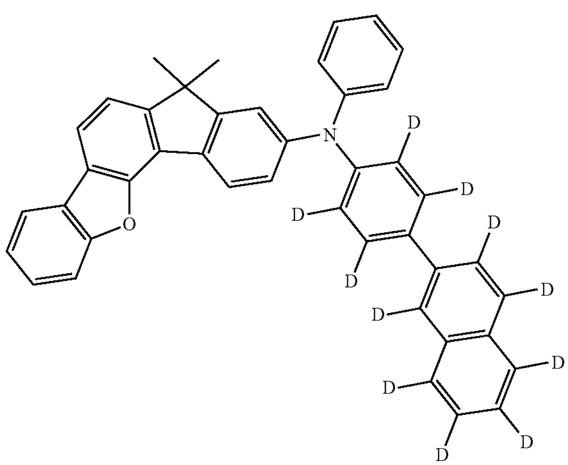

2-222

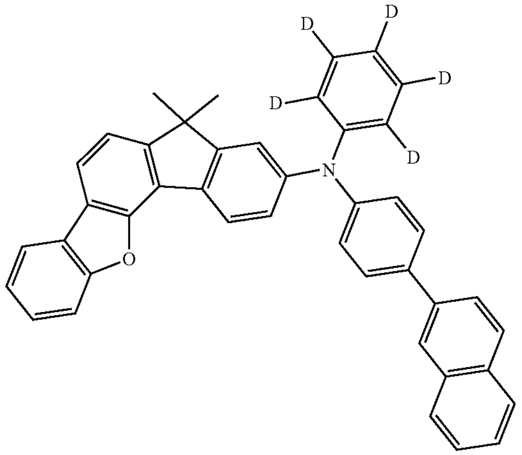

2-223

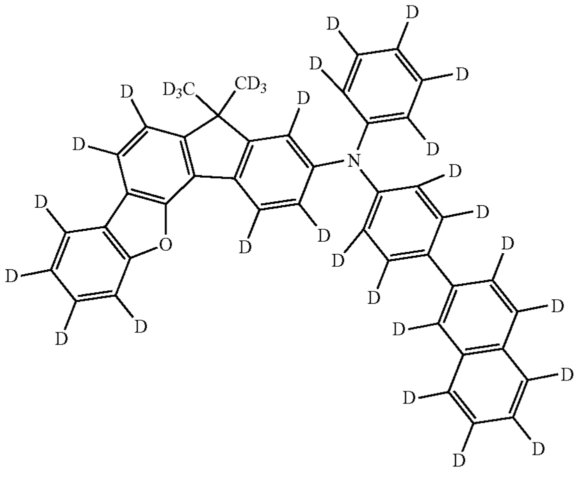

The first compound and the second compound may be included (e.g., mixed) in a weight ratio of, e.g., about 1:99 to about 99:1. Within the above range, bipolar characteristics may be implemented by adjusting an appropriate weight ratio using the electron transport capability of the first compound and the hole transport capability of the second compound, so that efficiency and life-span may be improved. Within the above range, the first compound and the second compound may be for example, included in a weight ratio of about 10:90 to about 90:10, about 20:80 to about 80:20, for example about 20:80 to about 70:30, about 20:80 to about 60:40, or about 30:70 to about 60:40. In an implementation, they may be included in a weight ratio of about 40:60, about 50:50, or about 60:40.

The composition for an organic optoelectronic device according to an embodiment may include, e.g., the compound represented by Chemical Formula 1-I or Chemical Formula 1-V as the first compound and the compound represented by Chemical Formula 2-IVB or Chemical Formula 2-XA as a second compound.

The composition for an organic optoelectronic device according to an embodiment may include, e.g., the compound represented by Chemical Formula 2-IVB-2 or Chemical Formula 2-XA-2 as the second compound.

One or more compounds may be further included in addition to the aforementioned first compound and second compound.

The aforementioned compound for an organic optoelectronic device or composition for an organic optoelectronic device may be a composition further including a dopant.

The dopant may be, e.g., a phosphorescent dopant, such as a red, green, or blue phosphorescent dopant. In an implementation, the dopant may be, e.g., a red or green phosphorescent dopant.

A dopant is a material that emits light by being mixed in a small amount with the compound or composition for an organic optoelectronic device. In general, the dopant may be a material such as a metal complex that emits light by multiple excitation into a triplet or more. The dopant may be, e.g., an inorganic, organic, or organic-inorganic compound, and may include one or two or more.

An example of the dopant may be a phosphorescent dopant, and examples of the phosphorescent dopant may include an organometallic compound including Ir, Pt, Os, Ti, Zr, Hf, Eu, Tb, Tm, Fe, Co, Ni, Ru, Rh, Pd, or a combination thereof. In an implementation, the phosphorescent dopant may be, e.g., a compound represented by Chemical Formula Z.

$L^7MX^5$ [Chemical Formula Z]

In Chemical Formula Z, M may be, e.g., a metal, and $L^7$ and $X^5$ may each independently be, e.g., ligands forming a complex compound with M.

M may be, e.g., Ir, Pt, Os, Ti, Zr, Hf, Eu, Tb, Tm, Fe, Co, Ni, Ru, Rh, Pd, or a combination thereof, and $L^7$ and $X^5$ may be, e.g., a bidentate ligand.

In an implementation, the ligand represented by $L^7$ and $X^5$ may be, e.g., a ligand of Group A.

[Group A]

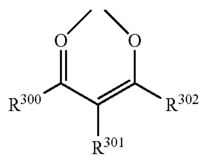

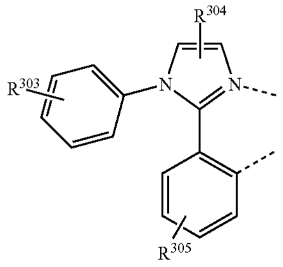

-continued
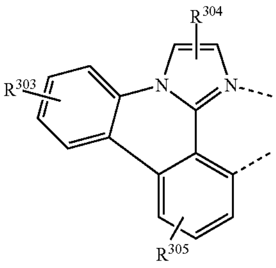
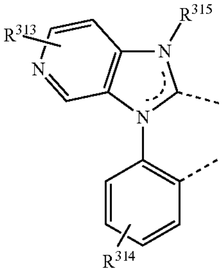
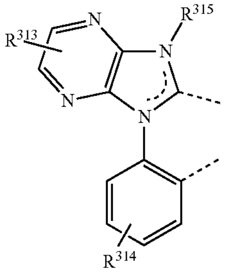
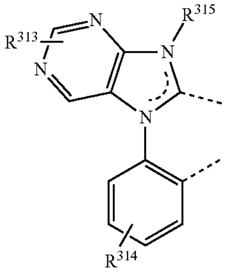
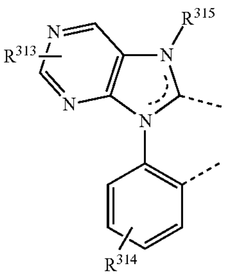
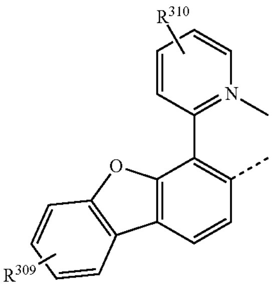
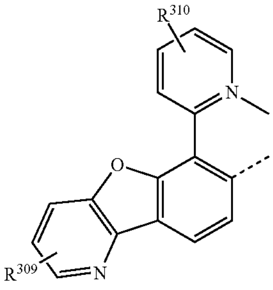
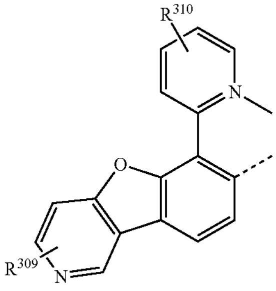
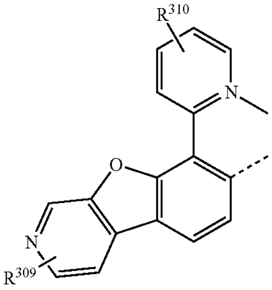
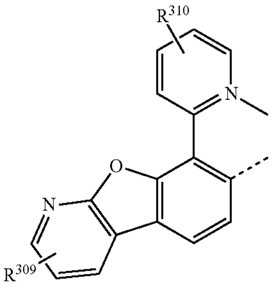
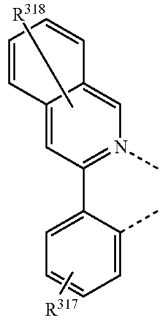
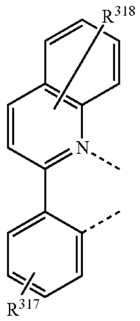
-continued
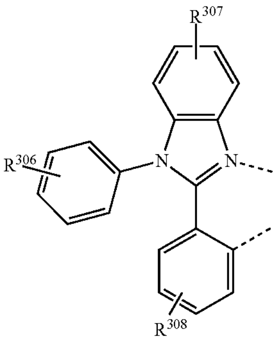
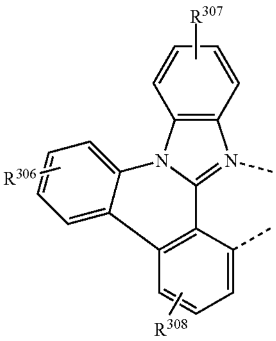
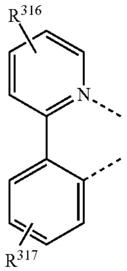
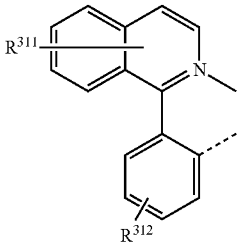
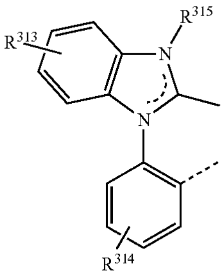
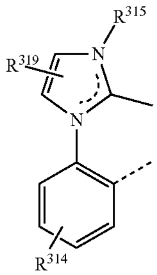
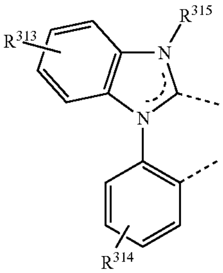
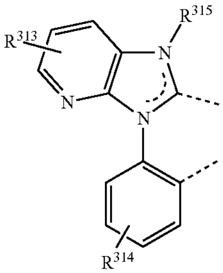
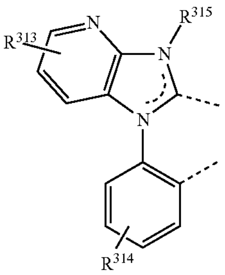
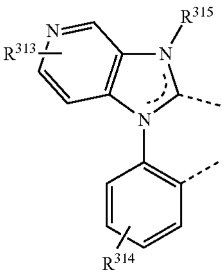
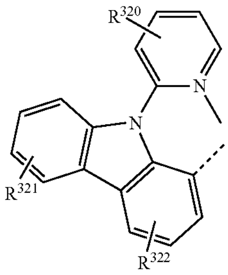
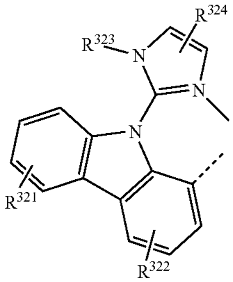

-continued

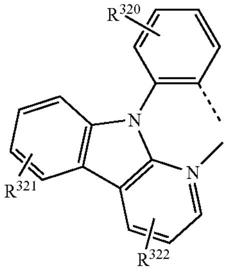

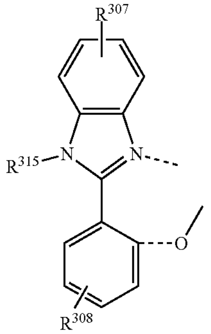

In Group A, $R^{300}$ to $R^{302}$ may each independently be, e.g., hydrogen, deuterium, a C1 to C30 alkyl group substituted or unsubstituted with a halogen, a C6 to C30 aryl group substituted or unsubstituted with a C1 to C30 alkyl group, or a halogen.

$R^{303}$ to $R^{324}$ may each independently be, e.g., hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C2 to C30 alkenyl group, a substituted or unsubstituted C6 to C30 aryl group, a substituted or unsubstituted C1 to C30 heteroaryl group, a substituted or unsubstituted C1 to C30 amino group, a substituted or unsubstituted C6 to C30 arylamino group, SFs, a trialkylsilyl group having a substituted or unsubstituted C1 to C30 alkyl group, a dialkylarylsilyl group having a substituted or unsubstituted C1 to C30 alkyl group and C6 to C30 aryl group, or a triarylsilyl group having a substituted or unsubstituted C6 to C30 aryl group.

In an implementation, the dopant may be represented by Chemical Formula V.

[Chemical Formula V]

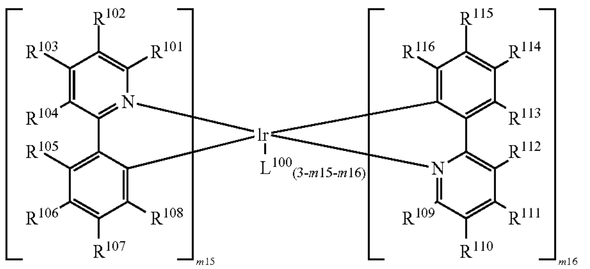

In Chemical Formula V, $R^{101}$ to $R^{116}$ may each independently be, e.g., hydrogen, deuterium, a C1 to C10 alkyl group, substituted or unsubstituted C6 to C30 aryl group, or $SiR^{132}R^{133}R^{134}$.

$R^{132}$ to $R^{134}$ may each independently be, e.g., a substituted or unsubstituted C1 to C6 alkyl group.

In an implementation, at least one of $R^{101}$ to $R^{116}$ may be a functional group represented by Chemical Formula V-1.

$L^{100}$ may be, e.g., bidentate ligand of monovalent anion, or a ligand that coordinates to iridium through a lone pair of electrons on a carbon or heteroatom.

m15 and m16 may each independently be, e.g., an integer of 0 to 3, m15+m16 may be, e.g., an integer of 1 to 3.

[Chemical Formula V-1]

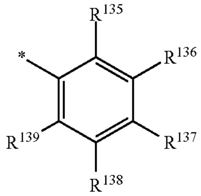

In Chemical Formula V-1, $R^{135}$ to $R^{139}$ may each independently be, e.g., hydrogen, deuterium, a C1 to C10 alkyl group, substituted or unsubstituted C6 to C20 aryl group, or $SiR^{132}R^{133}R^{134}$.

$R^{132}$ to $R^{134}$ may each independently be, e.g., a substituted or unsubstituted C1 to C6 alkyl group.

* indicates a linking point linked to carbon atom.

In an implementation, the dopant may be represented by Chemical Formula Z-1.

[Chemical Formula Z-1]

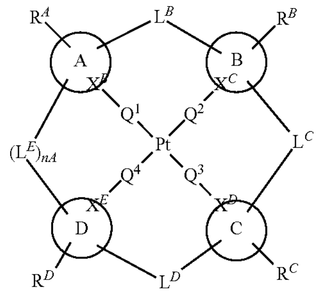

In Chemical Formula Z-1, rings A, B, C, and D may each independently be, e.g., 5- or 6-membered carbocyclic or heterocyclic rings.

$R^A$, $R^B$, $R^C$, and $R^D$ may independently indicate mono-substitution, disubstitution, trisubstitution, or tetrasubstitution, or unsubstitution.

$L^B$, $L^C$, and $L^D$ may each independently be, e.g., a direct bond, BR, NR, PR, O, S, Se, C═O, S═O, $SO_2$, CRR', SiRR', GeRR', or a combination thereof.

In an implementation, when nA is 1, $L^E$ may be, e.g., a direct bond, BR, NR, PR, O, S, Se, C═O, S═O, $SO_2$, CRR', SiRR', GeRR', or a combination thereof, and when nA is 0, $L^E$ is not present;

$R^A$, $R^B$, $R^C$, $R^D$, R, and R' may each independently be, e.g., hydrogen, deuterium, a halogen, an alkyl group, a cycloalkyl group, a heteroalkyl group, an arylalkyl group, an alkoxy group, an aryloxy group, an amino group, a silyl group, an alkenyl group, a cycloalkenyl group, a heteroalkenyl group, an alkynyl group, an aryl group, a heteroaryl group, an acyl group, a carbonyl group, a carboxylic acid group, an ester group, a nitrile group, an isonitrile group, a sulfanyl group, a sulfinyl group, a sulfonyl group, a phosphino group, or a combination thereof. In an implementation, adjacent groups of $R^A$, $R^B$, $R^C$, $R^D$, R, and R' may be arbitrarily linked with each other to form a ring; $X^B$, $X^C$, $X^D$, and $X^E$ may each independently be, e.g., carbon or nitrogen; and $Q^1$, $Q^2$, $Q^3$, and $Q^4$ may each independently be, e.g., oxygen or a direct bond.

In an implementation, the composition for the organic optoelectronic device according to an embodiment may include a dopant represented by Chemical Formula VI.

[Chemical Formula VI]

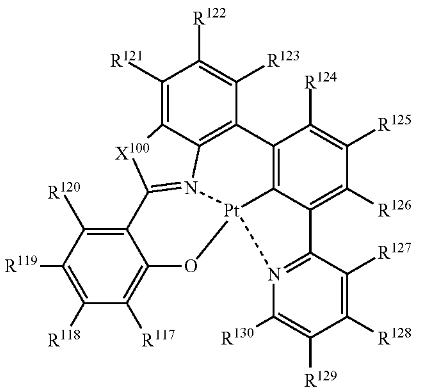

In Chemical Formula VI, $X^{100}$ may be, e.g., O, S, or $NR^{131}$.

$R^{101}$ to $R^{131}$ may each independently be, e.g., hydrogen, deuterium, a substituted or unsubstituted C1 to C10 alkyl group, a substituted or unsubstituted C6 to C20 aryl group, or $—SiR^{132}R^{133}R^{134}$.

$R^{132}$ to $R^{134}$ may each independently be, e.g., C1 to C6 alkyl group.

In an implementation, at least one of $R^{117}$ to $R^{131}$ may be, e.g., $—SiR^{132}R^{133}R^{134}$ or tert-butyl group.

Hereinafter, an organic optoelectronic device including the aforementioned compound for an organic optoelectronic device or composition for an organic optoelectronic device is described.

The organic optoelectronic device may be a suitable device to convert electrical energy into photoenergy and vice versa without particular limitation, and may be, e.g., an organic photoelectric device, an organic light emitting diode, an organic solar cell, or an organic photoconductor drum.

Herein, an organic light emitting diode as one example of an organic optoelectronic device is described referring to drawings.

The FIGURE is a cross-sectional view of an organic light emitting diode according to an embodiment.

Referring to the FIGURE, an organic light emitting diode 100 according to an embodiment may include an anode 120 and a cathode 110 facing each other and an organic layer 105 between the anode 120 and cathode 110.

The anode 120 may be made of a conductor having a large work function to help hole injection, and may be, e.g., a metal, a metal oxide, or a conductive polymer. The anode 120 may be, e.g., a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), or the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, or polyaniline.

The cathode 110 may be made of a conductor having a small work function to help electron injection, and may be, e.g., a metal, a metal oxide, or a conductive polymer. The cathode 110 may be, e.g., a metal such as magnesium, calcium, sodium, potassium, titanium, indium, yttrium, lithium, gadolinium, aluminum silver, tin, lead, cesium, barium, or the like, or an alloy thereof; a multi-layer structure material such as LiF/Al, $LiO_2$/Al, LiF/Ca, LiF/Al, or $BaF_2$/Ca.

The organic layer 105 may include the aforementioned compound for an organic optoelectronic device or composition for an organic optoelectronic device.

The organic layer 105 may include, e.g., the light emitting layer 130, and the light emitting layer 130 may include, e.g., the aforementioned compound for an organic optoelectronic device or composition for an organic optoelectronic device.

The composition for an organic optoelectronic device further including a dopant may be, e.g., a green light-emitting composition.

The light emitting layer 130 may include, e.g., the aforementioned compound for an organic optoelectronic device or composition for an organic optoelectronic device as a phosphorescent host, respectively.

The organic layer may further include a charge transport region in addition to the light emitting layer.

The charge transport region may be, e.g., the hole transport region 140.

The hole transport region 140 may further increase hole injection or hole mobility between the anode 120 and the light emitting layer 130 and block electrons.

In an implementation, the hole transport region 140 may include a hole transport layer between the anode 120 and the light emitting layer 130 and a hole transport auxiliary layer between the light emitting layer 130 and the hole transport layer, and at least one of compounds of Group B may be included in at least one of the hole transport layer and the hole transport auxiliary layer.

[Group B]

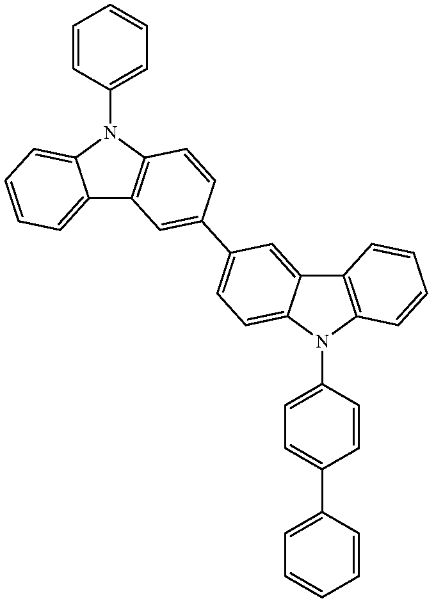

-continued
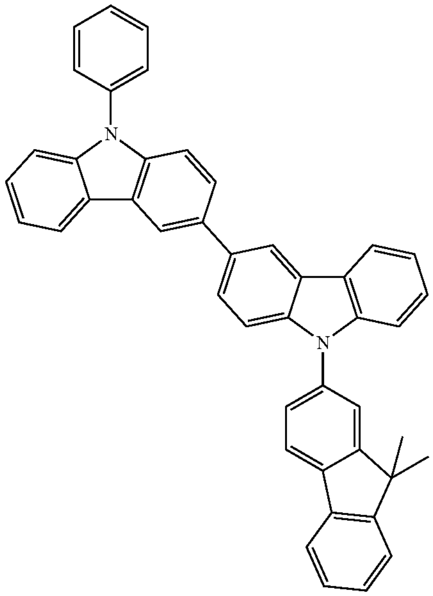
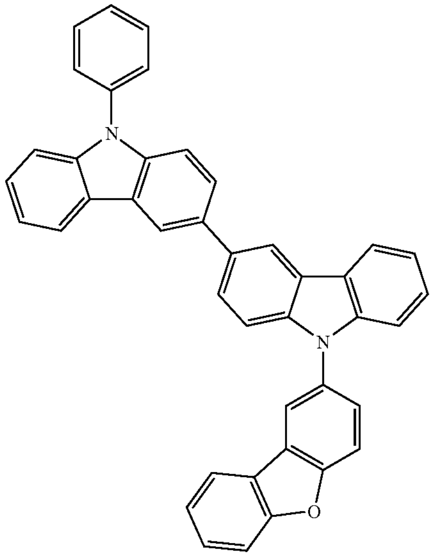
-continued
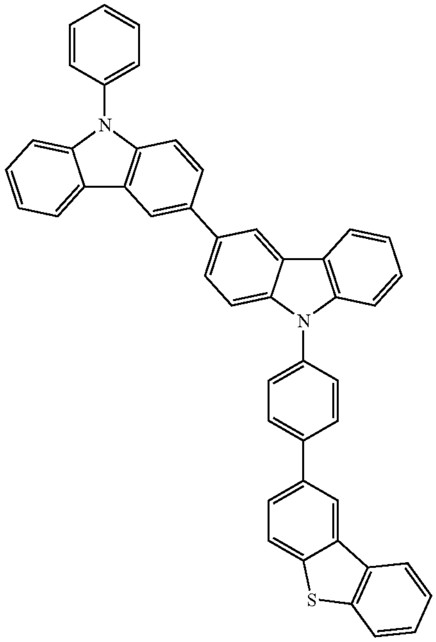
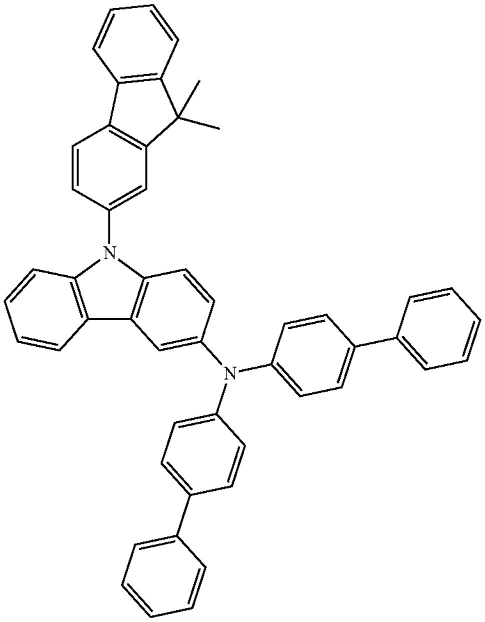

-continued
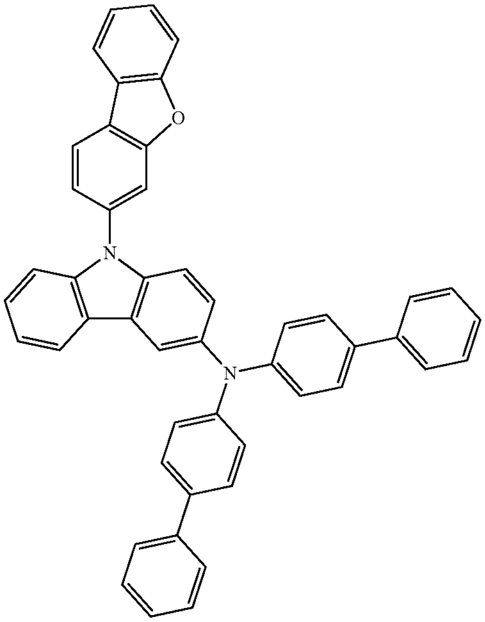
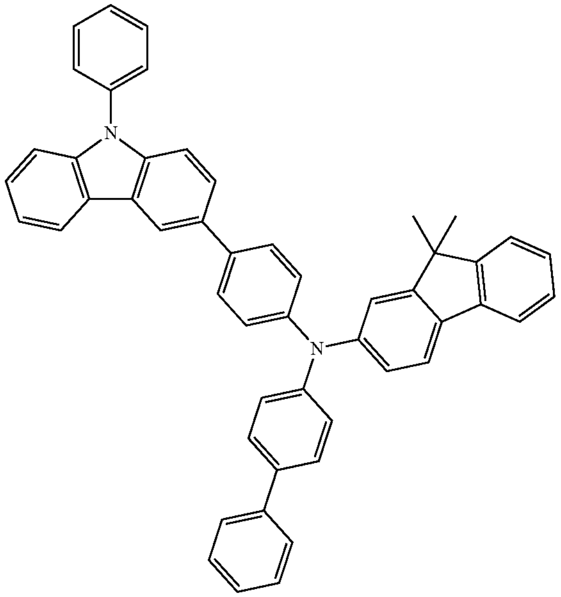
-continued
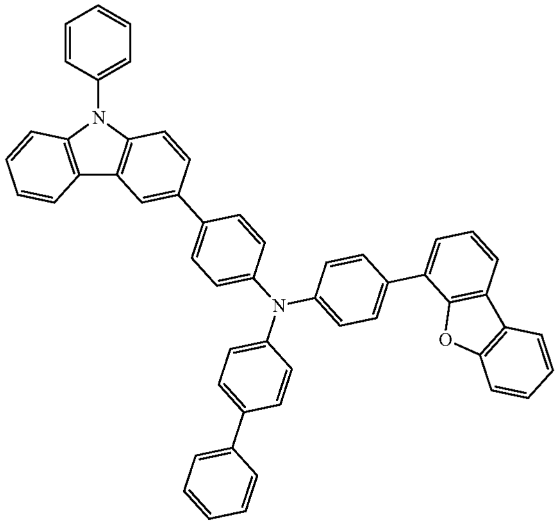
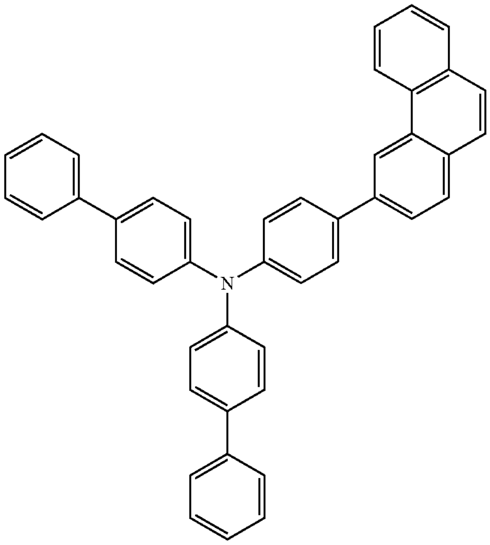
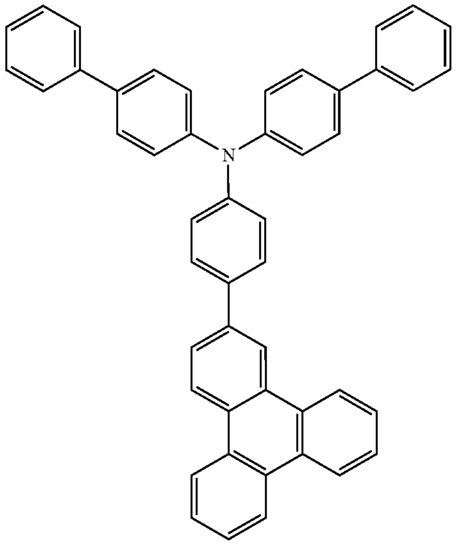

-continued
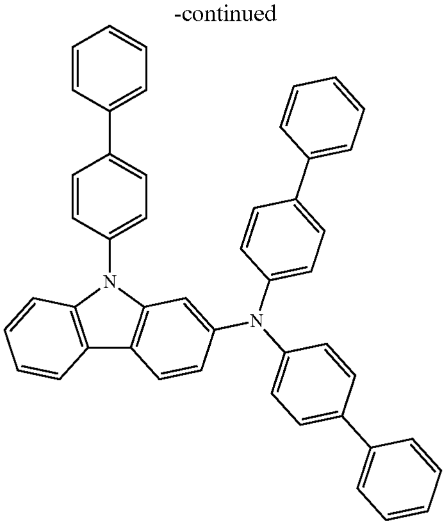
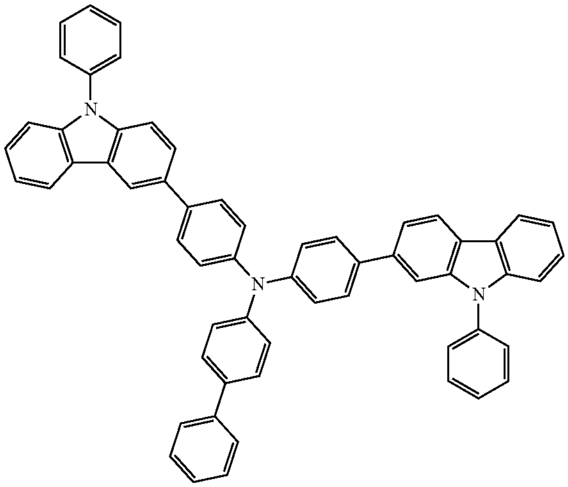
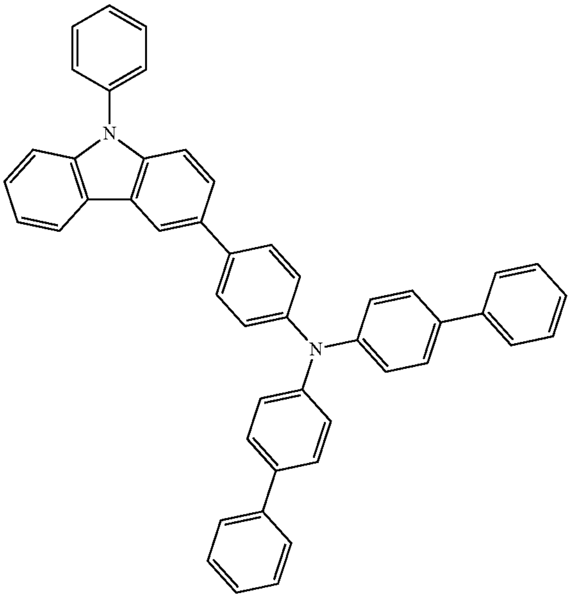
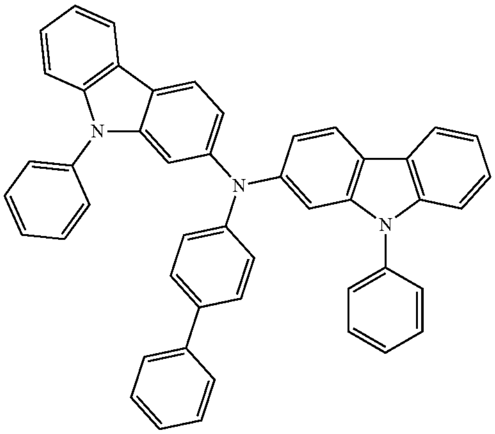
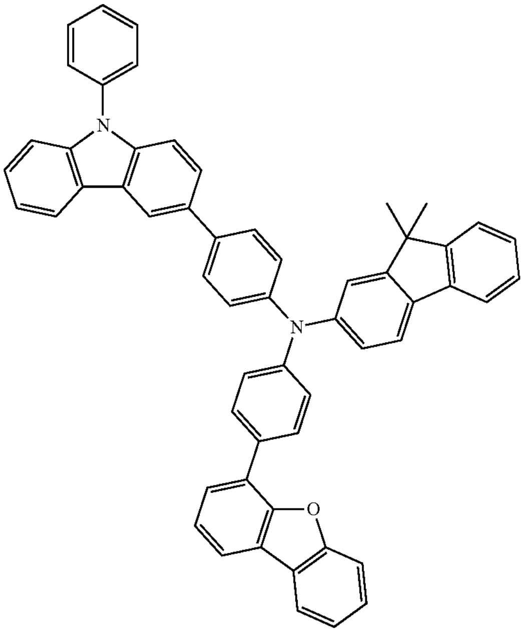
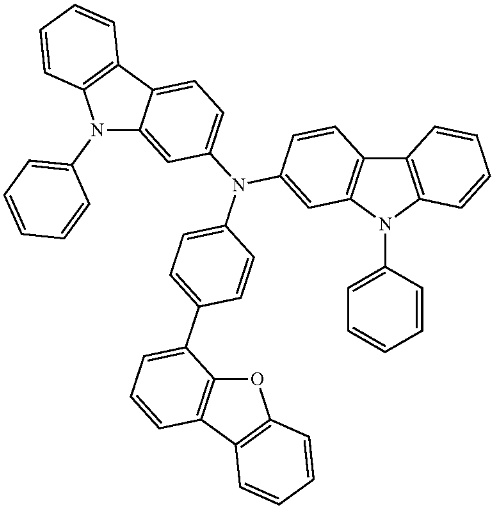
-continued -continued
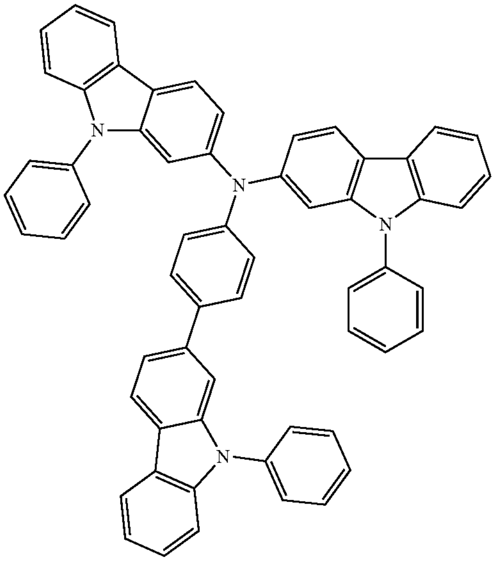
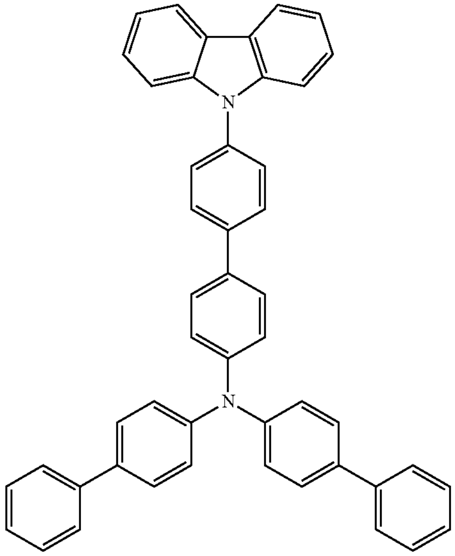
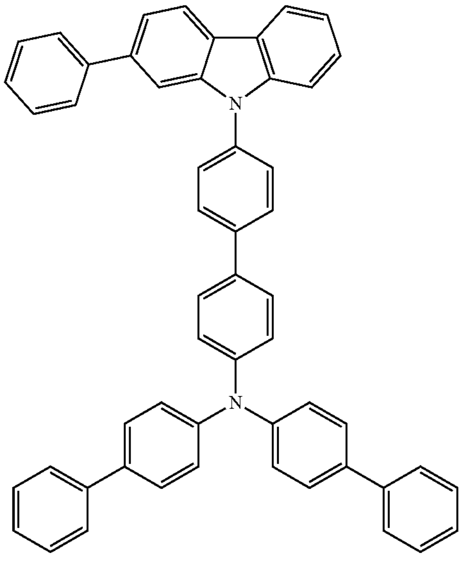
-continued
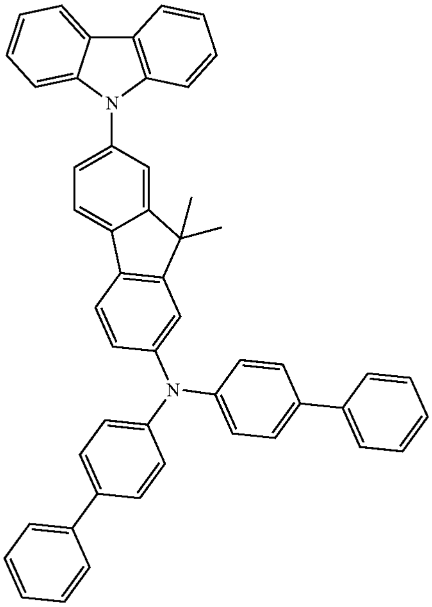
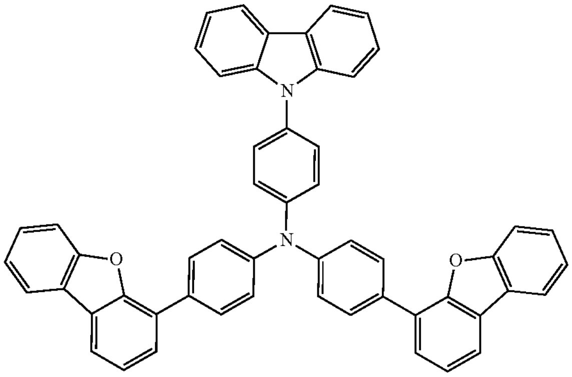
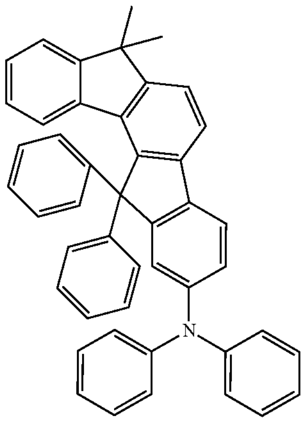

-continued
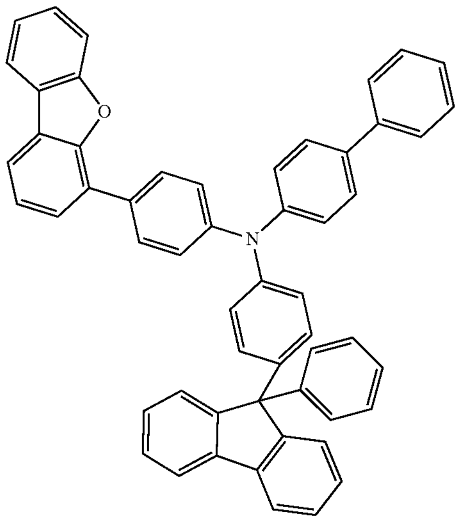
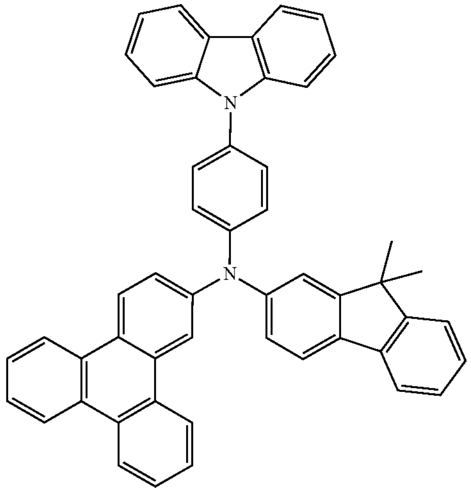
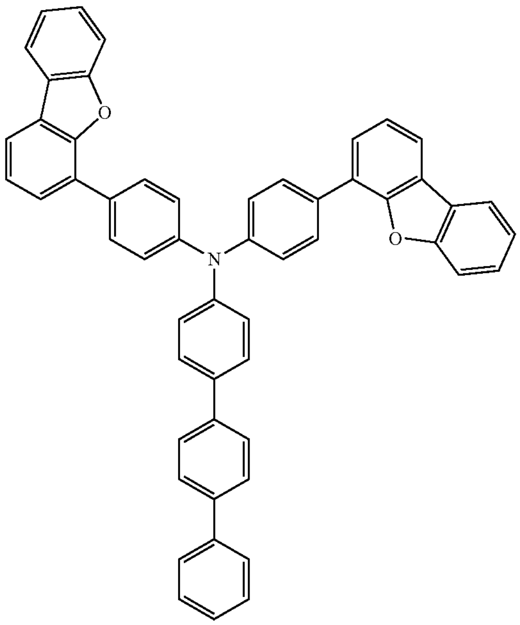
-continued
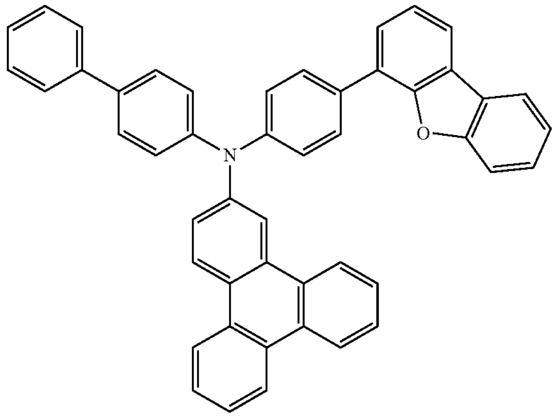
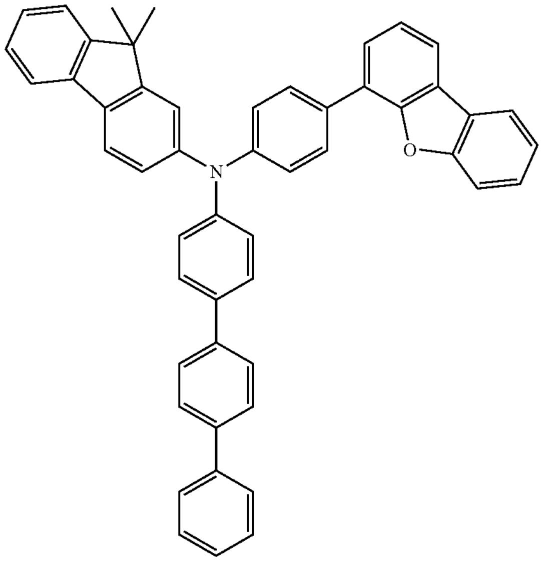
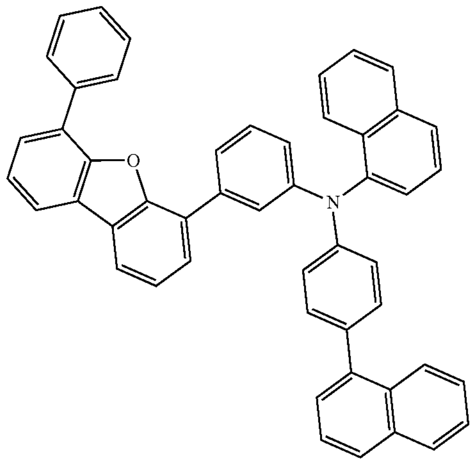

-continued
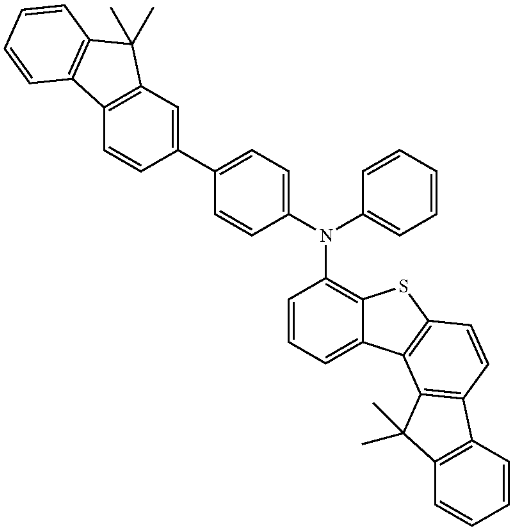
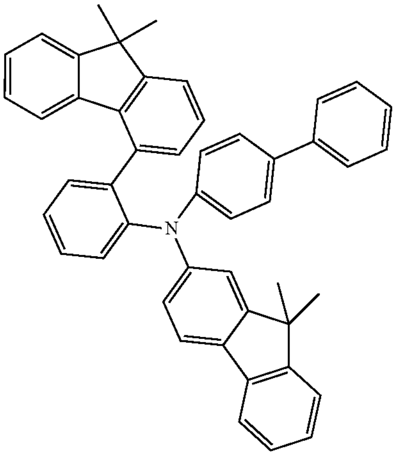
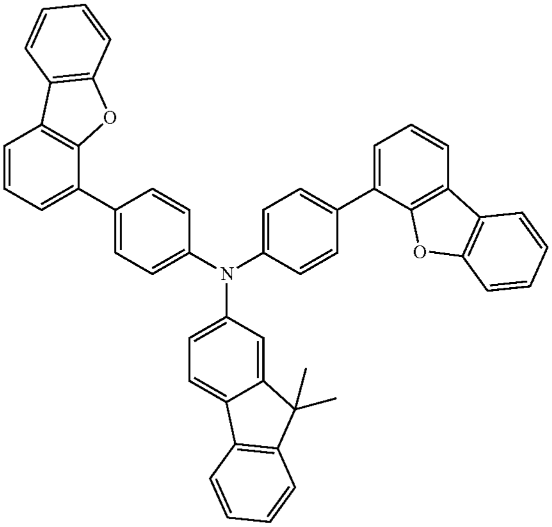
-continued
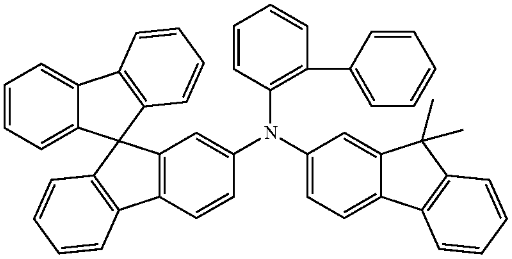
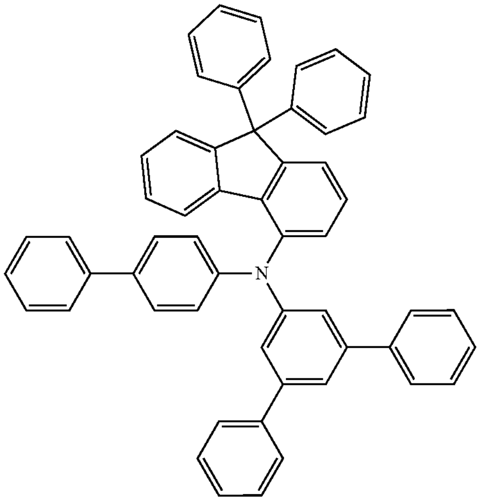
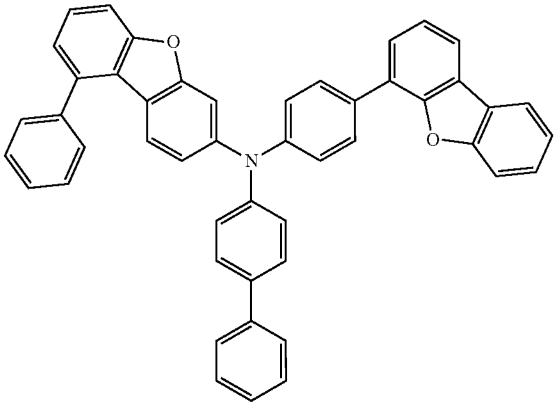
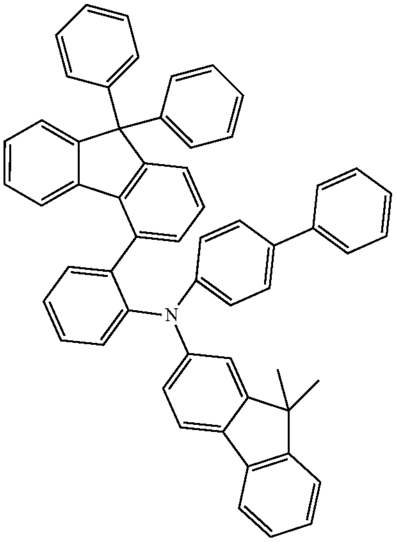

-continued
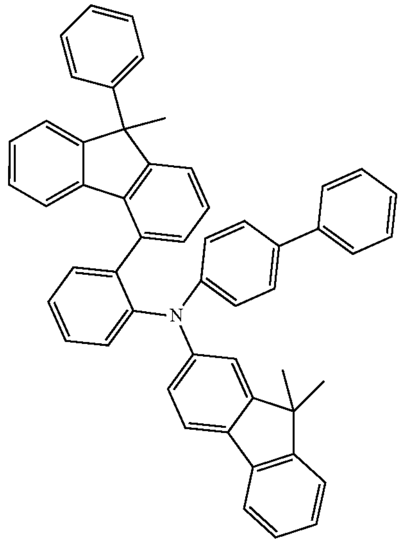
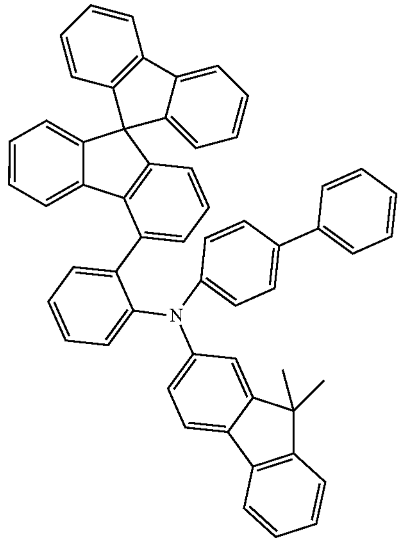
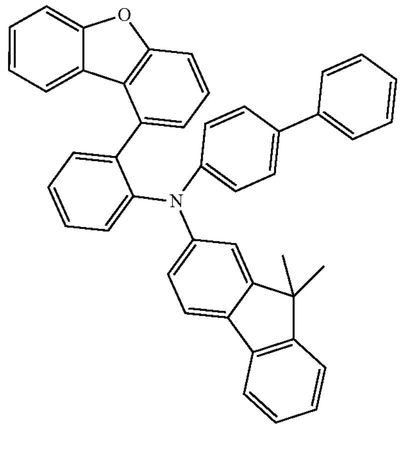
-continued
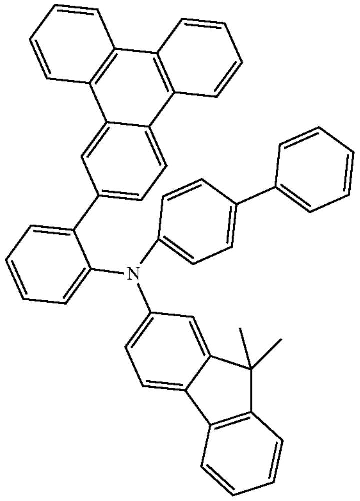
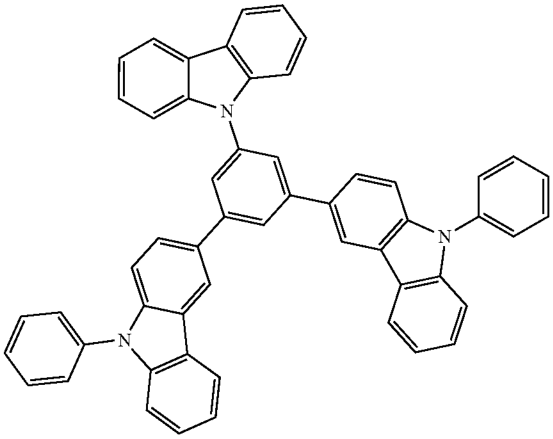
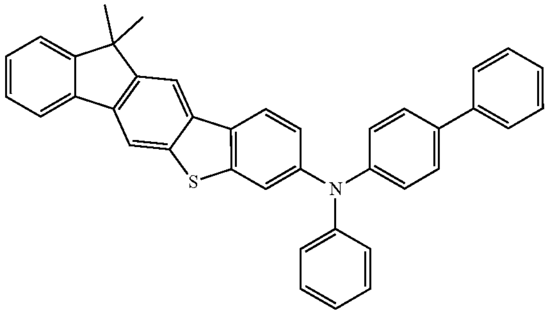

-continued
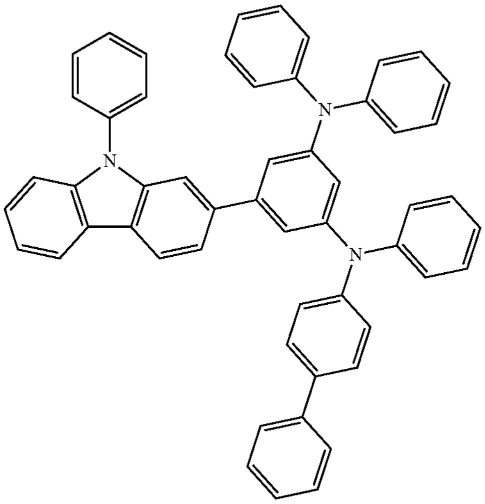
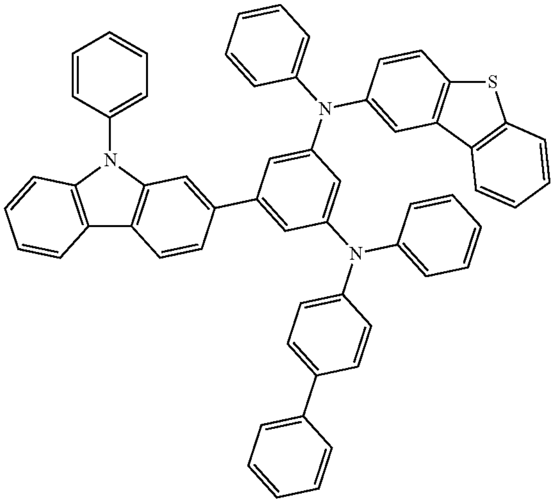
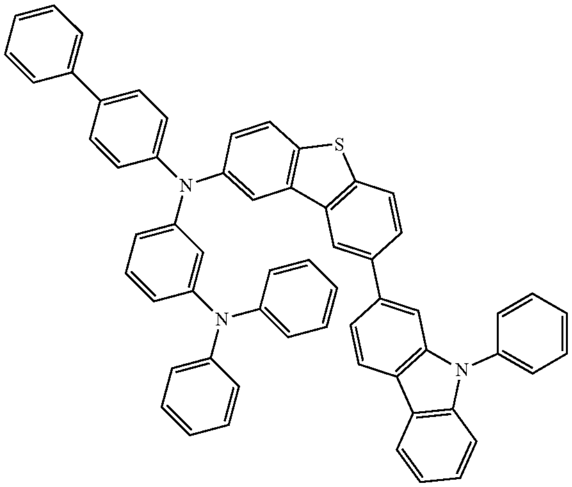
-continued
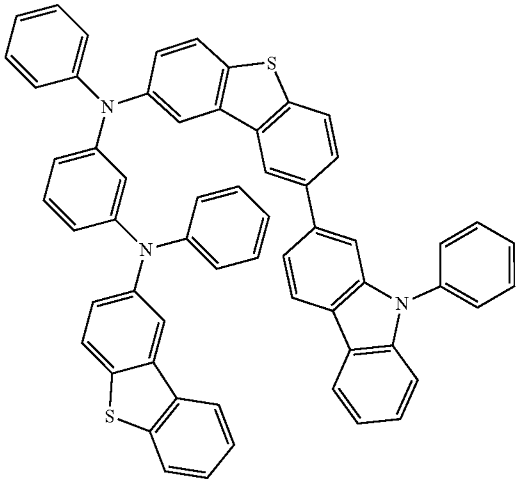
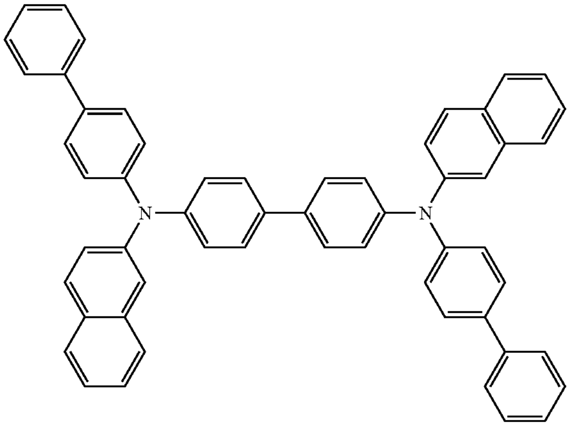
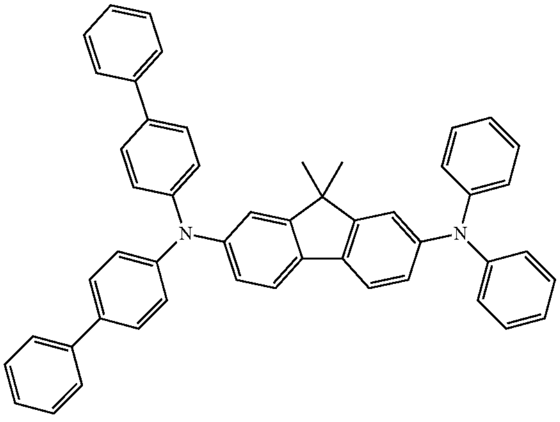

-continued
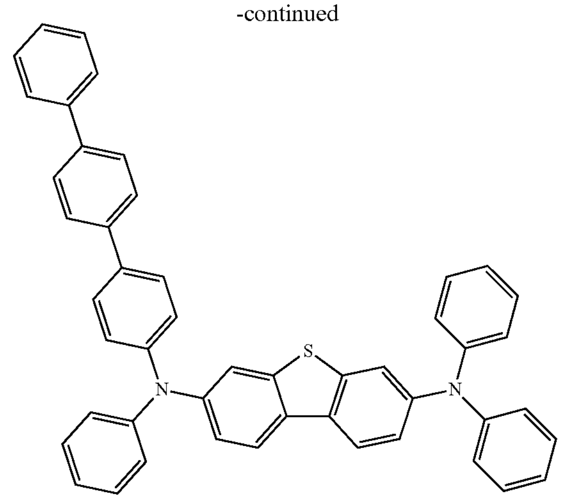
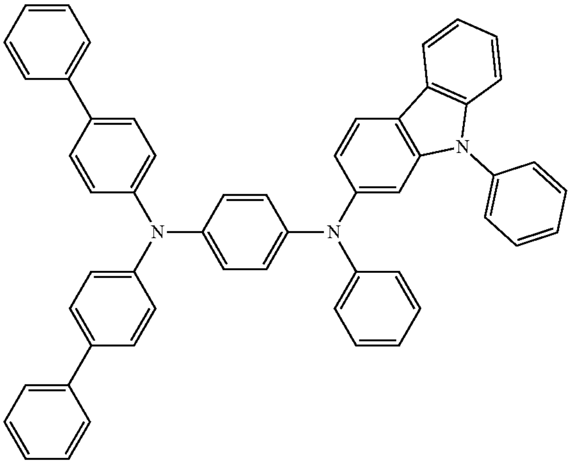
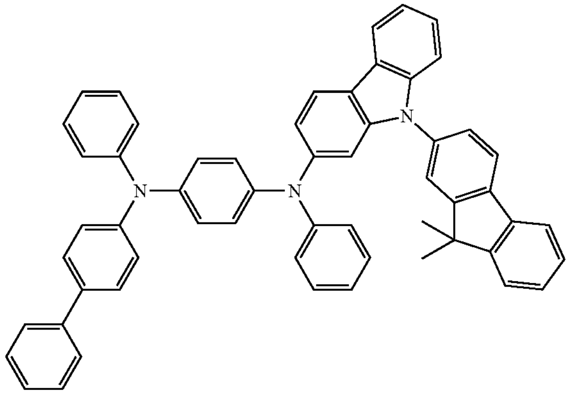
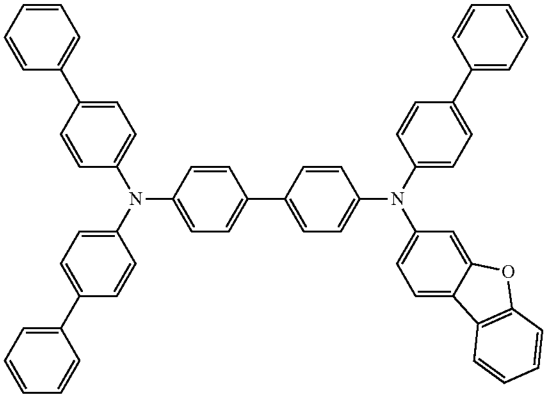
-continued
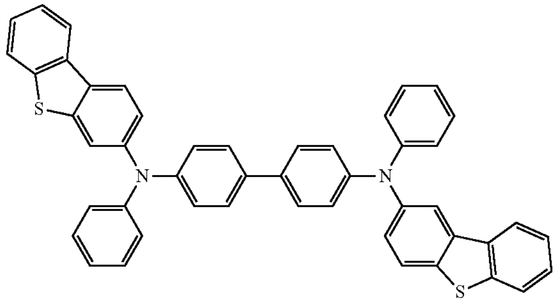
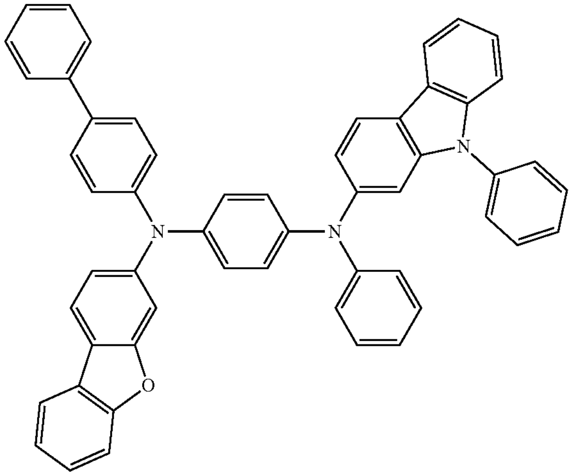
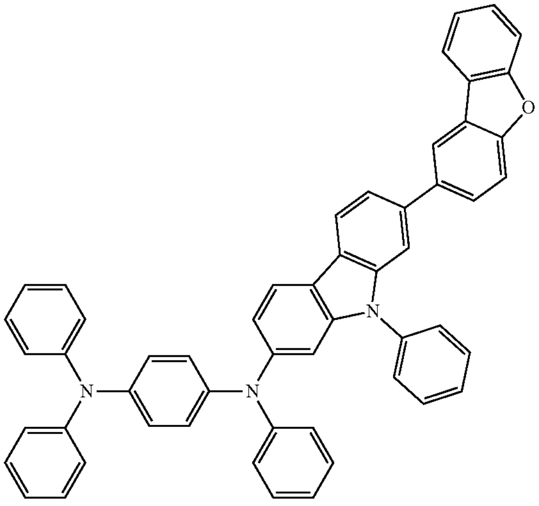

-continued
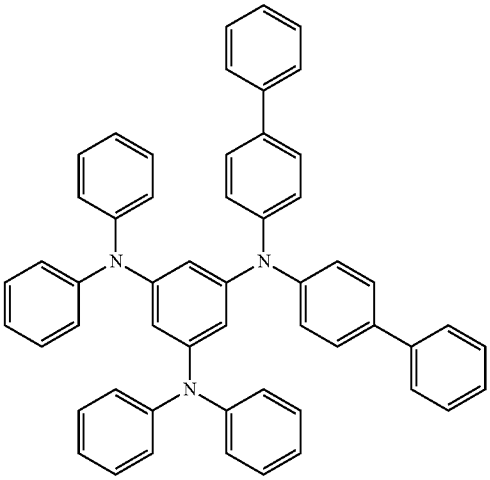
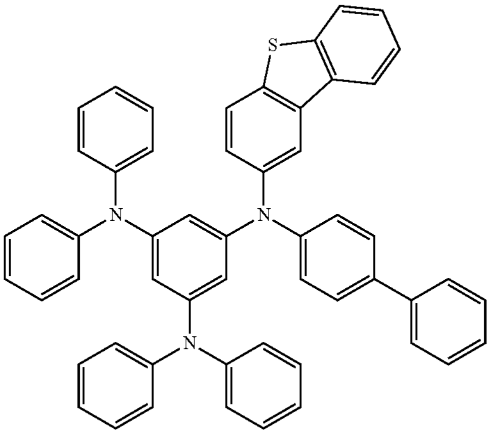
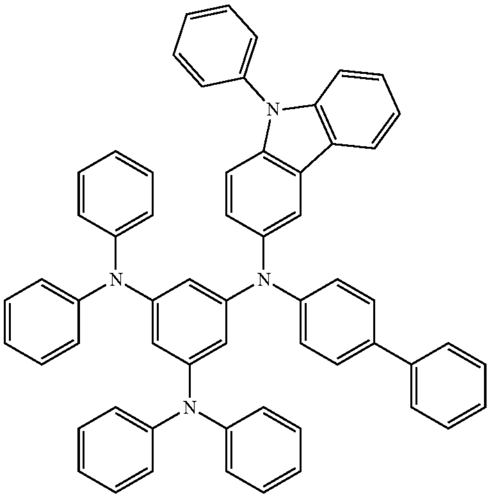
-continued
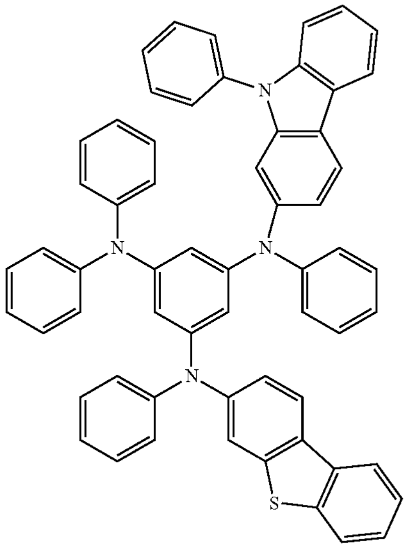
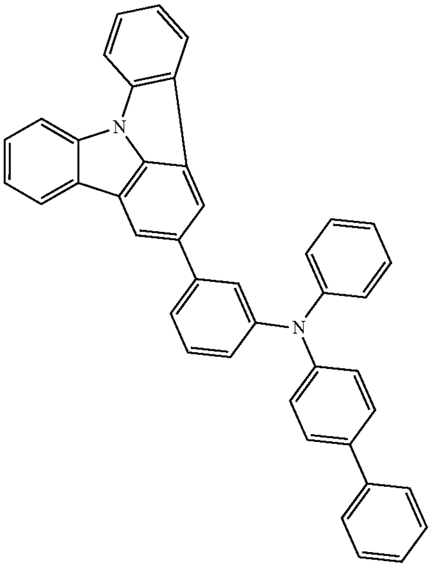
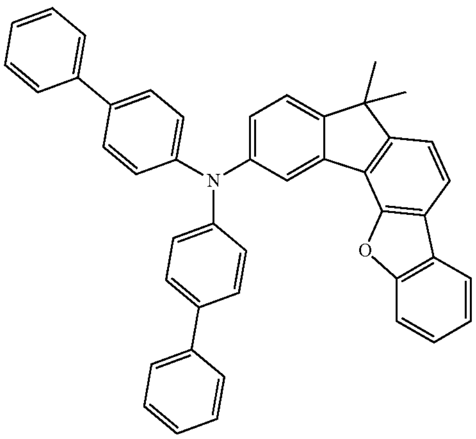

-continued
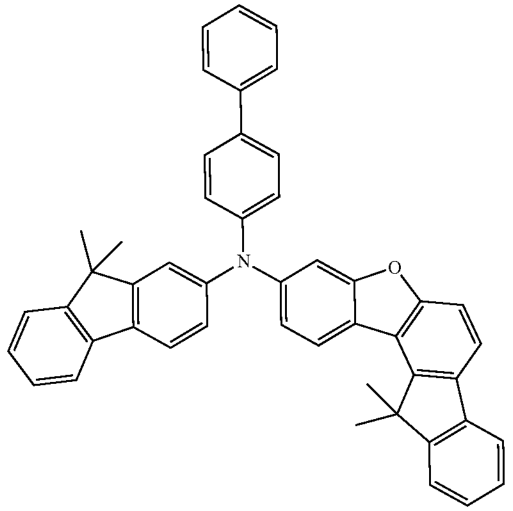
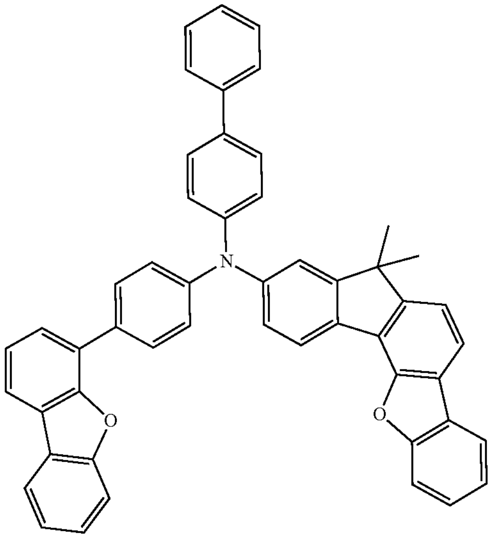
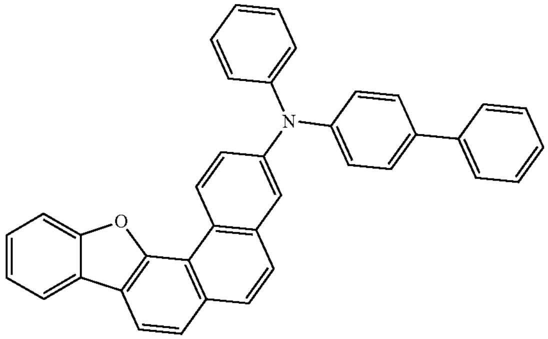
-continued
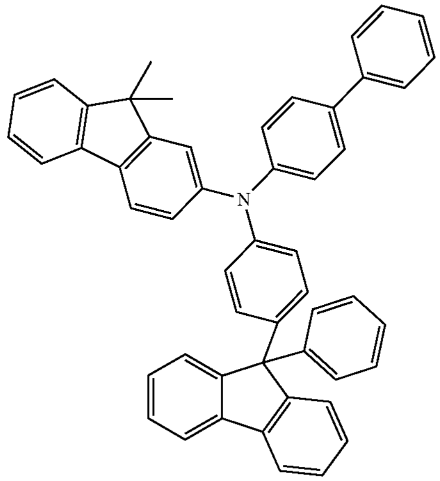
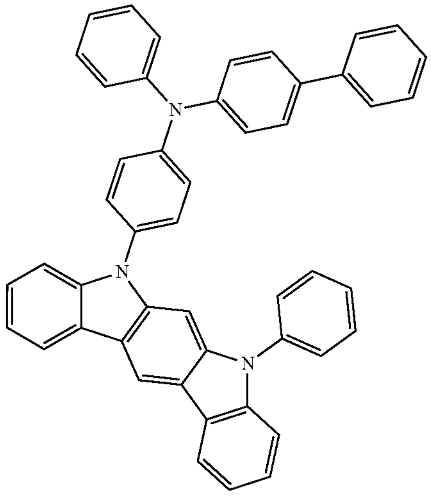
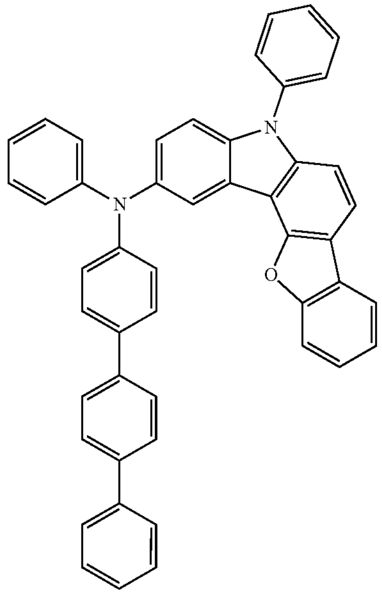

-continued
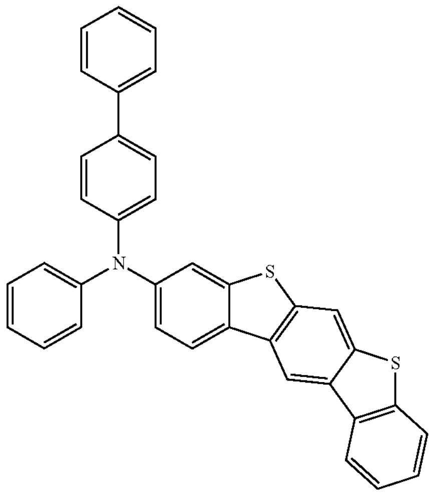
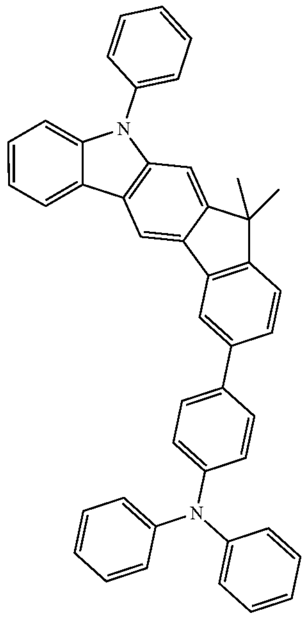
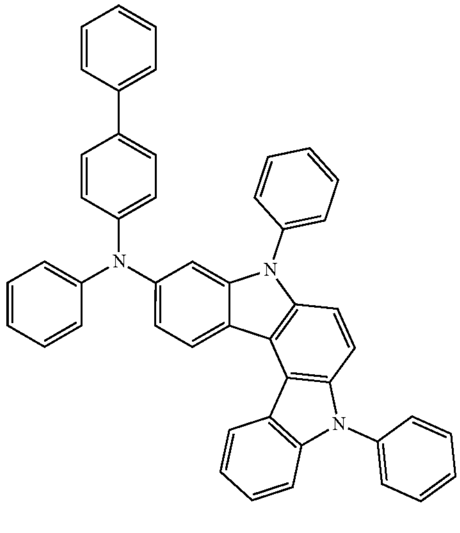
-continued
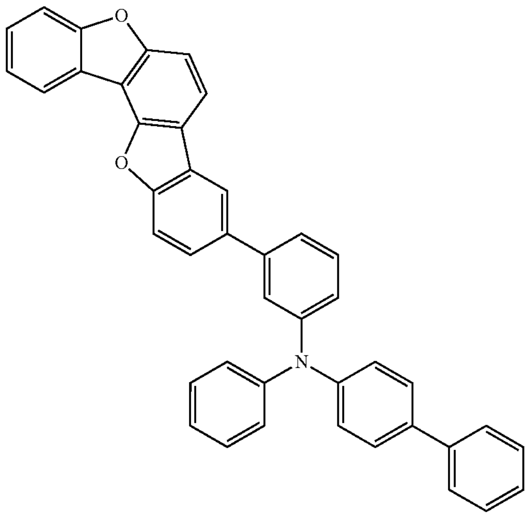
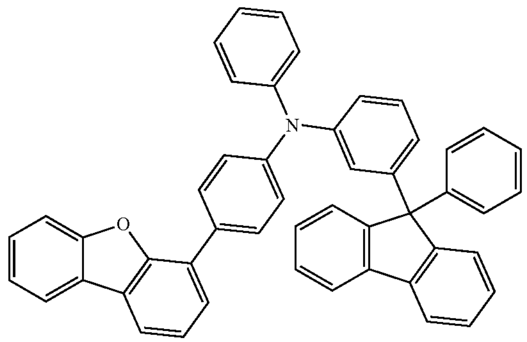
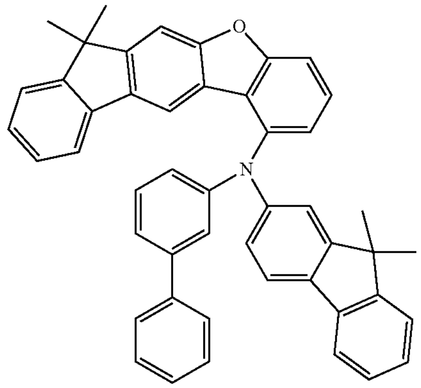
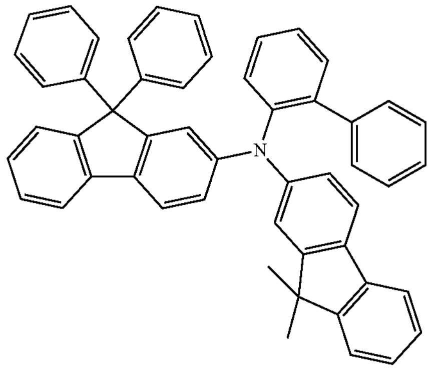

-continued
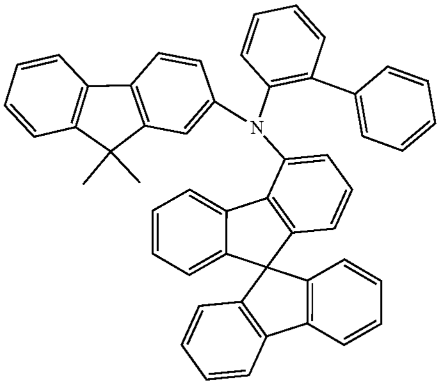
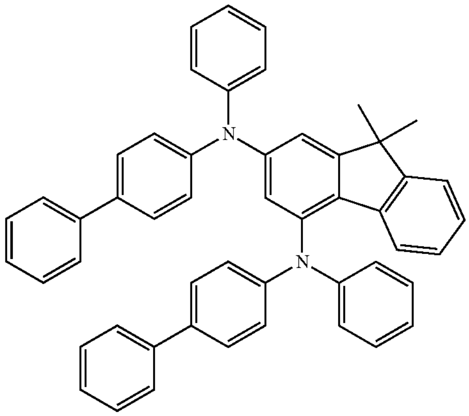
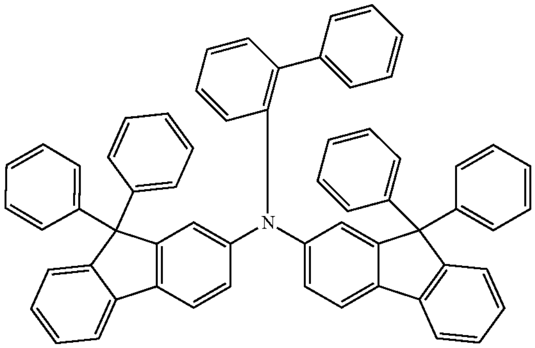
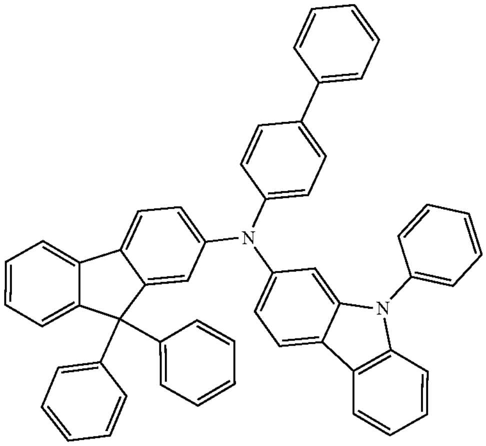
-continued
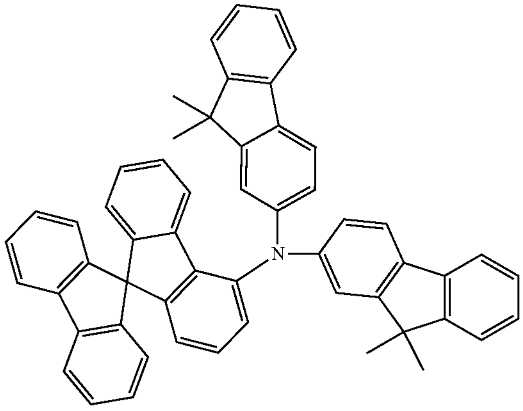
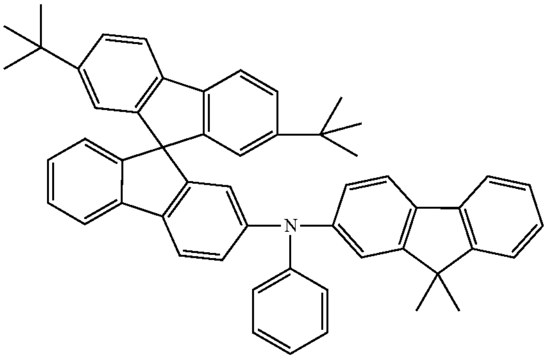
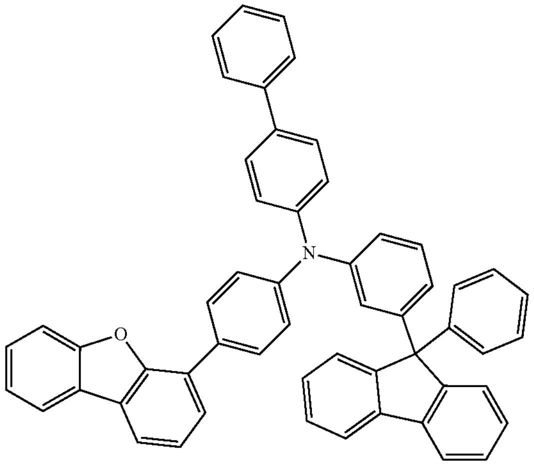
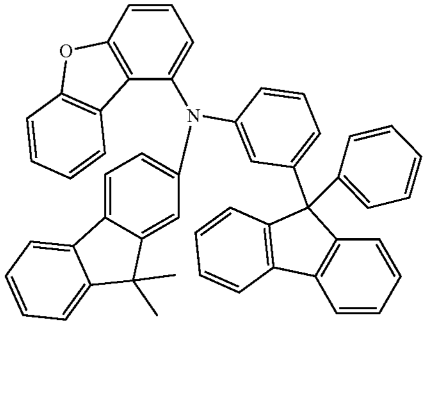

-continued
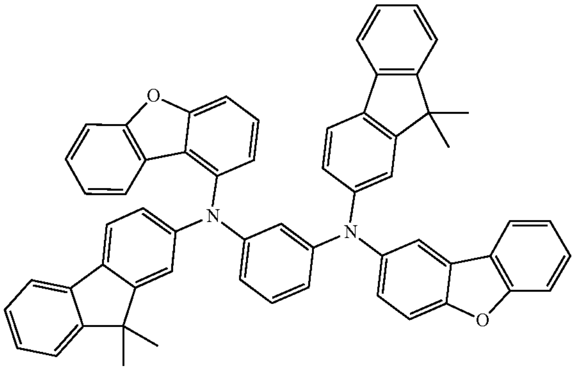
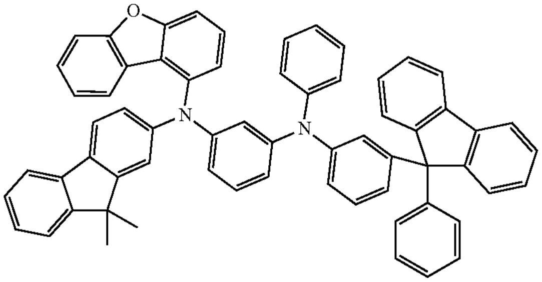
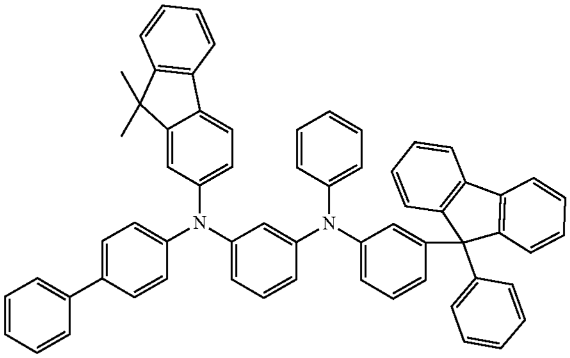
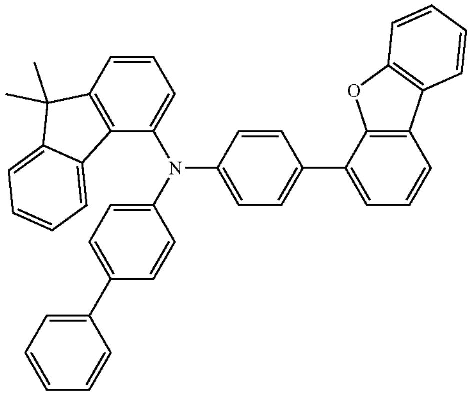
-continued
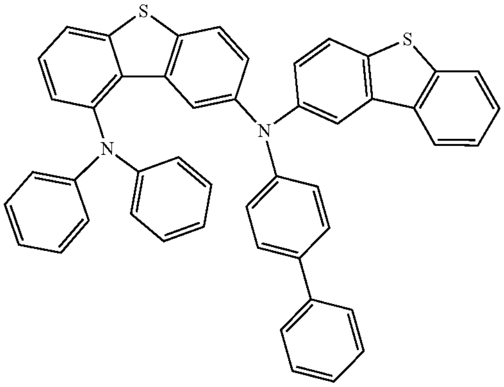
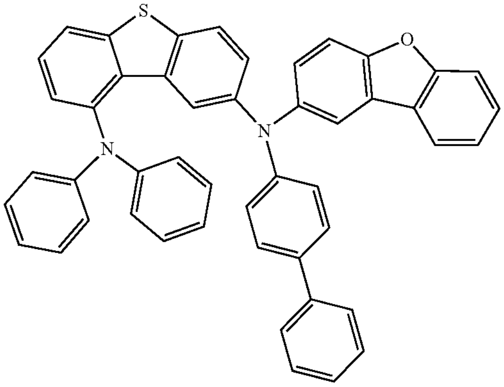
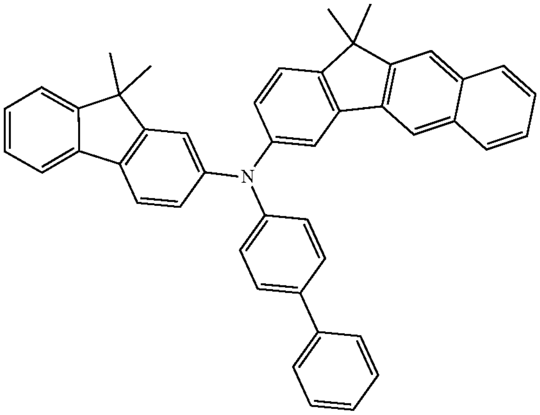
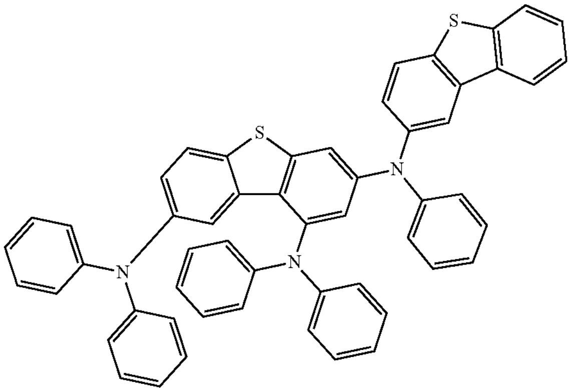

-continued

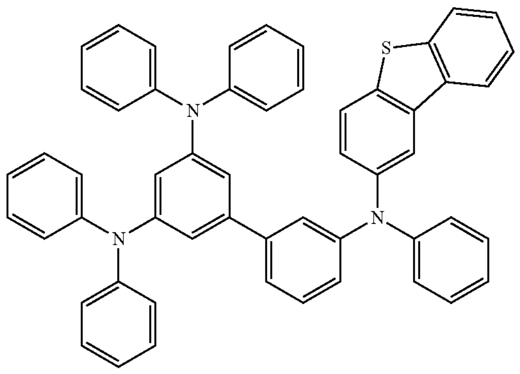

-continued

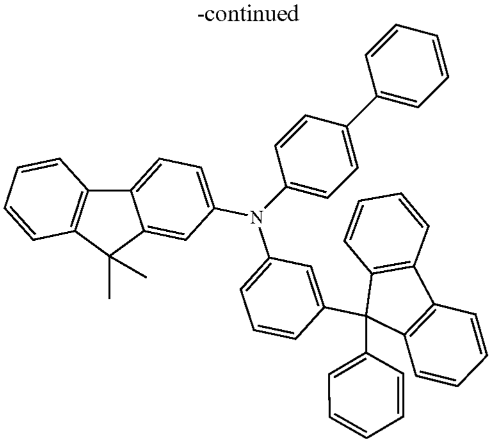

In the hole transport region 140, other suitable may be used in addition to the compounds above.

In an implementation, the charge transport region may be, e.g., the electron transport region 150.

The electron transport region 150 may further increase electron injection or electron mobility between the cathode 110 and the light emitting layer 130 and block holes.

In an implementation, the electron transport region 150 may include an electron transport layer between the cathode 110 and the light emitting layer 130, and an electron transport auxiliary layer between the light emitting layer 130 and the electron transport layer and at least one of the compounds of Group C may be included in at least one of the electron transport layer and the electron transport auxiliary layer.

[Group C]

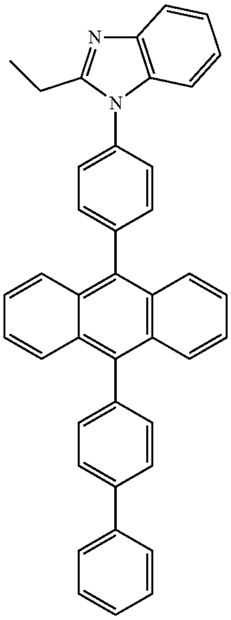

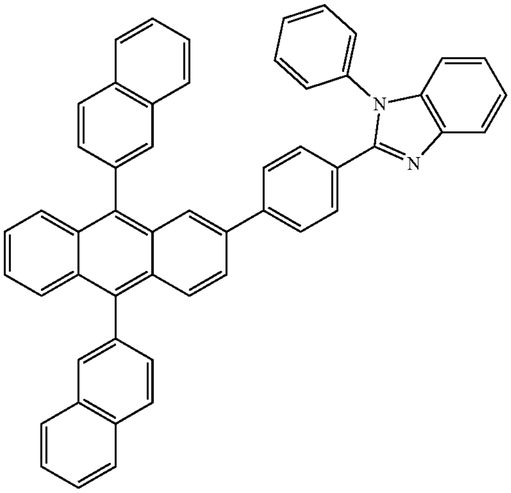

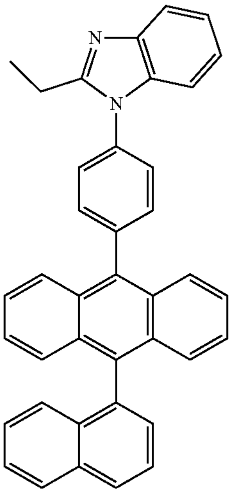

-continued
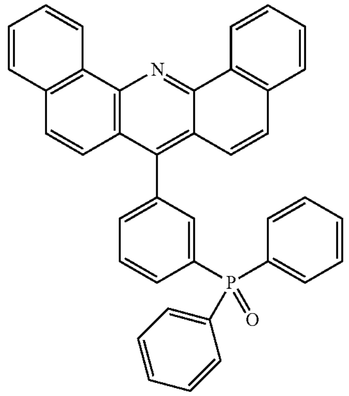
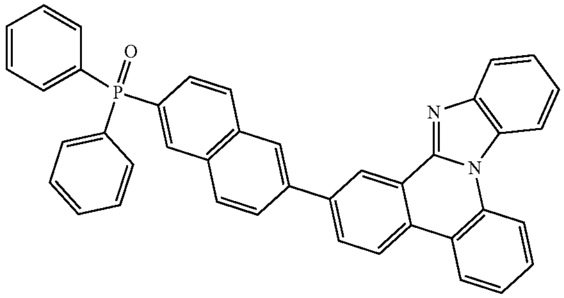
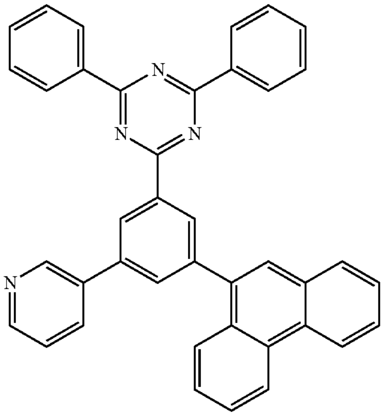
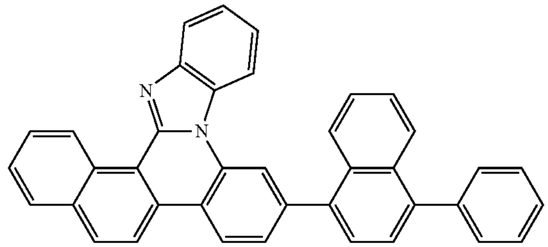
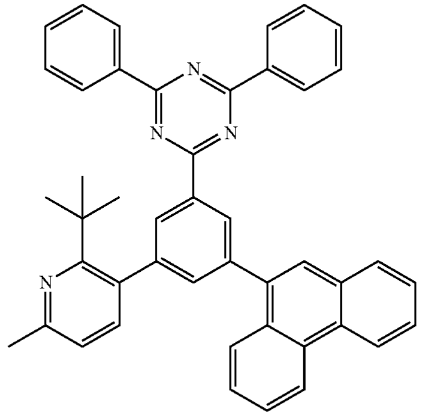
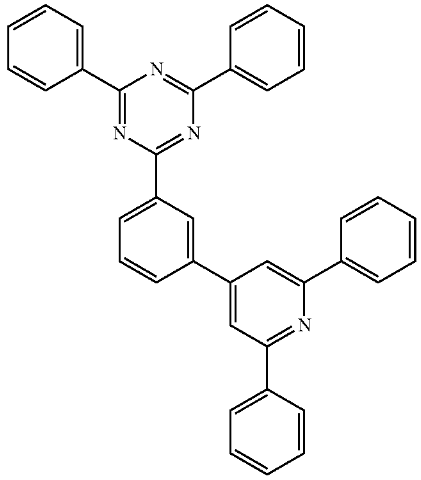
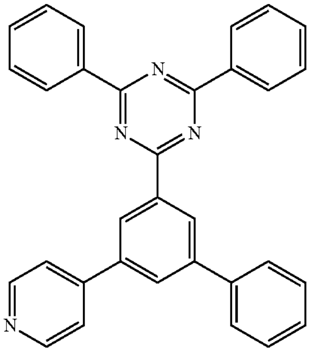
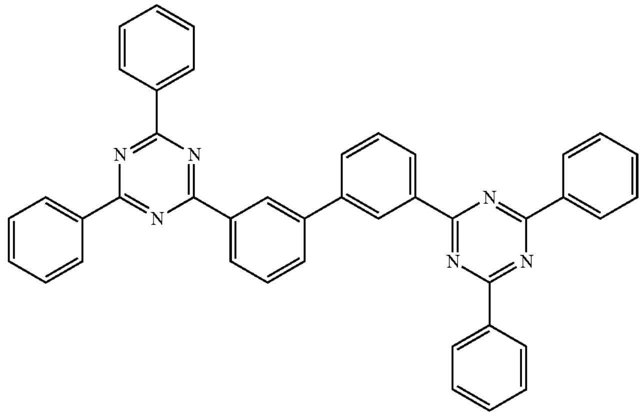

-continued
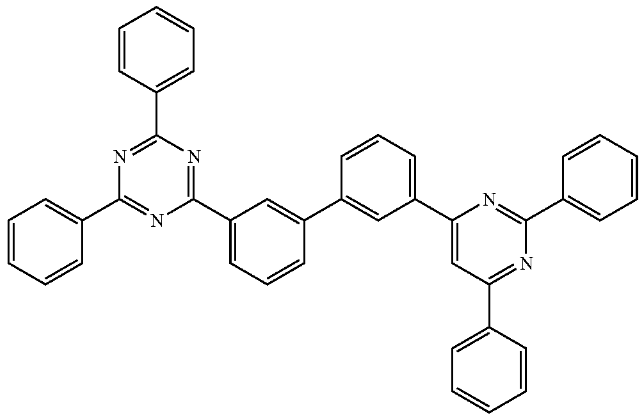
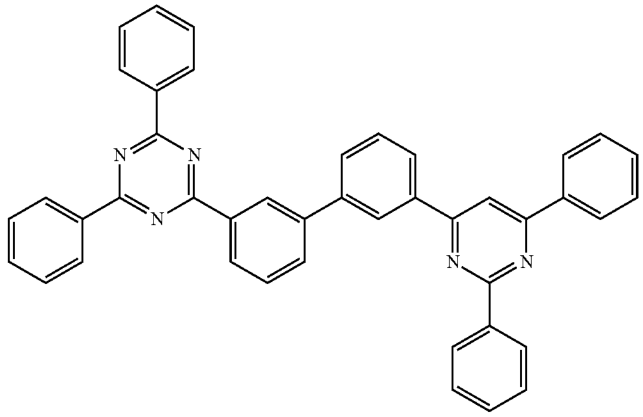
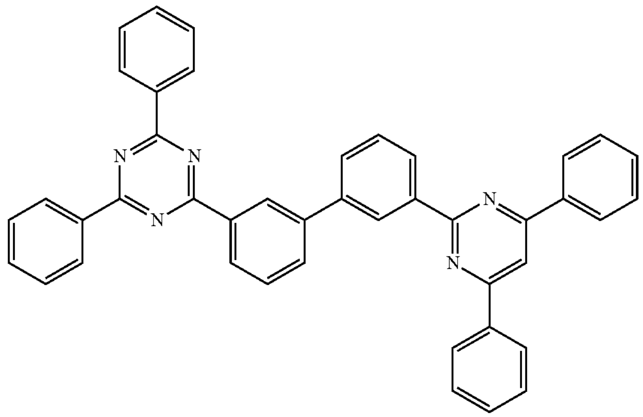
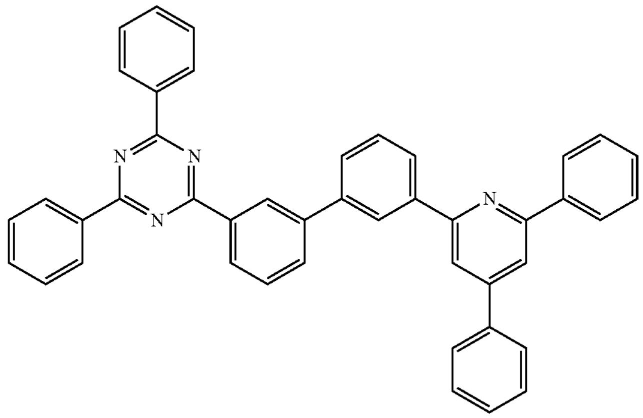

-continued
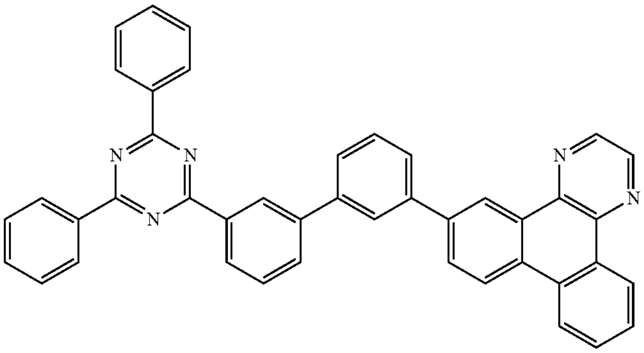
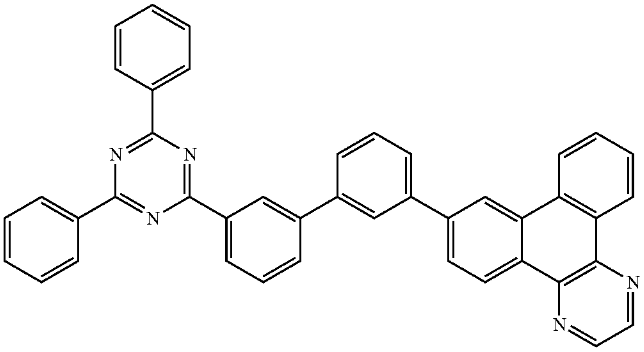
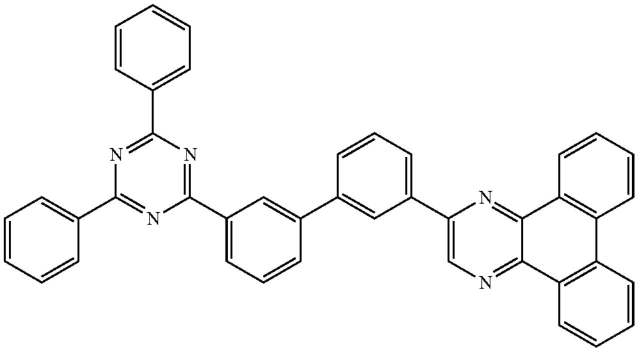
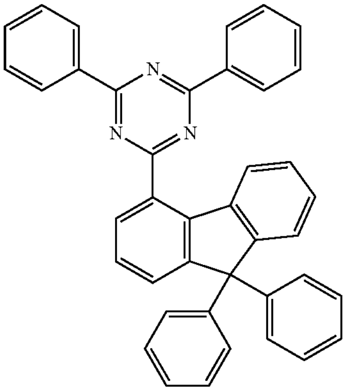
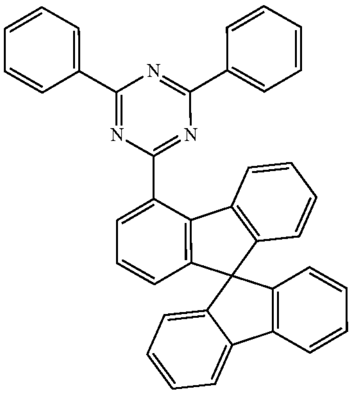
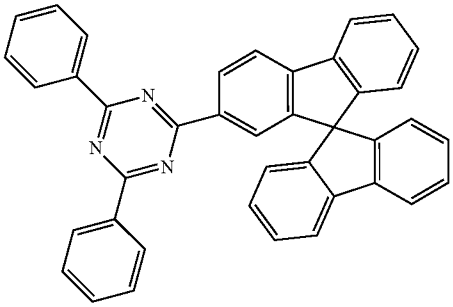

-continued
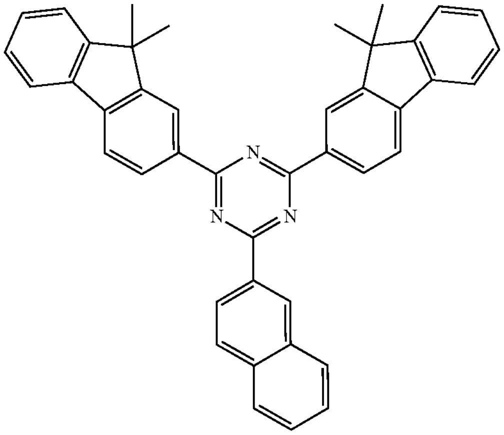
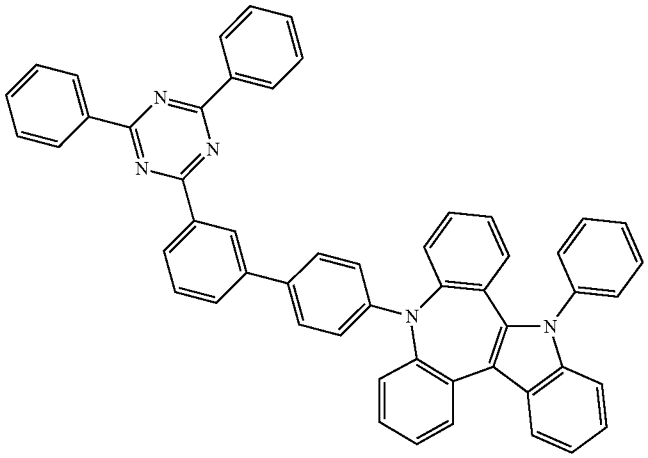
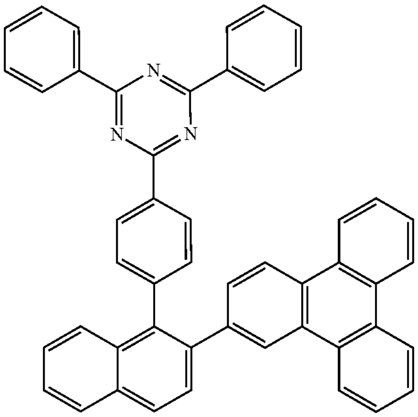
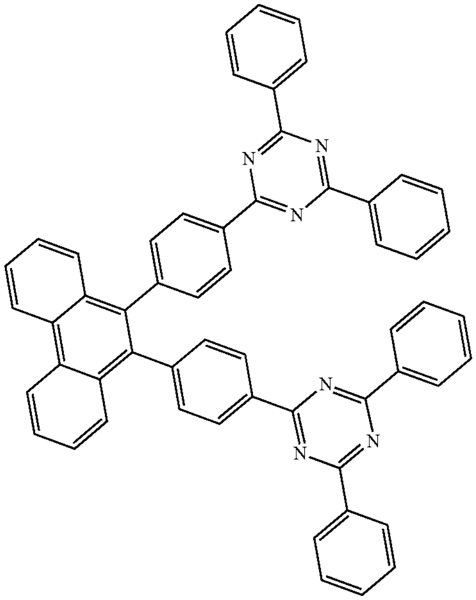
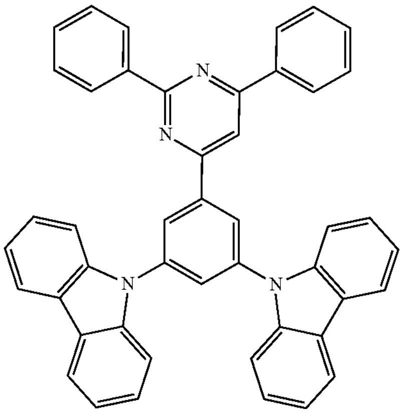
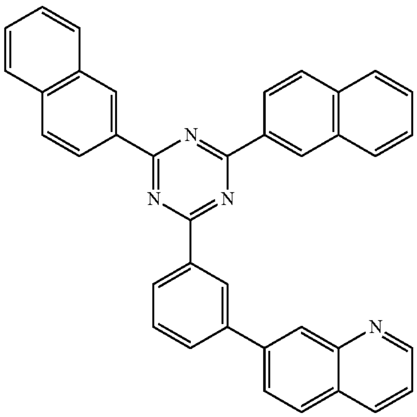

-continued
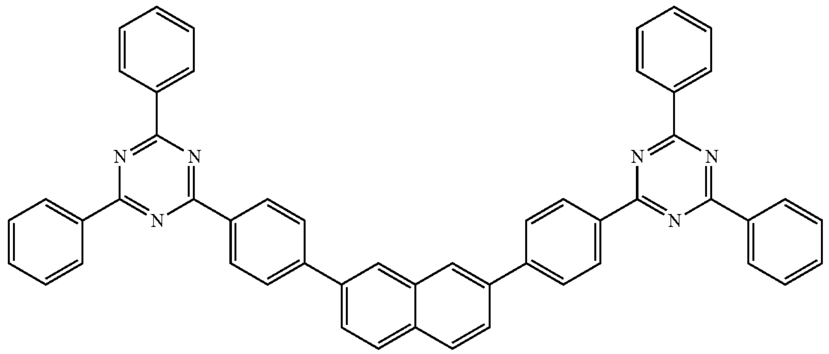
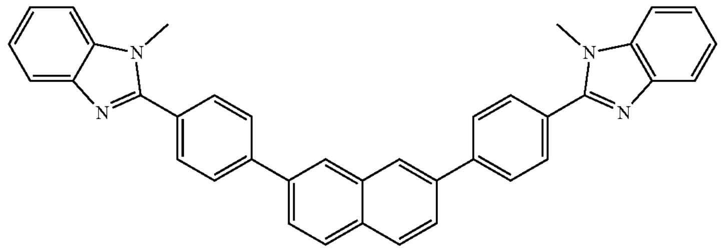
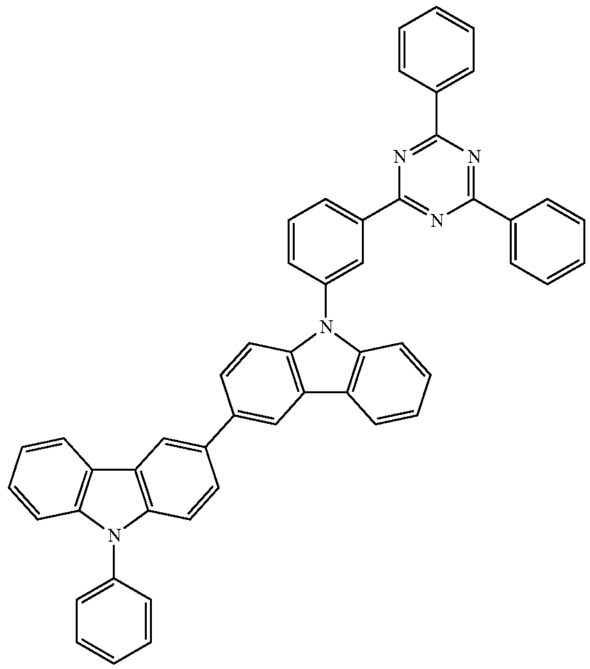
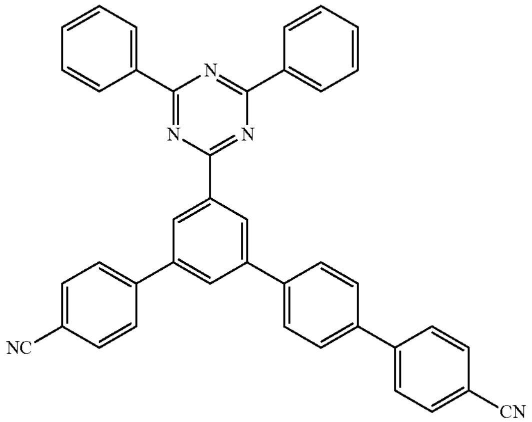

-continued
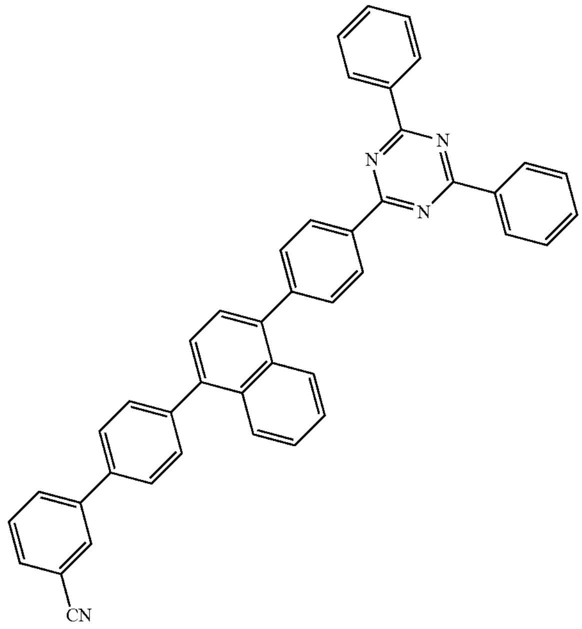
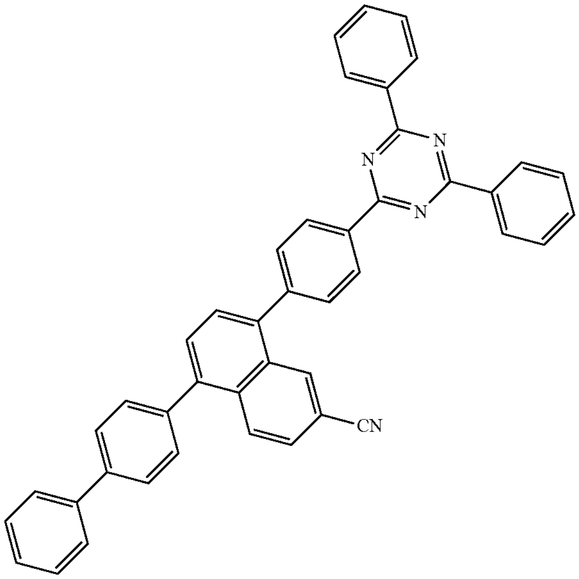
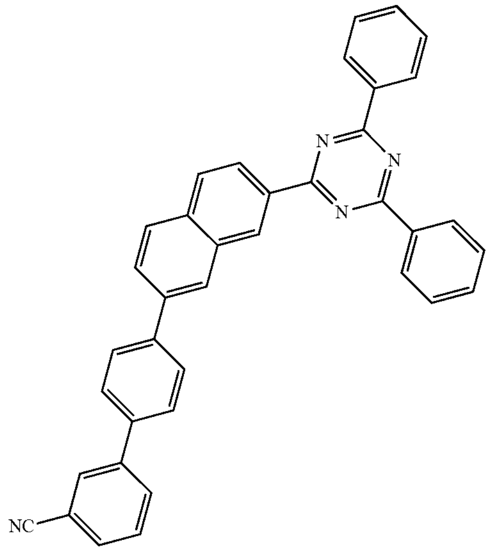
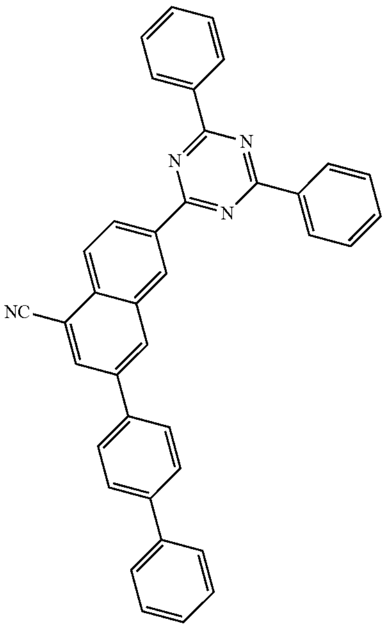

-continued
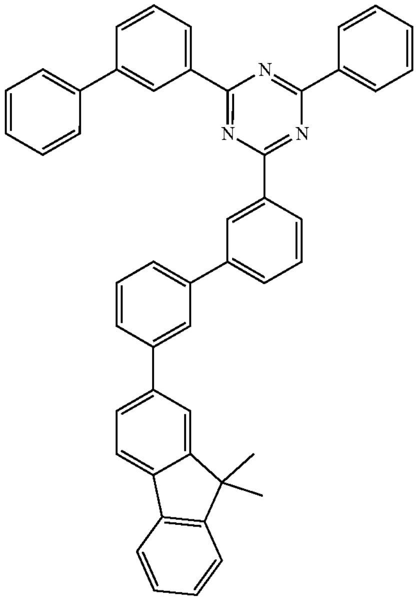
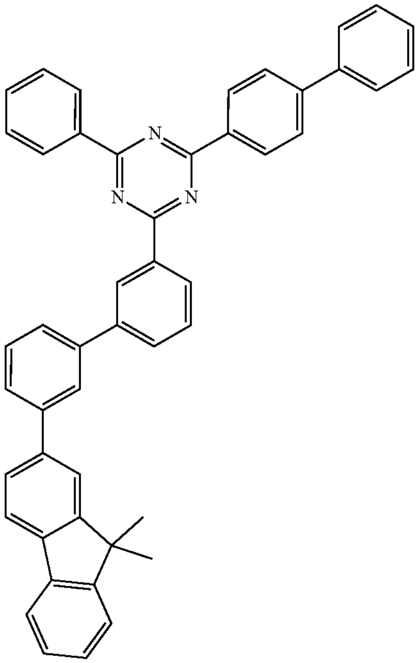
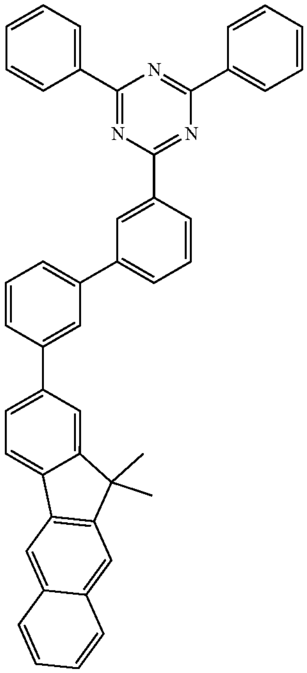
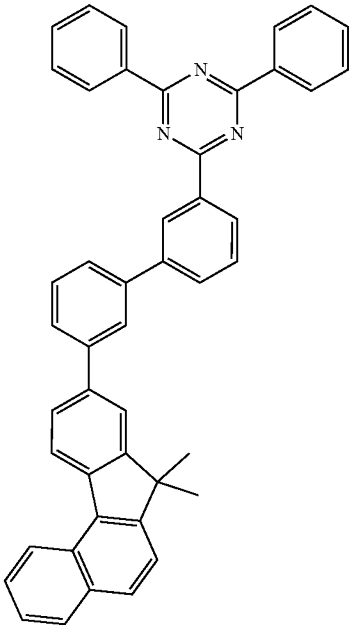
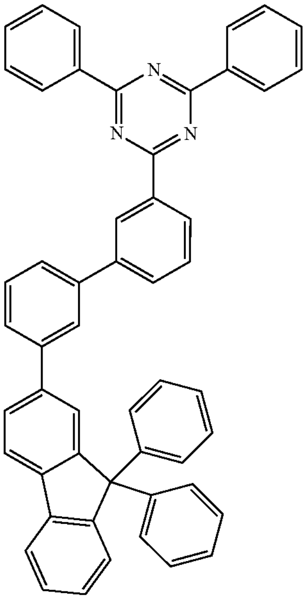

-continued
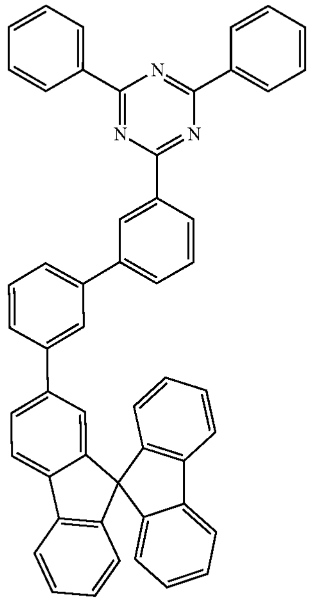
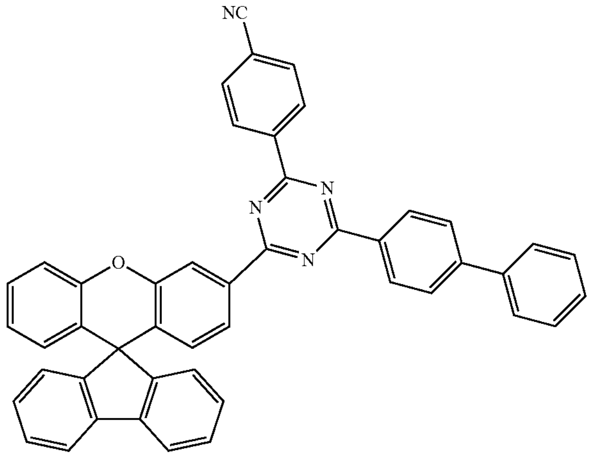
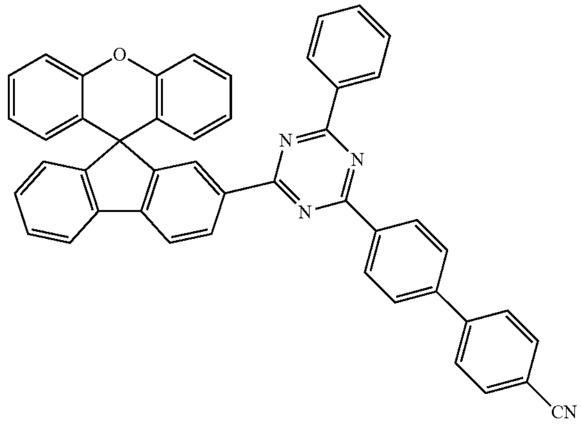
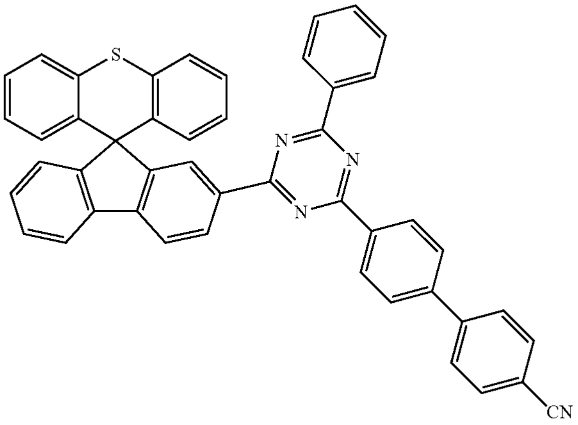
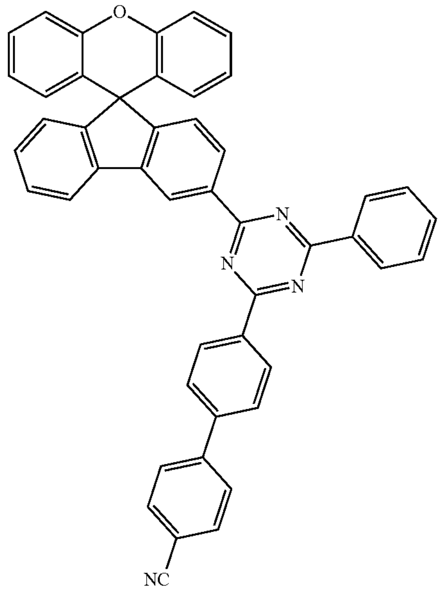
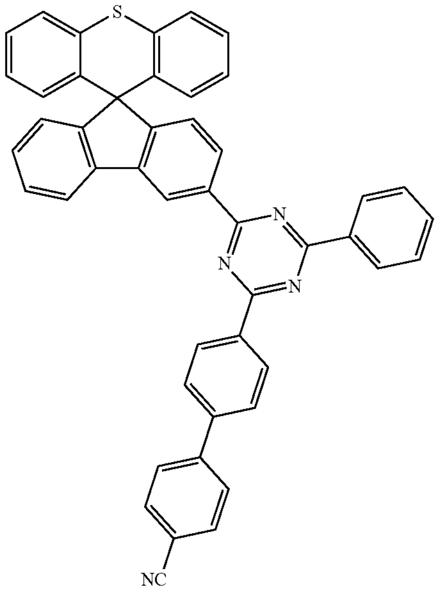

-continued
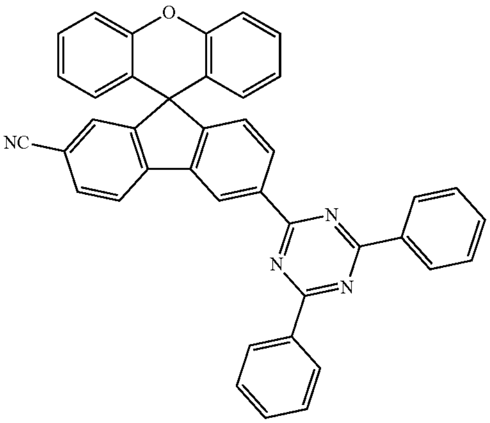
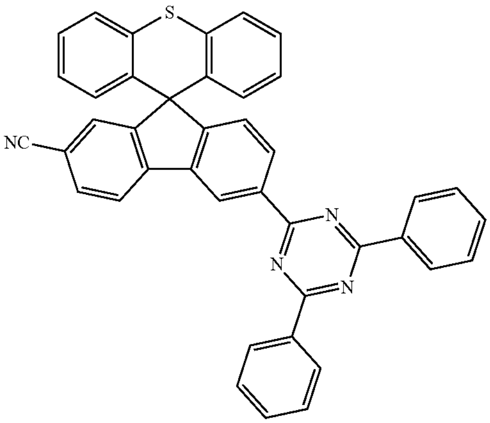
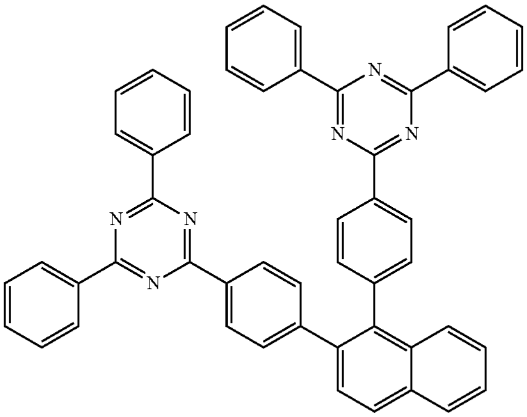
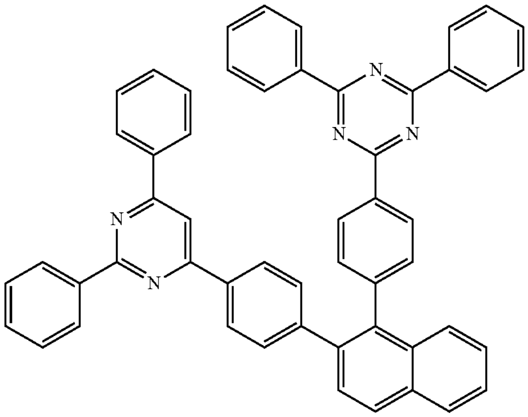
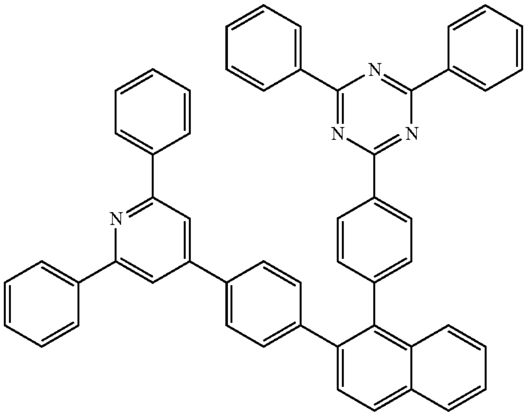
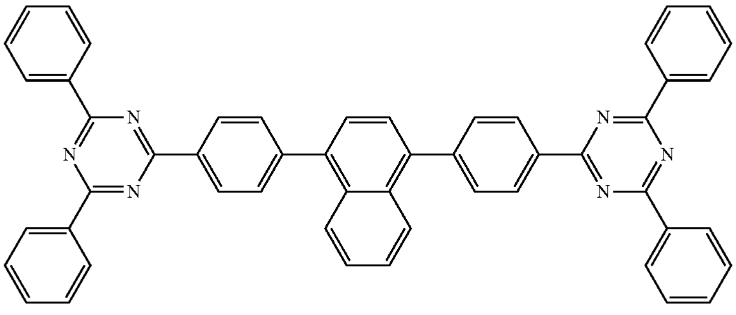

-continued

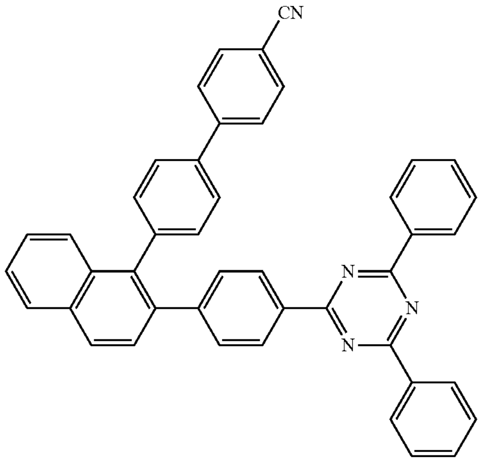

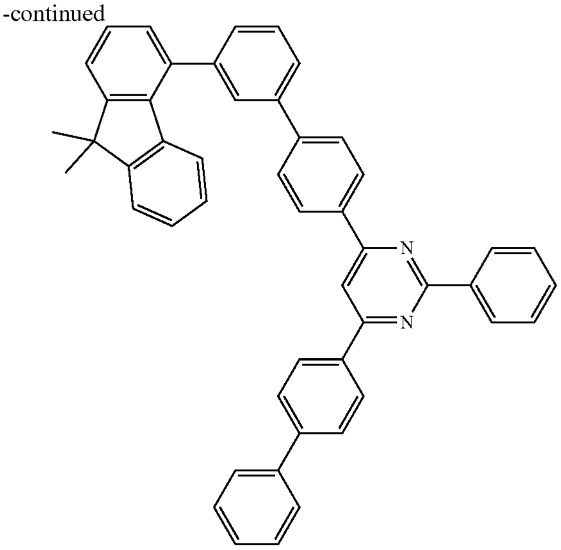

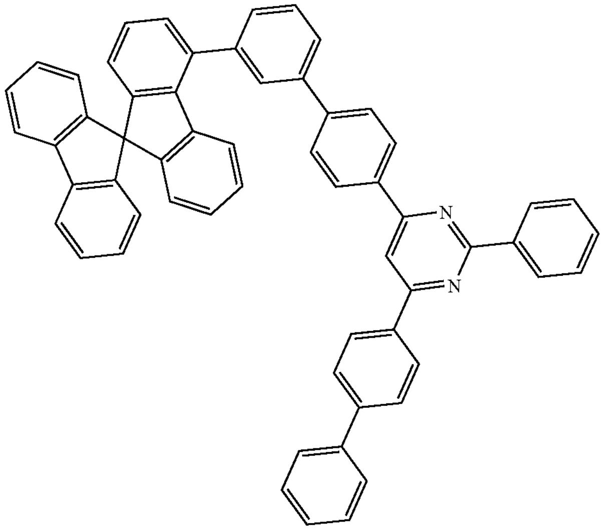

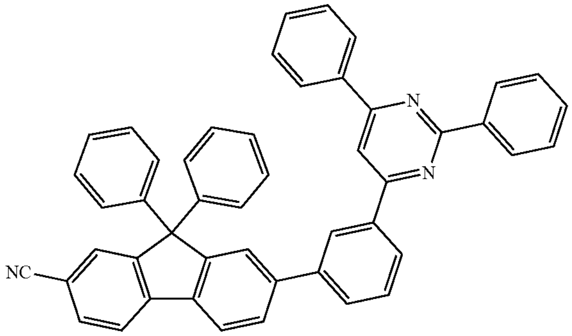

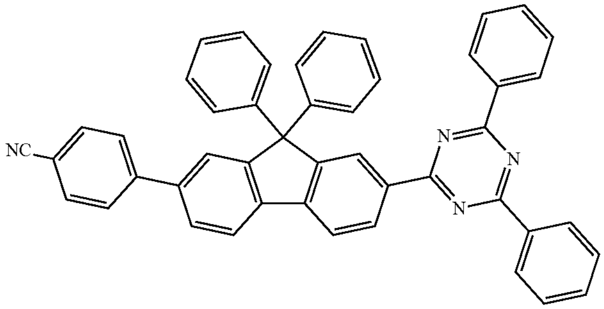

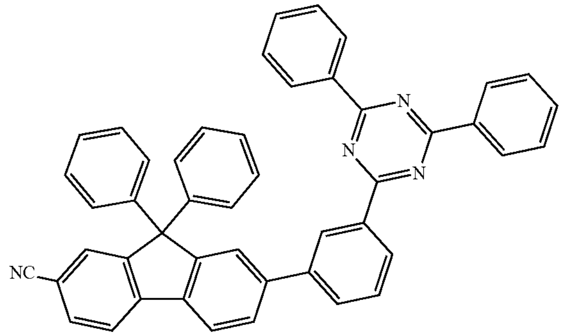

One embodiment may provide an organic light emitting diode including a light emitting layer as an organic layer.

Another embodiment may provide an organic light emitting diode including a light emitting layer and a hole transport region as an organic layer.

Another embodiment may provide an organic light emitting diode including a light emitting layer and an electron transport region as an organic layer.

The organic light emitting diode according to an embodiment may include a hole transport region 140 and an electron transport region 150 in addition to the light emitting layer 130 as the organic layer 105, as shown in the FIGURE.

In an implementation, the organic light emitting diode may further include an electron injection layer, a hole injection layer, or the like, in addition to the light emitting layer as the aforementioned organic layer.

The organic light emitting diode 100 may be produced by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in examples and synthesis examples were purchased from Sigma-Aldrich Co. Ltd., TCI Inc., or Tokyo Chemical Industry as far as there is no particular comment or were synthesized by known methods.

(Preparation of Compound for Organic Optoelectronic Device)

Synthesis Example 1: Synthesis of Compound 1-3

[Reaction Scheme 1]

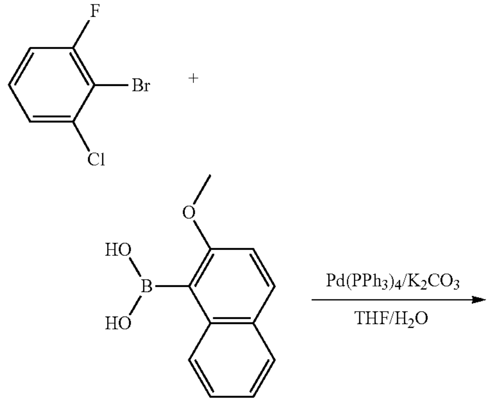

SM-1

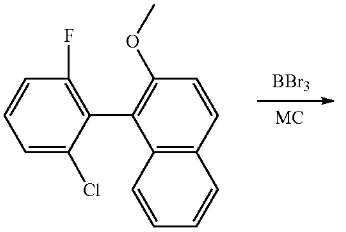

SM-2

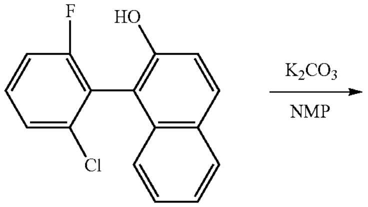

SM-3

-continued

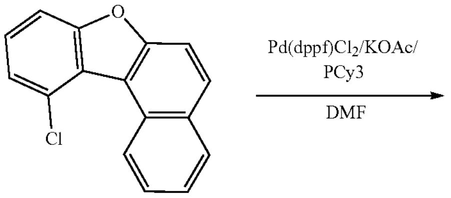

SM-4

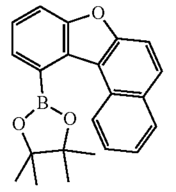

SM-5

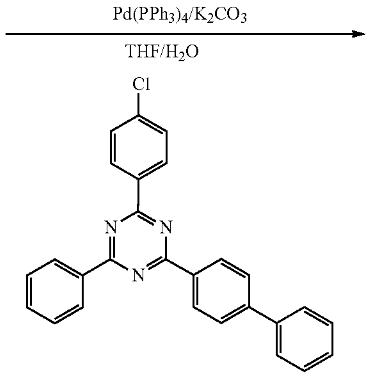

SM-6

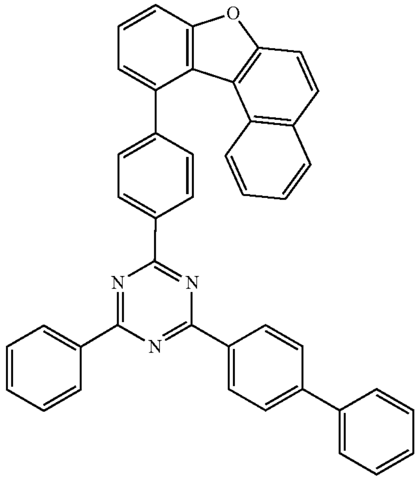

1-3

1st Step: Synthesis of SM-2

SM-1 (48 g, 239 mmol) was dissolved in 0.7 L of tetrahydrofuran (THF), and 2-bromo-1-chloro-3-fluorobenzene (50 g, 239 mmol) and tetrakis(triphenylphosphine) palladium (13.7 g, 11.9 mmol) were added thereto and then, stirred. Then, a saturated potassium carbonate (66 g, 478 mmol) solution in 250 mL of water was added and then, refluxed by heating at 80° C. for 12 hours. After completing a reaction, water was added to the reaction solution, and the mixture was extracted with ethyl acetate (EA) and then, treated with anhydrous magnesium sulfate to remove moisture, filtered, and concentrated under a reduced pressure. The obtained residue was separated and purified through flash column chromatography, obtaining 41 g (60%) of SM-2.

2nd Step: Synthesis of SM-3

SM-2 (41.4 g, 144.6 mmol) was dissolved in 720 mL of methylene chloride (MC), and $BBr_3$ (1 M) (217 ml, 217 mmol) was slowly added thereto in a dropwise fashion at an internal temperature of 0° C. and then, stirred at ambient temperature for 5 hours.

After slowly adding a potassium carbonate saturated aqueous solution thereto in a dropwise fashion at 0° C., until pH of the reaction solution reached 7, water was added to the reaction solution, and the mixture was extracted with methylene chloride (MC), treated with anhydrous magnesium sulfate to remove moisture, filtered, and concentrated under a reduced pressure. The obtained residue was separated and purified through flash column chromatography, obtaining 20 g (51%) of SM-3.

3rd Step: Synthesis of SM-4

SM-3 (40 g, 146.7 mmol) was dissolved in 430 mL of N-methyl-2-pyrrolidone (NMP), and potassium carbonate (40.6 g, 293.4 mmol) was added thereto and then, refluxed by heating at 130° C. for 12 hours. After completing a reaction, water was added to the reaction solution, and the mixture was extracted with ethyl acetate (EA), treated with anhydrous magnesium sulfate to remove water, filtered, and concentrated under a reduced pressure. The obtained residue was separated and purified through flash column chromatography, obtaining 36 g (97%) of SM-4.

4th Step: Synthesis of SM-5

SM-4 (37 g, 147 mmol) was dissolved in 300 mL of N,N-dimethylformamide (DMF), and bis(pinacolato)diboron (45 g, 177 mmol), [1,1'-bis(diphenylphosphino)ferrocene]dichloropalladium(II) (10.8 g, 14.8 mmol), potassium acetate (29 g, 295 mmol), and tricyclohexylphosphine (12.4 g, 44.3 mmol) were added thereto and then, refluxed by heating at 150° C. for 12 hours. After completing a reaction, water was added to the reaction solution, and the mixture was extracted with ethyl acetate (EA), treated with anhydrous magnesium sulfate to remove moisture, filtered, and concentrated under a reduced pressure. The obtained residue was separated and purified through flash column chromatography, obtaining 28 g (75%) of SM-5.

5th Step: Synthesis of Compound 1-3

SM-5 (10.6 g, 30.8 mmol) and SM-6 (13 g, 30.8 mmol) were dissolved in 140 mL of tetrahydrofuran (THF), and tetrakis(triphenylphosphine)palladium (2.1 g, 1.8 mmol) was added thereto and then, stirred. Subsequently, a saturated potassium carbonate (8.5 g, 62 mmol) solution in 30 ml of water was added, and then refluxed by heating at 80° C. for 12 hours. After completing a reaction, water was added to the reaction solution, and the mixture was extracted with ethyl acetate (EA), treated with anhydrous magnesium sulfate to remove moisture, filtered, and concentrated under a reduced pressure. This obtained residue was dissolved in heated xylene and then, silica-filtered. The filtered solution was concentrated under a reduced pressure and recrystallized by using a xylenes solvent, obtaining 15 g (81%) of Compound 1-3.

calcd. $C_{43}H_{27}N_3O$: C, 85.83; H, 4.52; N, 6.98; O, 2.66, found: C, 85.83; H, 4.52; N, 6.98; O, 2.66.

Synthesis Example 2: Synthesis of Compound 1-4

[Reaction Scheme 2]

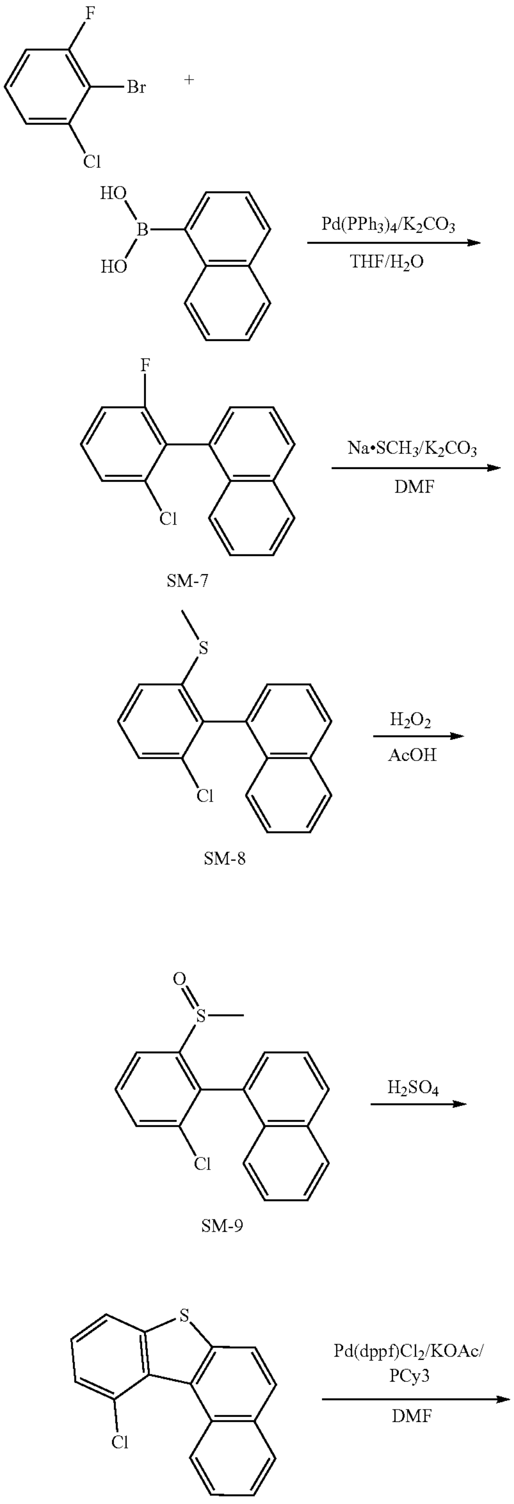

SM-7

SM-8

SM-9

SM-10

-continued

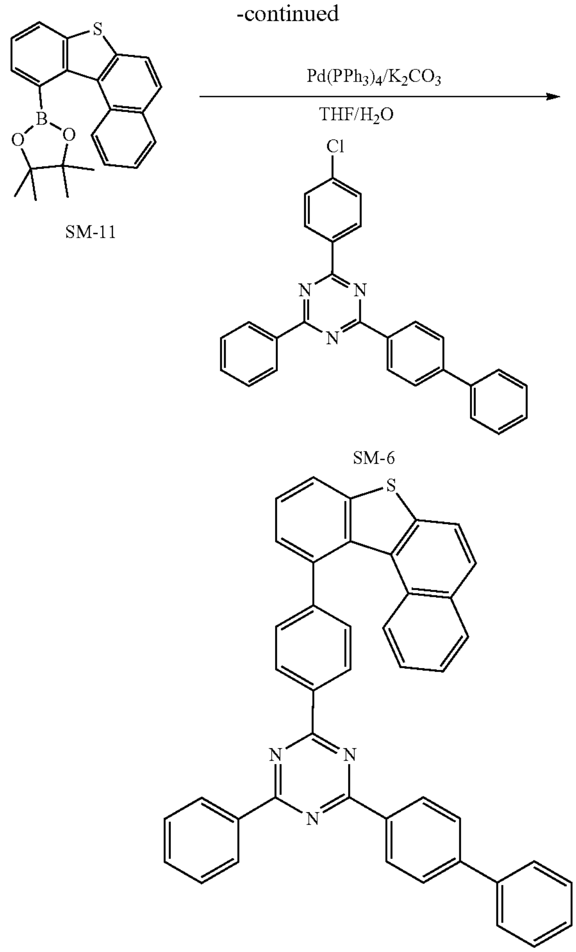

SM-11

SM-6

1-4

1st Step: Synthesis of SM-7

Compound SM-7 (72%) was synthesized in the same manner as the 1st step of Synthesis Example 1 except that naphthalen-1-ylboronic acid was used instead of SM-1.

2nd Step: Synthesis of SM-8

In a 1,000 mL round-bottomed flask, SM-7 (98.3 g, 273 mmol) was added to 550 mL of N,N-dimethylformamide (DMF), and an internal temperature thereof was set at 0° C. Subsequently, sodium thiomethoxide (21.1 g, 286.6 mmol) and potassium carbonate (56.5 g, 409.4 mmol) were slowly added thereto. Herein, the internal temperature was maintained at 0° C. The obtained mixture was heated at 80° C. under a nitrogen atmosphere. After 12 hours, the reaction solution was cooled down, ethyl acetate and water were added thereto and then, stirred, and an organic layer was separated therefrom, concentrated under a reduced pressure, and treated through column chromatography, obtaining 66.8 g (86%) of SM-8.

3rd Step: Synthesis of SM-9

SM-8 (66.3 g, 233 mmol) was added to 500 mL of acetic acid, and then, an internal temperature thereof was set at 0° C. Subsequently, 50 ml of hydrogen peroxide was slowly added thereto. Herein, the internal temperature was maintained at 0° C. The reaction solution was stirred at ambient temperature for 12 hours, placed in ice water and extracted with methylene chloride (MC), treated with anhydrous magnesium sulfate to remove moisture, filtered, and concentrated under a reduced pressure, obtaining 66.5 g (95%) of SM-9.

4th Step: Synthesis of SM-10

After adding SM-9 (66 g, 219 mmol) to 500 mL of sulfuric acid and then, stirring the mixture at ambient temperature for 20 hours, the reaction solution was placed in ice water and then, adjusted to pH 9 with a NaOH aqueous solution. The resultant was extracted with methylene chloride (MC), treated with anhydrous magnesium sulfate to remove moisture, filtered, and concentrated under a reduced pressure, obtaining 41 g (70%) of SM-10.

5th Step: Synthesis of SM-11

SM-11 (63%) was synthesized according to Reaction Scheme 2 in the same manner as Synthesis Example 1 except that SM-10 was used instead of SM-4 in the 4th step of Synthesis Example 1.

6th Step: Synthesis of Compound 1-4

Compound 1-4 (85%) was synthesized according to Reaction Scheme 2 in the same manner as Synthesis Example 1 except that SM-11 was used instead of SM-5 in the 5th step of Synthesis Example 1.

calcd. $C_{43}H_7N_3S$: C, 83.60; H, 4.41; N, 6.80; S, 5.19, found: C, 83.60; H, 4.41; N, 6.80; S, 5.19.

Synthesis Examples 3 to 8

Each compound was synthesized in the same manner as Synthesis Example 1 or 2 except that SM-5 or SM-11 of Synthesis Example 1 or Synthesis Example 2 was used as Int A as shown in Table 1, and Int B was used instead of SM-6 of Table 1.

TABLE 1

| Synthesis Example | Int A | Int B | Final product | Amount (yield) | Property data of final product |
|---|---|---|---|---|---|
| Synthesis Example 3 | SM-5 | Int B-1 | Compound 1-11 | 4.1 g, (75%) | calcd. C43H25N3O2: C, 83.88; H, 4.09; N, 6.83; O, 5.20, found: C, 83.88; H, 4.09; N, 6.83; O, 5.20 |
| Synthesis Example 4 | SM-11 | Int B-1 | Compound 1-12 | 5.4 g, (78%) | calcd. C43H25N3OS: C, 81.75; H, 3.99; N, 6.65; O, 2.53; S, 5.07 found: C, 81.75; H, 3.99; N, 6.65; O, 2.53; S, 5.07 |

TABLE 1-continued

| Synthesis Example | Int A | Int B | Final product | Amount (yield) | Property data of final product |
|---|---|---|---|---|---|
| Synthesis Example 5 | SM-5 | Int B-2 | Compound 1-17 | 6.5 g, (77%) | calcd. C45H31N3OSi: C, 82.16; H, 4.75; N, 6.39; O, 2.43; Si, 4.27 found: C, 82.16; H, 4.75; N, 6.39; O, 2.43; Si, 4.27 |
| Synthesis Example 6 | SM-5 | Int B-3 | Compound 1-30 | 4.3 g, (70%) | calcd. C47H27N3O2: C, 84.79; H, 4.09; N, 6.31; O, 4.81 found: C, 84.79; H, 4.09; N, 6.31; O, 4.81 |
| Synthesis Example 7 | SM-5 | Int B-4 | Compound 1-34 | 6.4 g, (80%) | calcd. C47H27N3O2: C, 84.79; H, 4.09; N, 6.31; O, 4.81 found: C, 84.79; H, 4.09; N, 6.31; O, 4.81 |
| Synthesis Example 8 | SM-5 | Int B-5 | Compound 1-39 | 5.3 g, (74%) | calcd. C47H27N3O2: C, 84.79; H, 4.09; N, 6.31; O, 4.81 found: C, 84.79; H, 4.09; N, 6.31; O, 4.81 |

<Int B>

Int B-1

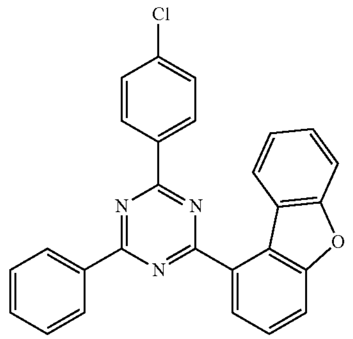

Int B-2

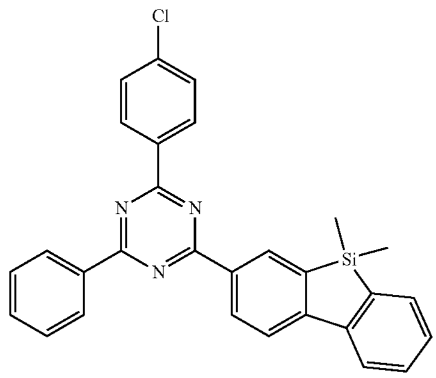

-continued

Int B-3

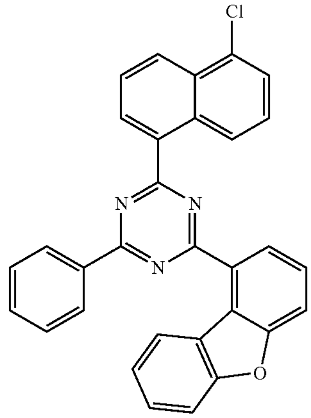

Int B-4

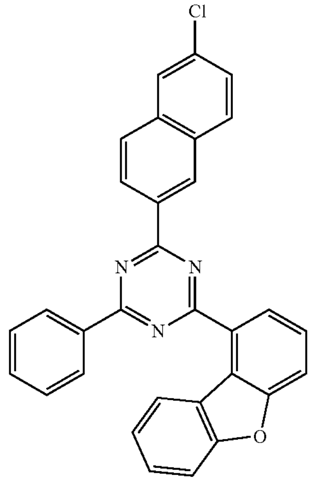

-continued

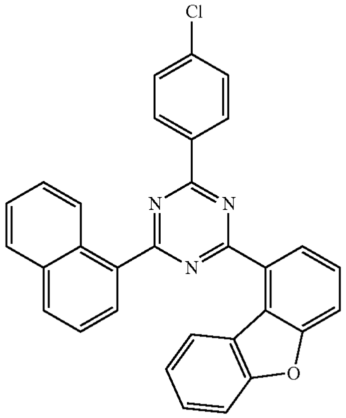

Int B-5

Synthesis Example 9: Synthesis of Compound A-28

[Reaction Scheme 3]

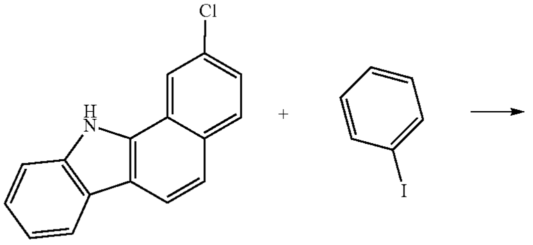

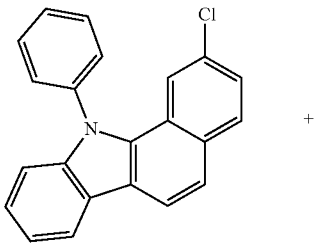

Int-17

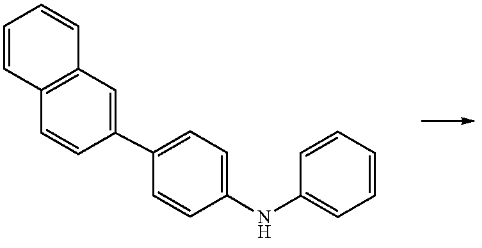

-continued

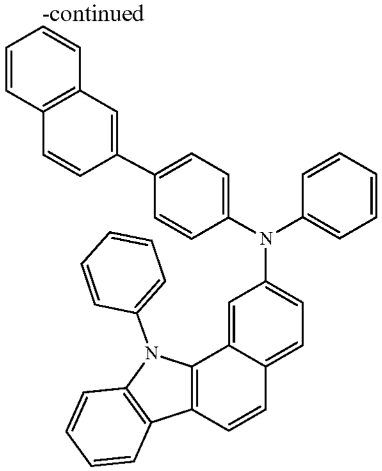

A-28

$1^{st}$ Step: Synthesis of Int-17

20 g (79.46 mmol) of 2-chloro-11H-benzo[a]carbazole, 19.45 g (95.35 mmol) of iodobenzene, 19.09 g (198.64 mmol) of sodium t-butoxide, and 3.22 g (15.89 mmol) of tri-tert-butylphosphine were dissolved in 260 ml of toluene, and 3.64 g (3.97 mmol) of $Pd(dba)_2$ was added thereto and then, stirred under reflux for 12 hours under a nitrogen atmosphere. When a reaction was completed, after extracting with toluene and distilled water, an organic layer therefrom was dried with anhydrous magnesium sulfate and filtered, and a filtrate therefrom was concentrated under a reduced pressure. A product therefrom was purified with normal hexane/dichloromethane (a volume ratio of 2:1) through silica gel column chromatography, obtaining 23.7 g (91%) of a target compound Int-17 as a white solid.

$2^{nd}$ Step: Synthesis of Compound A-28

20 g (61.01 mmol) of Int-17, 18.92 g (64.06 mmol) of 4-(2-naphthalenyl)-N-phenylbenzenamine, 14.66 g (152.53 mmol) of sodium t-butoxide, and 2.47 g (12.20 mmol) of tri-tert-butylphosphine were dissolved in 200 ml of toluene, and 2.79 g (3.05 mmol) of $Pd(dba)_2$ was added thereto and then, stirred under reflux for 12 hours under a nitrogen atmosphere. When a reaction was completed, after extracting with toluene and distilled water, an organic layer therefrom was dried with anhydrous magnesium sulfate and filtered, and a filtrate therefrom was concentrated under a reduced pressure. A product therefrom was purified with normal hexane/dichloromethane (a volume ratio of 2:1) through silica gel column chromatography, obtaining 31.5 g (88%) of a target compound A-28 as a white solid.

Synthesis Example 10: Synthesis of Compound 2-92

[Reaction Scheme 4]

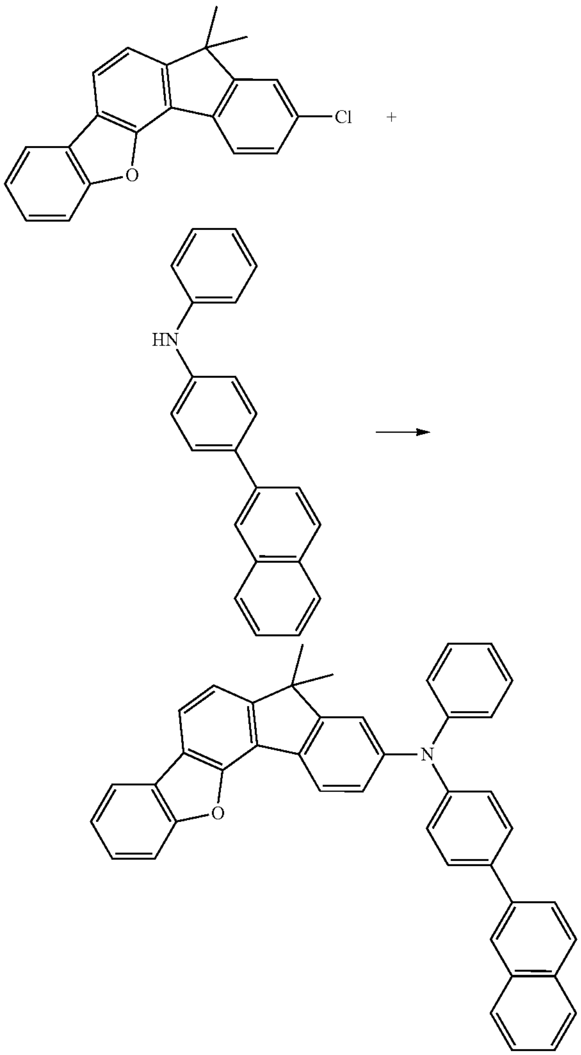

2-92

20 g (62.74 mmol) of 10-chloro-8,8-dimethyl-8H-benzo[b]fluoreno[4,3-d]furan, 19.46 g (65.87 mmol) of 4-(2-naphthalenyl)-N-phenylbenzenamine, 15.07 g (156.84 mmol) of sodium t-butoxide, and 2.54 g (12.55 mmol) of tri-tert-butylphosphine were dissolved in 300 ml of toluene, and 2.87 g (3.14 mmol) of $Pd(dba)_2$ was added thereto and then, stirred under reflux for 12 hours under a nitrogen atmosphere. When a reaction was completed, after extracting with toluene and distilled water, an organic layer therefrom was dried with anhydrous magnesium sulfate and filtered, and a filtrate therefrom was concentrated under a reduced pressure. A product therefrom was purified with normal hexane/dichloromethane (a volume ratio of 2:1) through silica gel column chromatography, obtaining 31.5 g (87%) of a target compound 2-92 as a white solid.

Comparative Synthesis Example 1: Synthesis of Compound Host1

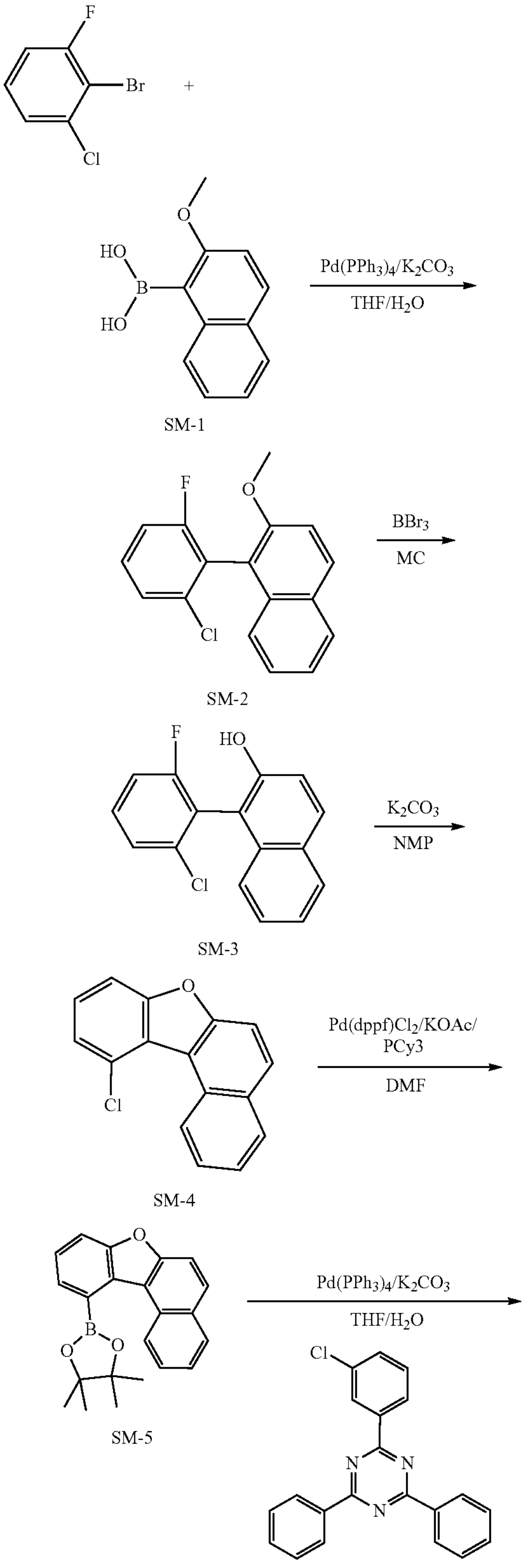

+

SM-1

SM-2

SM-3

SM-4

SM-5

SM-12

-continued

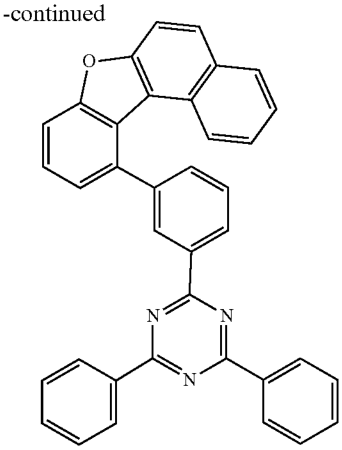

Host 1

Compound Host 1 (80%) according to Comparative Synthesis Example 1 was synthesized in the same manner as Synthesis Example 1 except that SM-12 was used instead of SM-6.

caled. C37H23N3O: C, 84.55; H, 4.41; N, 7.99; O, 3.04, found: C, 84.55; H, 4.41; N, 7.99; O, 3.04.

Comparative Synthesis Example 2: Synthesis of Compound Host2

Host 2

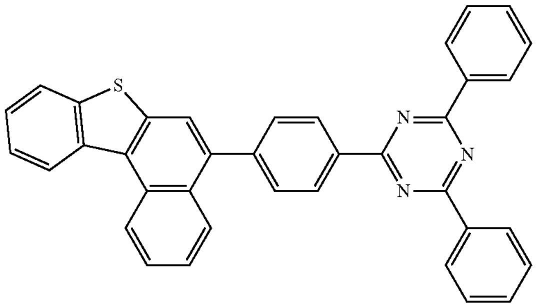

Compound Host 2 (89%) was synthesized with reference to KR 10-1814875.

calcd. C37H23N3S: C, 82.04; H, 4.28; N, 7.76; S, 5.92, found: C, 82.04; H, 4.28; N, 7.76; S, 5.92.

(Manufacture of Organic Light Emitting Diode)

Example 1

The glass substrate coated with ITO (indium tin oxide) at a thickness of 1,500 Å was washed with distilled water and ultrasonic waves. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A doped with 3% NDP-9 (commercially available from Novaled) was vacuum-deposited on the ITO substrate to form a 100 Å-thick hole injection layer, and then Compound A was deposited to be 1,300 Å-thick to form a hole transport layer. Compound B was deposited on the hole transport layer to a 700 Å-thick hole transport auxiliary layer. A 400 Å-thick light emitting layer was formed by using Compound 1-3 obtained in Synthesis Example 1 as a host, and 2 wt % of [Ir(piq)$_2$acac] as a dopant by vacuum deposition on the hole transport auxiliary layer. Subsequently, on the light emitting layer, a 300 Å-thick electron transport layer was formed by simultaneously vacuum-depositing Compound D and LiQ in a weight ratio of 1:1. On the electron transport layer, LiQ and Al were sequentially vacuum-deposited to be 15 Å-thick and 1,200 Å-thick, manufacturing an organic light emitting diode.

A structure of ITO/Compound A (3% NDP-9 doping, 100 Å)/Compound A (1,300 Å)/Compound B (700 Å)/EML [Compound 1-3 (98 wt %), [Ir(piq)$_2$acac] (2 wt %)](400 Å)/Compound D: Liq (300 Å)/LiQ (15 Å)/Al (1,200 Å)

Compound A: N-(biphenyl-4-yl)-9,9-dimethyl-N-(4-(9-phenyl-9H-carbazol-3-yl)phenyl)-9H-fluoren-2-amine Compound B: N,N-di([1,1'-biphenyl]-4-yl)-7,7-dimethyl-7H-fluoreno[4,3-b]benzofuran-10-amine Compound C: 2-(3-(3-(9,9-dimethyl-9H-fluoren-2-yl)phenyl)phenyl)-4,6-diphenyl-1,3,5-triazine Compound D: 8-(4-(4,6-di(naphthalen-2-yl)-1,3,5-triazin-2-yl)phenyl)quinoline Examples 2 to 10 and Comparative Examples 1 and 2

Diodes of Examples 2 to 10 and Comparative Examples 1 and 2 were manufactured in the same manner as in Example 1, except that the host was changed as shown in Table 2.

Example 11

The glass substrate coated with ITO (indium tin oxide) at a thickness of 1,500 Å was washed with distilled water and ultrasonic waves. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A doped with 3% NDP-9 (commercially available from Novaled) was vacuum-deposited on the ITO substrate to form a 100 Å-thick hole injection layer, and then Compound A was deposited to be 1,300 Å-thick to form a hole transport layer. Compound B was deposited on the hole transport layer to a 700 Å-thick hole transport auxiliary layer. A 400 Å-thick light emitting layer was formed by using Compound 1-3 obtained in Synthesis Example 1 and Compound 2-92 obtained in Synthesis Example 10 as a host simultaneously, and 2 wt % of [Ir(piq)$_2$acac] as a dopant by vacuum deposition on the hole transport auxiliary layer. Herein, Compound 1-3 and Compound 2-92 were used in a weight ratio of 5:5. Subsequently, on the light emitting layer, a 300 Å-thick electron transport layer was formed by simultaneously vacuum-depositing Compound D and LiQ in a weight ratio of 1:1. On the electron transport layer, LiQ and Al were sequentially vacuum-deposited to be 15 Å-thick and 1,200 Å-thick, manufacturing an organic light emitting diode.

A structure of ITO/Compound A (3% NDP-9 doping, 100 Å)/Compound A (1,300 Å)/Compound B (700 Å)/EML [98 wt % of host (Compound 1-3: Compound 2-92=5:5 w/w), 2 wt % of [Ir(piq)$_2$acac]] (400 Å)/Compound D: Liq (300 Å)/LiQ (15 Å)/Al (1,200 Å).

Examples 12 to 18 and Comparative Examples 3 to 6

Diodes of Examples 12 to 18 and Comparative Examples 3 to 6 were manufactured in the same manner as in Example 11, except that the host was changed as shown in Table 3.

Evaluation

Luminous efficiency and life-span characteristics of the organic light emitting diodes of Examples 1 to 18 and Comparative Examples 1 to 6 were evaluated.

Specific measurement methods are as follows, and the results are shown in Tables 2 and 3.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Luminous efficiency (cd/A) at the same current density (10 mA/$cm^2$) were calculated by using the luminance and current density from the items (1) and (2) and voltage.

The relative values based on the luminous efficiency of Comparative Example 2 were calculated and shown in Table 2.

The relative values based on the luminous efficiency of Comparative Example 6 were calculated and shown in Table 3.

(4) Measurement of Life-Span

The organic light emitting diodes of Examples 1 to 18, and Comparative Examples 1 to 6 were measured with respect to T95 life-spans by emitting light at initial luminance (cd/$m^2$) of 6,000 cd/$m^2$ and measuring luminance decreases over time to obtain when the luminance decreased down to 95% of the initial luminance as T95 life-span.

The relative values based on the T95 life-span of Comparative Example 2 were calculated and shown in Table 2.

The relative values based on the T95 life-span of Comparative Example 6 were calculated and shown in Table 3.

TABLE 2

| | Host | T95 life-span (%) | Efficiency (%) |
|---|---|---|---|
| Example 1 | 1-3 | 152 | 107 |
| Example 2 | 1-4 | 155 | 108 |
| Example 3 | 1-7 | 145 | 102 |
| Example 4 | 1-11 | 158 | 109 |
| Example 5 | 1-12 | 159 | 106 |
| Example 6 | 1-17 | 142 | 106 |
| Example 7 | 1-30 | 120 | 112 |
| Example 8 | 1-34 | 140 | 105 |
| Example 9 | 1-35 | 144 | 104 |
| Example 10 | 1-39 | 135 | 104 |
| Comparative Example 1 | Host 1 | 39 | 97 |
| Comparative Example 2 | Host 2 | 100 | 100 |

TABLE 3

| | Host | | T95 | |
|---|---|---|---|---|
| | First host | Second host | life-span (%) | Efficiency (%) |
| Example 11 | 1-3 | 2-92 | 122 | 117 |
| Example 12 | 1-4 | 2-92 | 119 | 115 |
| Example 13 | 1-11 | 2-92 | 125 | 117 |
| Example 14 | 1-17 | 2-92 | 117 | 114 |
| Example 15 | 1-30 | 2-92 | 108 | 121 |
| Example 16 | 1-39 | 2-92 | 107 | 114 |
| Example 17 | 1-3 | A-28 | 143 | 111 |
| Example 18 | 1-4 | A-28 | 146 | 109 |
| Comparative Example 3 | Host 1 | 2-92 | 34 | 105 |
| Comparative Example 4 | Host 2 | 2-92 | 82 | 104 |
| Comparative Example 5 | Host 1 | A-28 | 53 | 100 |
| Comparative Example 6 | Host 2 | A-28 | 100 | 100 |

Referring to Table 2, the compounds according to the Examples exhibited improved efficiency and life-span as a single host, compared with the Comparative Examples. Referring to Table 3, when combined with a second host, overall efficiency and life-span were greatly improved.

One or more embodiments may provide a compound for an organic optoelectronic device capable of implementing an organic optoelectronic device having high efficiency and a long life-span.

An organic optoelectronic device having high efficiency and a long life-span may be realized.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A composition for an organic optoelectronic device, the composition comprising:

a first compound represented by Chemical Formula 1; and a second compound represented by Chemical Formula 2-IVB:

[Chemical Formula 1]

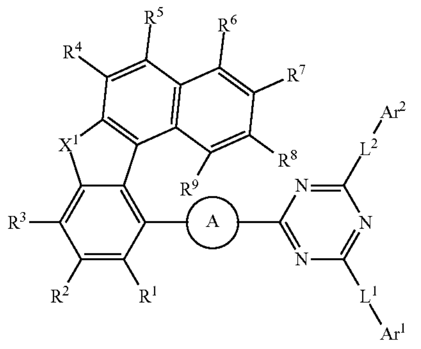

wherein, in Chemical Formula 1, $X^1$ is O or S, $L^1$ and $L^2$ are each independently a single bond or a substituted or unsubstituted C6 to C20 arylene group, $Ar^1$ and $Ar^2$ are each independently a substituted or unsubstituted C6 to C30 aryl group or a substituted or unsubstituted C2 to C30 heterocyclic group, $R^1$ to $R^9$ are each independently hydrogen, deuterium, a halogen, a substituted or unsubstituted C1 to C20 alkyl group, or a substituted or unsubstituted C6 to C20 aryl group, and A is a linking group of Group I,

[Group I]

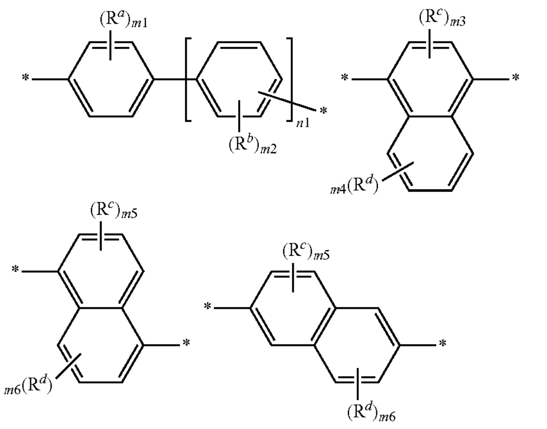

wherein, in Group I, $R^a$, $R^b$, $R^c$, and $R^d$ are each independently hydrogen, deuterium, or a substituted or unsubstituted C1 to C10 alkyl group, n1 is 0 or 1, m1, m2, and m4 are each independently an integer of 1 to 4, m3 is 1 or 2, m5 and m6 are each independently an integer of 1 to 3, and

* is a linking point,

[Chemical Formula 2-IVB]

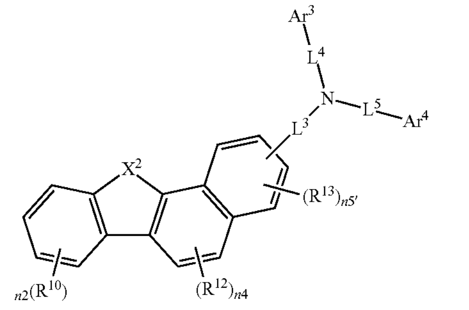

wherein, in Chemical Formula 2-IVB, $X^2$ is N-$L^a$-$R^e$, $L^a$ is a single bond or a substituted or unsubstituted C6 to C12 arylene group, $R^e$ and $R^{10}$ are each independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, n2 is an integer of 1 to 4, $R^{12}$ and $R^{13}$ are each independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, n4 is an integer of 1 or 2, n5' is an integer of 1 to 3, $L^3$ to $L^5$ are each independently a single bond or a substituted or unsubstituted C6 to C30 arylene group, $Ar^3$ is a substituted or unsubstituted naphthyl group, $Ar^4$ is a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, a substituted or unsubstituted triphenylene group, a substituted or unsubstituted chrysenyl group, a substituted or unsubstituted fluorenyl group, a substituted or unsubstituted benzophenanthrenyl group, a substituted or unsubstituted carbazolyl group, a substituted or unsubstituted dibenzofuranyl group, a substituted or unsubstituted dibenzothiophenyl group, a substituted or unsubstituted benzofuranofluorenyl group, or a substituted or unsubstituted benzothiophenefluorenyl group, and

* is a linking point.

2. The composition as claimed in claim 1, wherein:

the first compound represented by Chemical Formula 1 is represented by one of Chemical Formula 1-I to Chemical Formula 1-VI:

[Chemical Formula 1-I]

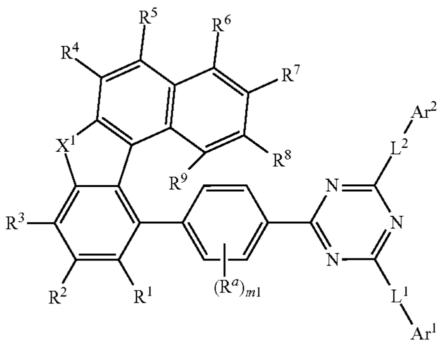

[Chemical Formula 1-II]

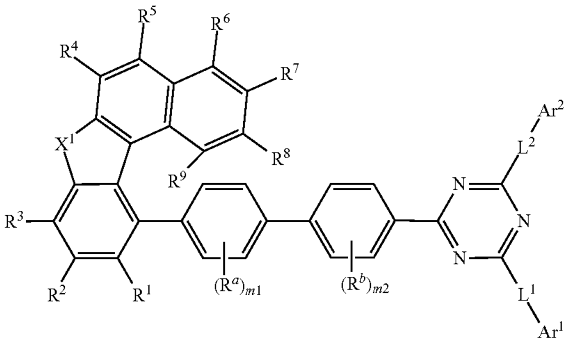

-continued

[Chemical Formula 1-III]

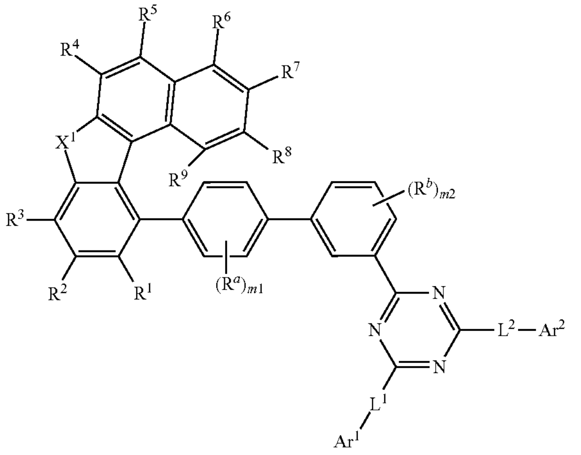

[Chemical Formula 1-IV]

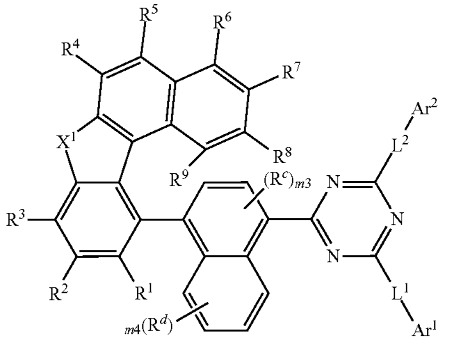

[Chemical Formula 1-V]

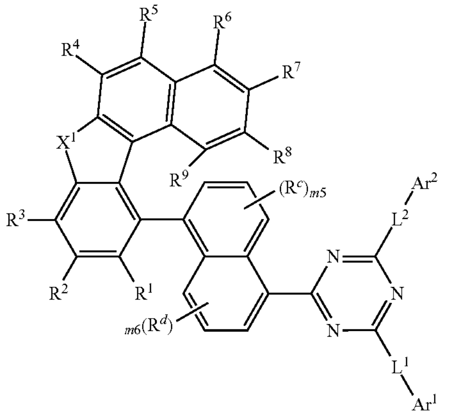

-continued

[Chemical Formula 1-VI]

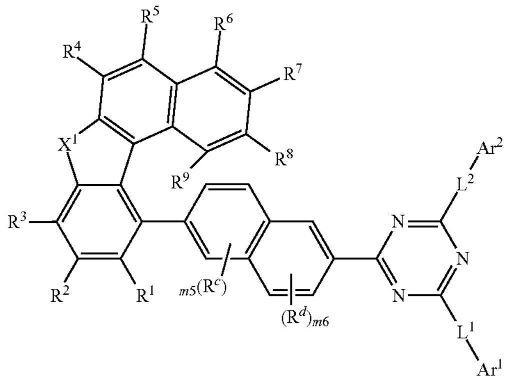

in Chemical Formula 1-I to Chemical Formula 1-VI, $X^1$, $L^1$, $L^2$, $Ar^1$, $Ar^2$, $R^1$ to $R^9$, $R^a$, $R^b$, $R^c$, $R^d$, and m1 to m6 are defined the same as those of Chemical Formula 1.

3. The composition as claimed in claim 1, wherein $Ar^1$ and $Ar^2$ are each independently a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, a substituted or unsubstituted chrysenyl group, or a substituted or unsubstituted triphenylene group, a substituted or unsubstituted fluorenyl group, a substituted or unsubstituted dibenzofuranyl group, a substituted or unsubstituted dibenzothiophenyl group, or a substituted or unsubstituted dibenzosilolyl group.

4. The composition as claimed in claim 1, wherein:

moieties *-$L^1$-$Ar^1$ and *-$L^2$-$Ar^2$ of Chemical Formula 1 are each independently a moiety of Group II:

[Group II]

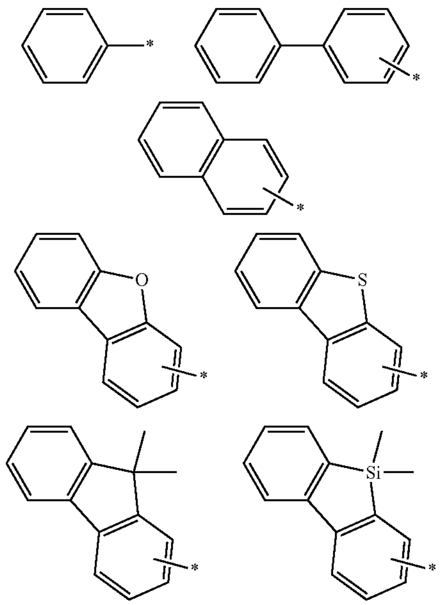

-continued
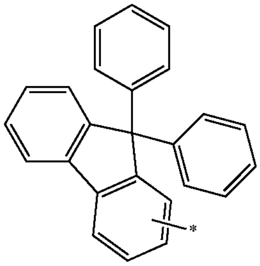
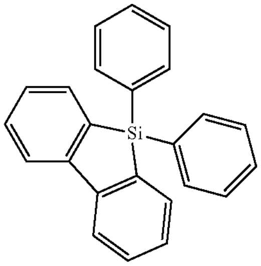
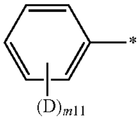
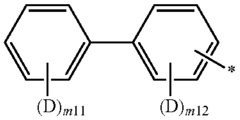
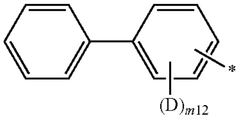
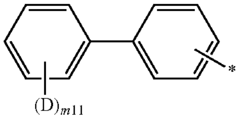
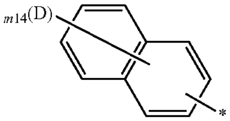
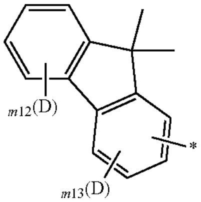
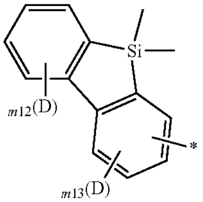
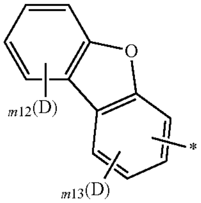
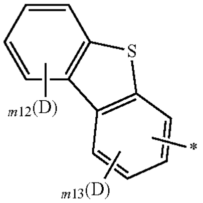
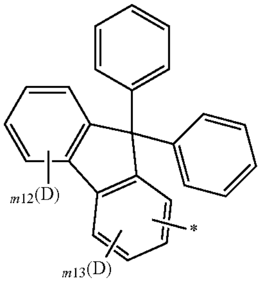
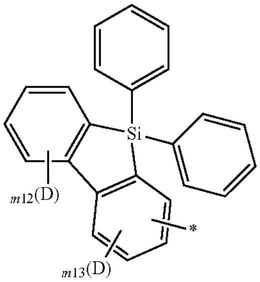
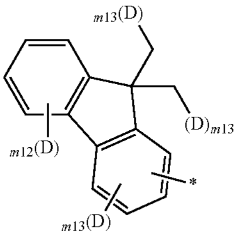
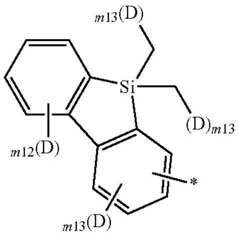
-continued
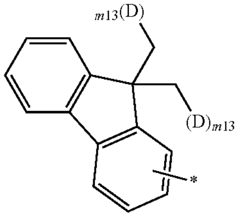
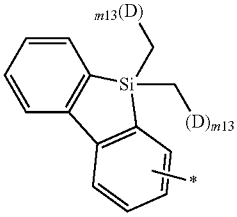
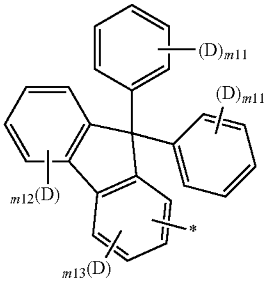
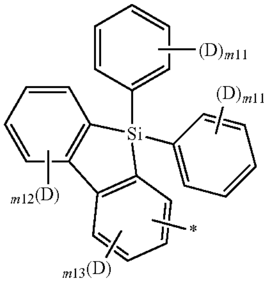
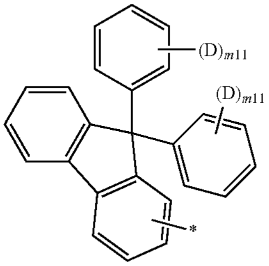
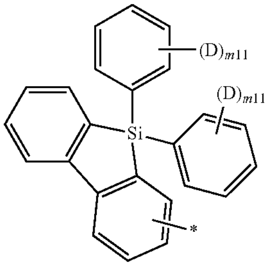
in Group II,
D is a deuterium,
m11 is an integer of 1 to 5,
m12 is an integer of 1 to 4,
m13 is an integer of 1 to 3,
m14 is an integer of 1 to 7, and
* is a linking point.
5. The composition as claimed in claim 1, wherein the first compound represented by Chemical Formula 1 is a compound of Group 1:
[Group 1]
[1-1]
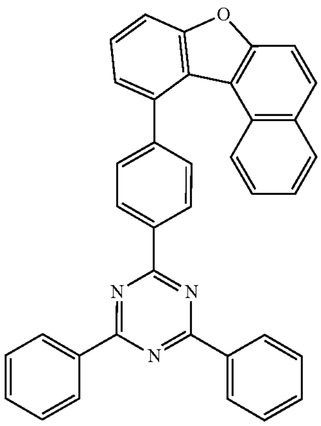

-continued
[1-2]
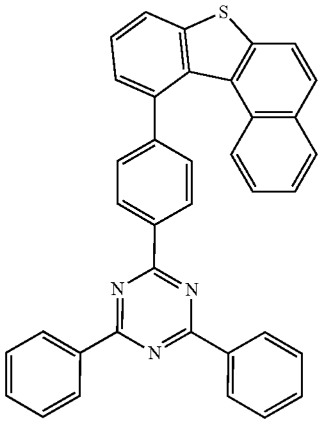
[1-3]
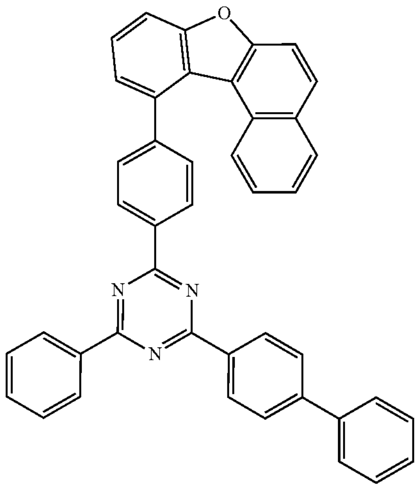
[1-4]
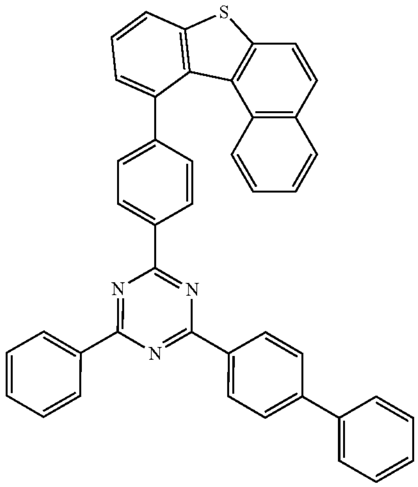
-continued
[1-5]
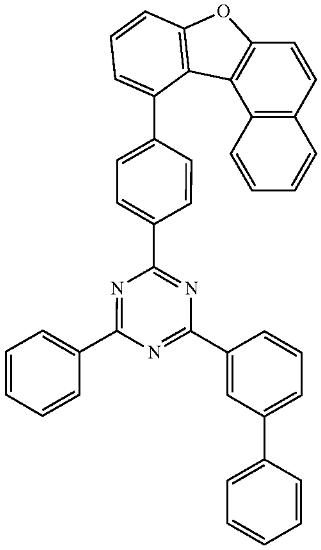
[1-6]
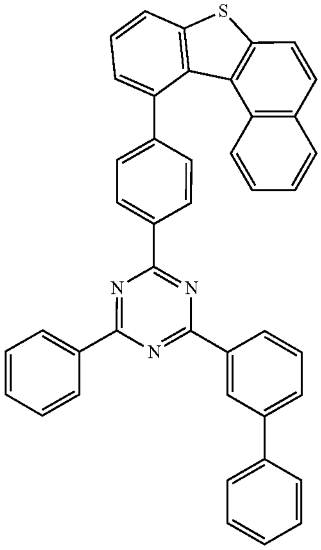
[1-7]
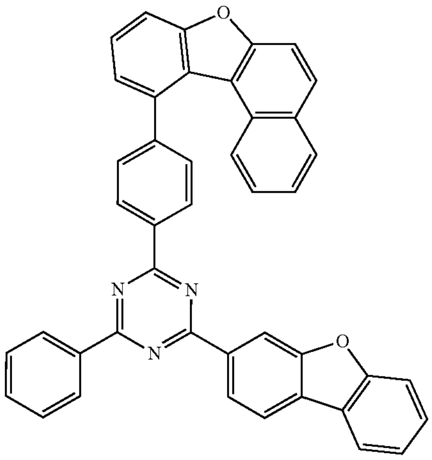

-continued
[1-8]
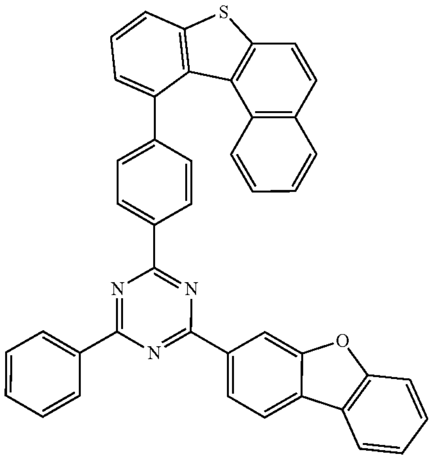
[1-9]
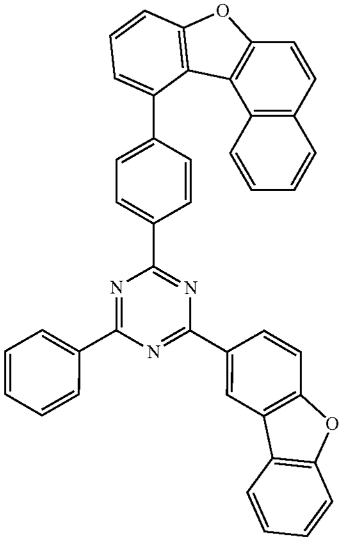
[1-10]
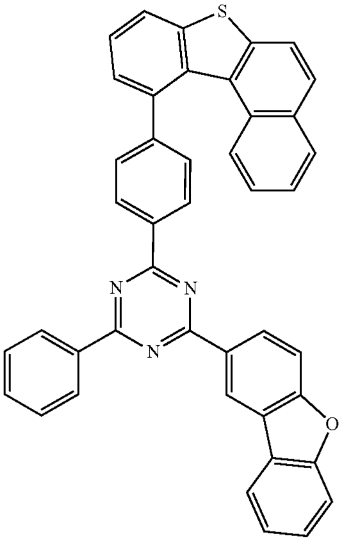
-continued
[1-11]
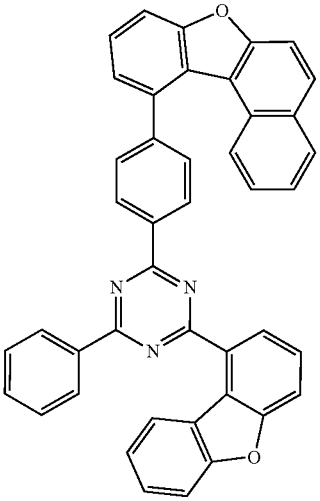
[1-12]
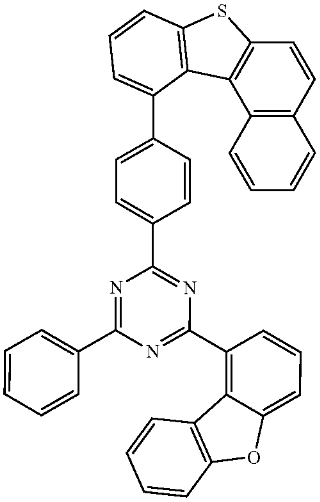
[1-13]
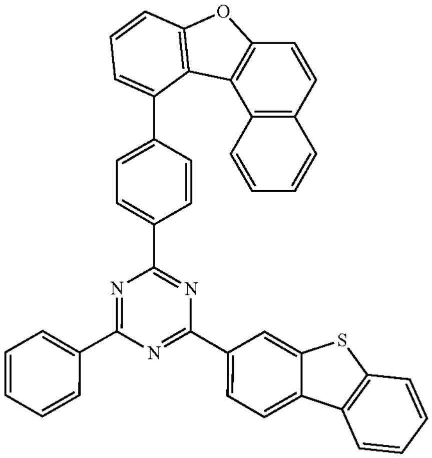

-continued
[1-14]
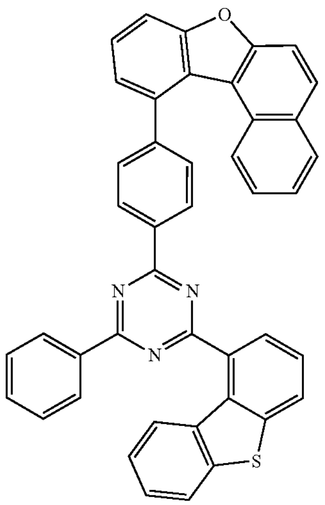
[1-15]
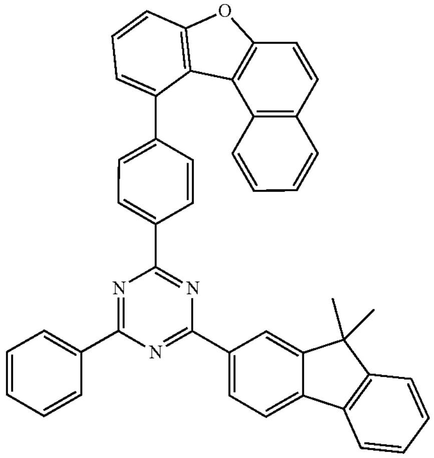
[1-16]
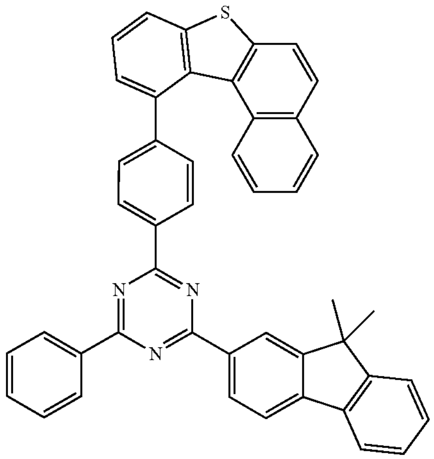
-continued
[1-17]
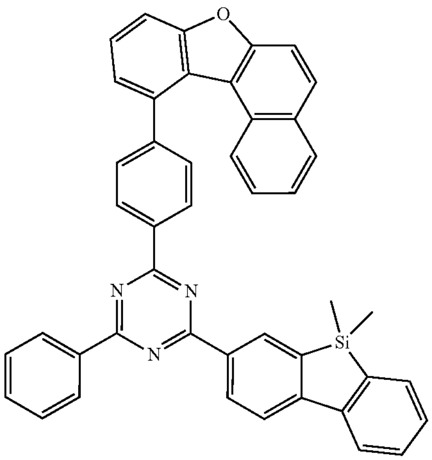
[1-18]
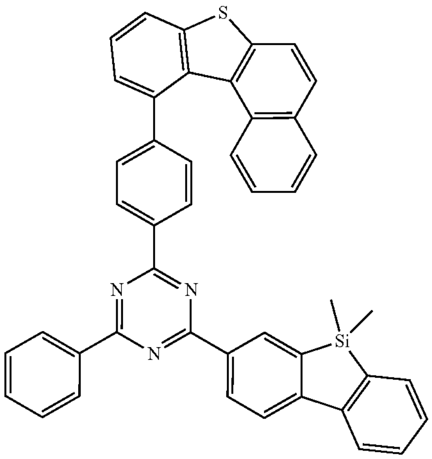
[1-19]
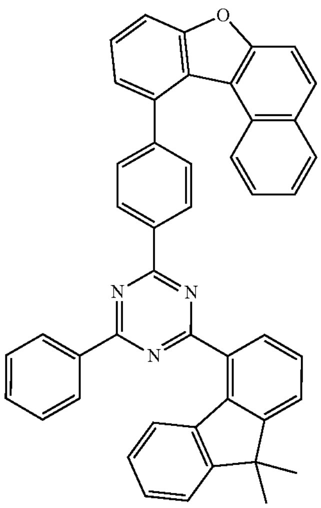

-continued
[1-20]
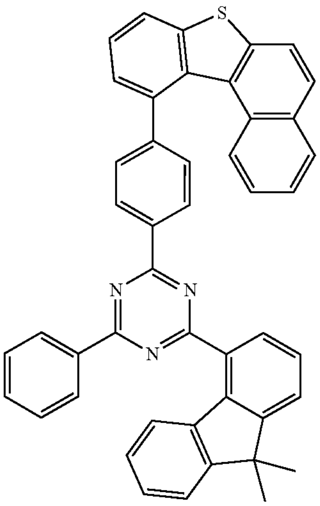
[1-21]
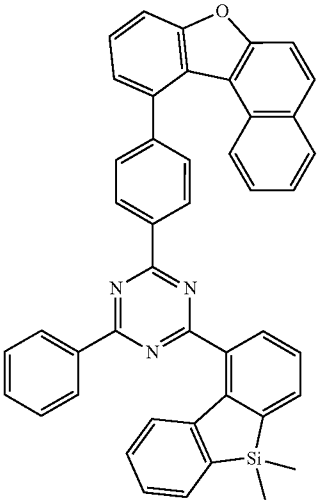
[1-22]
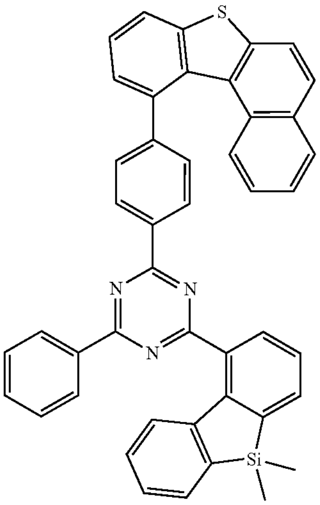
-continued
[1-23]
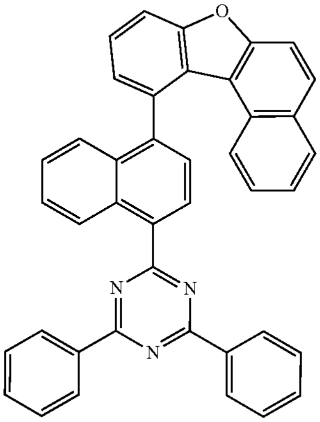
[1-24]
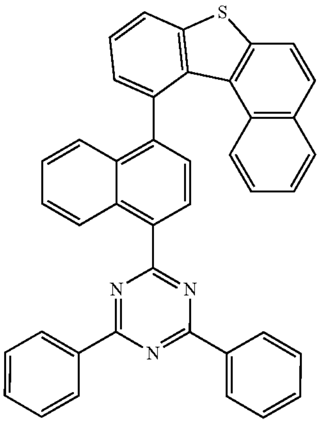
[1-25]
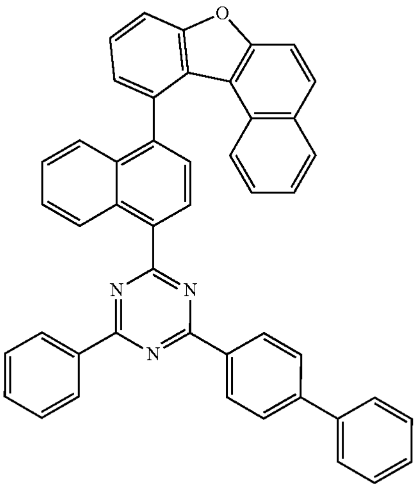

-continued
[1-26]
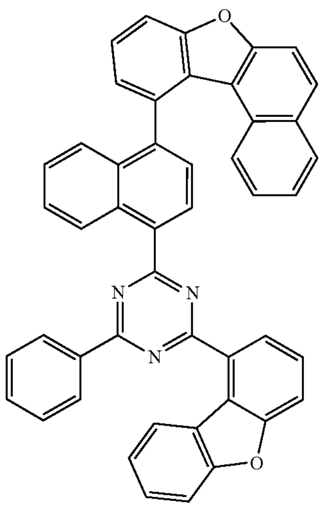
[1-27]
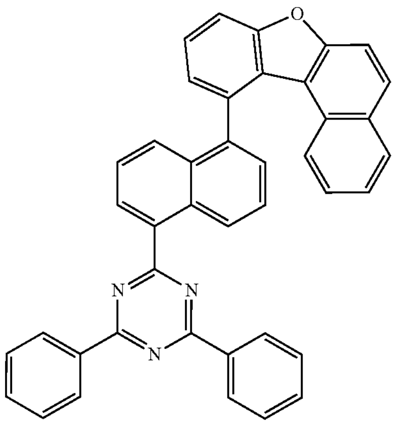
[1-28]
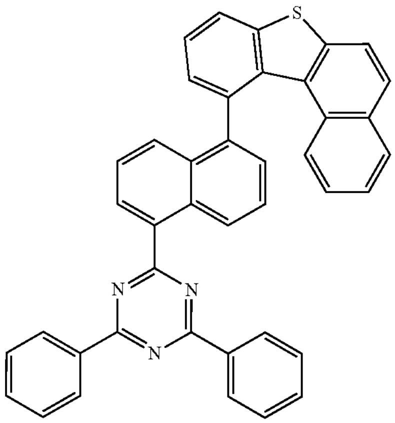
-continued
[1-29]
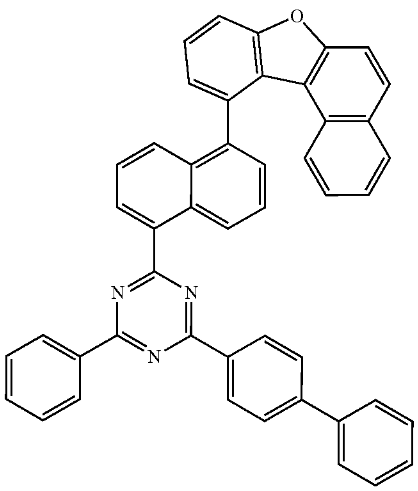
[1-30]
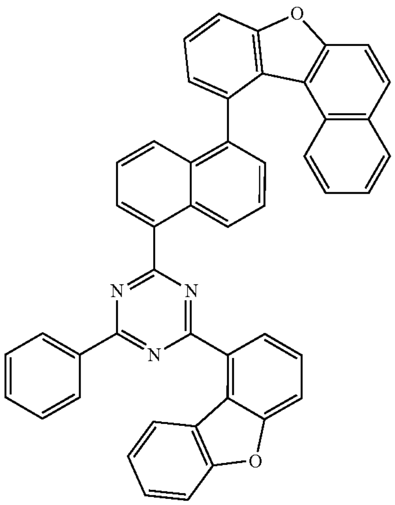
[1-31]
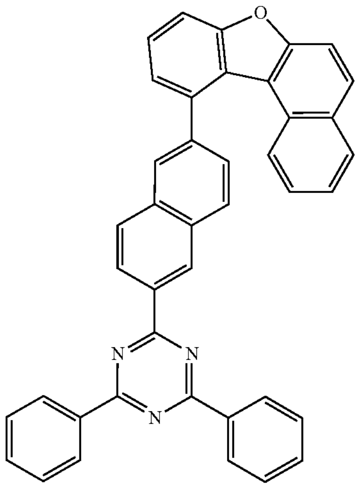

[1-32]
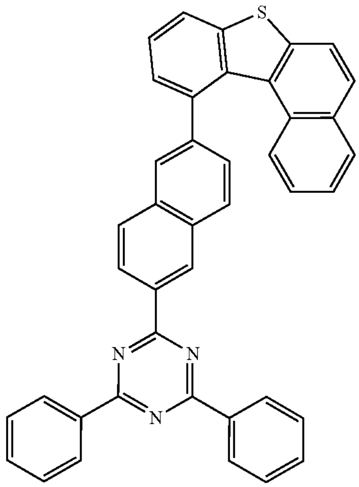
[1-33]
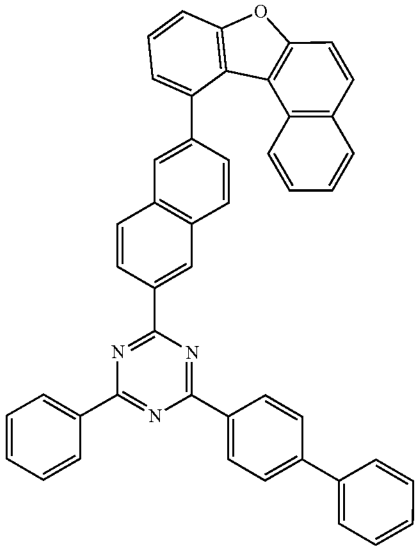
[1-34]
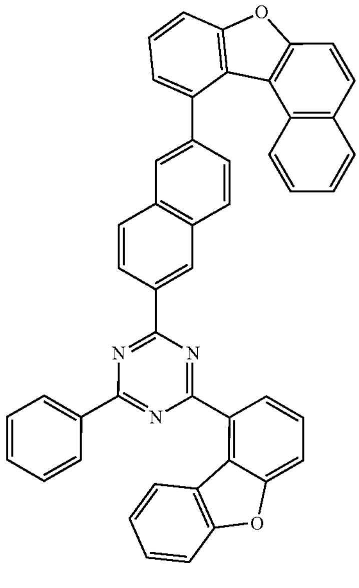
[1-35]
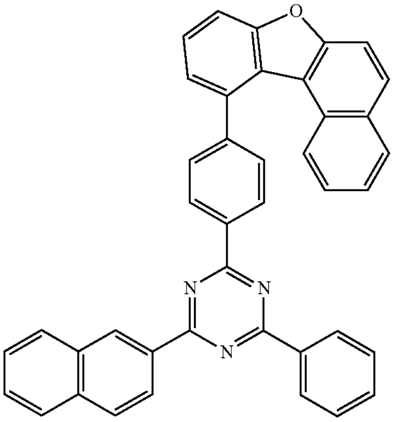
[1-36]
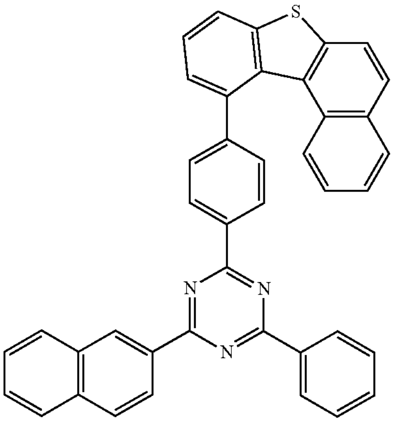
[1-37]
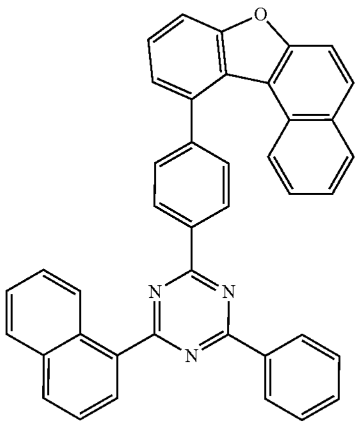

-continued
[1-38]
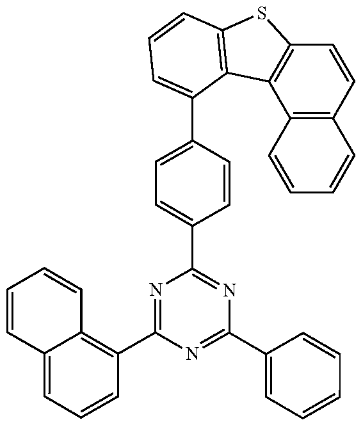
[1-39]
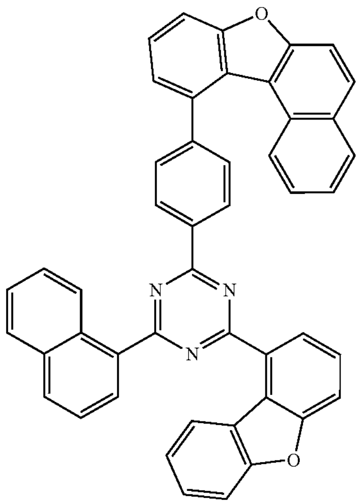
[1-40]
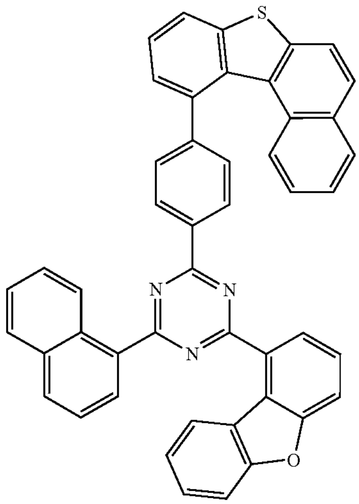
-continued
[1-41]
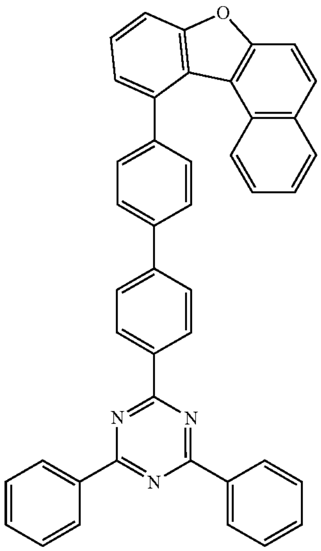
[1-42]
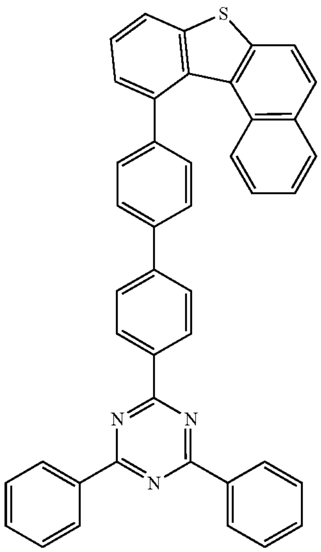
[1-43]
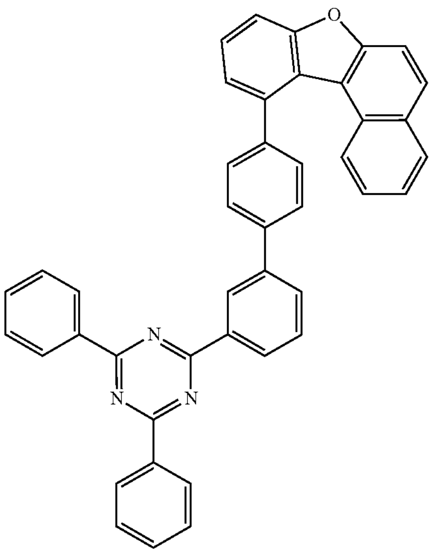

-continued
[1-44]
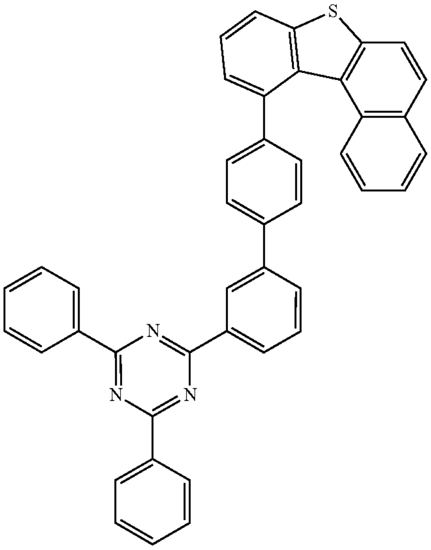
[1-45]
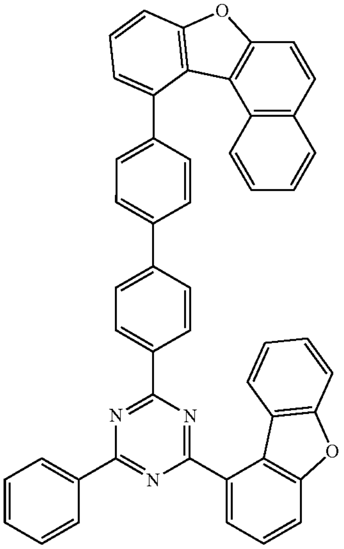
[1-46]
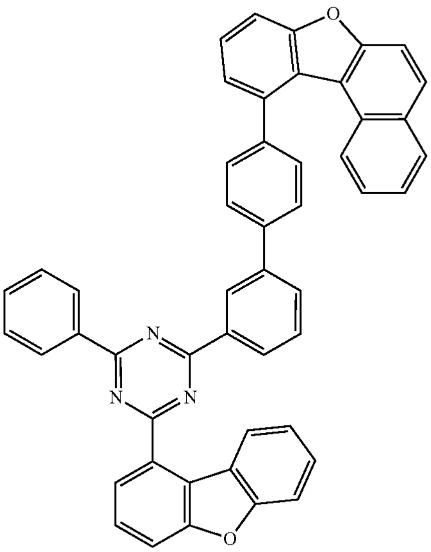
-continued
[1-47]
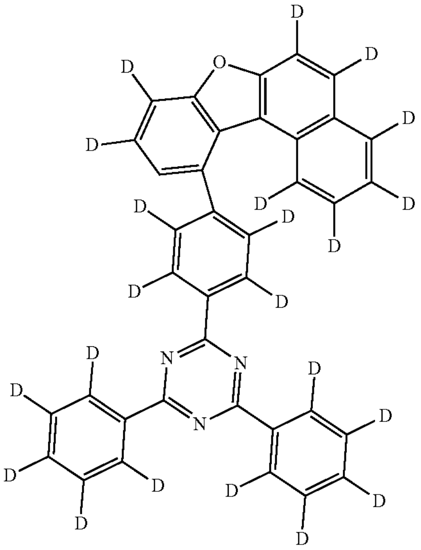
[1-48]
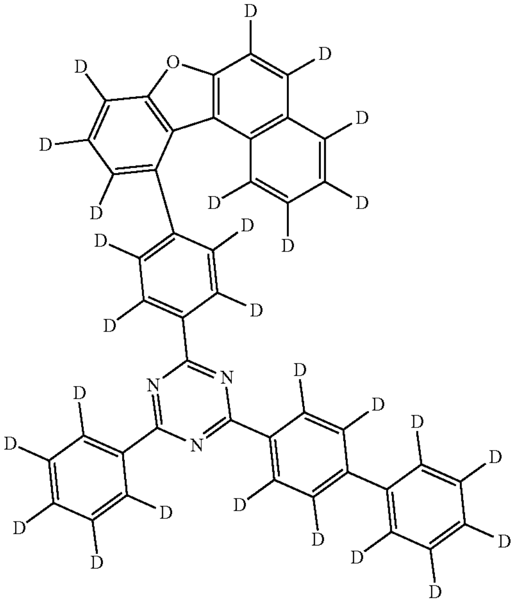

-continued
[1-49]
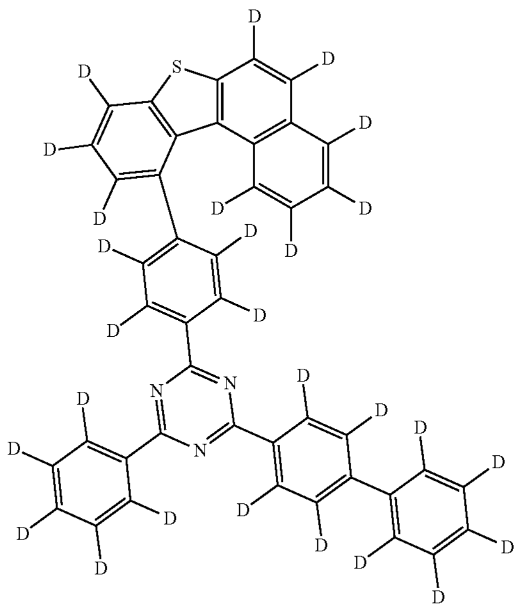
[1-50]
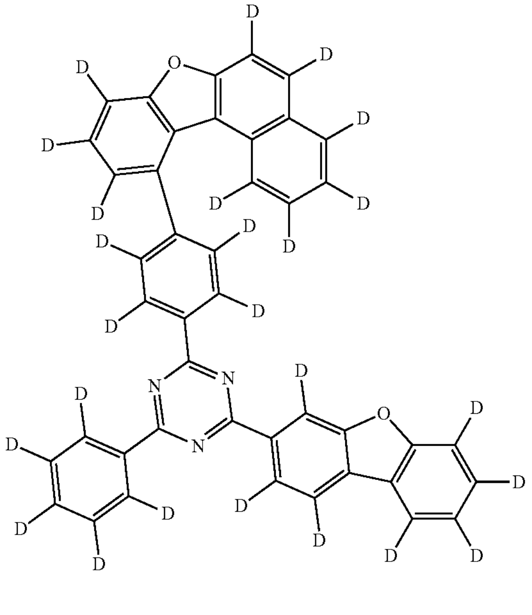
-continued
[1-51]
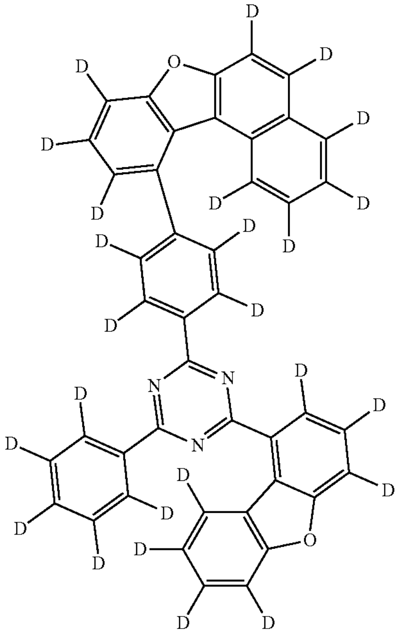
[1-52]
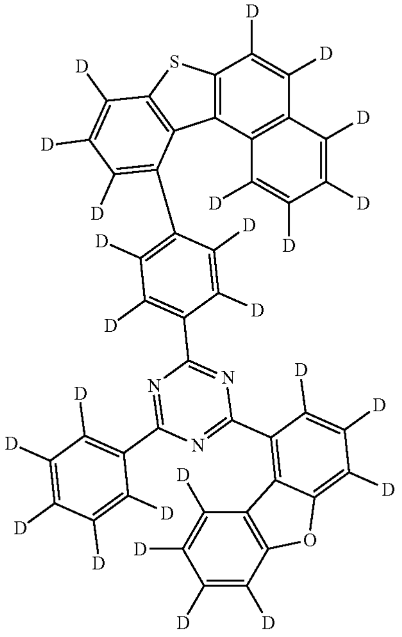

-continued
[1-53]
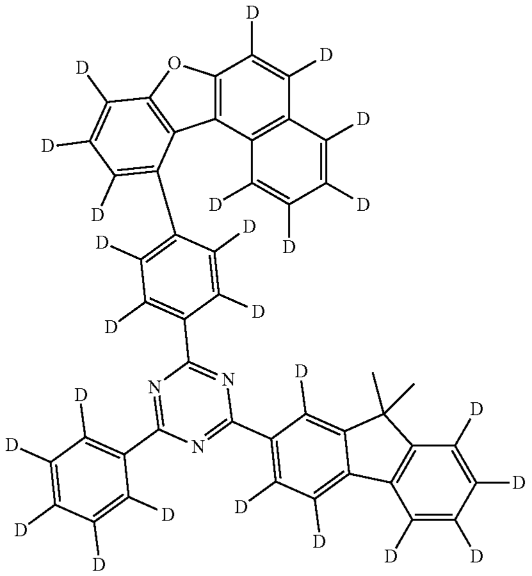
[1-54]
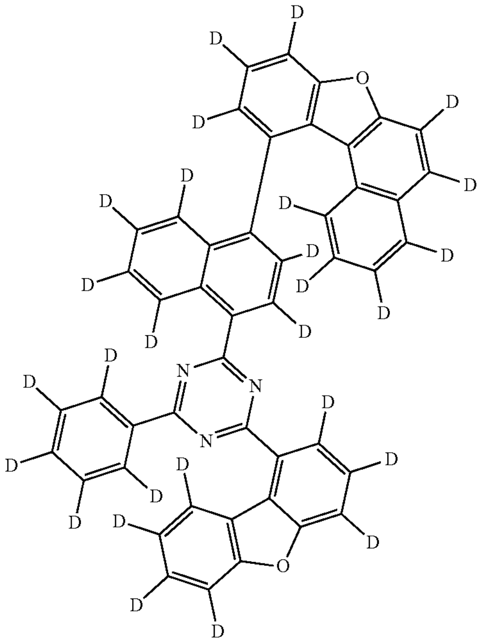
-continued
[1-55]
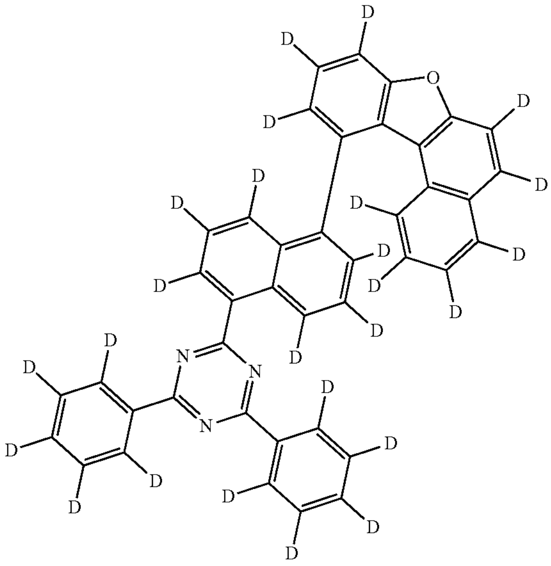
[1-56]
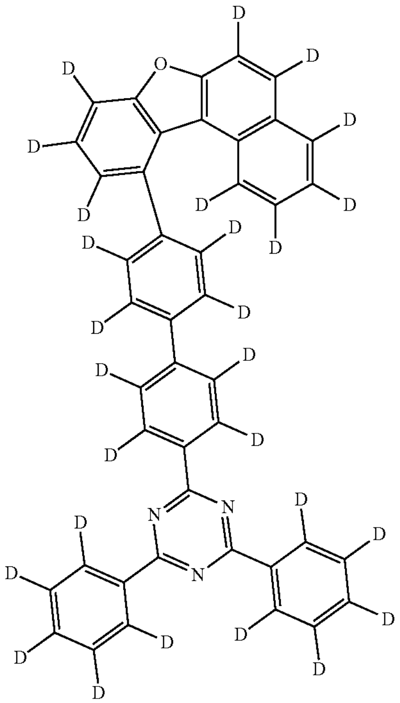

-continued

[1-57]

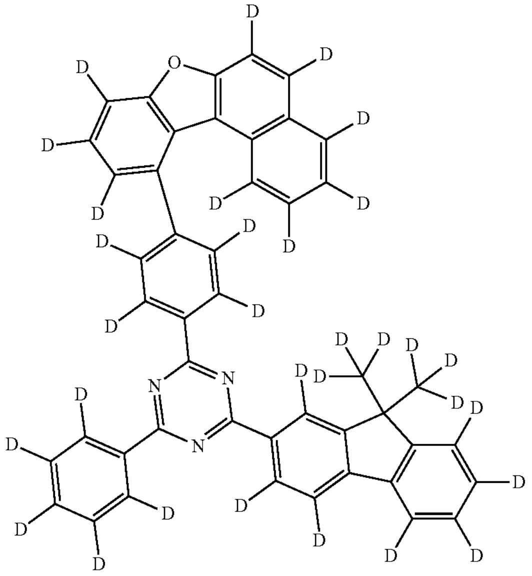

[1-58]

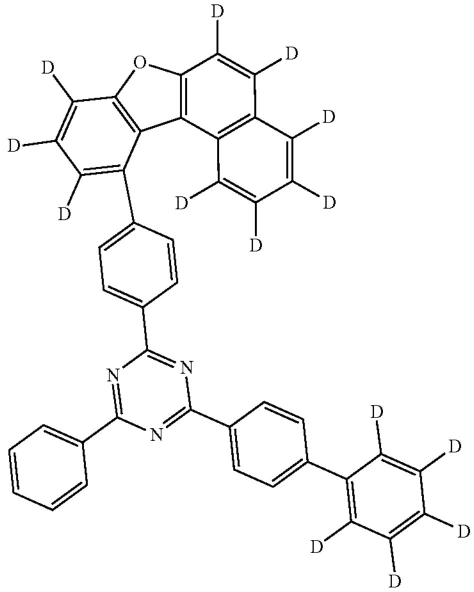

-continued

[1-59]

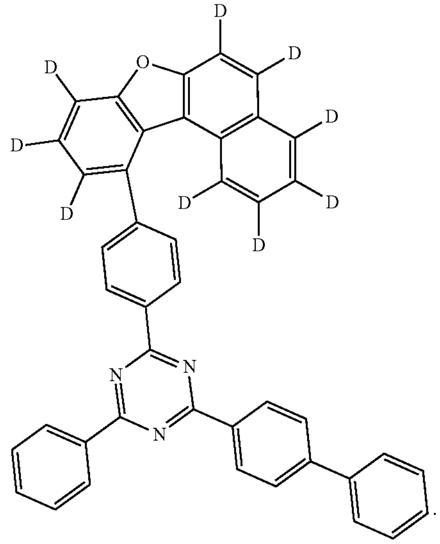

6. The composition as claimed in claim 1, wherein $R^{10}$, $R^{12}$, and $R^{13}$ are each independently hydrogen, deuterium, a substituted or unsubstituted C1 to C30 alkyl group, or a substituted or unsubstituted C6 to C30 aryl group.

7. The composition as claimed in claim 1, wherein:

the second compound represented by Chemical Formula 2-IVB is represented by Chemical Formula 2-IVB-2:

[Chemical Formula 2-IVB-2]

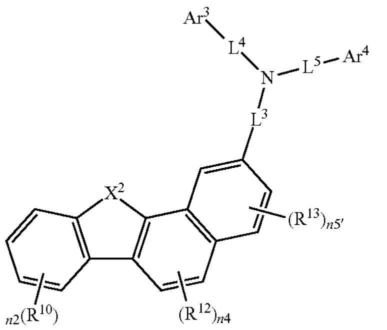

in Chemical Formula 2-IVB-2 $X^2$, $R^{10}$, $R^{12}$, $R^{13}$, $L^3$ to $L^5$, $Ar^3$, $Ar^4$, n2, n4, and n5', are defined the same as those of Chemical Formula 2-IVB.

8. The composition as claimed in claim 1, wherein the second compound represented by Chemical Formula 2-IVB is a compound of Group 2:

[Group 2]
A-10
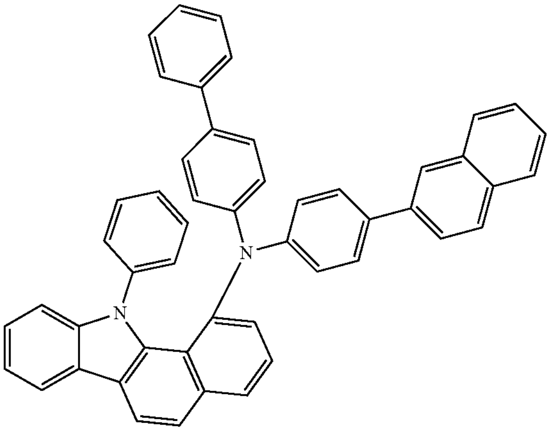
A-11
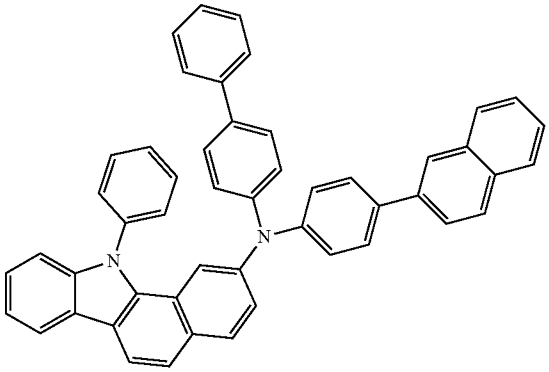
A-12
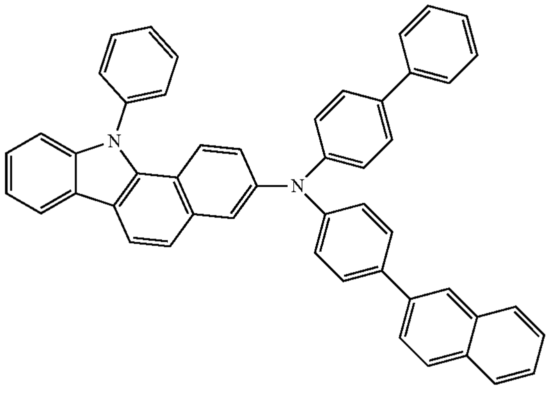
-continued
A-13
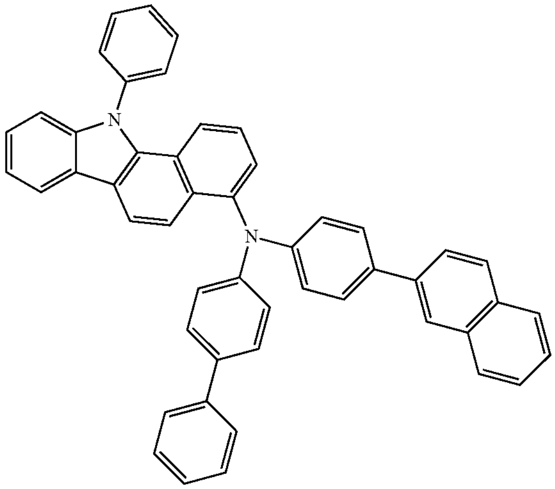
A-19
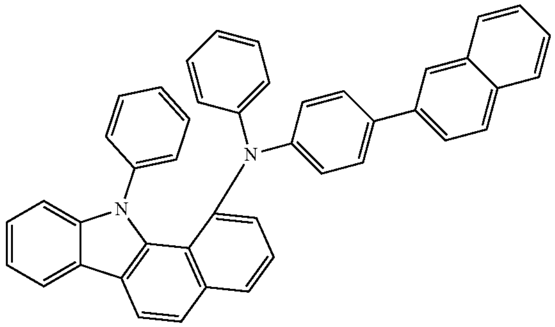
A-20
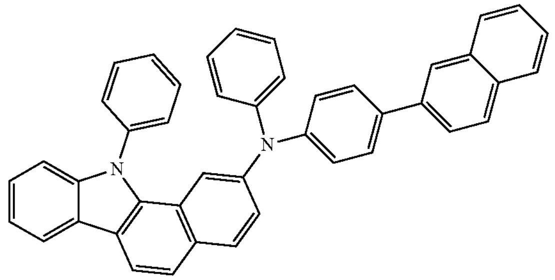
A-21
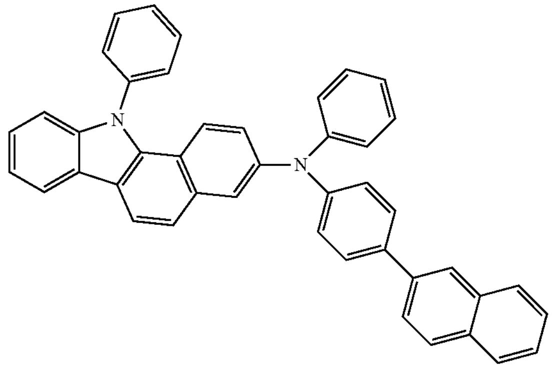

-continued
A-22
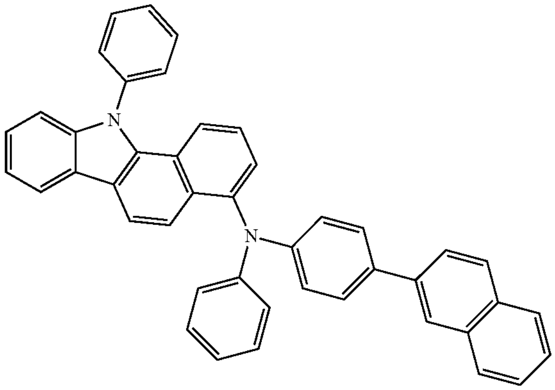
A-28
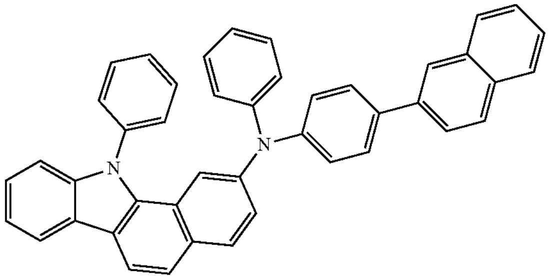
A-46
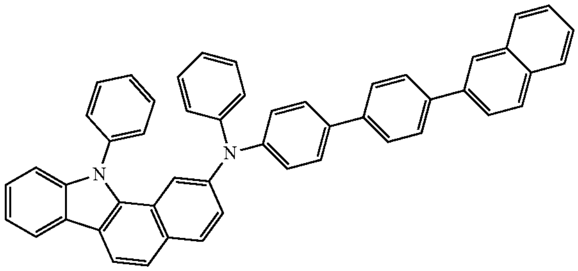
A-84
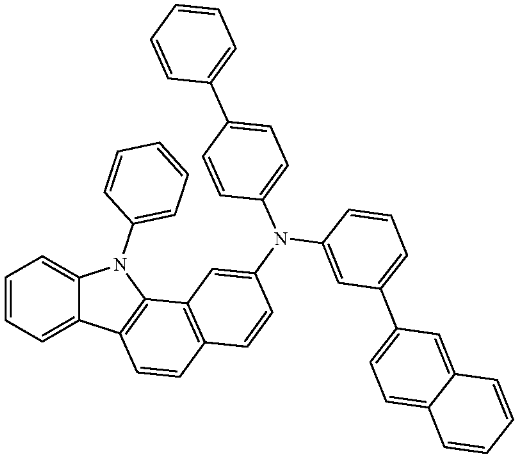
-continued
2-210
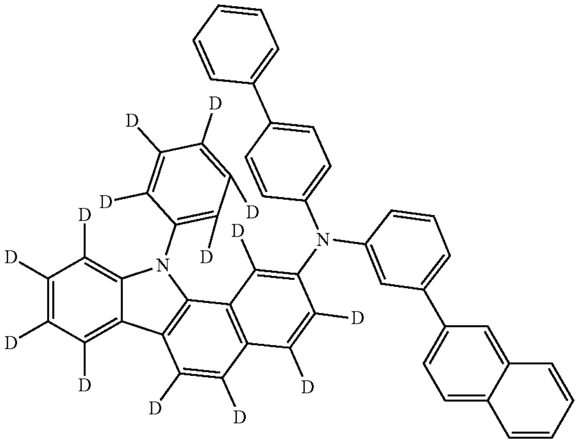
2-211
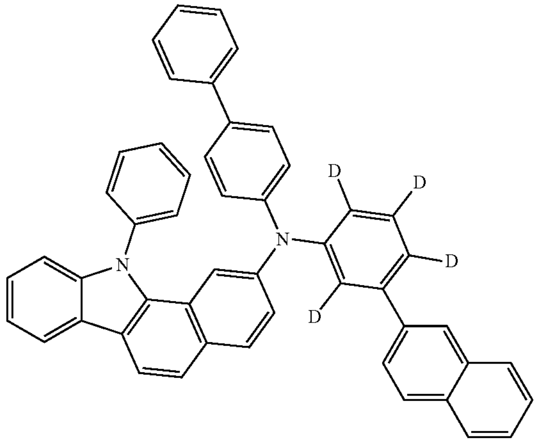
2-212
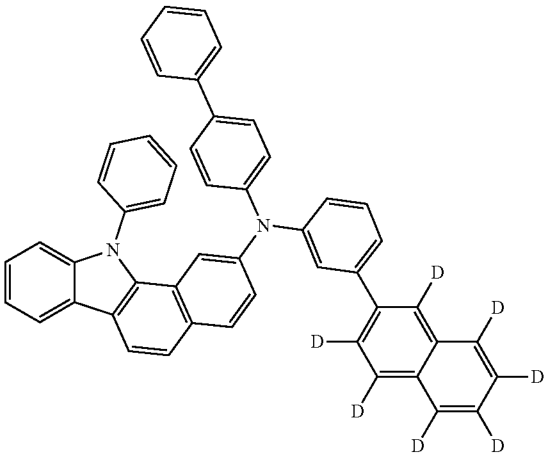

-continued 2-213

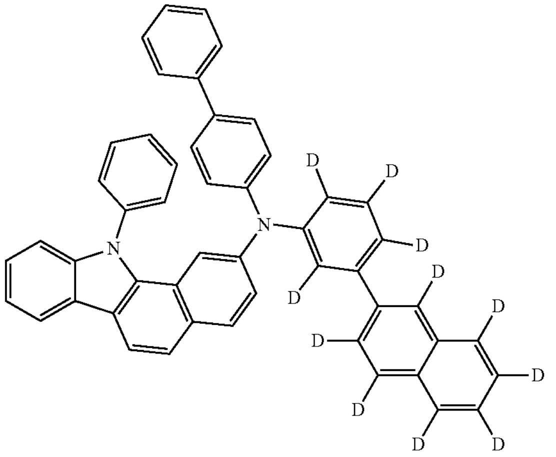

2-214

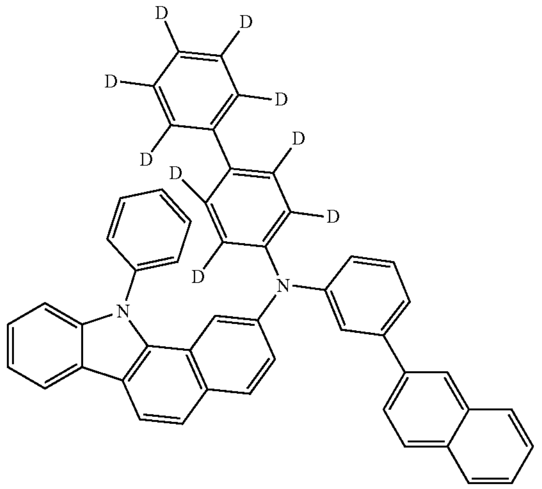

2-215

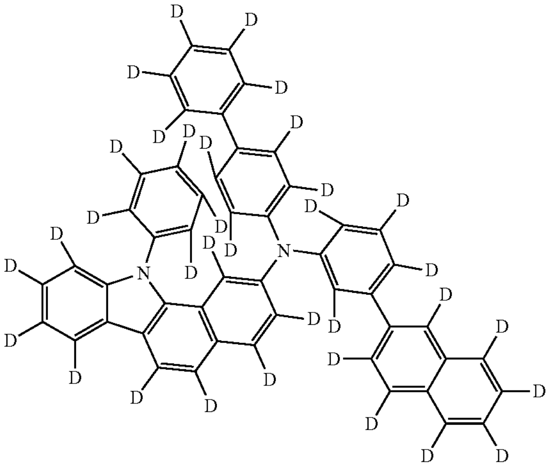

-continued 2-216

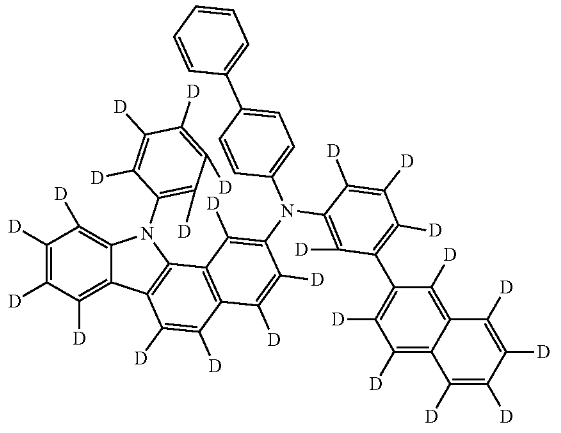

2-217

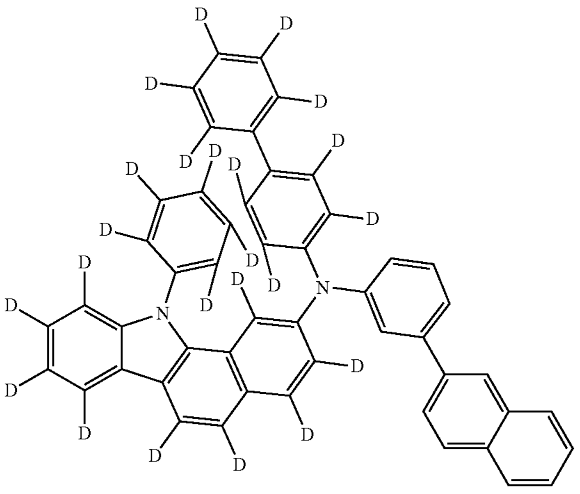

9. An organic optoelectronic device, comprising:

an anode and a cathode facing each other, and at least one organic layer between the anode and the cathode, wherein the at least one organic layer includes the composition for an organic optoelectronic device as claimed in claim 1.

10. The organic optoelectronic device as claimed in claim 9, wherein:

the at least one organic layer includes a light emitting layer, and the light emitting layer includes the composition for an organic optoelectronic device.

11. A display device comprising the organic optoelectronic device as claimed in claim 9.

* * * * *